(12) United States Patent
Dalton et al.

(10) Patent No.: US 9,624,161 B2
(45) Date of Patent: *Apr. 18, 2017

(54) ESTROGEN RECEPTOR LIGANDS AND METHODS OF USE THEREOF

(71) Applicant: GTx, Inc., Memphis, TN (US)

(72) Inventors: James T. Dalton, Ann Arbor, MI (US); Mitchell S. Steiner, Germantown, TN (US); Christopher C. Coss, Barlett, TN (US); Robert H. Getzenberg, Memphis, TN (US)

(73) Assignee: GTX, INC., Memphis, TN (US)

( * ) Notice: Subject to any disclaimer, the term of this patent is extended or adjusted under 35 U.S.C. 154(b) by 22 days.

This patent is subject to a terminal disclaimer.

(21) Appl. No.: 14/523,333

(22) Filed: Oct. 24, 2014

(65) Prior Publication Data

US 2015/0087712 A1 Mar. 26, 2015

Related U.S. Application Data

(63) Continuation-in-part of application No. 14/139,201, filed on Dec. 23, 2013, which is a (Continued)

(51) Int. Cl.
| | |
|---|---|
| *A61K 31/165* | (2006.01) |
| *C07C 235/64* | (2006.01) |

(Continued)

(52) U.S. Cl.
CPC .......... *C07C 235/64* (2013.01); *A61K 31/136* (2013.01); *A61K 31/137* (2013.01);
(Continued)

(58) Field of Classification Search
USPC .................................................. 514/170, 617
See application file for complete search history.

(56) References Cited

U.S. PATENT DOCUMENTS

| | | |
|---|---|---|
| 3,413,339 A | 11/1968 | Scherrer |
| 3,625,972 A | 12/1971 | Schulenberg |

(Continued)

FOREIGN PATENT DOCUMENTS

| | | |
|---|---|---|
| DE | 269213 | 1/1914 |
| DE | 2228351 | 12/1972 |

(Continued)

OTHER PUBLICATIONS

Bolla et al.; "Long-term results with immediate androgen suppression and external irradiation in patients with locally advance prostate cancer (an EORTC stud): a phase III randomized trial", The Lancet vol. 360, Jul. 2002, pp. 103-108.

(Continued)

*Primary Examiner* — San-Ming Hui
(74) *Attorney, Agent, or Firm* — Mark S. Cohen; Pearl Cohen Zedek Latzer Baratz LLP

(57) ABSTRACT

The present invention relates to methods for reducing testosterone levels in a male subject and methods of treating, suppressing, reducing the incidence, reducing the severity, or inhibiting prostate cancer, advanced prostate cancer, castration resistant prostate cancer (CRPC), metastatic castration resistant prostate cancer (mCRPC), and methods of reducing high or increasing PSA levels and/or increasing SHBG levels in a subject suffering from prostate cancer, advanced prostate cancer, castration resistant prostate cancer (CRPC) and metastatic castration resistant prostate cancer (mCRPC). The compounds of this invention suppress free or total testosterone levels despite castrate levels secondary to ADT and reduce high or increasing PSA levels. This reduction in testosterone levels may be used to treat prostate cancer, advanced prostate cancer, CRPC and mCRPC without causing bone loss, decreased bone mineral density, (Continued)

increased risk of bone fractures, increased body fat, hot flashes and/or gynecomastia.

15 Claims, 60 Drawing Sheets

Related U.S. Application Data continuation-in-part of application No. 13/766,535, filed on Feb. 13, 2013, which is a continuation-in-part of application No. 13/713,345, filed on Dec. 13, 2012, which is a continuation-in-part of application No. 13/215,679, filed on Aug. 23, 2011, which is a continuation-in-part of application No. PCT/US2010/025032, filed on Feb. 23, 2010.

(60) Provisional application No. 61/154,707, filed on Feb. 23, 2009, provisional application No. 61/168,983, filed on Apr. 14, 2009, provisional application No. 61/261,669, filed on Nov. 16, 2009, provisional application No. 61/380,113, filed on Sep. 3, 2010.

(51) Int. Cl.

| | | |
|---|---|---|
| *C07C 233/75* | (2006.01) | |
| *C07C 215/50* | (2006.01) | |
| *C07C 215/82* | (2006.01) | |
| *A61K 45/06* | (2006.01) | |
| *A61K 31/167* | (2006.01) | |
| *A61K 31/137* | (2006.01) | |
| *A61K 31/136* | (2006.01) | |
| *C07D 295/088* | (2006.01) | |

(52) U.S. Cl.
CPC .......... *A61K 31/167* (2013.01); *A61K 45/06* (2013.01); *C07C 215/50* (2013.01); *C07C 215/82* (2013.01); *C07C 233/75* (2013.01); *C07D 295/088* (2013.01)

(56) References Cited

U.S. PATENT DOCUMENTS

| | | |
|---|---|---|
| 3,838,131 A | 9/1974 | Gauthier et al. |
| 3,838,134 A | 9/1974 | Gauthier et al. |
| 3,960,886 A | 6/1976 | Schulenberg |
| 4,373,017 A | 2/1983 | Maukawa et al. |
| 5,081,112 A | 1/1992 | Tsutsumi et al. |
| 5,480,656 A | 1/1996 | Okada et al. |
| 5,491,173 A | 2/1996 | Toivola et al. |
| 5,575,987 A | 11/1996 | Kamei et al. |
| 5,631,020 A | 5/1997 | Okada et al. |
| 5,643,607 A | 7/1997 | Okada et al. |
| 5,716,640 A | 2/1998 | Kamei et al. |
| 5,814,342 A | 9/1998 | Okada et al. |
| 6,036,976 A | 3/2000 | Takechi et al. |
| 6,166,013 A | 12/2000 | Coghlan et al. |
| 6,262,098 B1 | 7/2001 | Heubner et al. |
| 6,518,301 B1 | 2/2003 | Barlaam et al. |
| 6,632,447 B1 | 10/2003 | Steiner et al. |
| 6,762,205 B1 | 7/2004 | Koizumi et al. |
| 7,001,911 B2 | 2/2006 | Salvati et al. |
| 7,118,552 B2 | 10/2006 | Shaw et al. |
| 7,220,247 B2 | 5/2007 | Shaw et al. |
| 7,500,964 B2 | 3/2009 | Shaw et al. |
| 8,158,828 B2 | 4/2012 | Dalton et al. |
| 8,546,451 B2 | 10/2013 | Dalton et al. |
| 8,637,706 B2 | 1/2014 | Dalton et al. |
| 9,051,267 B2 | 6/2015 | Dalton et al. |
| 2002/0119953 A1 | 8/2002 | Brugnara et al. |
| 2002/0156301 A1 | 10/2002 | Kaneko et al. |
| 2002/0192310 A1 | 12/2002 | Bland et al. |
| 2003/0147936 A1 | 8/2003 | Sahadevan |
| 2003/0153625 A1 | 8/2003 | Steiner |
| 2004/0082813 A1 | 4/2004 | Iwakuma et al. |
| 2005/0182143 A1 | 8/2005 | Anttila |
| 2006/0088887 A1 | 4/2006 | Kato |
| 2006/0287282 A1 | 12/2006 | Steiner et al. |
| 2006/0287359 A1 | 12/2006 | Danso-Danquah et al. |
| 2007/0265296 A1 | 11/2007 | Dalton et al. |
| 2009/0062341 A1 | 3/2009 | Dalton et al. |
| 2009/0156614 A1 | 6/2009 | Dalton et al. |
| 2010/0267773 A1 | 10/2010 | Dalton et al. |
| 2012/0077845 A1 | 3/2012 | Dalton et al. |
| 2014/0057985 A1 | 2/2014 | Dalton et al. |
| 2014/0187641 A1 | 7/2014 | Dalton et al. |
| 2016/0031797 A1 | 2/2016 | Dalton et al. |

FOREIGN PATENT DOCUMENTS

| | | |
|---|---|---|
| EP | 0501656 | 9/1992 |
| EP | 1193250 | 4/2002 |
| EP | 1593665 A1 | 11/2005 |
| FR | 4333 | 9/1966 |
| FR | 1.536.400 | 7/1967 |
| FR | 1.557.928 | 2/1969 |
| FR | 7699 | 2/1970 |
| FR | 2.098.587 | 4/1972 |
| GB | 2126576 | 3/1984 |
| GB | 2305173 | 2/1997 |
| GB | 2305177 | 2/1997 |
| JP | 49127938 A | 12/1974 |
| JP | 11-71332 | 3/1999 |
| JP | 2002-322162 | 11/2002 |
| JP | 2004-307380 | 11/2004 |
| JP | 2005-247961 | 9/2005 |
| JP | 2005-255981 | 9/2005 |
| JP | 2008-156239 A | 7/2008 |
| WO | WO 96/07402 | 3/1996 |
| WO | WO 96/08240 | 3/1996 |
| WO | WO 97/30047 | 8/1997 |
| WO | WO 99/37309 | 7/1999 |
| WO | WO 01/44161 | 6/2001 |
| WO | WO 02/00653 | 1/2002 |
| WO | WO 02/28853 | 4/2002 |
| WO | WO 2004/009552 | 1/2004 |
| WO | WO 2004/026823 | 4/2004 |
| WO | WO 2007/062230 | 5/2007 |
| WO | WO 2008/130571 | 10/2008 |
| WO | WO 2008/147418 | 12/2008 |
| WO | WO 2010/096801 A1 | 8/2010 |

OTHER PUBLICATIONS

Denham et al.; Short-term androgen deprivation and radiotherapy for locally advance prostate cancer: results from the Trans-Tasman Radiation Oncology Group 96.01 randomised controlled trial; The Lancet vol. 6, Nov. 2005, pp. 841-850.

Pilepich et al.; "Androgen Deptrivation with Radiation Therapy compared with Radiation Therapy Alone for Locally Advances Prostatic Carcinoma: a Randomized Coparative Trial of the Radiation Therapy Oncology Group"; Urology vol. 45, No. 4, Apr. 1995, pp. 616-623.

Advanced Prostate Cancer, Fact Sheet downloaded from http//:www.urologyhealth.org/urology/articles/_notes/AdvPCFactSheet.pdf.

Prostate Cancer—Treatment Options; downloaded from http//:cancer.net/cancertypes/prostate-cancer(treatment-options).

Wei et al. "Synthesis of triphenylamine-cored dendritic two-photon absorbing chromophores", Org Lett. Jul. 21, 2005;7(15):3199-202.

Advanced Prostate Cancer, Fact Sheet downloaded from http//:www.urologyhealth.org/urology/articles/_notes/AdvPCFactSheet.pdf, 2011.

Prostate Cancer—Treatment Options; downloaded from http//:cancer.net/cancer-types/prostate-cancer(treatment-options), 2015.

Alibhai et al "Prevention and Management of Osteoporosis in Men Receiving Androgen Deprivation Therapy: A Survey of Urologists and Radiation Oncologists", Urology, vol. 68, pp. 126-131. (2006).

(56) References Cited

OTHER PUBLICATIONS

Angelo et al. "Nouvelles solutions ioniques radiclaires et leur emplol.", Bull de la Soc. Chim. De France, No. 9, 3855-3856. (1968).
Anonymous; "GTx-758: The Potential for a Best in Class", Feb. 11, 2009, Retrieved online: URL:http://www.gtxinc.com/Pipeline/GTx758.aspx?Sid=5.
Australian Office Action cited dated Oct. 25, 2011 reference in AU Patent Application No. 2006318400, D21 RN 663217-19-14, Benzamide, N-[3, 5-bis (I,I-dimethylethyl)-4-hydroxyphenyl]-2-chloro-N-(4-methylphenyl), Chemical Library Supplier, Mar. 15, 2004.
Australian Office Action dated Oct. 25, 2011 cited reference in AU Patent Application No. 2006318400, D19 CAS RN- 79777-72-1, Benzamide, 2,4-dichloro-N, N-bis (2 -chlorophenyl), Chemical Library, Dec. 15, 2004.
Australian Office Action dated Oct. 25, 2011 cited reference in AU Patent Application No. 2006318400, D31 CAS RN 300668-84-4, Benzamide, N-(3-bromophenyl_-N-(4- bromophenyl)-2-nitro, Chemical Library Supplier, Nov. 1, 2000.
Australian Office Action dated Oct. 25, 2011cited reference in AU Patent Application No. 2006318400, D22 CAS RN 409111-68-8, Benzeneacetic acid, 2, 2'-[4- chlorobenzoyll)iminio]bis-, dimethylester.
Banker et al.; "Modern Pharmaceutics", 3 Ed. pp. 451 and 596 (1996).
Berthelot et al; "Stereochimie des complexes du chlorure d'iode avec les bases carbonylees", Can. J. Chem, vol. 63, 1985, pp. 958-962. (1985).
Birchall et al.; "Rearrangements of Diphenylamine Derivatives, II, Rearrangement of Some N- aroyldiphenylamines and the Intermolecular Character of the Reaction", Journal of the Chemical Society [Section] C: Organic 1968, vol. 23, pp. 2900-2904.
Boltze et al., "The Chemistry of Etofenamate, a Novel Anti-inflammatory Agent from the Series N-arylanthranilic Acid Derivatives", Arzneimittel-Forschung, 1977, vol. 27, No. 6B, pp. 1300-1312.
Carter et al. John, Willey & Sons, 2nd Edition, pp. 361-365, (1981).
Carter et al.; "Arylation with 1,3-dinitroarnes and copper (I) tert-butoxide Scope and Limitations", Journal of Chemical Reserch, Synopses, 1958, vol. 5, pp. 136-137.
Chadwick et al. "Identification of pathway-selective estrogen receptor ligands that inhibit NF-kB transcriptional activity", PNAS, vol. 102, No. 7, pp. 2543-2548. (2005).
Chapman et al. "New method for preparing substituted diphenylamines", Journal of the Chemical Society, pp. 569-72, 1929.
Chapman et al.; "Beckmann Change, I, The Spontaneous Rearrangement of oxime picryl ethers", Journal of the Chemical Society, 1933, pp. 806-811.
Clark et al."Synthetic studies on 5-(3,4-dimethoxyphenyl)-5, 6-dihydrophenanthridin-6-ol, an analog of perloline", Australian Journal of Chemistry, 35(8), pp. 1645-1653, (1982).
Coss et al.; "Preclinical Characterization of a Novel Diphenal Benzamide Selective ER[Alpha] Agonist for Hormone Therapy in Prostate Cancer—Supplemental data", Endocrinology, vol. 153, No. 3, Jan. 31, 2012, pp. 1070-1081.
Coss et al.; "Preclinical Characterization of a Novel Diphenal Benzamide Selective ER[Alpha] Agonist for Hormone Therapy in Prostate Cancer", Endocrinology, vol. 153, No. 3, Jan. 31, 2012, pp. 1070-1081.
Daniell. "Osteoperosis due to androgen deprivation therapy in men with prostate cancer", Urology 58, supplement 2A, pp. 101-106, (2001).
Datta et al. "Studies on Enamides. Part 4. Photochemical Investigations of N-Aroyldiphenylamines", Tetrahedron, 46(19), 6821-30, (1990).
Demeter et al. "Dual fluorescence and intramolecular charge transfer with N-Phenylphenanthridinones", Journal of Physical Chemistry a, 105 (19), 4611-4621, (2001).

El-Taweel et al., "Studies with polyfunctionally substituted heteroarenes: New synthesis of benzo[c]quinolinones and pyrano[3,2,c]quinoline derivatives", Bollettino Chimico Farmaceutico, 137(8), pp. 325-333, (1998).
Eurasian Search Report of Application No. 200801461; Date of Mailing Oct. 29, 2008.
Fong et al. "The effect of side chain confirmation on the carbon-13 substituent chemical shifts of N-substituted benzamides", Australian Journal of Chemistry, 34(6), 1205-1214, (1981).
Fotsis et al. "Genistein, a Dietary-Derived Inhibitor of in vitro Angiogensis." PNAS, vol. 90, pp. 2690-2694. (1993).
Froehlich et al.; "Process for Preparaton of Anthranilamides", Ger (East), 1989, p. 7.
Gilman et al.; "Synthesis of some 5, 10-dihydrophenazasiline derivatives", Journal of Organic Chemistry, 1961, vol. 26, pp. 2013-2017.
Gilman; "Inositol: Goodman's and Gilman's Pharmacological Basis of Therapeutics", vol. 4, 2006.
Grease et al. "Photochemical Synthesis of N-Arylbenzophenanthridine Selective Estrogen Receptor Modulators (SERMS)", J. Med. Chem. 44, 2857-2860. (2001).
Grigorovskii et al.; "The Formation of 9-Chloroacridines from Diphenylamine-2-Carboxylic Acids and Phosphorus Oxychlorid", Zhurnal Prikladnoi Khimii, 1950, vol. 23, pp. 197-204.
Grimshaw et al. "Intramolecular Cyclisation during the reduction of 2-chloro-NN-diphenylbenzamides", Electrochemical Reactions, Part 20, vol. 22, p. 2456. (1977).
GTx-758 on Serum prostate-specific antigen (PSA) in men with castrate resistant prostate cancer. Clinicaltrials.gov (online), retrieved from: http://clinicaltrials.gov/archive/NCT01420861/2011_08_19. Aug. 19, 2008.
Gustafson. "ERb scientific visions translate to clinical uses." Climacteric, vol. 9, pp. 156-160. (2006).
Harris et al. "Evaluation of an Estrogen Receptor-b Agonist in Animal Models of Human Disease." Endocrinology, vol. 144, No. 10, pp. 4241-4249. (2006).
Harris et al., "Sequential N-Arylation of primary amines as a route to alkyldiarylamines", Journal of Organic Chemistry, vol. 64, 1999, pp. 6019-6022.
Harris. "Estrogen Receptor-b: Recent Lessons from in Vivo Studies", Molecular Endocrinology, vol. 21, No. 1, pp. 1-13. (2006).
Harris; "The unexpected science of estrogen receptor-b selective agonists: a new class of anti-inflammatory agents?", Nuclear Receptor Signaling, vol. 4, 012-016. (2006).
Hayashi et al.; "Genistein, a Protein Tyrosine Kinase Inhibitor, Ameliorates Retinal Degeneration After Ischemia-Reperfusion Injury in a Rat.", Investigative Ophthalmology and Visual Science, vol. 38, No. 6, pp. 1193-1202. (1997).
Heim et al.; "They Phytoestrogen Genistein Enhances Osteogenesis and Represses Adipogenic Differentiation of Human Primary Bone Marrow Stromal Cells", Endocrinology, vol. 145, No. 2, pp. 848-859. (2006).
Heine et al.; "The reactions of an o-Quinone Monoimide with some phenols", Journal of Organic Chemistry, vol. 55, No. 13, 1990, pp. 4039-4043.
Hellwinkel et al."Heterocyclic synthese via carbanionically induced rearrangement reactions", Tetrahedron, 39(12), 2073-84, (1983).
Hellwinkel et al., "Ein bequemes Eintopfverfahren zur Synthese von 1,2-Benzisothiazol-1, 1-dioxiden", No. 5, 1989, pp. 394-395.
Hellwinkel et al.; "Carbanionically induced [1,3]-migrations of π-and Corrdinatively Unsaturated Groups", Chemische Berichte, 1983, vol. 116, No. 10, pp. 3375-3405.
Hey et al., "Internuclear cyclization. XIII. Decomposition of diazonium salts prepared from N-(0-aminobenzoyl) diphenylamines. New molecular rearrangement", Journal of the Chemistry Society, pp. 1563-1572, (1959).
Ho et al. "Estrogens and Anti-Estrogens: Key Mediators of Prostat Carcinogenesis and New Therapeutic Candidates", Journal of Cellular Biochemistry, vol. 91, pp. 491-503. (2004).
Hoeft et al.; "Reactions of nitrogen-containing compounds with molecular oxygen II. Partially hydrogenated, benxocondensed isoquinolines", justus Liebids Annalen de Chemie, 697, pp. 181-187, (1966).

(56) References Cited

OTHER PUBLICATIONS

Huhtaniemi et al.; "Will GnRH antagonists improve prostate cancer treatment?", Trends in Endocrinology and Metabolism, vol. 20 No. 1, pp. 43-50.
International Search Report of Application No. PCT/US06/45451; Date of Mailing Feb. 29, 2008.
International Search Report of Application No. PCT/US08/04908; Date of Mailing Sep. 26, 2008.
International Search Report of Application No. PCT/US10/25032; Date of Mailing Apr. 8, 2010.
Ivakhnenko et al.; "Synthesis and Transformations of Phenoxyl Biradicals", Zhurnal Organicheskoi Khimii, 1990, vol. 26(3), pp. 616-623.
Jamison et al. "Optical activation of acids and a new resolution process depending on it", Journal of the Chemical Society, 164-76, (1940).
Jamison et al.; "Some Derivatives of Diphenylamine and a New Synthesis of N-arylanthranilic Acids and of Acridones", Journal of the Chemical Society, 1937, pp. 1954-1959.
Joseph et al., "Rearrangement of nitrones to amides using chlorosulfonyl isocyanate", Tetrahedron, 42(21), 5979-83, (1986).
Kai et al.; "Soybean Isoflavones Eliminate Nifedipine-Induced Flushing of Tail Skin in Ovariectomized Mice", J Pharmacol. Sci., vol. 95, pp. 476-478. (2004).
Kenetth et al.; "The kinetics of the thermal rearrangement of phenyl benzanilimino ethers", Journal of the American Chemical Society, 77, 2205-9, (1955).
Korpachev et al.; "A postmenopausal metabolic syndrome and methods for its correction", Health of Ukraine, No. 10/1, Jun. 2007, pp. 60-61.
Lam et al., "Copper-promoted C—N. bond cross-coupling with phenylstannane", Tetrahedron Letters 43, 2002, 3091-3094.
Levy et al. "Reactivity of some secondary amines", Memorial des Services de l'Etat, 32, pp. 62-66, 2005.
Lupron FDA label, 2005.
Lutty et al. "Changes in Choriocapillaris and Retinal Pigment Epithelium (RPE) in Age-Related Macular Degeneration", Molecular Vision, vol. 5, No. 35, (1999).
Migel et al., "Estimate of the energy characteristics of the electronic-vibrational interactions in N-methylphenanthridone molecules", Zhurnal Fizicheskoi Khimii, 62(9), pp. 2533-2537, (1986).
Miller et al.; "Phase III, randomized, placebo-controlled study of once-daily oral zibotentan (ZD4054) in patients with non-metastatic castration-resistant prostate cancer", 2013, Prostate Canc Prost Dis. Feb.; 16:187-192.
Mintas et al.; "Sterically hindered N-aryl-2 (1H)-quinolones and N-aryl-6-(5H)-phenanthridinones: separation of enantiomers and barriers to racemization", Journal of the Chemical Society, Perkin Transactions 2: Physical Organic Chemistry (4), 1990, pp. 619-624, (1972-1999).
Mohler et al.; "Hydroxysteroid Dehydrogenase (17beta -HSD3, 17beta-HSD5, and 3alpha- HSD3) Inhibitors: Extragonadal Regulation of Intracellular Sex Steroid Hormone Levels", Recent Patents on Endocrine, Metabolic & Immune Drug Discovery, 1, 000-000, (2007).
Morani et al. "Lung dysfunction causes systematic hypoxia in estrogen receptor b knockout (ERb-/-) mice." PNAS. vol. 103, No. 18, pp. 7165-7169. (2006).
Morote et al., "Behavior of free testosterone in patients with prostate cancer on androgen deprivation therapy" Int J Biomarkers, 20:119-122, (2005).
Moynehan et al., Proceedings of the Chemical Society, Lodon 209, (1957).
Nakajima et al.; "Normalization of Retinal Vascular Permeability in Experimental Diabetes with Genistein", Investigative Ophthalmology and Visual Science, vol. 42, No. 9, pp. 2110-2114. (2001).
Norman et al. "Benzopyrans Are Selective Estrogen Receptor b Agonists with Novel Activity in Models of Benign Prostate Hyperplasia", J Med. Chem., vol. 49, pp. 6155-6157.(2006).

Office Action for Russian Patent Application No. 2011137324 issued on Jan. 30, 2014.
Ohnmacht et al.; "N-Aryl-3,3,3-trifluoro-2-hydroxy-2-methylpropanamides: potassium Channel Openers. Modifications on the Western Region", J. Med. Chem., 39, 4592-4601, (1996).
Ohta et al.; "Reaction of N,O-Diacylarylhydroxylamine with carbon nucleophiles", 1978, Tetrahedron Letters, pp. 1983-1986.
Penson et al. "The economic burden of metastatic and prostate specific antigen progression in patients with prostate cancer: findings from a retrospective analysis of health plan data", J. Urol. 171: 2250-2254, (2004).
Piutti et al.; "Azione dell'anidride ftalica sulla p- e m-ossidif-fenilammina", Gazzetta Chimica Italiana, vol. 28, 1898, pp. 370-382.
Presti; "Estrogen Therapy for Prostate Carcinoma", JAMA. 275(15): 1153-6, (1996).
Rhodes et al. "ERb-selective SERMs produce mnemonic-enhancing effects in the inhibitory avoidance and water maze tasks", Neurobiology of Learning and Memory, vol. 85, pp. 183-191. (2005).
Safe et al.; "The role of xenoestrogenic compounds in the development of breast cancer", Trends in Pharmacological Sciences, vol. 27, No. 8. (2006).
Scherowsky et al. "Reactions of heterocyclic onium salts with electron-rich multiple bond systems", Chemische Berichte, 116(1), pp. 186-196, (1983).
Scherr et al.; "The nonsteroidal effects of diethylstilbestrol: the rationale for androgen deprivation therapy without estrogen deprivation in the treatment of prostate cancer", J Urol.; 170(5):1703-8. Nov. 2003.
Schroeter et al.; "Dimolecular Anhydrides of Anthranilic Acid", Justis Liebigs Annalen der Chemie, 367, pp. 101-168, (1909).
Sharifi et al.; "Androgen Deprivation Therapy for Prostate Cancer", JAMA. 294(2): 238-244, (2005).
Shen et al.; "Expression of Estrogen Receptors-a and -b in Bladder Cancer Cell Lines and Human Bladder Tumor Tissue", American Cancer Society. (2006).
Simpkins et.al.; "Similarities between morphine withdrawal in the rat and the menopausal hot flush"Life Sci.; 32(17):1957-66. Apr. 25, 1983.
Smith; "Androgen Deprivation Therapy and Risk for Diabetes and Cardiovascular Disease in Prostate Cancer Survivors", Current Prostate Reports, 6:149-154, (2008).
Steigman et al.; "The Anhydrides of N-aryl Anthranilic Acids II", Journal of Organic Chemistry, 1937, vol. 2, pp. 211-212.
Suzuki et al.; "Current topics and perspectives relating to hormone therapy for prostate cancer", Int. J. Clin. Oncol. 13: 401-410, (2008).
Testa; "Predicting drug metabolism: concepts and challenges", Pure Appl. Chem., vol. 76, No. 5, pp. 907-914, (2004).
Townsend et al.; "Bone Fractures Associated with Luteinizing Hormone—Releasing Hormone Agonists Used in the Treatment of Prostate Carcinoma", Cancer, vol. 79, No. 3, pp. 545-550, (1997).
Tozer et al.; "Rearrangement of the o-Carbamyl Derivatives of Diphenyl ether", Journal of the Chemical Society, 1938, pp. 2052-2056.
Trotter et al.; "Design and Synthesis of Novel Isoquinoline-3-nitrilies as Orally Bioavailable Kv1.5 Antagonists for the Treatment of Atrial Fibrillation", American Chemical Society, (2006).
Tsourdi et al.; "The effect of selective estrogen receptor modulator administration on the hypothalamic-pituitarytesticular axis in men with idiopathic oligozoospermia", Fertility and Sterility doi: 10.1016, (2008).
Vivacqua et al.; "The G Protein-Coupled Receptor GPR30 Mediates the Proliferative Effects Induced by 17b-Estradiol and Hydroxytamoxifen in Endometrial Cancer Cells", Molecular Endocrinology, vol. 20, No. 3, pp. 631-646. (2006).
Walf et al.; "Aggression, mood and affect", Frontiers in Neuroendocrinology, vol. 27. (2006).
Werbel et al.; "Potential Antimalarial Substances. Amides of o-Ethoxy-and p-Isopropylbenzoic Acids", J. Med. Chem, 10(3), pp. 508-509., (1967).

(56) References Cited

OTHER PUBLICATIONS

West; "Solid state chemistry and its applications", Wiley, pp. 358 and 365, (1988).
Whitesel; "The Case for Diethylstilbestrol", The Journal of Urology, vol. 169, 290-291, Jan. 2003.
Wolff; "Burger's Medicinal Chemistry 5th Ed. Part I", Wiley, pp. 975-977M, (1996).
Wolff; "Burger's Medical Chemistry 4th Ed. Part I", Wiley: New York, 336-337, (1979).
Xu et al.; "Effects of genistein on angiotensin-converting enzyme in rats", Life Sciences, vol. 79, pp. 828-837. (2006).
Yu et al.; "Salutary effects of estrogen receptor-b agonist on lung injury after trauma-hemorrhage", Am. J. Physiol. Lung Cell Mol. Physiol., vol. 290, pp. L1004-L1009. (2006).
Belikov "Pharmaceutical chemistry", high school, 1993, vol. 1, pp. 43-47.
Office Action issued on Apr. 13, 2015 for Russian Patent Application No. 2012151846.
Sharifi et al. "Secondary hormonal therapy for prostate cancer: what lies on the horizon'?", BJU Int. Feb. 2008;101(3):271-4.

| Clinical Trial | Dose(s) | Patient Population | Time | Endpoint(s) |
|---|---|---|---|---|
| Study 1 | 609, 986, 1450 mg QD, Solutions | healthy males 18-40 yr, N=20/arm | 28d | Total T < 50 ng/dL (FL, castration) |
| Study 2 | 1000, 2000 mg QD, or 4-month Lupron Depot Injection | prostate cancer pts 45-80 yr, n=52/arm | 360d | Total T < 50 ng/dL (FL, castration) |
| Study 3 (early term.) | 2000 mg QD concurrent ADT | castrated prostate cancer pts on ADT for >6 month with rising PSA, n=25 | PSA inc. >25% | Serum PSA, Free T Progression (SL, SHBG↑) |
| Study 4 | 1000, 1500, 2000 mg QD | healthy males 50-80 yr, N=5/arm | 39d | Total T < 50 ng/dL (FL, castration) |
| Study 5 (early term.) | 1000 mg BID/LD, 1000 mg QD/MD<br>1000 mg BID/LD, 2000 mg QD/MD<br>1500 mg BID/LD, 1000 mg QD/MD<br>1500 mg BID/LD, 2000 mg QD/MD | prostate cancer pts 45-80 yr, n=26/arm | 28d(LD) 28d(MD) | Total T < 50 ng/dL (FL, castration) |
| Study 6 (upcoming) | Dose Escalation 125, 250, 500 mg QD concurrent ADT | castrated prostate cancer pts on ADT for >6 month with rising PSA, n=25 | 30d per DL AE based | Serum PSA, Free T Progression (SL, SHBG↑) |

FL - first line therapy
SL - second line therapy
DL - dose level
AE - adverse event
LD - loading dose
MD - maintenance dose

FIGURE 26

A
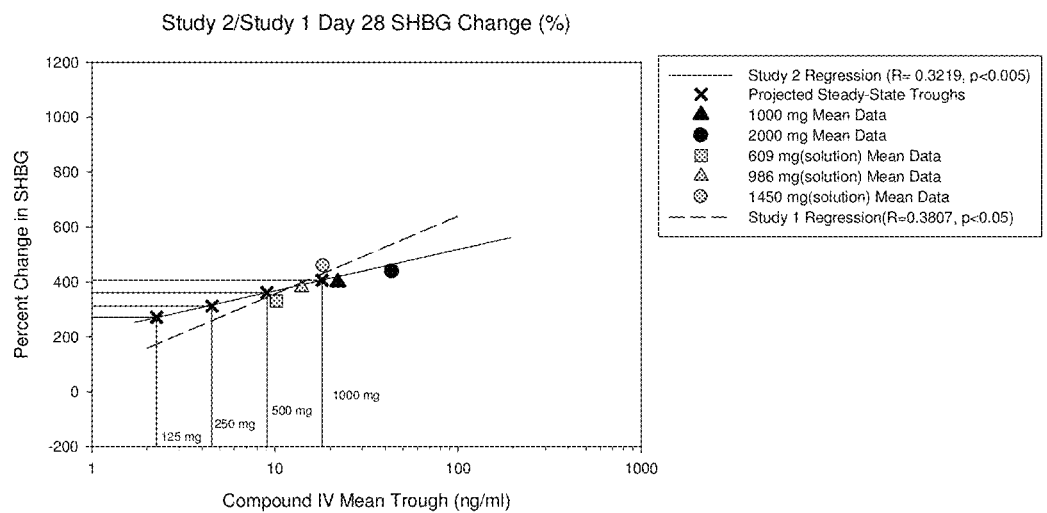
B
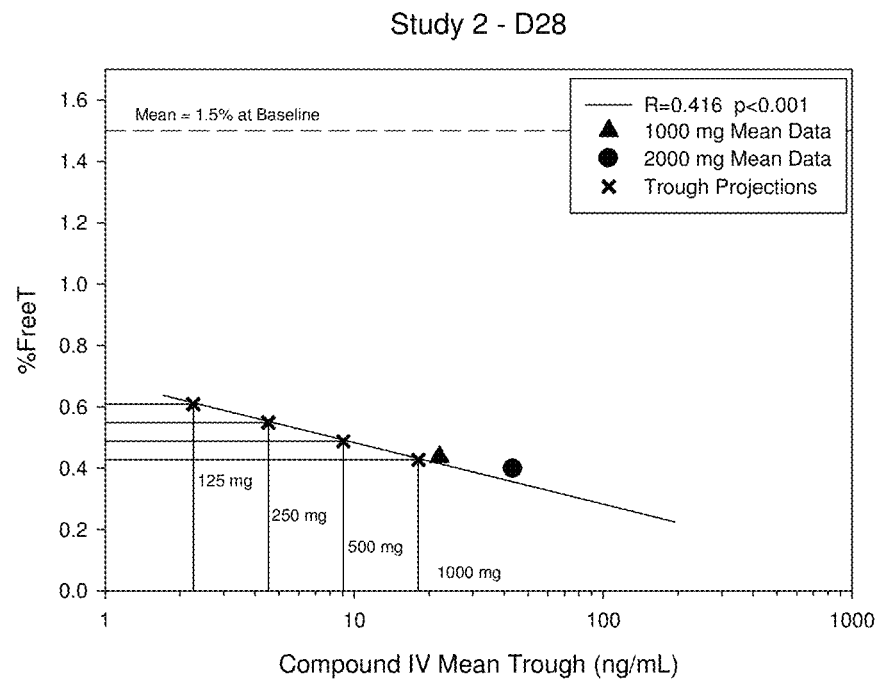
FIGURE 32

FIGURE 33

*Data was not collected from each patient at each of the time points after baseline

ESTROGEN RECEPTOR LIGANDS AND METHODS OF USE THEREOF

CROSS REFERENCE TO RELATED APPLICATIONS

This is a Continuation in Part of U.S. application Ser. No. 14/139,201, filed Dec. 23, 2013, which is a Continuation in Part of U.S. application Ser. No. 13/766,535, filed Feb. 13, 2013, which is a Continuation in Part of U.S. application Ser. No. 13/713,345, filed Dec. 13, 2012, which is a Continuation in Part of U.S. application Ser. No. 13/215,679, filed Aug. 23, 2011 which is Continuation in Part of International Application Number PCT/US10/25032, filed Feb. 23, 2010 which claims priority to United-States Ser. No. 61/154,707, filed Feb. 23, 2009; and U.S. Ser. No. 61/168,983 filed Apr. 14, 2009; and U.S. Ser. No. 61/261,669, filed Nov. 16, 2009; and U.S. application Ser. No. 13/215,679 claims priority from U.S. Ser. No. 61/380,113, filed Sep. 3, 2010; each of which is hereby incorporated by reference in its entirety.

FIELD OF THE INVENTION

The present invention relates to methods for treating, suppressing, reducing the incidence, reducing the severity, or inhibiting the progression of advanced prostate cancer or castration resistant prostate cancer (CRPC) or metastatic castration resistant prostate cancer (mCRPC) or high risk non-metastatic castration resistant prostate cancer (nm-CRPC) and their symptoms, or increasing the survival of men with advanced prostate cancer, CRPC or metastatic castration resistant prostate cancer (mCRPC) or high risk non-metastatic castration resistant prostate cancer (nm-CRPC), and to methods for lowering serum Prostate Specific Antigen (PSA) levels and serum testosterone levels in a male subject suffering from castration resistant prostate cancer (CRPC) or metastatic castration resistant prostate cancer (mCRPC) or high risk non-metastatic castration resistant prostate cancer (nmCRPC). Therapeutic goals include increasing radiographic progression free survival (rPFS) in metastatic cancers, increasing metastasis-free survival (MFS) in non-metastatic cancers, and decreasing symptomatic bone fractures in subjects suffering from CRPC, mCRPC and/or nmCRPC.

BACKGROUND OF THE INVENTION

Estrogens refer to a group of endogenous and synthetic hormones that are important for and used for tissue and bone maintenance. Estrogens are endocrine regulators in the cellular processes involved in the development and maintenance of the reproductive system. The role of estrogens in reproductive biology, the prevention of postmenopausal hot flashes, and the prevention of postmenopausal osteoporosis are well established. Estradiol is the principal endogenous human estrogen, and is found in both women and men.

The biological actions of estrogens and antiestrogens are manifest through two distinct intracellular receptors, estrogen receptor alpha (ERα) and estrogen receptor beta (ERβ). Endogenous estrogens are typically potent activators of both receptor subtypes. For example estradiol acts as an ERα agonist in many tissues, including breast, bone, cardiovascular and central nervous system tissues. Selective estrogen receptor modulators commonly act differently in different tissues. For example, a SERM may be an ERα antagonist in the breast, but may be a partial ERα agonist in the uterus, bone and cardiovascular systems. Compounds that act as estrogen receptor ligands are, therefore, useful in treating a variety of conditions and disorders.

Prostate cancer is one of the most frequently diagnosed noncutaneous cancers among men in the US and is the second most common cause of cancer deaths with 241,740 new cases and 28,472 deaths expected in 2012 in the United States. Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

Patients with advanced prostate cancer undergo androgen deprivation therapy (ADT), either by luteinizing hormone releasing hormone (LHRH) agonists, LHRH antagonists or by bilateral orchiectomy.

Androgen deprivation therapy (ADT) improves disease-free survival in men with advanced prostate cancer, but patients develop castration resistant prostate cancer (CRPC) one of the major causes of which is incomplete castration. Castration, as defined by orchiectomy, results in total testosterone (T) levels much lower than 50 ng/dL, the cut off set over 40 years ago based on the lower limit of detection of those older assays. Current T assays are more accurate and measuring free (unbound) T is a better reflection of the T available to androgenic tissues including prostate cancer. Although 20 ng/dL total T has been suggested as a new cut off to achieve for effective castration, in men treated with LHRH, the mean chemical castration of 20 ng/dL was only reached in approximately 43% of the men. The level of free T that was found to correspond to this level of total T was 0.5 pg/mL, and 43% of the men on LHRH were similarly below this level (Morote et al., *Int J Biomarkers*, 20:119-122, 2005).

Primary ADT, which causes castration (serum total testosterone levels of <50 ng/dL), is used to initially treat patients with metastatic hormone naïve prostate cancer. Symptoms improve with ADT, but ADT does not cure these patients. Unfortunately, prostate cancer cells eventually become castration resistant and these men develop progressive disease. Men with mCRPC have a very poor prognosis, severe cancer related symptoms, and a life expectancy of less than 16 months.

In males Androgen Deprivation Therapy not only reduces testosterone levels, but also estrogen levels, since estrogen is derived from the aromatization of testosterone, which levels are depleted by ADT. As a result, ADT also reduces estrogen to "castrate" levels.

Androgen deprivation therapy-induced estrogen deficiency causes significant side effects which include hot flashes, gynecomastia and mastalgia, bone loss, decreases in bone quality and strength, osteoporosis and life-threatening fractures, adverse lipid changes and higher cardiovascular disease and myocardial infarction, and depression and other mood changes. It is believed that many of the estrogen deficiency side effects of ADT are mediated by ERα.

Leuprolide acetate (Lupron®) is a synthetic nonapeptide analog of naturally occurring gonadotropin-releasing hormone (GnRH or LHRH). Leuprolide acetate is an LHRH superagonist that eventually suppresses LH secretion by the pituitary. Leuprolide acetate acts as a potent inhibitor of gonadotropin secretion, resulting in suppression of ovarian and testicular steroidogenesis. In humans, administration of leuprolide acetate results in an initial increase in circulating levels of luteinizing hormone (LH) and follicle stimulating hormone (FSH), leading to a transient increase in levels of the gonadal steroids (testosterone and dihydrotestosterone in males, and estrone and estradiol in premenopausal females). However, continuous administration of leuprolide acetate results in decreased levels of LH and FSH. In males, testosterone is reduced to castrate levels (below 50 ng/dL). In premenopausal females, estrogens are reduced to postmenopausal levels. Testosterone is a known stimulus for cancerous cells of the prostate. Suppressing testosterone secretion or inhibiting the actions of testosterone is thus a necessary component of prostate cancer therapy. Leuprolide acetate can be used for LH suppression, which is the reduction and lowering of serum testosterone to castrate levels to treat prostate cancer.

Prior to the introduction of LHRH agonists, castrate testosterone levels were achieved by increasing estrogen activity in the pituitary via estrogens, primarily diethylstilbestrol (DES). DES was equally effective as LHRH agonists at suppressing testosterone to castrate levels. Patients treated with DES did not have hot flashes or bone loss, but did have gynecomastia at higher rates than ADT with LHRH agonists. Unfortunately, highly potent, pure estrogens, like DES and estradiol, are often associated with a high risk of severe cardiovascular and thromboembolic complications which have limited their clinical use.

The compounds of this invention are nonsteroidal selective ERα agonists. In the treatment of CRPC and metastatic CRPC (mCRPC) patients, these novel small molecules further suppress testosterone levels for patients on ADT (i.e., these patients' testosterone levels are already at castrate levels) by increasing levels of serum sex or steroidal hormone binding globulin (SHBG) thereby reducing the circulating levels of serum free testosterone, the form of testosterone that stimulates prostate growth and prostate cancer. Because they are ERα agonists, the compounds of this invention also improve the side effects of estrogen deficiency including the ability to maintain bone, reduce the incidence of hot flashes, and avoid the insulin resistance and adverse lipid changes that are commonly associated with LHRH agonists and antagonists.

SUMMARY OF THE INVENTION

In one embodiment, this invention provides a method for lowering serum free testosterone concentration to levels comparable to those achieved in a male subject who has undergone surgical orchiectomy, in a male subject suffering from high risk advanced prostate cancer or at high risk for progression to castration resistant prostate cancer (CRPC), comprising administering a therapeutically effective amount of a compound represented by the structure of formula I, or its isomer, pharmaceutical acceptable salt, pharmaceutical product, polymorph, hydrate or any combination thereof:

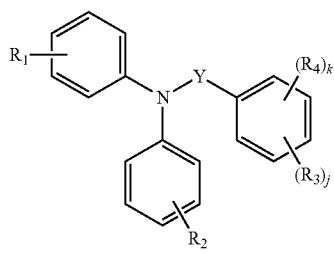

(I)

wherein
Y is C(O) or $CH_2$;
$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;
$R_3$, $R_4$ are independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;
R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;
$R_5$ and $R_6$ are independently hydrogen, phenyl, an alkyl group of 1 to 6 carbon atoms, a 3 to 7 membered cycloalkyl, a 3 to 7 membered heterocycle, a 5 to 7 membered aryl; or $R_5$ and $R_6$ form a 3 to 7 membered ring with the nitrogen atom;
j and k are independently 1-4; and
Alk is linear alkyl of 1-7 carbons, branched alkyl of 1-7 carbons, or cyclic alkyl of 3-8 carbons.

In another embodiment, said subject further receives androgen deprivation therapy (ADT).

In one embodiment, this invention is directed to a method of treating, suppressing, reducing the incidence, reducing the severity, or inhibiting the progression to castration resistant prostate cancer (CRPC) and its symptoms, or increasing the overall or progression-free survival of men with advanced or castration resistant prostate cancer (CRPC) comprising administering a therapeutically effective amount of a compound of formula I, or its isomer, pharmaceutical acceptable salt, pharmaceutical product, polymorph, hydrate or any combination thereof. In another embodiment, said subject further receives androgen deprivation therapy (ADT). In another embodiment, the CRPC is metastatic CRPC (mCRPC). In another embodiment, the CRPC is non-metastatic CRPC (nmCRPC). In another embodiment, the nmCRPC is high-risk nmCRPC In one embodiment, this invention provides a method of lowering serum PSA levels in a male subject suffering from advanced prostate cancer or castration resistant prostate cancer (CRPC) comprising administering a therapeutically effective amount of a compound of formula I, or its isomer, pharmaceutical acceptable salt, pharmaceutical product, hydrate or any combination thereof. In another embodiment, said subject further receives androgen deprivation therapy (ADT). In another embodiment, the CRPC is metastatic CRPC (mCRPC). In another embodiment, the CRPC is non-metastatic CRPC (nmCRPC). In another embodiment, the nmCRPC is high-risk nmCRPC.

In one embodiment, this invention provides a method of increasing serum concentrations of sex or steroid hormone binding globulin (SHBG) in a subject suffering from advanced prostate cancer or castration resistant prostate cancer (CRPC) comprising administering a therapeutically effective amount of a compound of formula I, or its isomer, pharmaceutical acceptable salt, pharmaceutical product, polymorph, hydrate or any combination thereof. In another embodiment, said subject further receives androgen deprivation therapy (ADT). In another embodiment, the CRPC is metastatic CRPC (mCRPC). In another embodiment, the CRPC is non-metastatic CRPC (nmCRPC). In another embodiment, the nmCRPC is high-risk nmCRPC In one embodiment, this invention provides a method of reducing the levels of bone turnover markers in a male subject suffering from advanced prostate cancer or castration resistant prostate cancer (CRPC) comprising administering a therapeutically effective amount of a compound of formula I, or its isomer, pharmaceutical acceptable salt, pharmaceutical product, polymorph, hydrate or any combination thereof. In another embodiment, said subject further receives androgen deprivation therapy (ADT). In another embodiment, the CRPC is metastatic CRPC (mCRPC). In another embodiment, the CRPC is non-metastatic CRPC (nm-CRPC). In another embodiment, the nmCRPC is high-risk nmCRPC.

In another embodiment, the compound is Compound IV as described herein below.

In another embodiment, the methods of this invention make use of a compound of formula I, wherein said compound of formula I is selected from:

II.
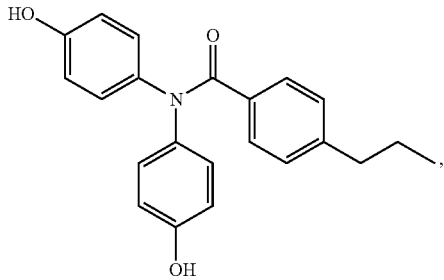

III.
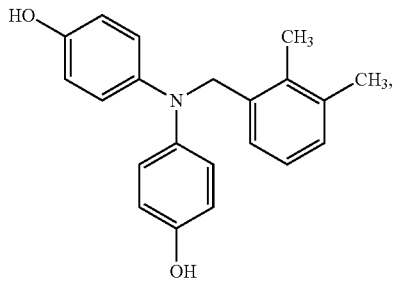

IV.
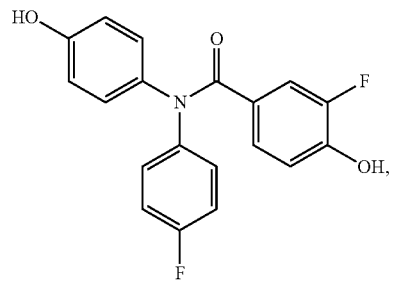

V.
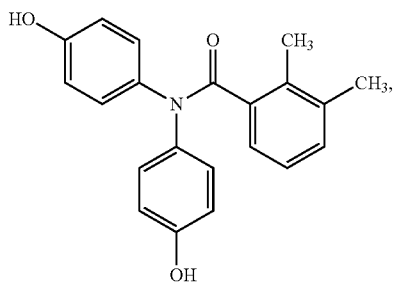

VII.
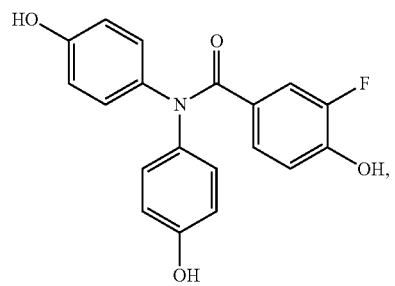

VIII.
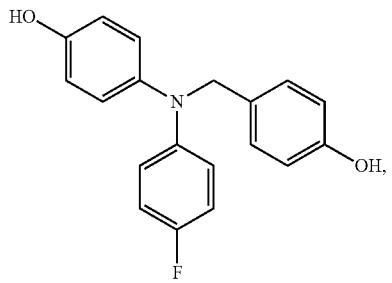

XI.
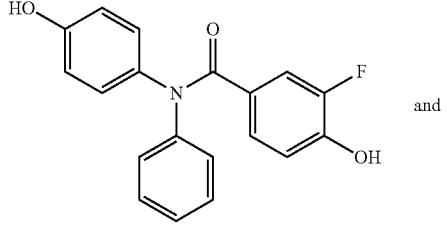

and

XII.
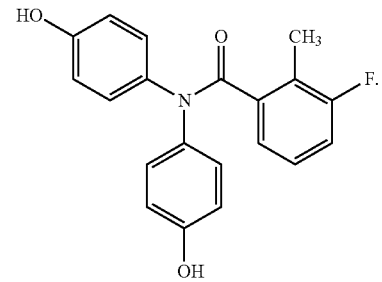

In another embodiment, the methods of this invention are directed to a subject which undergone ADT treatment. In another embodiment, the methods of this invention are directed to a subject which undergone a surgical castration.

In one embodiment, the methods of this invention increase radiographic progression free survival (rPFS) in a subject having metastatic cancer.

In one embodiment, the methods of this invention increase metastasis-free survival (MFS) in a subject having non-metastatic cancer.

In one embodiment, the methods of this invention include administering a compound of this invention or its isomer, pharmaceutical acceptable salt, pharmaceutical product, hydrate or any combination thereof, at a dose of 40 mg per day, 80 mg per day, 125 mg per day, 250 mg per day, 500 mg per day, 1000 mg per day, 1500 mg per day, 2000 mg per day, or 2500 mg per day.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 3:
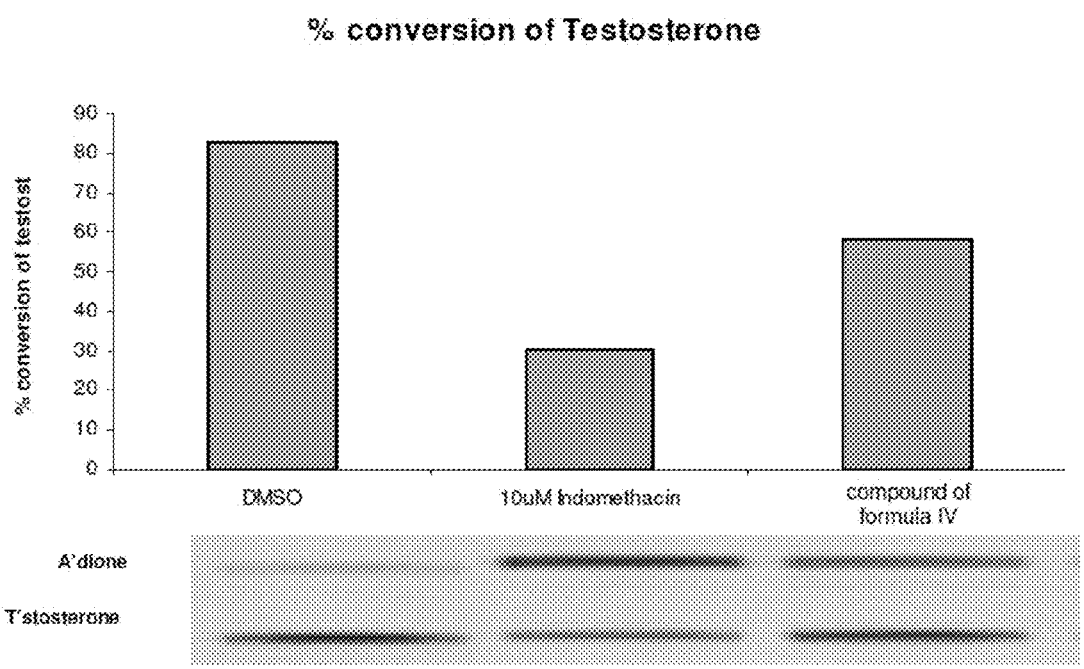

FIG. 3 depicts the inhibitory effect of Compound IV on 17β-HSD5 enzyme activity. (See Example 12.)

Figure 4:
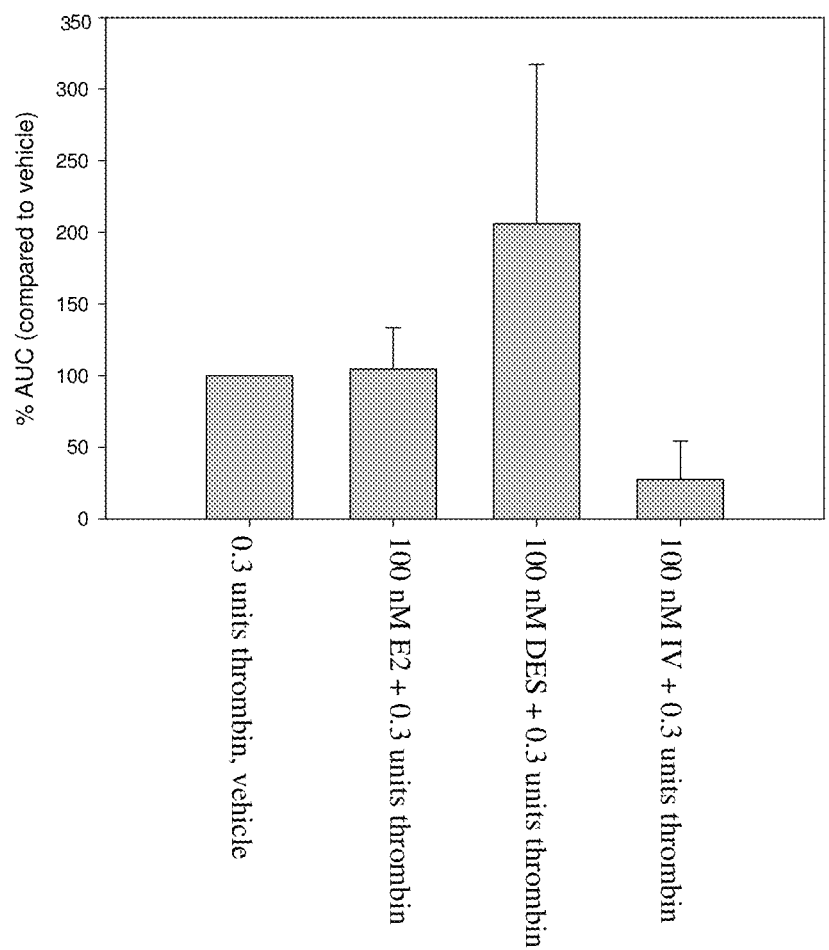

FIG. 4 depicts in vitro aggregation of human platelets in the presence of DES, 17β-estradiol (E2), and Compound IV. Platelet Rich Plasma (PRP) was incubated with vehicle, E2, DES, or Compound IV for 30 seconds before inducing aggregation with 0.3 units of thrombin. Aggregation was monitored for 5 minutes and expressed as a percentage of vehicle control. (See Example 13.)

Figure 5:
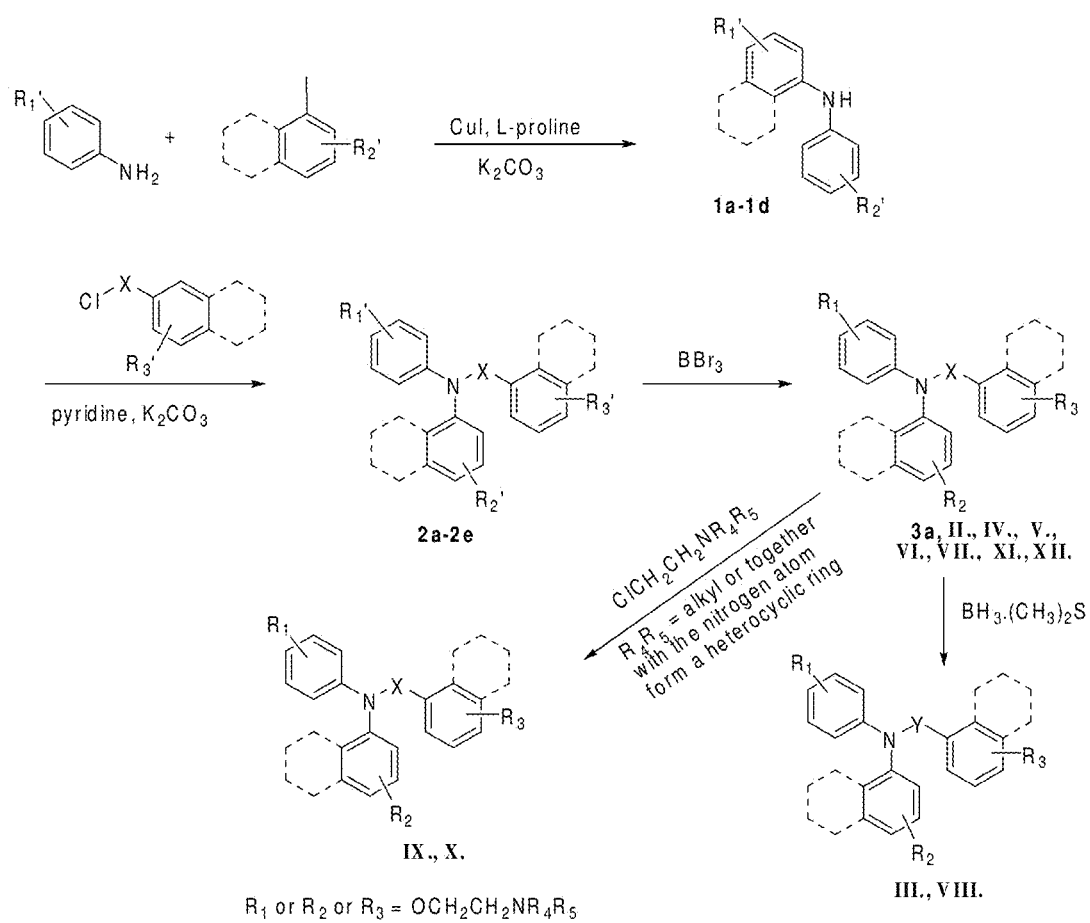

FIG. 5 depicts the generic synthetic scheme for the preparation of Compounds II-XII. (See Example 1.)

Figure 6:
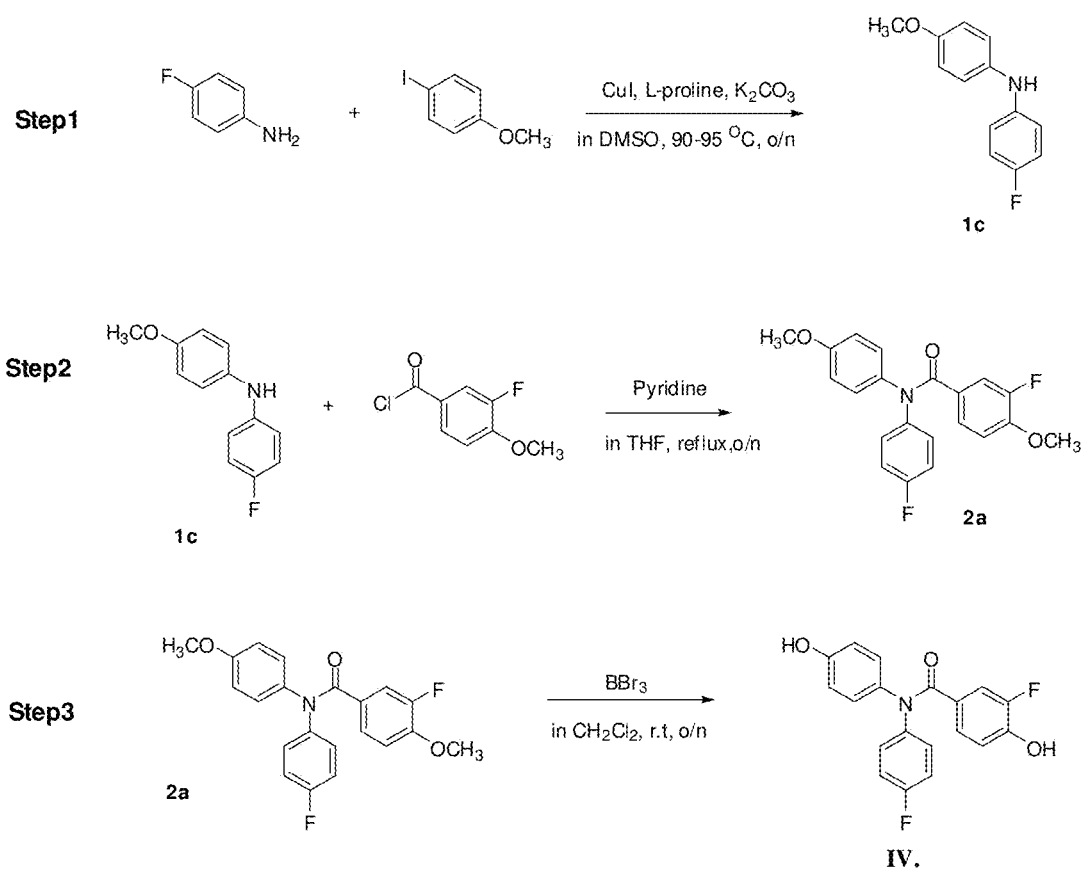

FIG. 6 depicts the synthetic scheme for the preparation of Compound IV. (See Example 2.)

Figure 7:
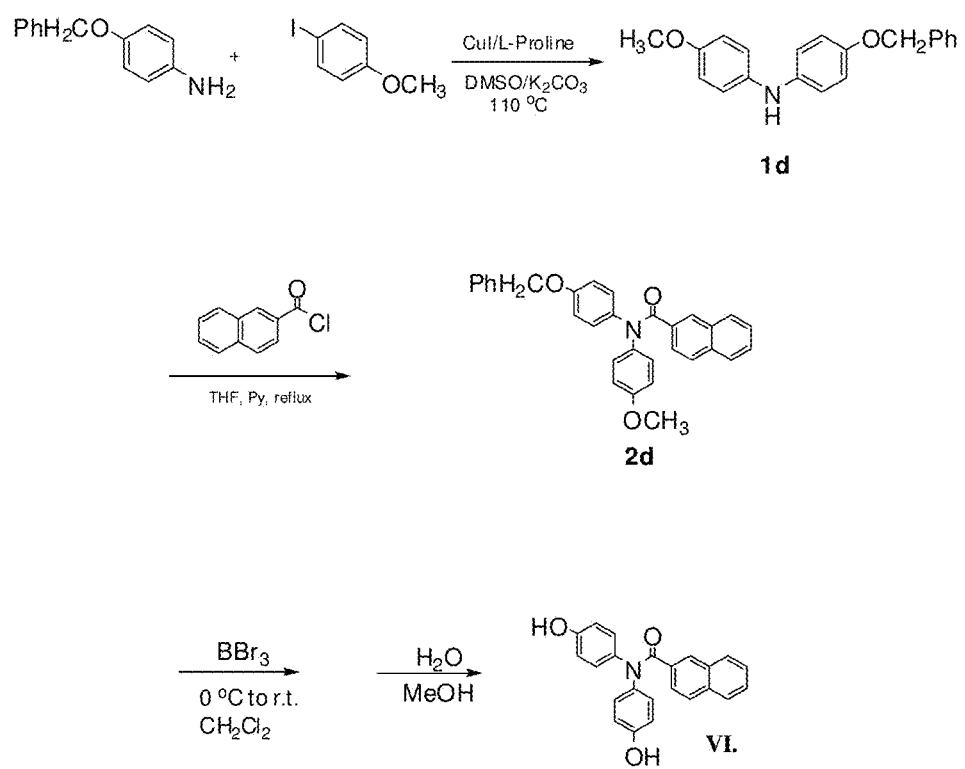

FIG. 7 depicts the synthetic scheme for the preparation of Compound VI. (See Example 3.)

Figure 8:
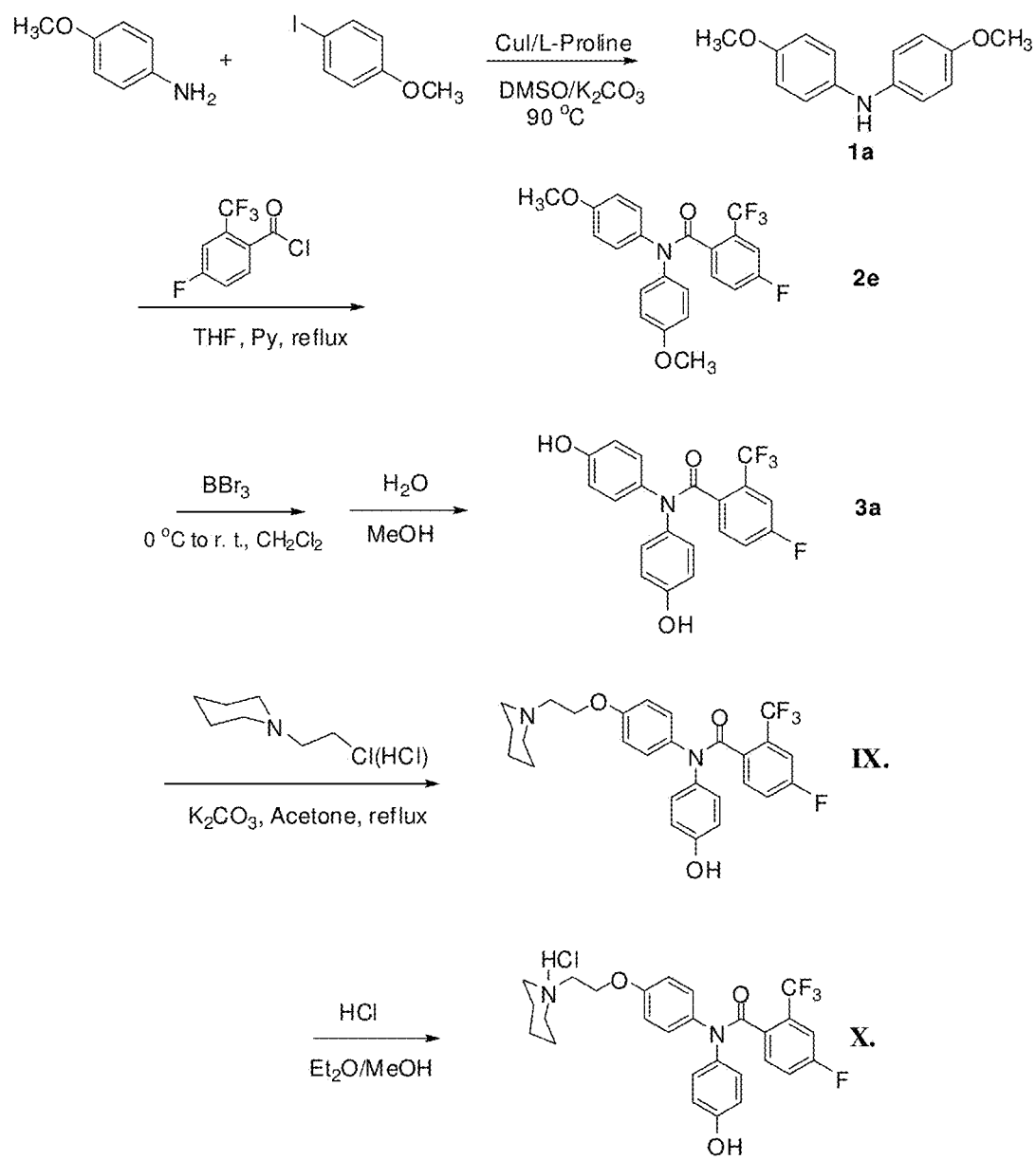

FIG. 8 depicts the synthetic scheme for the preparation of Compounds IX and X. (See Example 5.)

Figure 9:
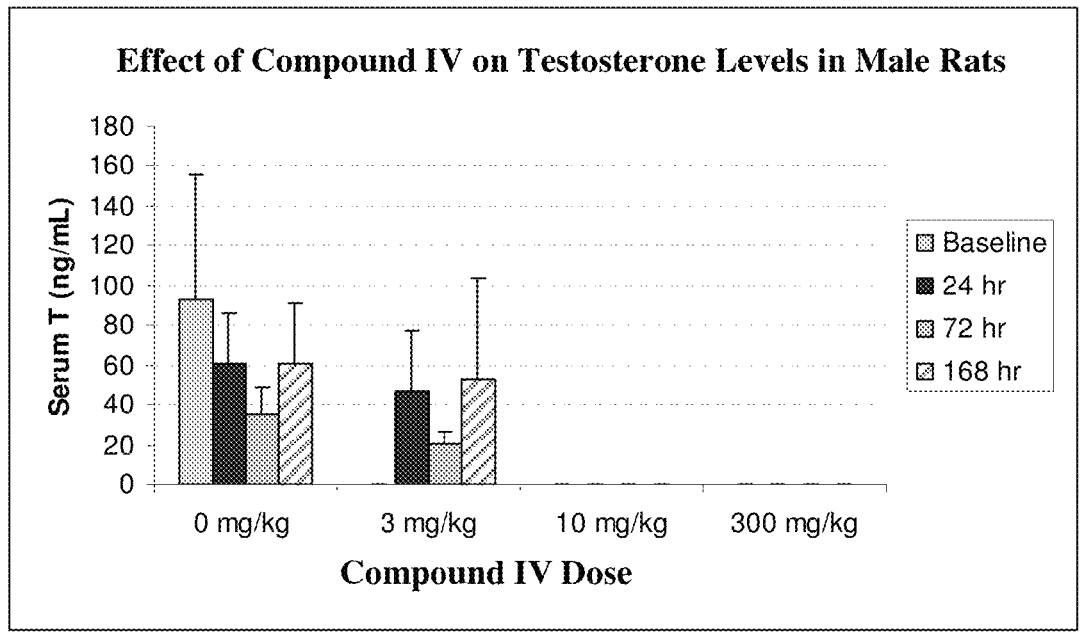
Figure 10A:
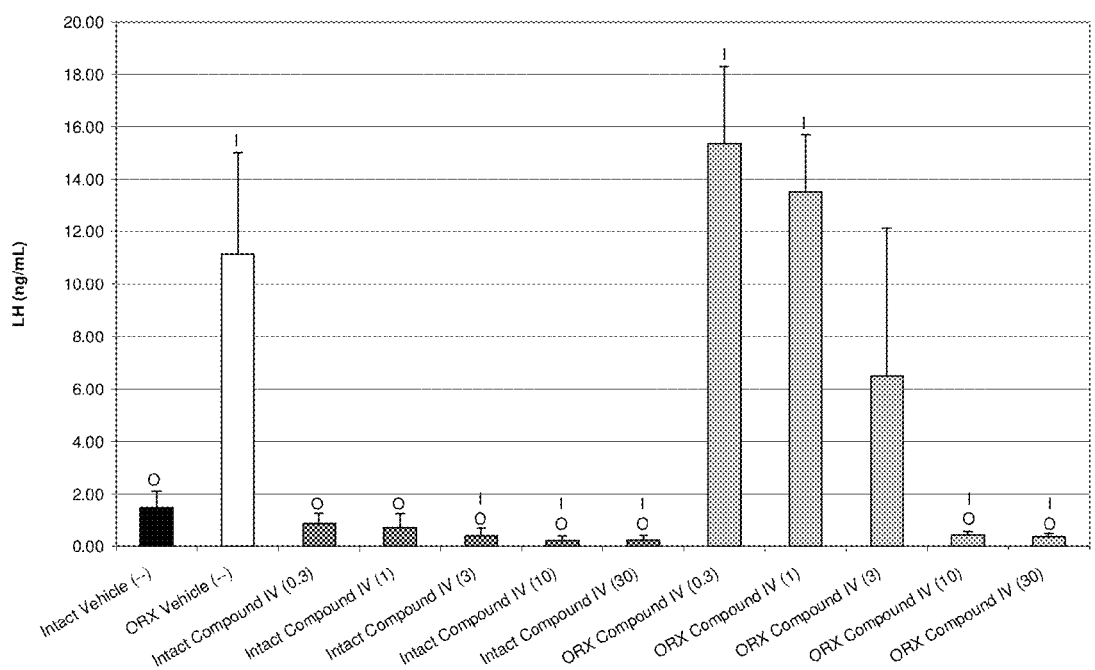
Figure 10B:
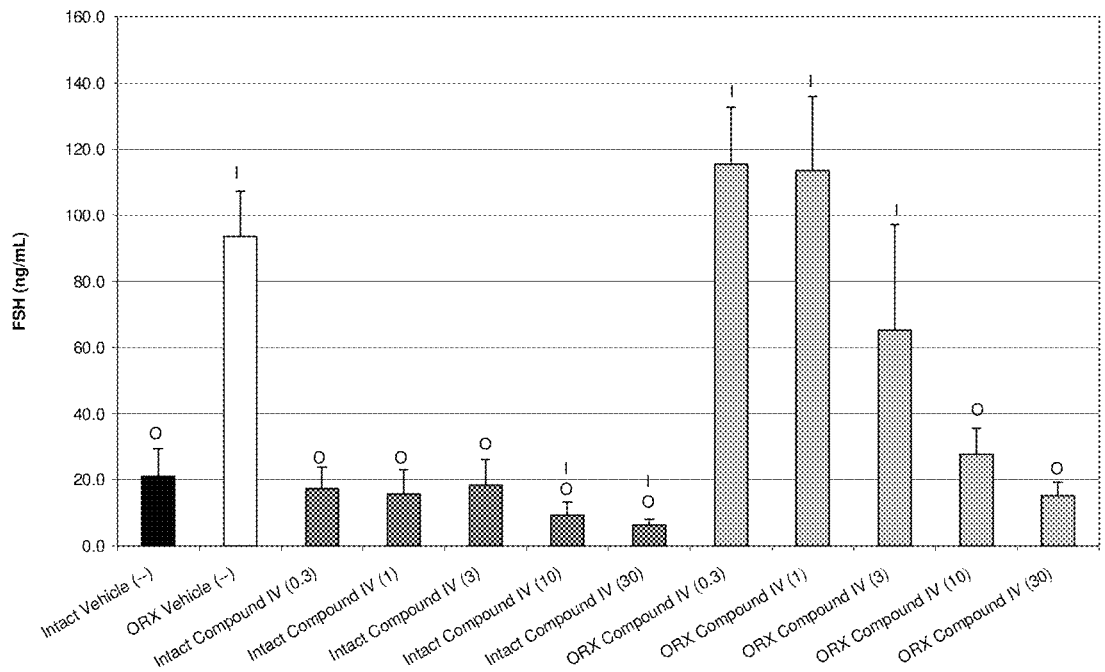
Figure 10C:
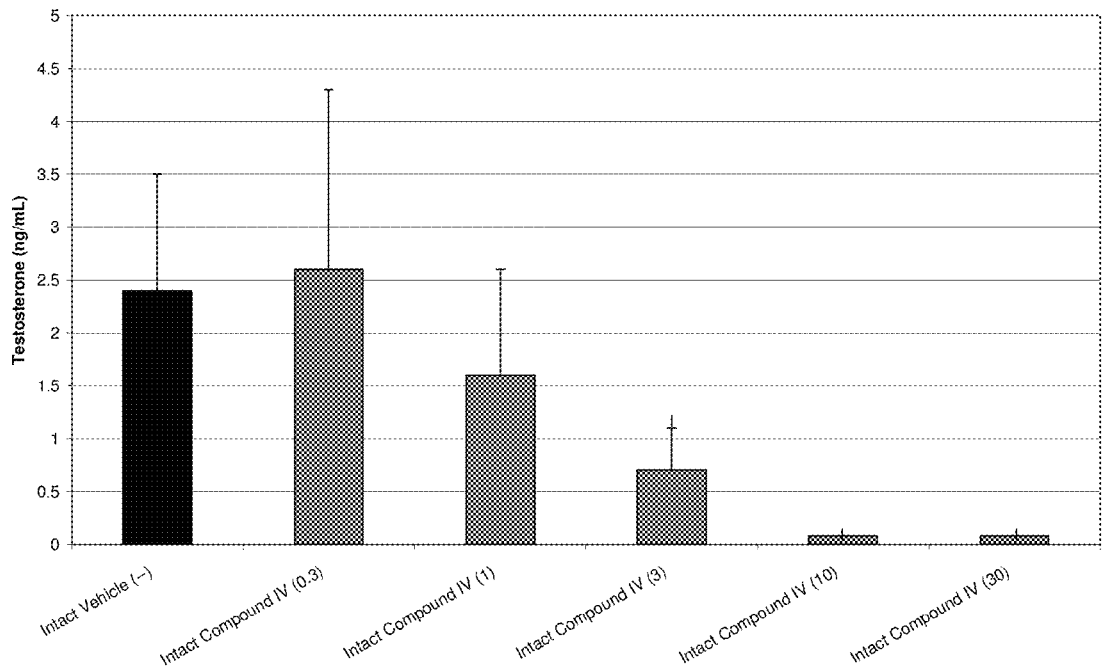
Figure 10D:
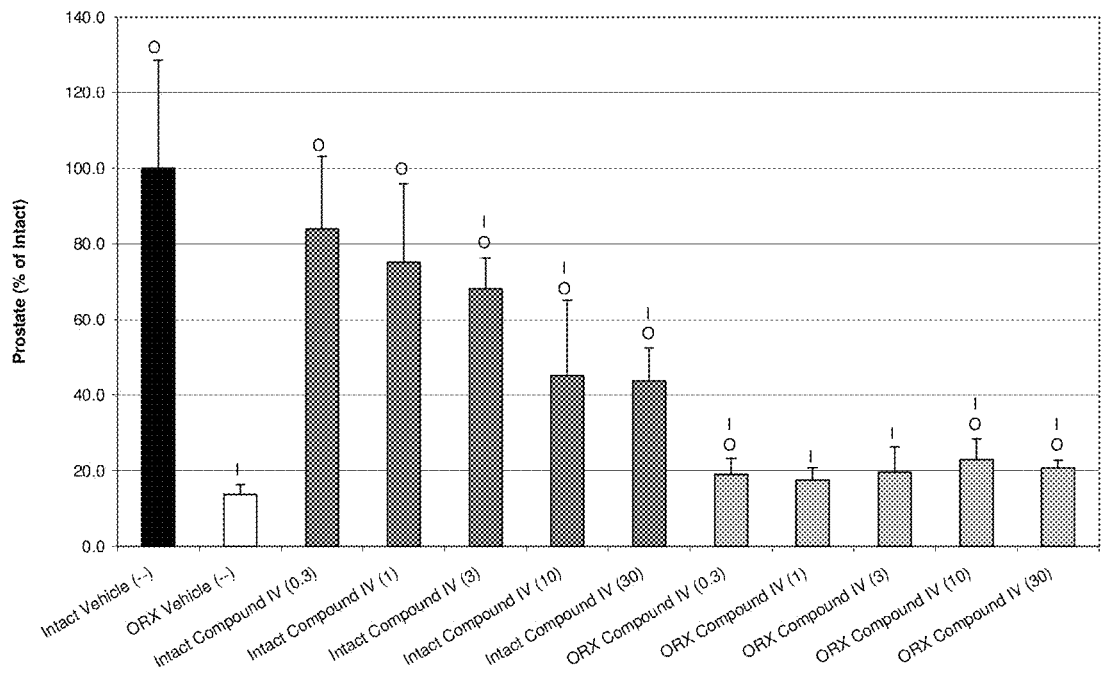
Figure 10E:
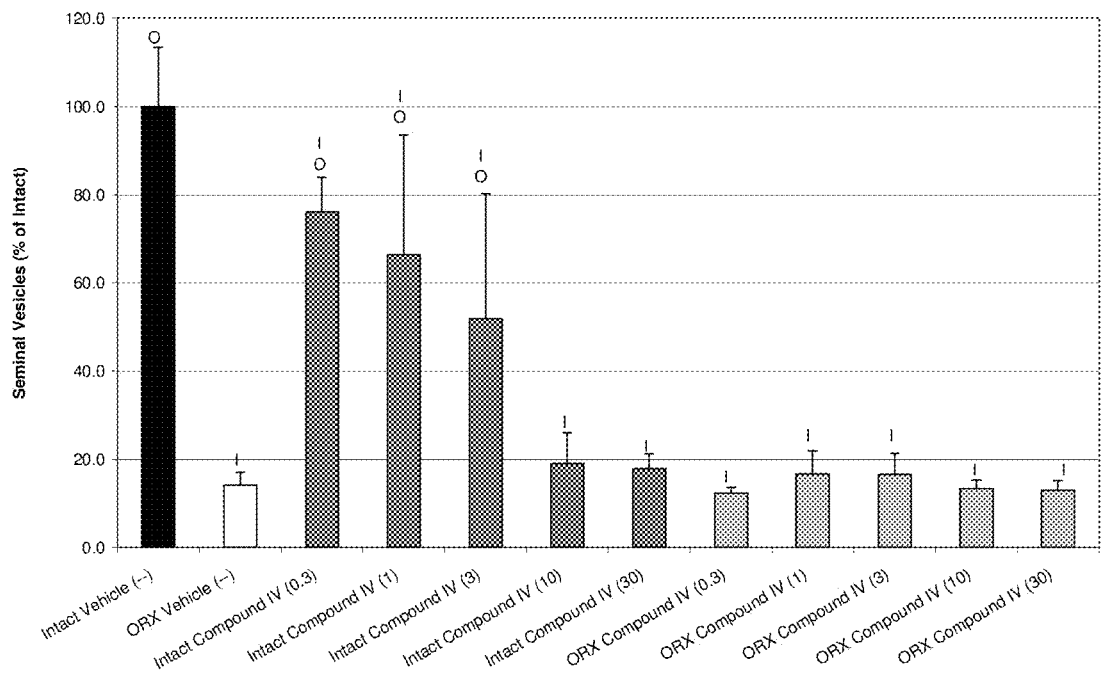
Figure 10F:
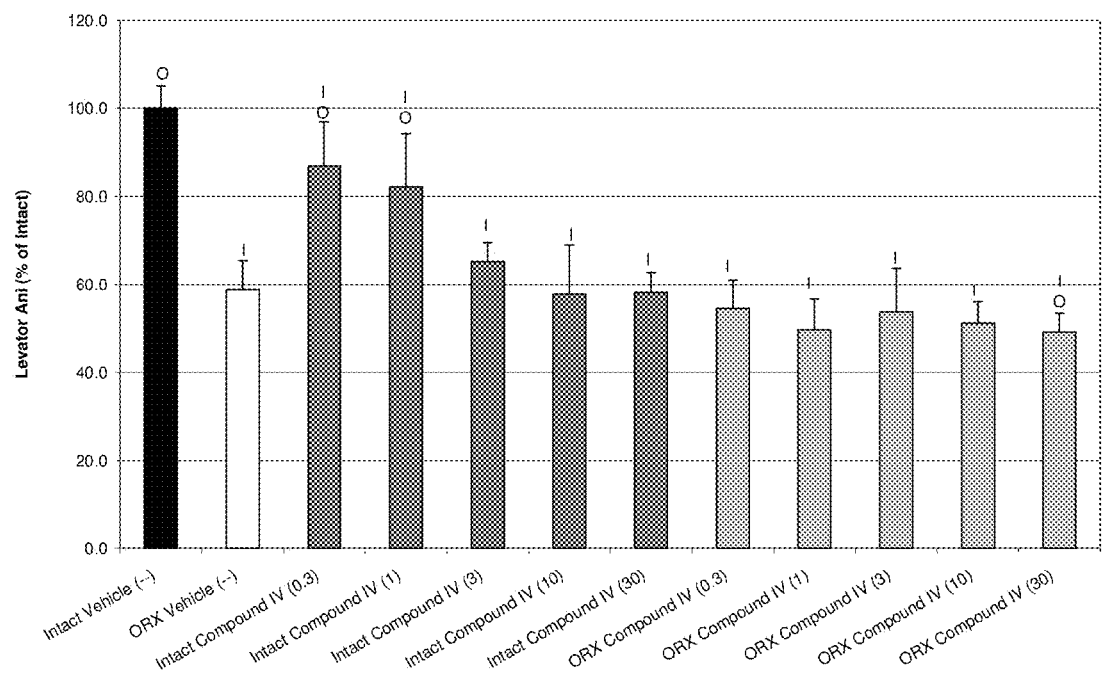

FIG. 9 depicts testosterone levels in intact rats treated with Compound IV after 24 h, 72 h and 168 h with dosages of 3 mg/kg, 10 mg/kg and 300 mg/kg. (See Example 9)

FIGS. 10A-10F depict LH levels (FIG. 10A), FSH levels (FIG. 10B), testosterone levels (FIG. 10C), prostate weight levels (FIG. 10D), seminal vesicle weight levels (FIG. 10E) and levator ani weight (FIG. 10F) of treated intact and orchidectomized (ORX) rats with 0.3 mg/kg, 1 mg/kg, 3 mg/kg, 10 mg/kg and 30 mg/kg dosages of Compound IV. $^I$denotes P<0.05 vs. intact vehicle controls. $^O$denotes P<0.05 vs. ORX vehicle controls BLOQ values are represented graphically at the limit of quantitation 0.08 ng/mL. (See Example 9.)

Figure 11A:
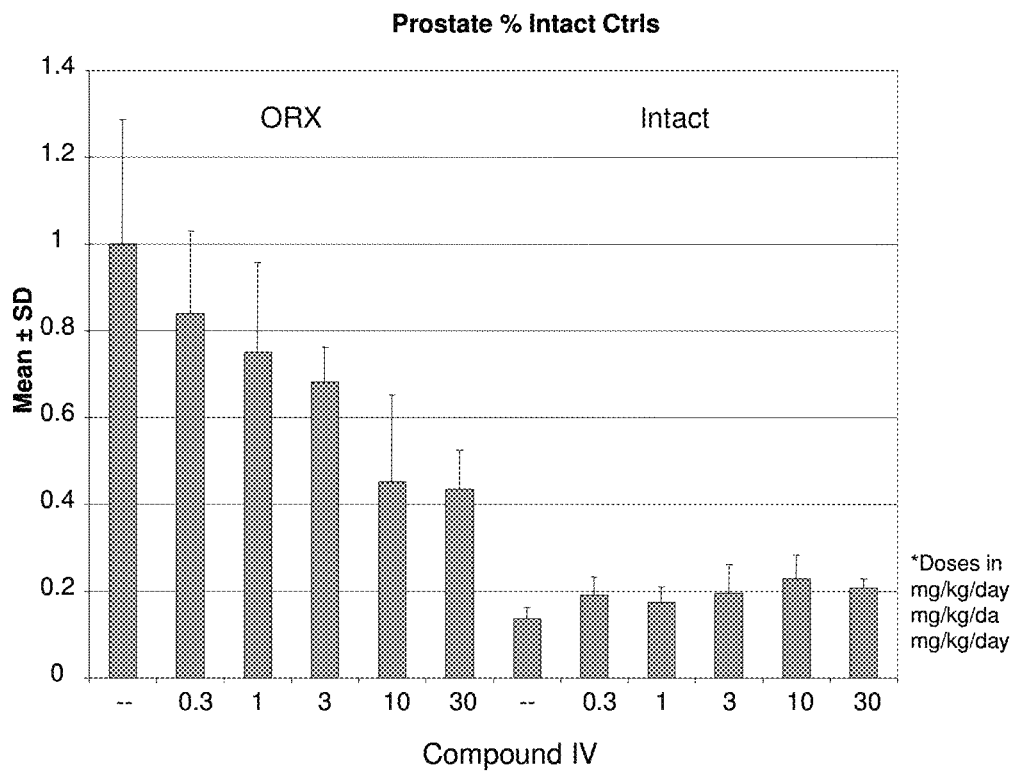
Figure 11B:
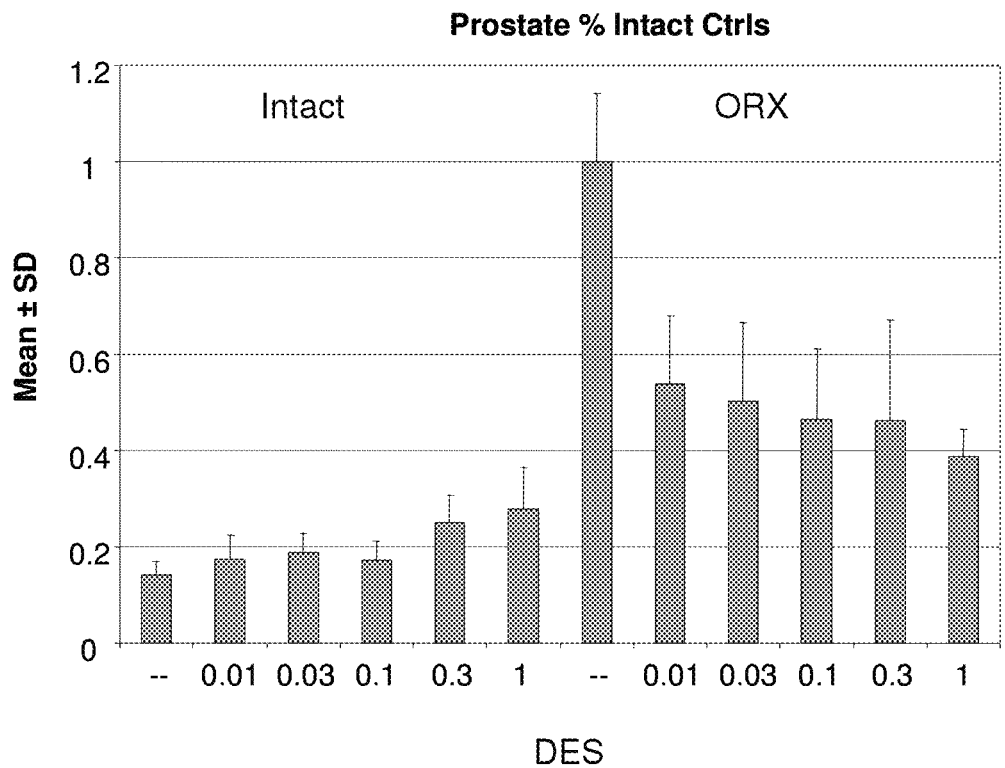

FIGS. 11A-11B depict prostate size in intact and ORX rats by administering Compound IV (FIG. 11A) and DES (FIG. 11B) at different dosages. (See Example 15.)

Figure 12A:
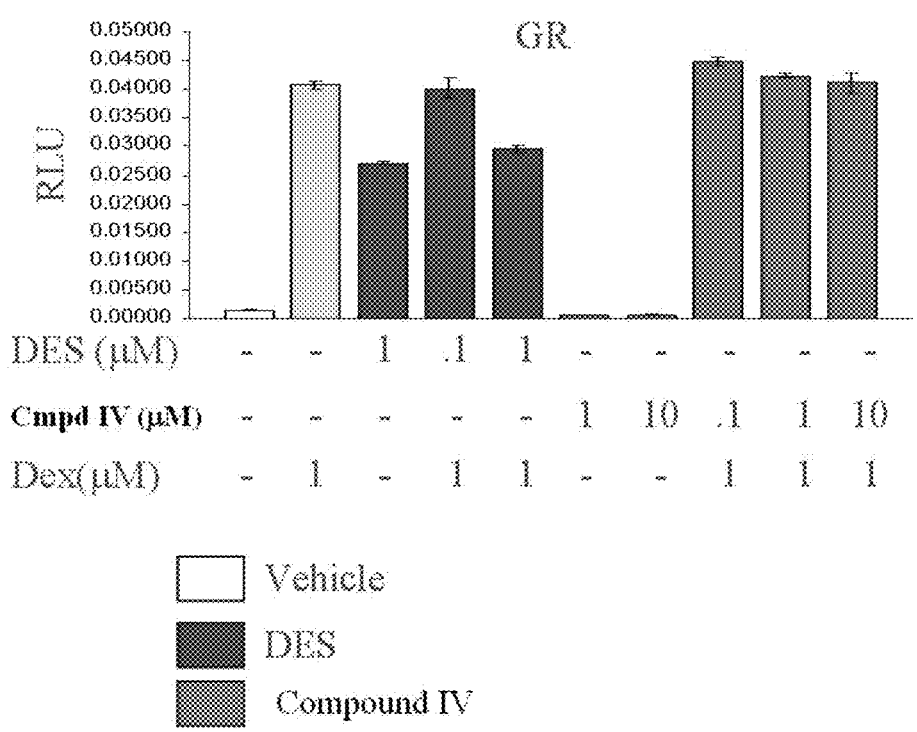
Figure 12B:
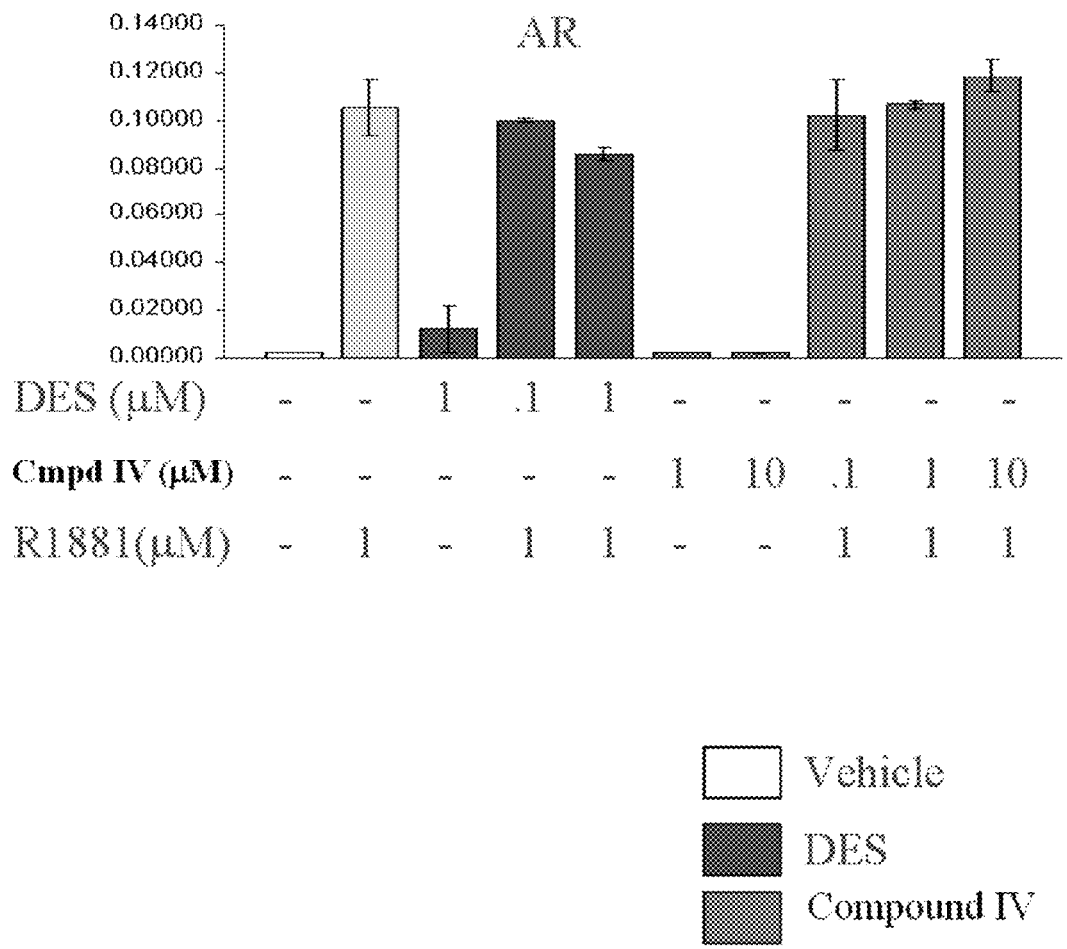
Figure 12C:
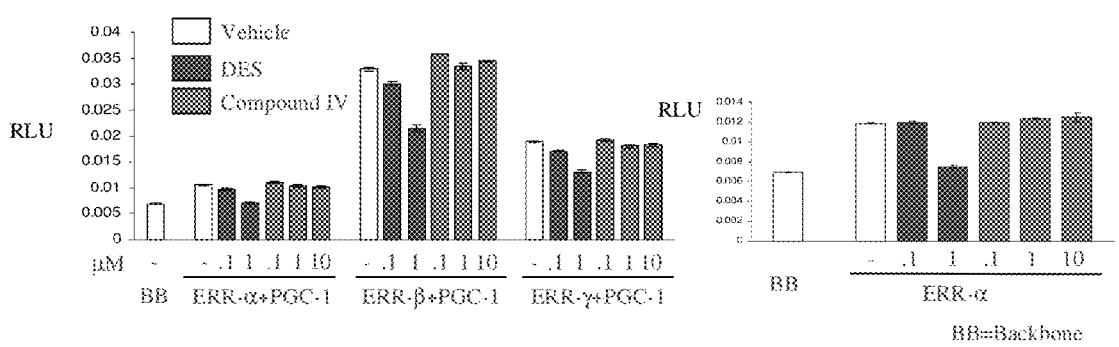

FIGS. 12A-12C depict differences between DES and Compound IV; DES crossreacts with glucocorticoid receptor (GR) while Compound IV does not (FIG. 12A). DES crossreacts with androgen receptor (AR). It mildly stimulates AR action and mildly inhibits (i.e., it is a partial agonist/antagonist) while Compound IV does not (FIG. 12B). DES abrogates estrogen related receptor (ERR) transactivation, while Compound IV does not (FIG. 12C). (See Example 15.)

Figure 13:
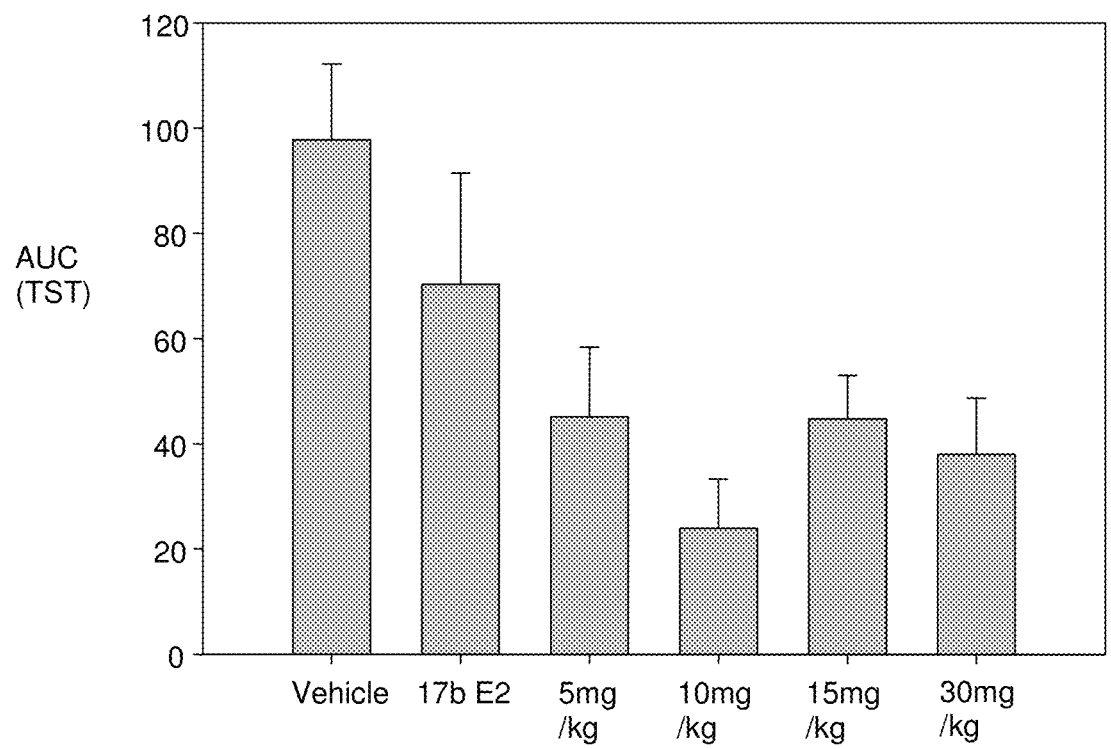

FIG. 13 depicts effect of Compound IV on attenuation of hot flashes in morphine withdrawal model with 5 mg/kg, 10 mg/kg, 15 mg/kg and 30 mg/kg dosages. N=7 animals per group. 17β-E2 was used at 5 mg/kg in 100% DMSO. (See Example 14.)

Figure 14:
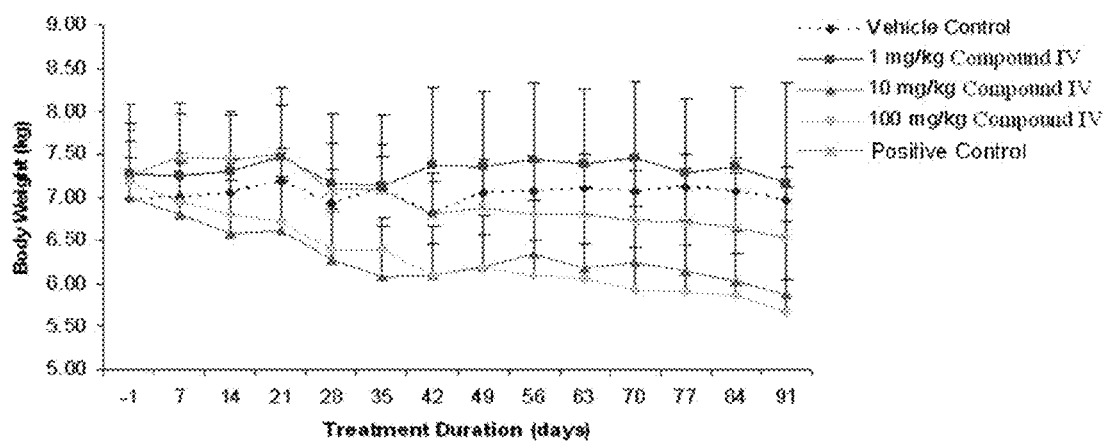

FIG. 14 depicts dose dependent body weight (kg) reductions of monkeys (~20% at 100 mg/kg) by administering Compound IV for 91 days. No sign of gynecomastia or hyperestrogenicity was observed. (See Example 16.)

Figure 15:
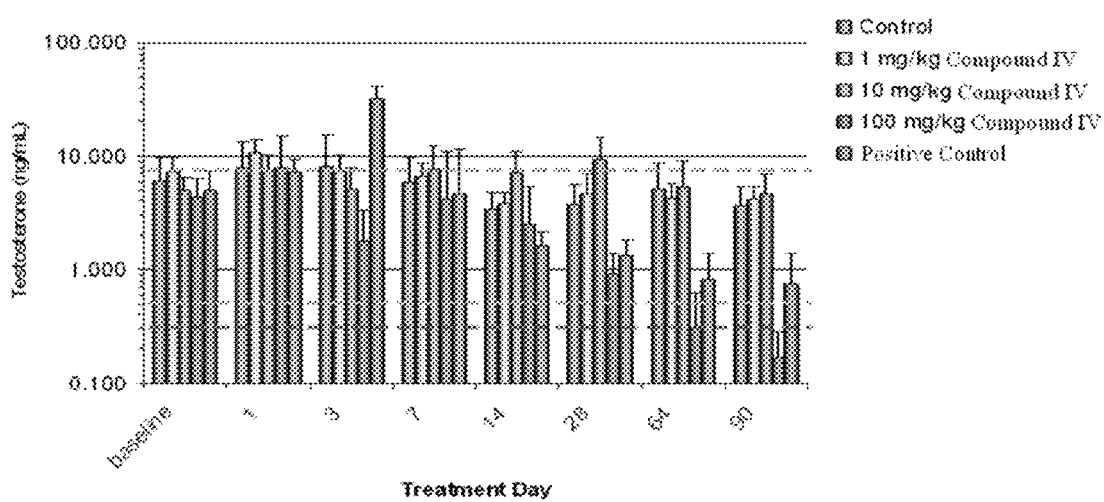

FIG. 15 depicts dose dependent serum testosterone level reductions (ng/mL) in monkeys after daily oral administration of Compound IV compared to positive control (LHRH agonist). Dotted line indicates the testosterone level of chemically castrated patients and the bold dashed line indicates the testosterone level of surgically castrated monkeys. (See Example 16.)

Figure 16:
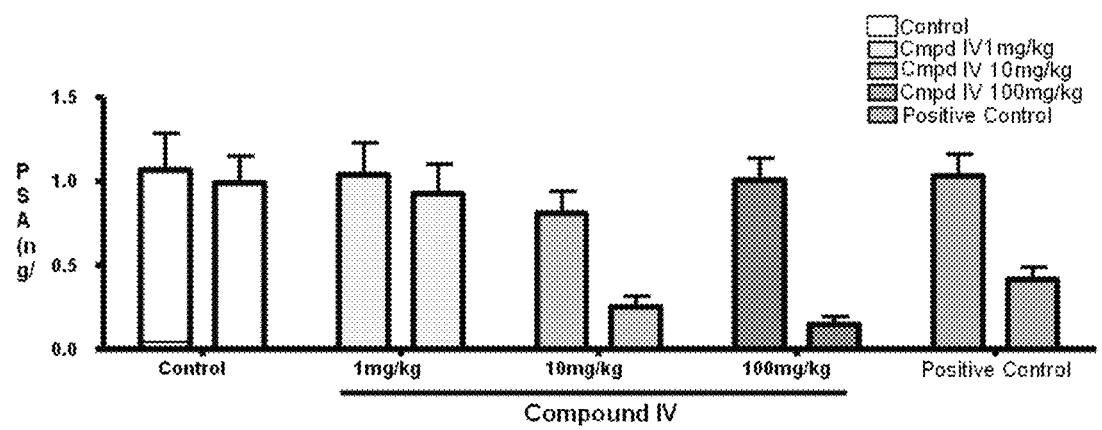

FIG. 16 depicts dose dependent prostate-specific antigen (PSA) levels (ng/mL) in monkeys by administering Compound IV at baseline and at day 28. PSA levels were significantly decreased with Compound IV treatment. (See Example 16.)

Figure 17:
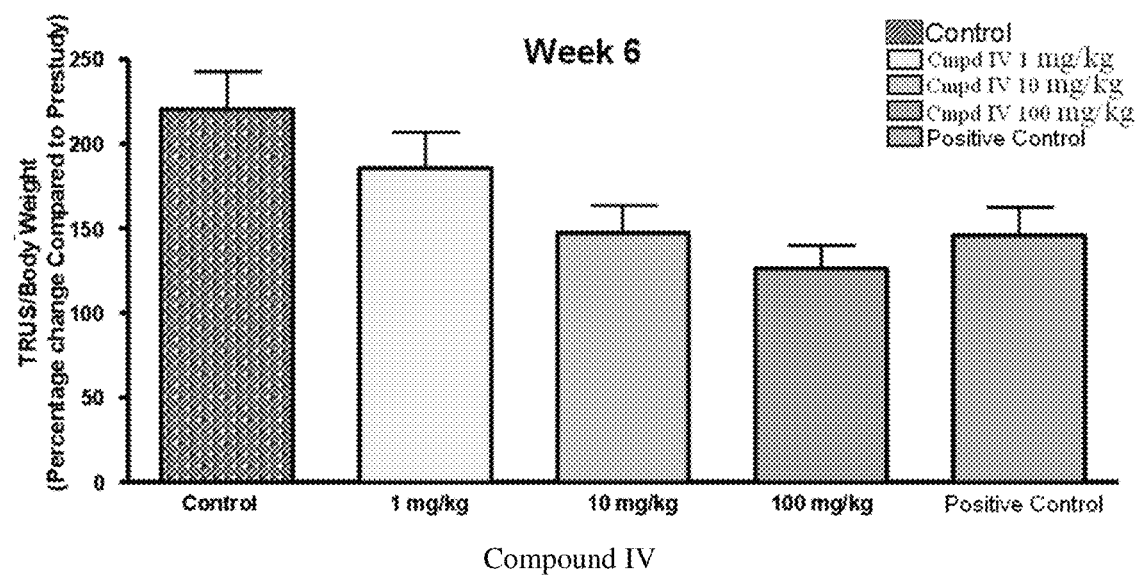

FIG. 17 depicts dose dependent prostate volume using transrectal ultrasound (TRUS) in monkeys compared to positive control (LHRH agonist), by administering Compound IV at week 6. (See Example 16.)

Figure 18A:
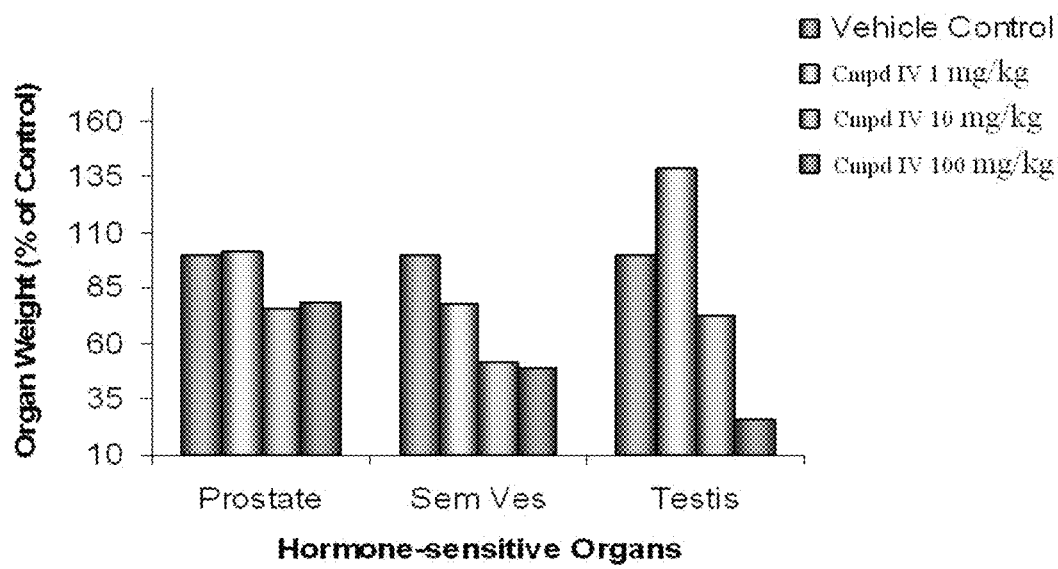
Figure 18B:
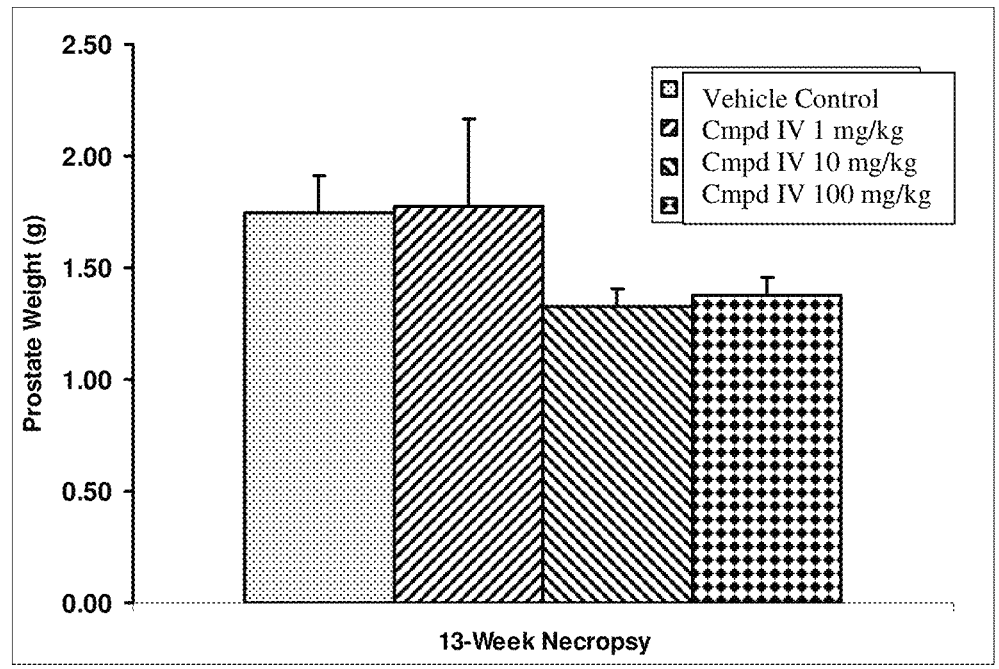

FIGS. 18A-18B depict dose dependent organ weights (prostate, seminal vesicle and testis) as percent of control monkeys at day 90, by administering Compound IV (FIG. 18A). Prostate weights at 13-week necropsy in monkeys after daily oral administration of Compound IV (FIG. 18B). (See Example 16.)

Figure 19:
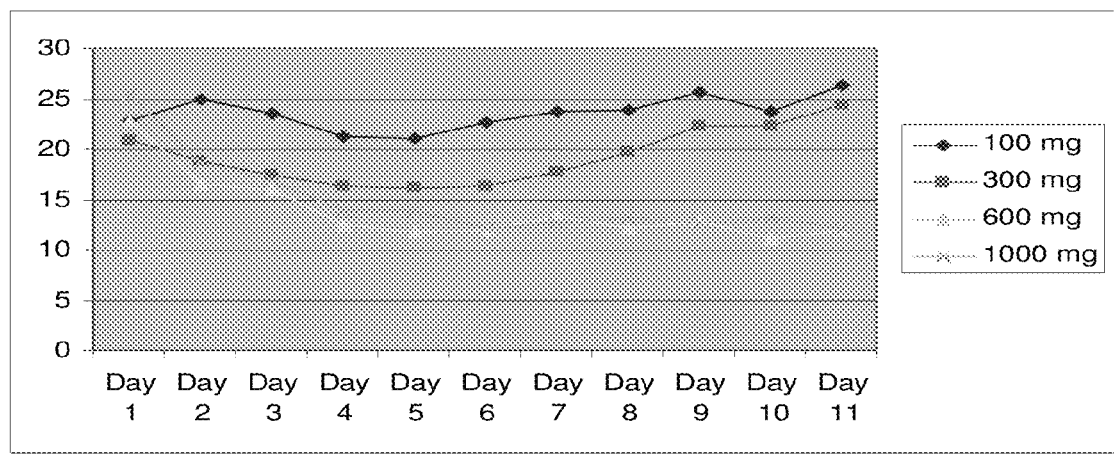

FIG. 19 depicts dose dependent mean total testosterone levels (nmol/L) in humans for a period between 1-11 days by administering Compound IV (100 mg, 300 mg, 600 mg and 1000 mg). (See Example 17.)

Figure 20:
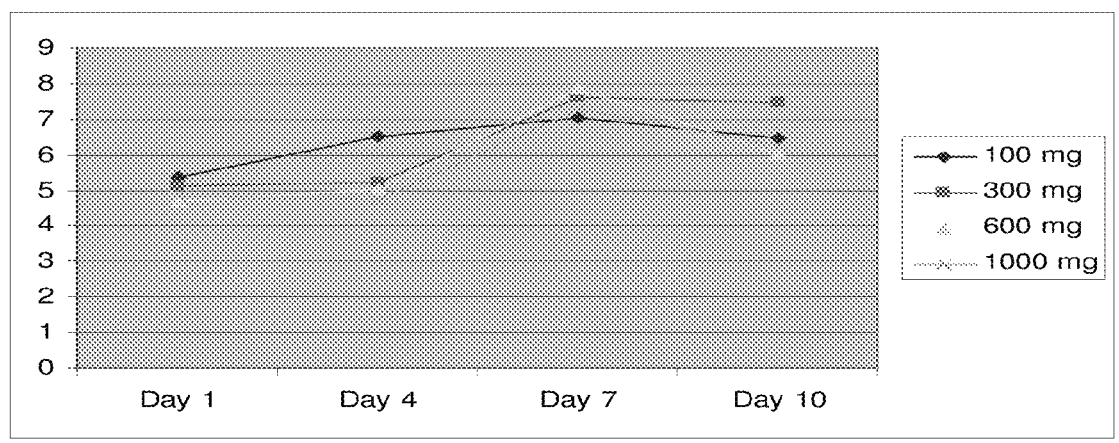

FIG. 20 depicts dose dependent mean LH levels (IU/L) in humans for a period between 1-10 days by administering compound IV (100 mg, 300 mg, 600 mg and 1000 mg. (See Example 17.)

Figure 21:
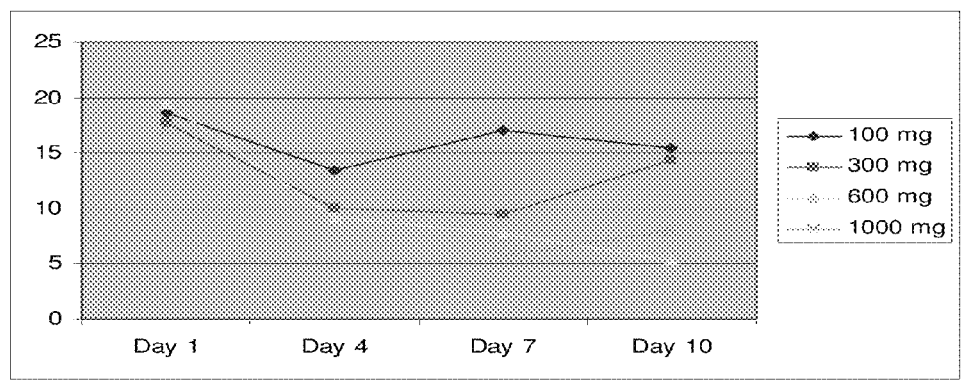

FIG. 21 depicts dose dependent mean free testosterone levels (pg/mL) in humans for a period between 1-10 days by administering compound IV (100 mg, 300 mg, 600 mg and 1000 mg. (See Example 17.)

Figure 22:
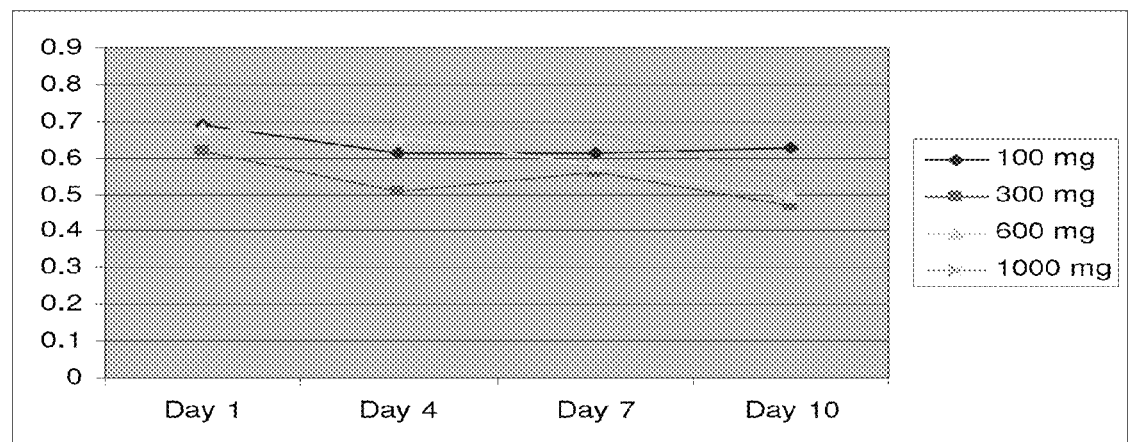

FIG. 22 depicts dose dependent mean PSA levels (μg/L) in humans for a period between 1-10 days by administering compound IV (100 mg, 300 mg, 600 mg and 1000 mg). (See Example 17.)

Figure 23:
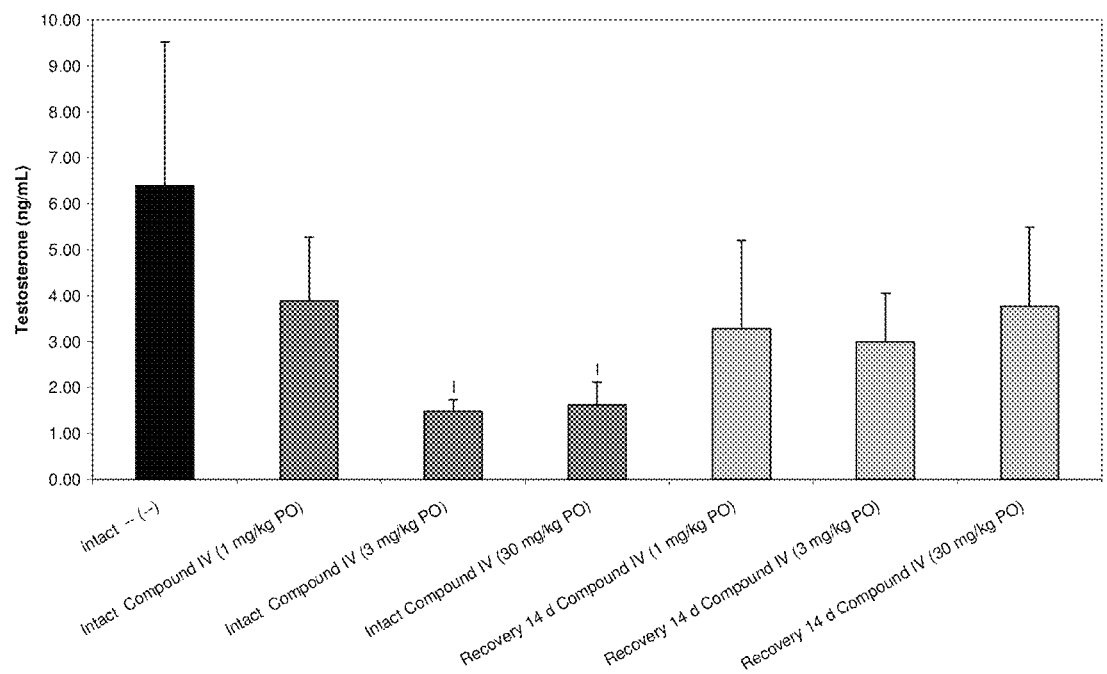

FIG. 23 depicts dose dependent serum testosterone levels (ng/mL) in intact rats after 14 days recovery of administering Compound IV. $^I$denotes P<0.05 vs Intact controls. (See Example 10.)

Figure 24:
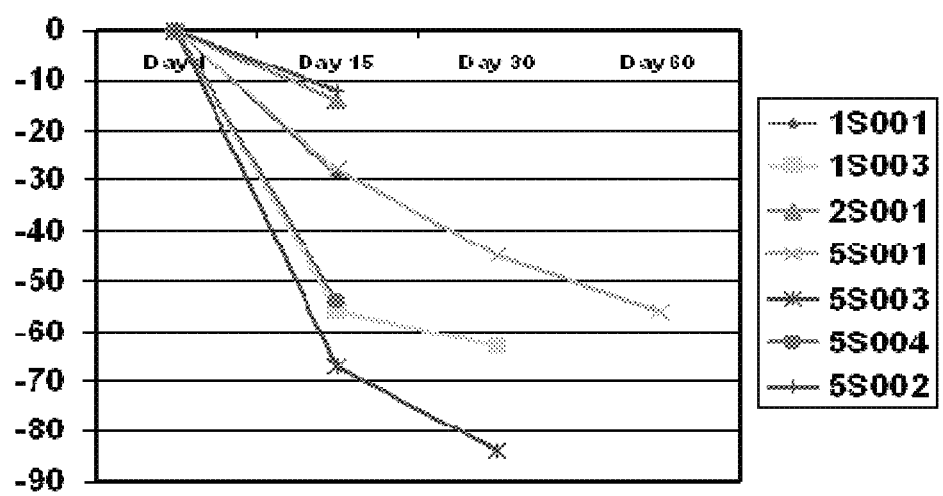

FIG. 24 depicts the percent reduction in serum PSA in seven subjects with castration resistant prostate cancer (CRPC) that were treated with 2000 mg Compound IV (Study 3; Example 26).

Figure 25:
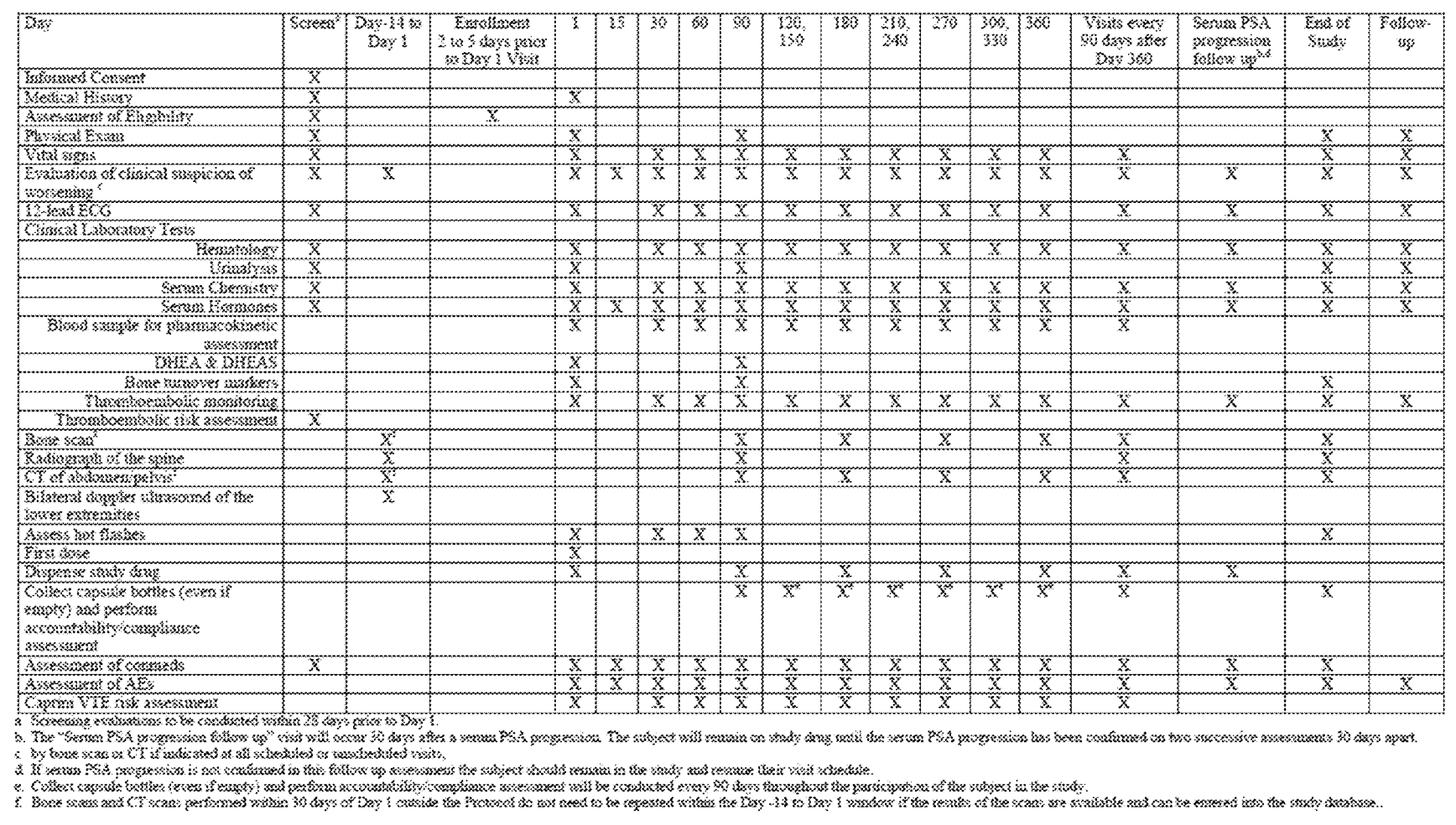

FIG. 25 depicts a flow chart describing Study 6 procedures (Example 27).

FIG. 26 depicts the study details for each of the Compound IV clinical studies in human subjects: healthy, treatment naïve prostate cancer patients and castration resistant prostate cancer patients (Examples 25-30).

Figure 27A:
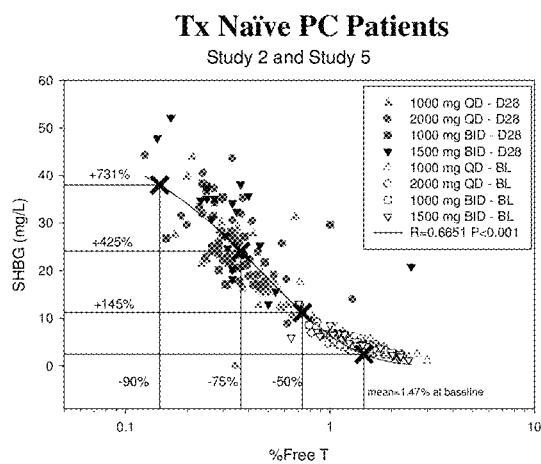
Figure 27B:
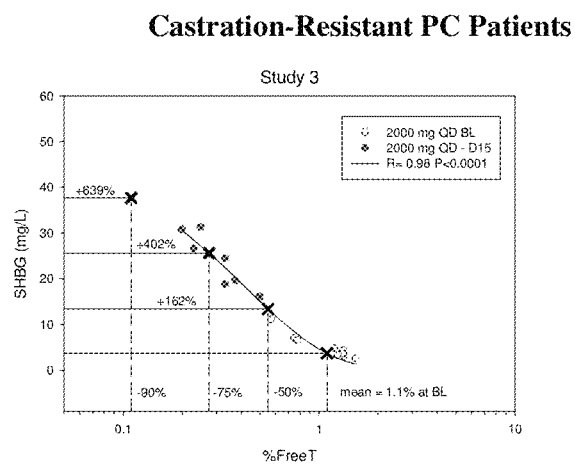

FIGS. 27A-27B depict the SHBG induction by Compound IV and the relationship between SHBG and free testosterone percentage (% FreeT) in treatment naive patients from Study 2 and Study 5 (FIG. 27A) and in CRPC patients on concurrent ADT from Study 3 (FIG. 27B). In Study 2 and Study 5 trials, baseline SHBG is induced by ~150-700% after 28 days of Compound IV therapy (FIG. 27A). SHBG induction is strongly correlated with reductions in % FreeT [Free T (pg/mL)/Total T (pg/mL)*100]. The regression of the relationship shows that a ~400% induction in SHBG is associated with ~75% reductions in % FreeT. A large number of treatment naive patients cluster in this range across all doses of Compound IV. Importantly this strong relationship is maintained in CRPC patients on concurrent ADT from Study 3 (FIG. 27B) even when looking at only 15 days of Compound IV therapy. Open symbols represent baseline (BL) and closed symbols are treated with Compound IV as described herein below (Example 26).

FIGS. 28A-28D depict the change in free testosterone percentage vs. the change in PSA in the treatment naïve prostate cancer patients from Studies 2 and 5 at day 7 (FIG. 28A); day 14 (FIG. 28B); day 21 (FIG. 28C) and day 28 (FIG. 28D) of Compound IV treatment (Example 25).

Figure 29:
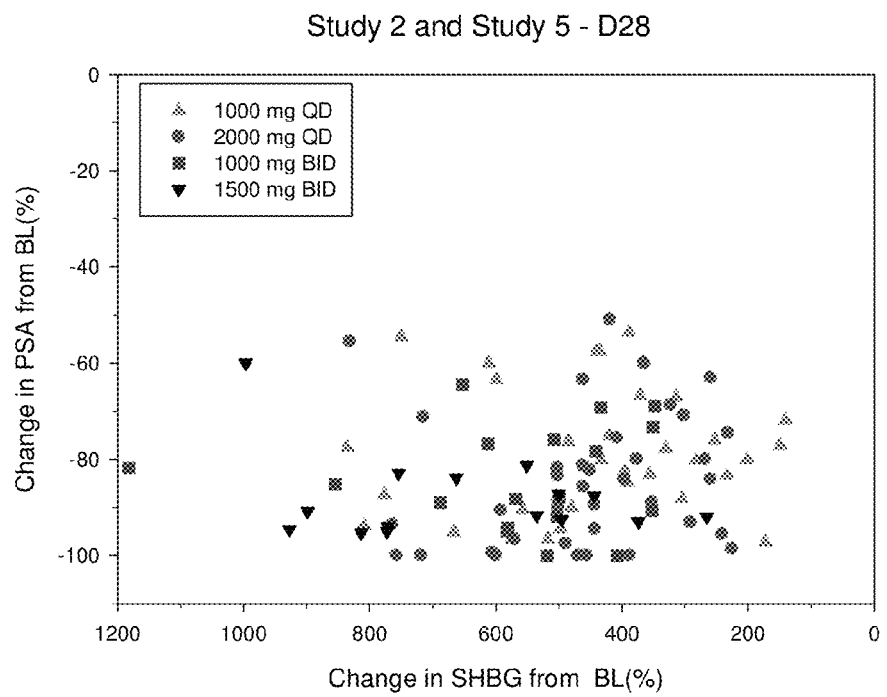

FIG. 29 depicts the change in PSA vs. the change in SHBG in the treatment naïve prostate cancer patients from Studies 2 and 5 at day 28. Wide range of SHBG induction is capable of greater than 50% reduction in PSA (Example 25).

Figure 30:
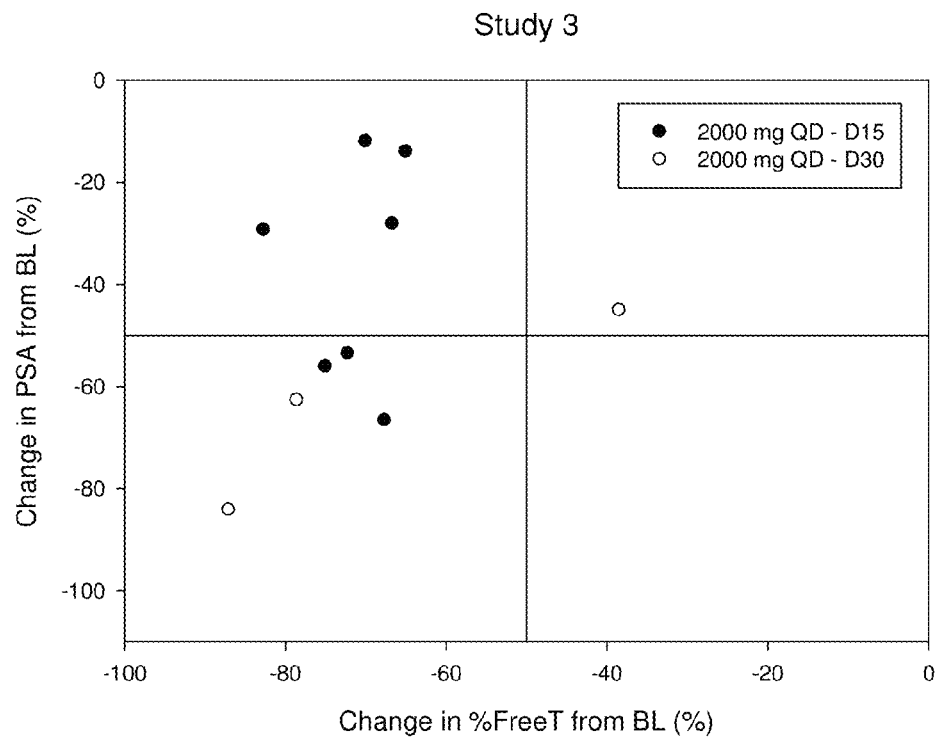

FIG. 30 depicts the change in free testosterone percentage vs. the change in PSA in the castration resistant prostate cancer patients from Study 3 at day 15 (7 subjects) and day 30 (3 subjects) (Example 26).

Figure 31:
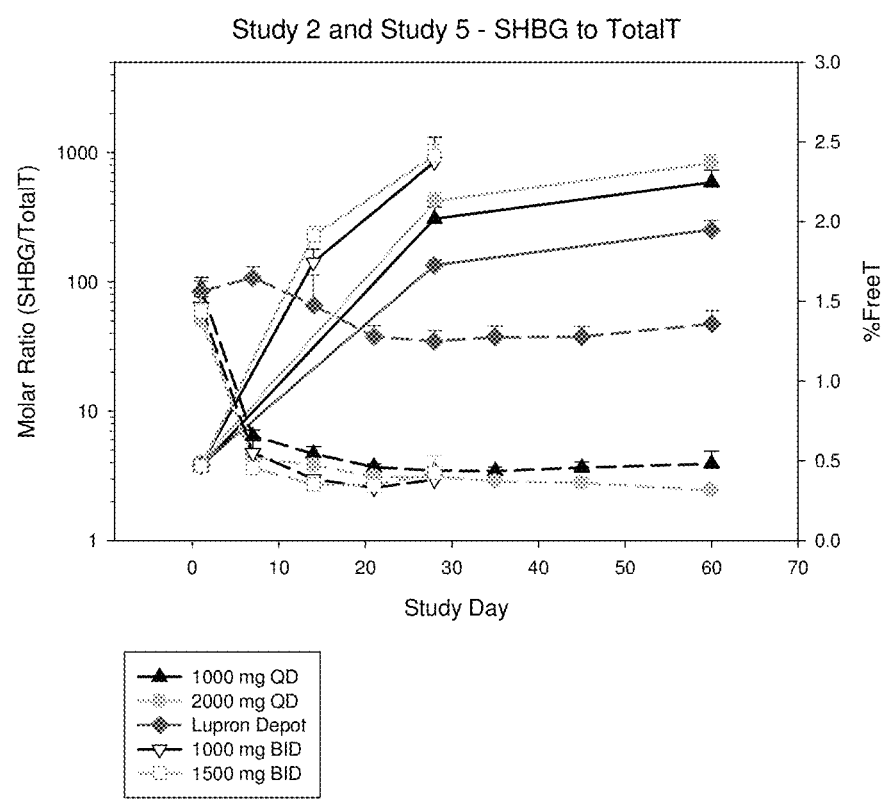

FIG. 31 depicts the molar ratio of SHBG to total testosterone as a function of time in the treatment naive prostate cancer patients from Studies 2 and 5 (solid line). The dotted line represents the free testosterone percentage (% FreeT) as a function of time (Example 25).

FIG. 32 depicts the percent change in SHBG vs. Compound IV mean trough as calculated based on Study 1 and Study 2 results at day 28, and extrapolation to lower doses of 125 mg, 250 mg and 500 mg. This suggests that even at lower doses of Compound IV, SHBG can be elevated enough to significantly suppress % freeT and PSA (Example 25).

Figure 33:
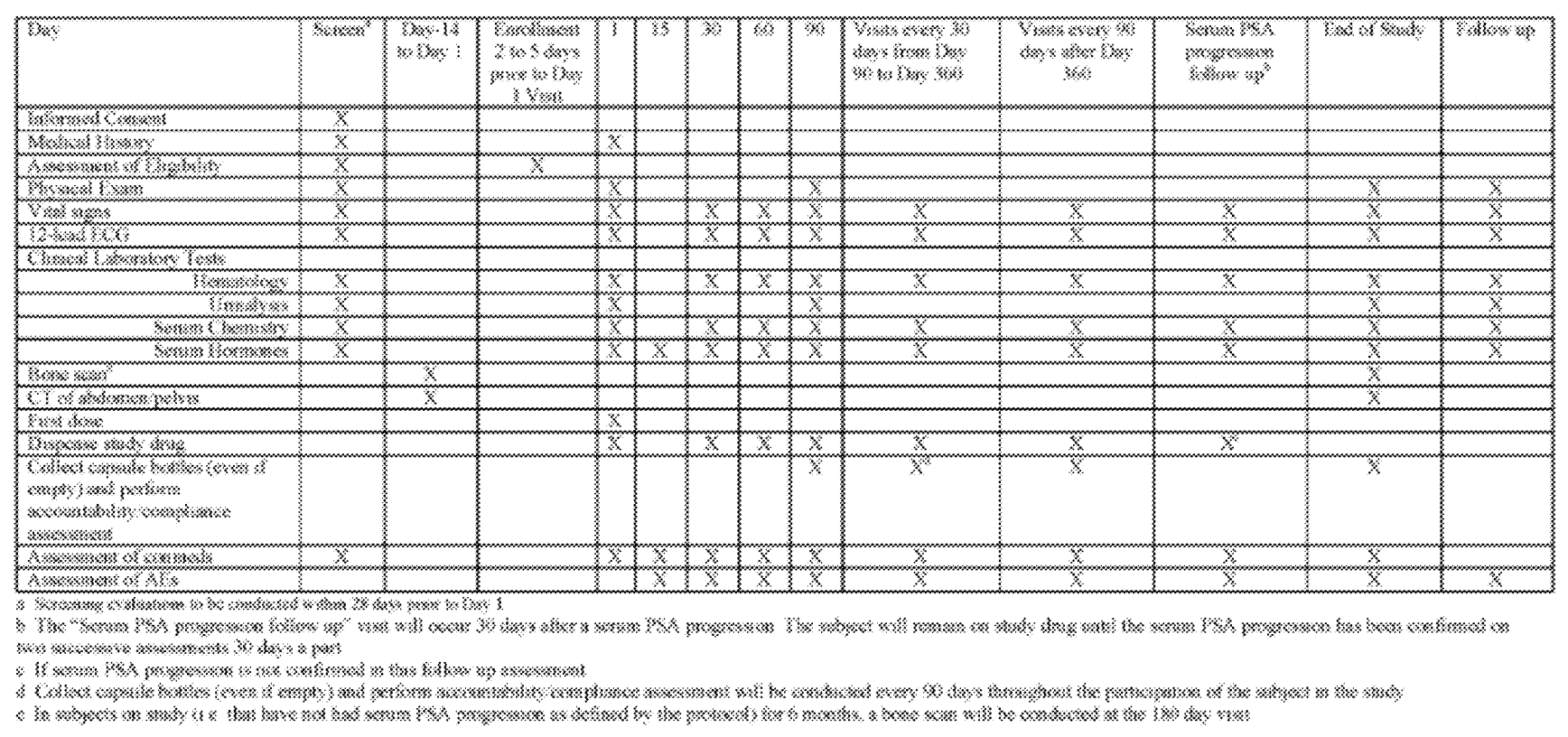

FIG. 33 depicts a flow chart describing Study 3 procedures (Example 26).

Figure 34:
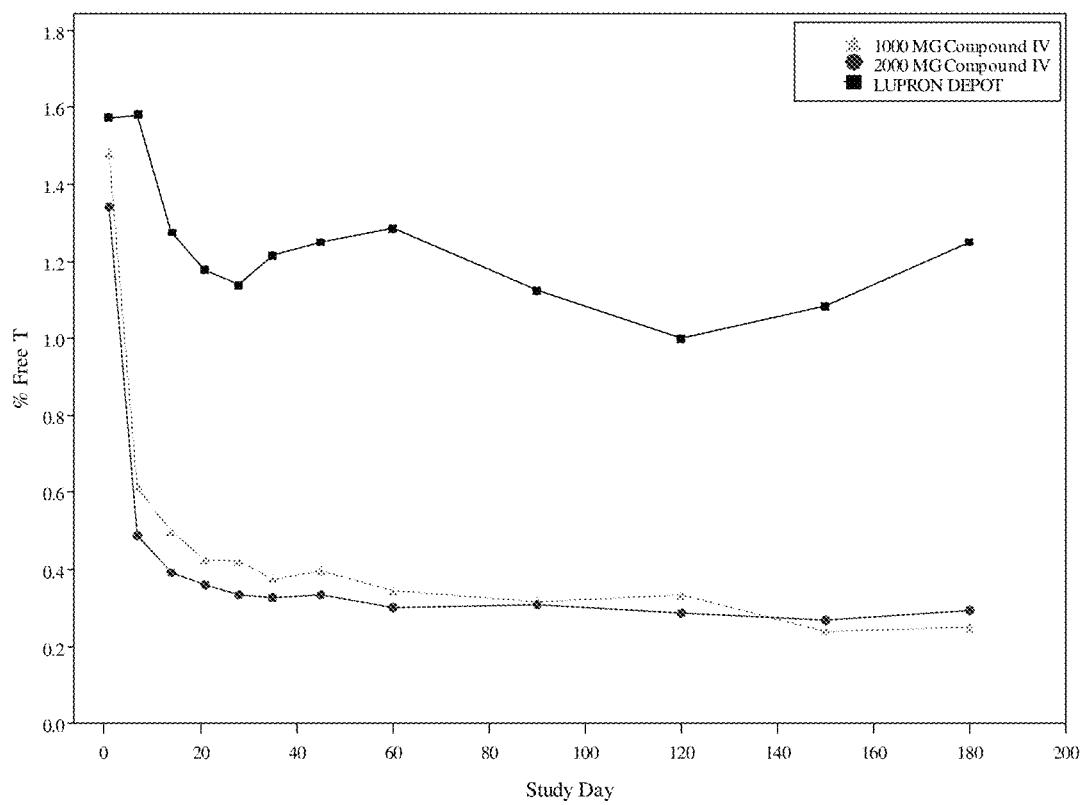

FIG. 34 depicts changes in the percentage free testosterone (% Free T) in response to treatment with Compound IV over time. Compound IV lowers the percentage free testosterone rapidly and to a dramatically greater extent than leuprolide acetate. (Example 25, Study 2).

Figure 35:
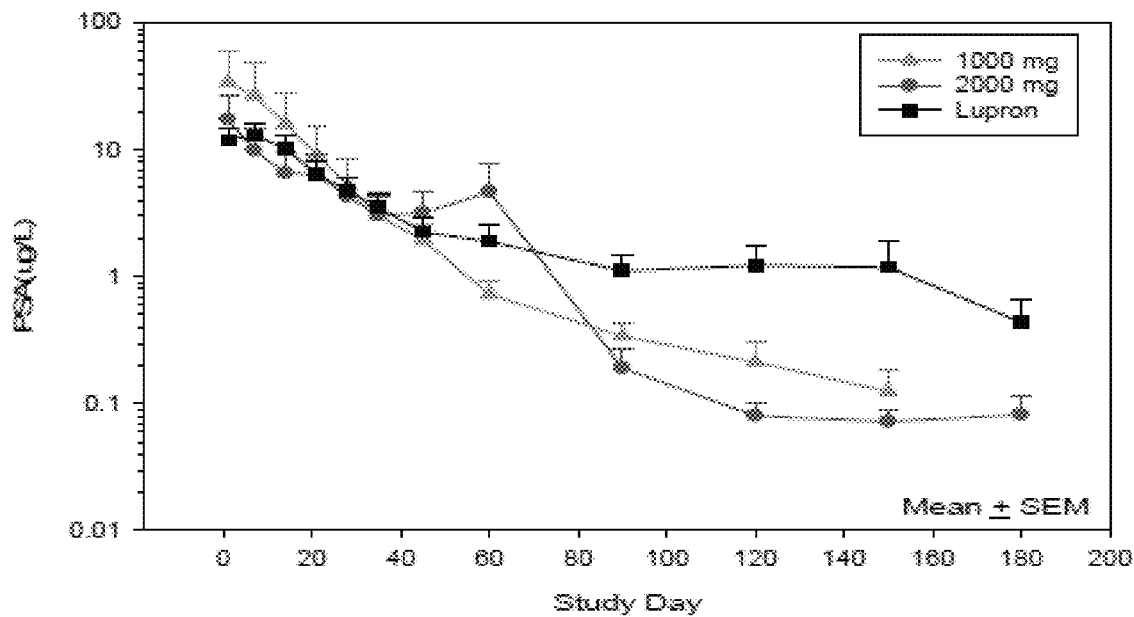

FIG. 35 depicts changes in the percentage PSA levels. On average, men treated with Compound IV reach "undetectable" (<0.2 μg/L) PSA levels. (Study 2)

Figure 36:
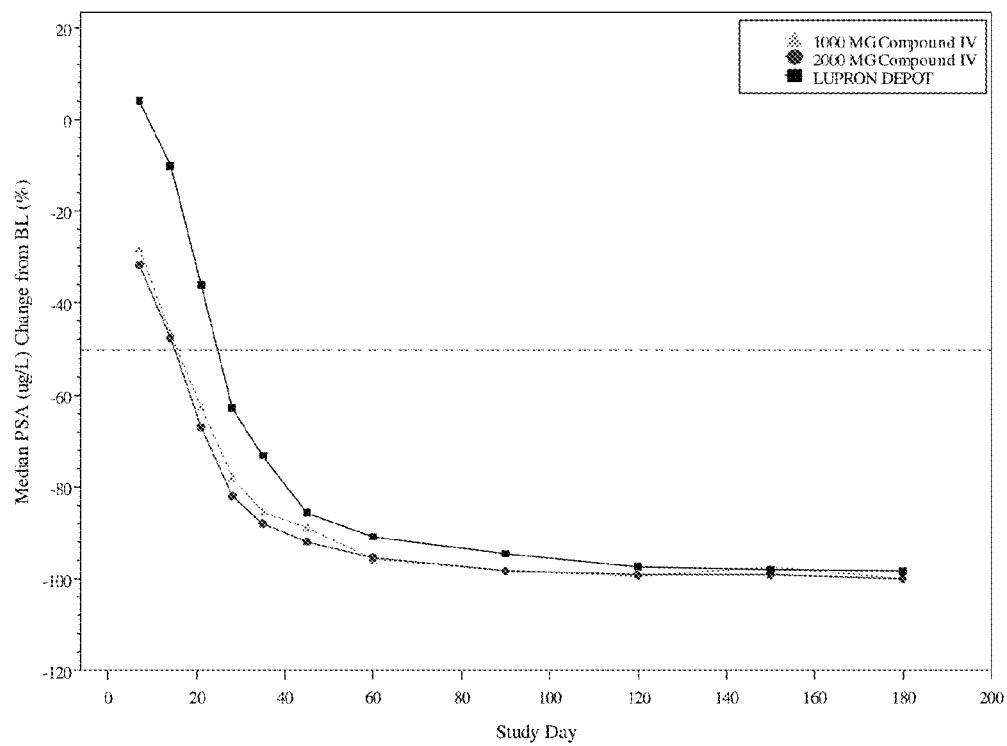

FIG. 36 depicts changes in the percentage PSA in response to treatment with Compound IV from baseline vs. time. (Example 25, Study 2)

Figure 37:
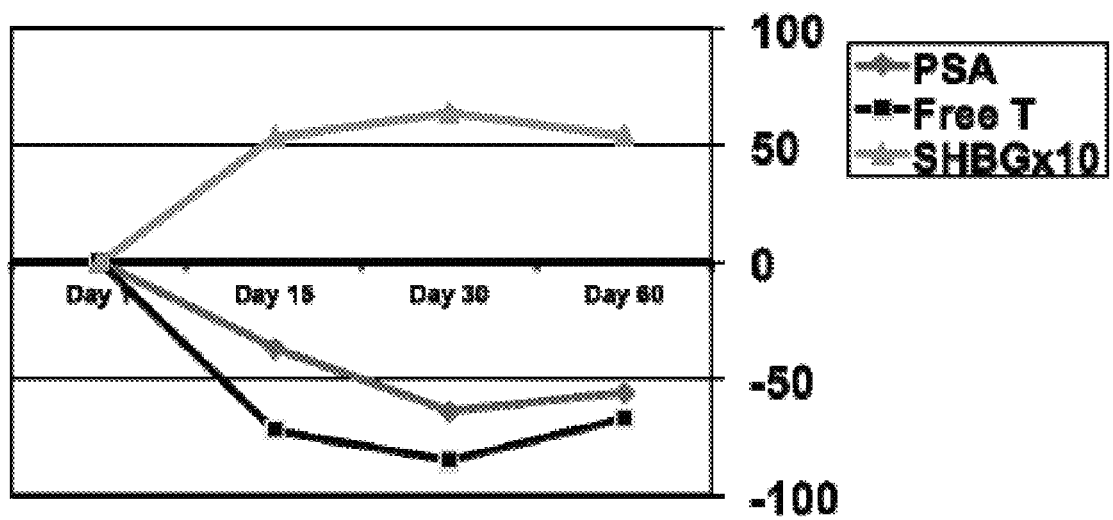

FIG. 37 depicts relationship of mean SHBG, Free Testosterone, and PSA (all patients). Mean SHBG for PSA responders (>50% reduction)=399%+85%. (Study 2)

Figure 38:
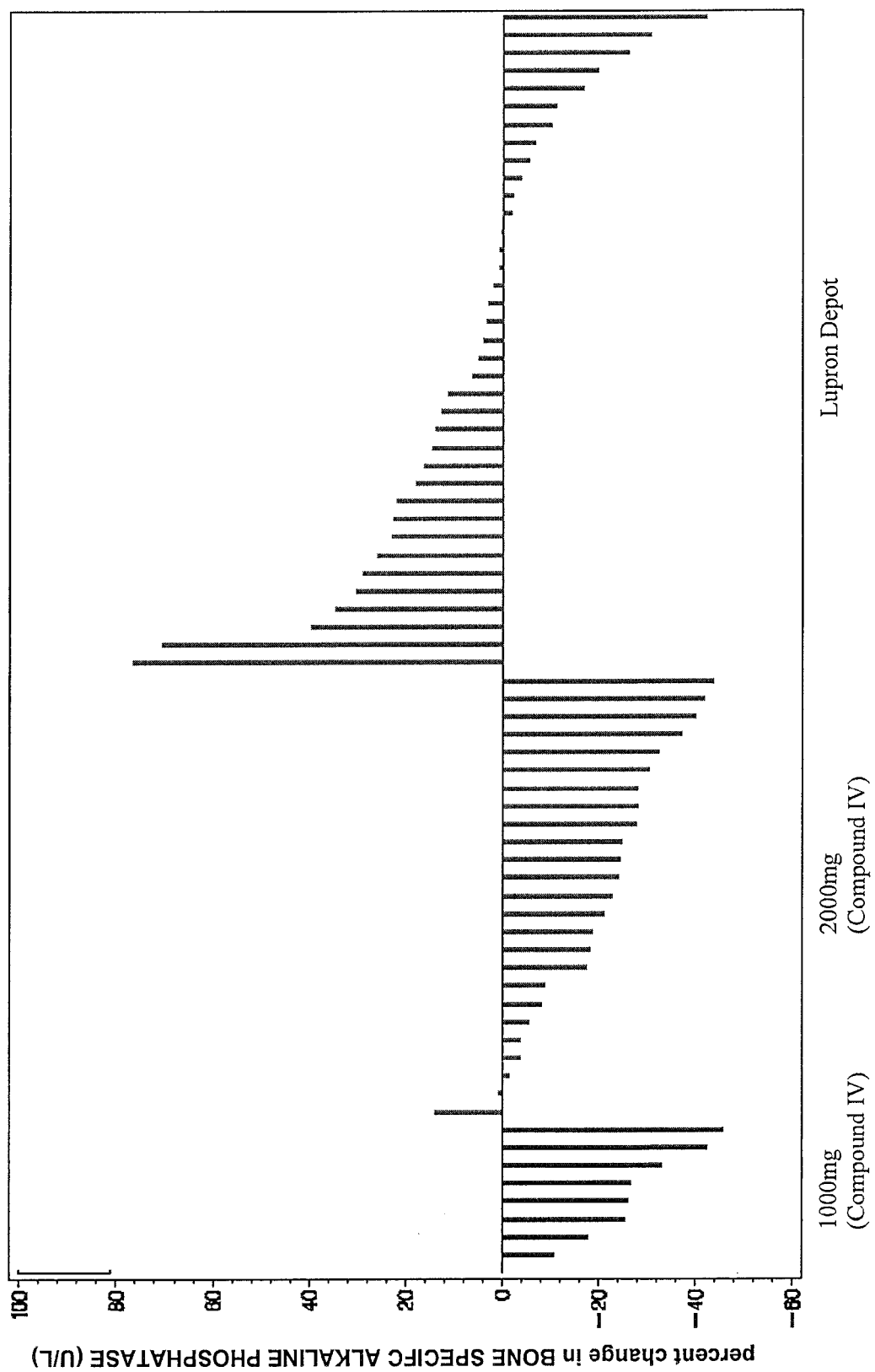

FIG. 38 depicts bone turnover marker percentage change of bone specific alkaline phosphatase from baseline to day 120 for Compound IV vs leuprolide treated patients. (Example 25, Study 2)

Figure 39:
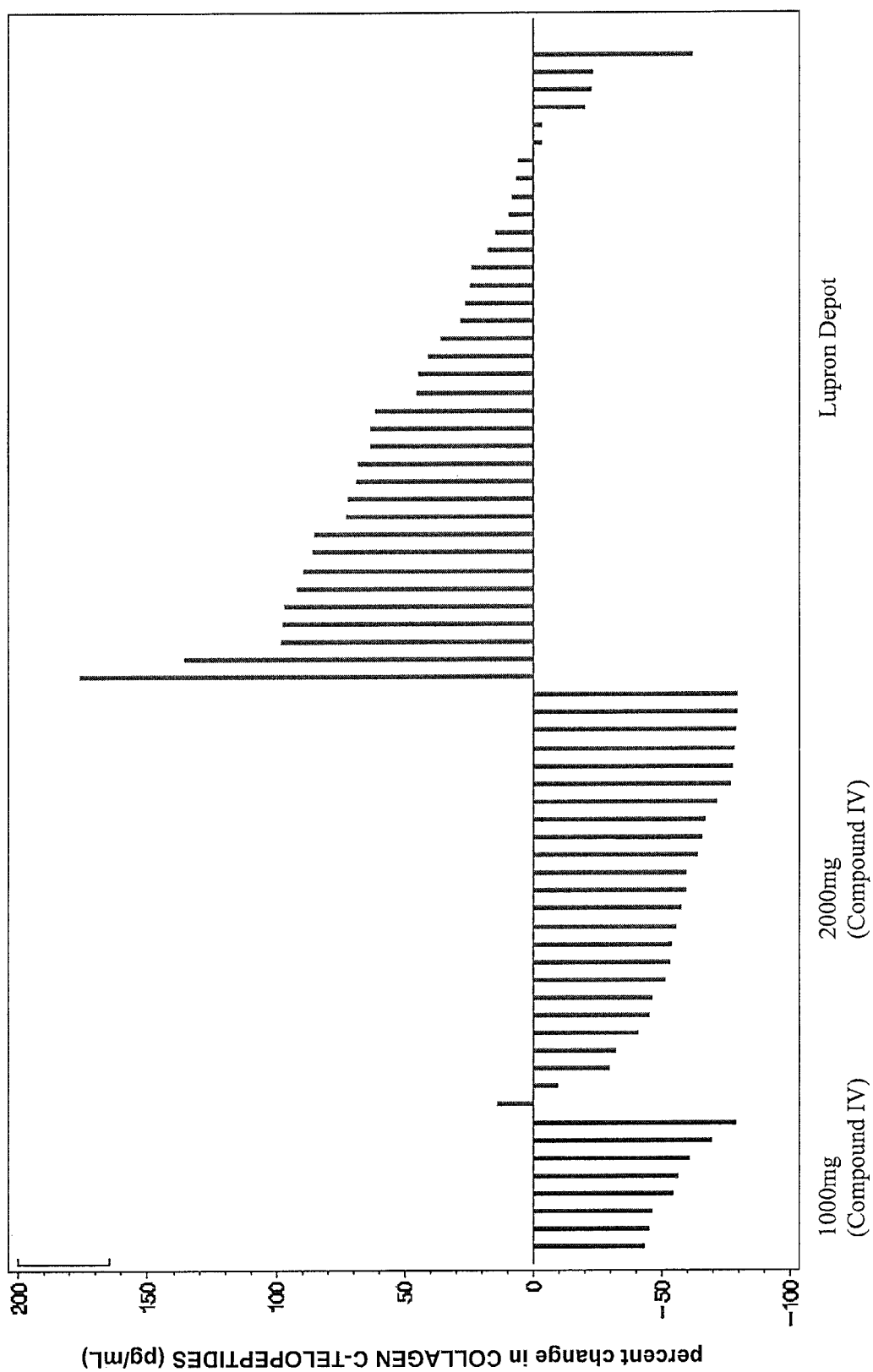

FIG. 39 depicts bone turnover marker percentage change of collagen C-telopeptides from baseline to day 120 for Compound IV vs leuprolide treated patients. (Example 25, Study 2)

Figure 40:
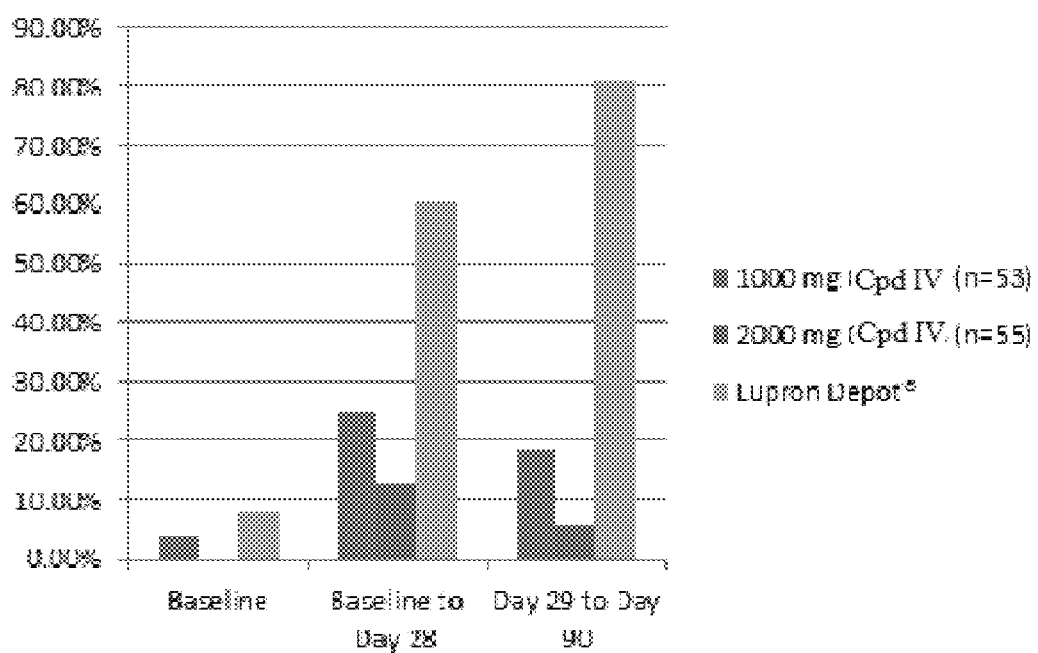

FIG. 40 depicts incidence and severity of hot flashes for Compound IV vs leuprolide treated patients. (Example 25, Study 2)

Figure 41:
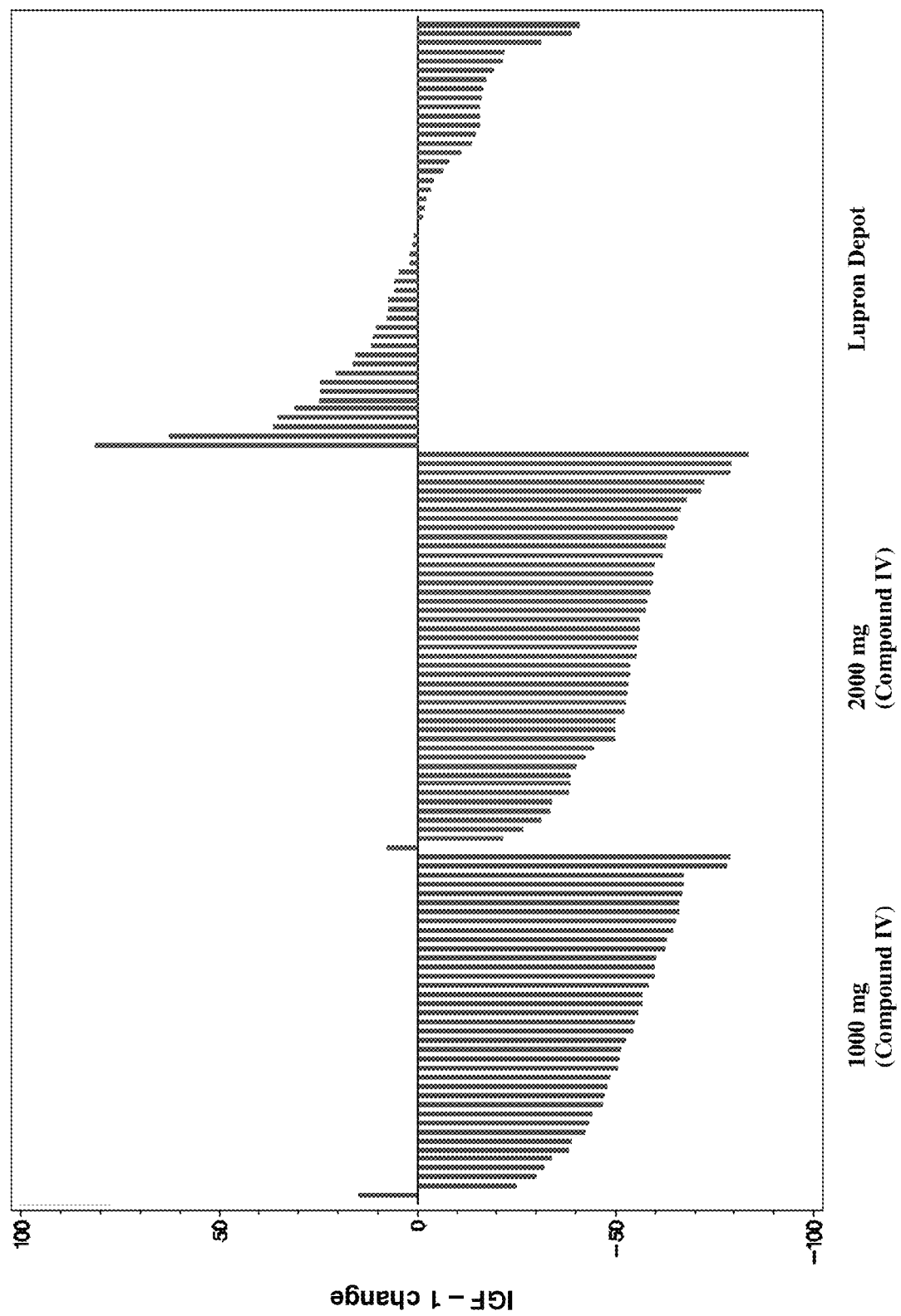

FIG. 41 depicts a waterfall plot of IGF-1 change from baseline to day 60 in the study (Example 29, Study 2).

Figure 42:
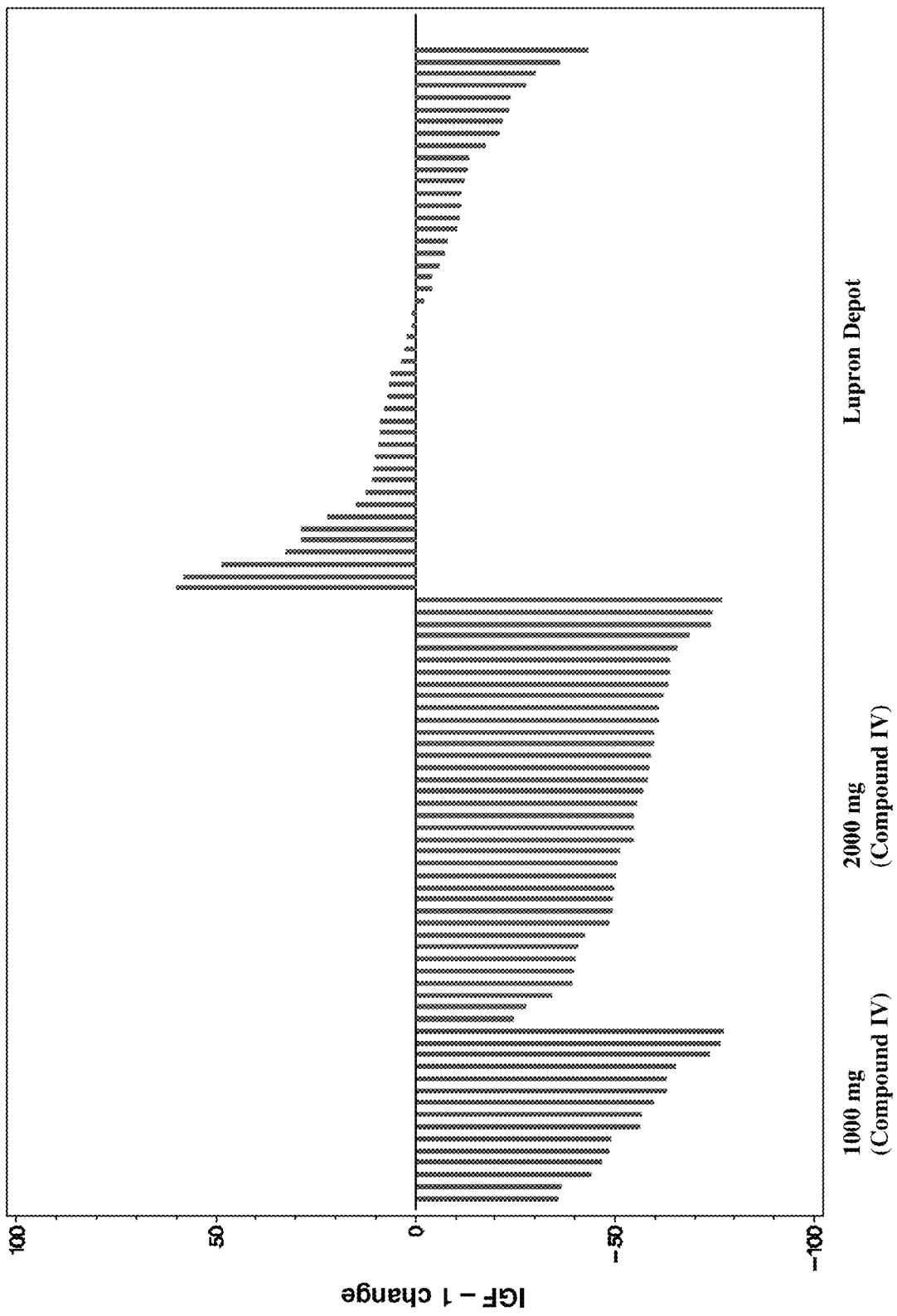

FIG. 42 depicts a waterfall plot of IGF-1 change from baseline to day 90 in the study (Example 29, Study 2).

Figure 43:
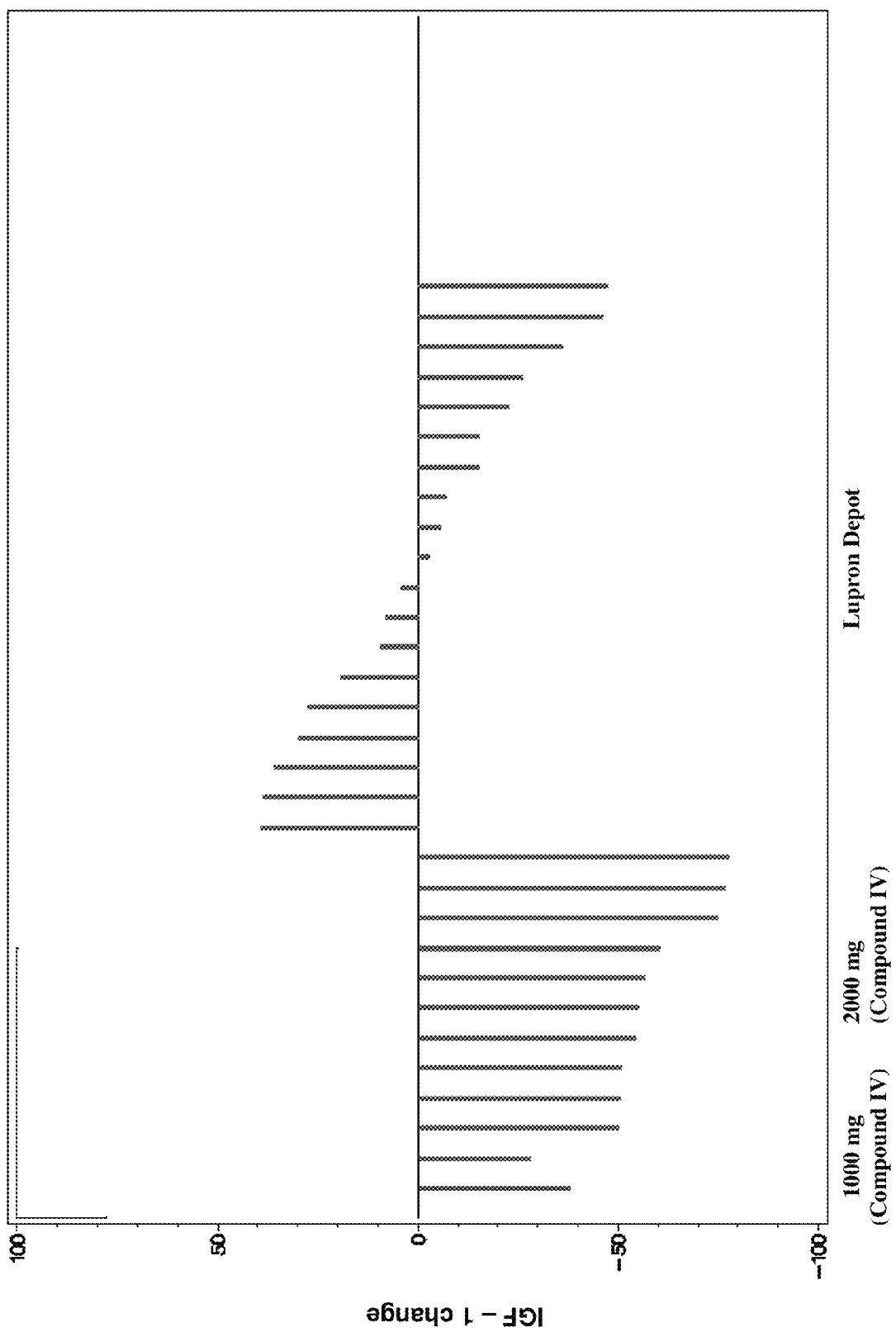

FIG. 43 depicts a waterfall plot of IGF-1 change from baseline to day 180 in the study (Example 29, Study 2).

Figure 44:
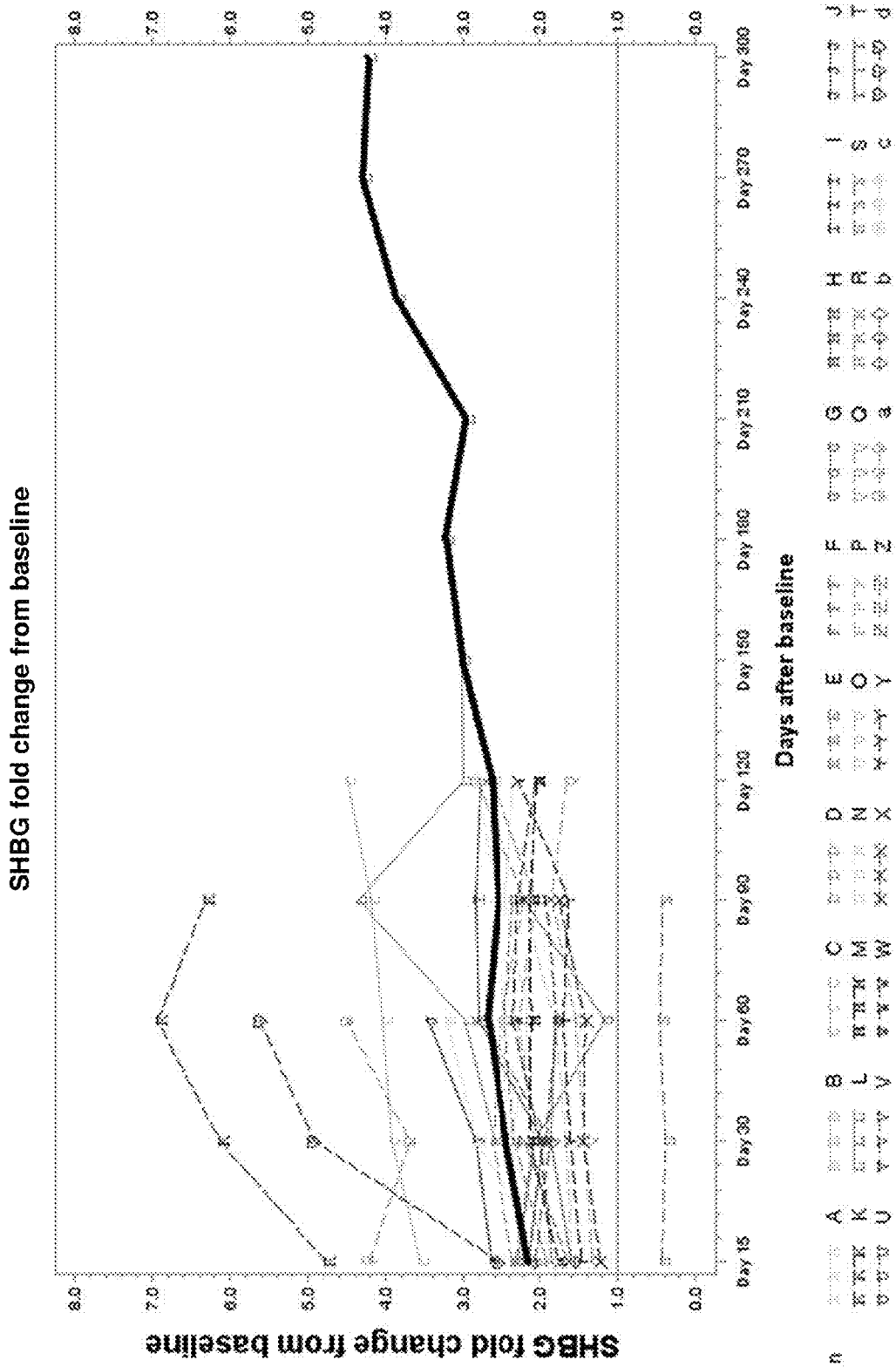

FIG. 44 depicts SHBG fold change from baseline for men with mCRPC treated with Compound IV, 125 mg, for at least 90 days. All treated men had SHBG levels increased to ≥150% of Day 0. (Example 30, Study 6)

Figure 45:
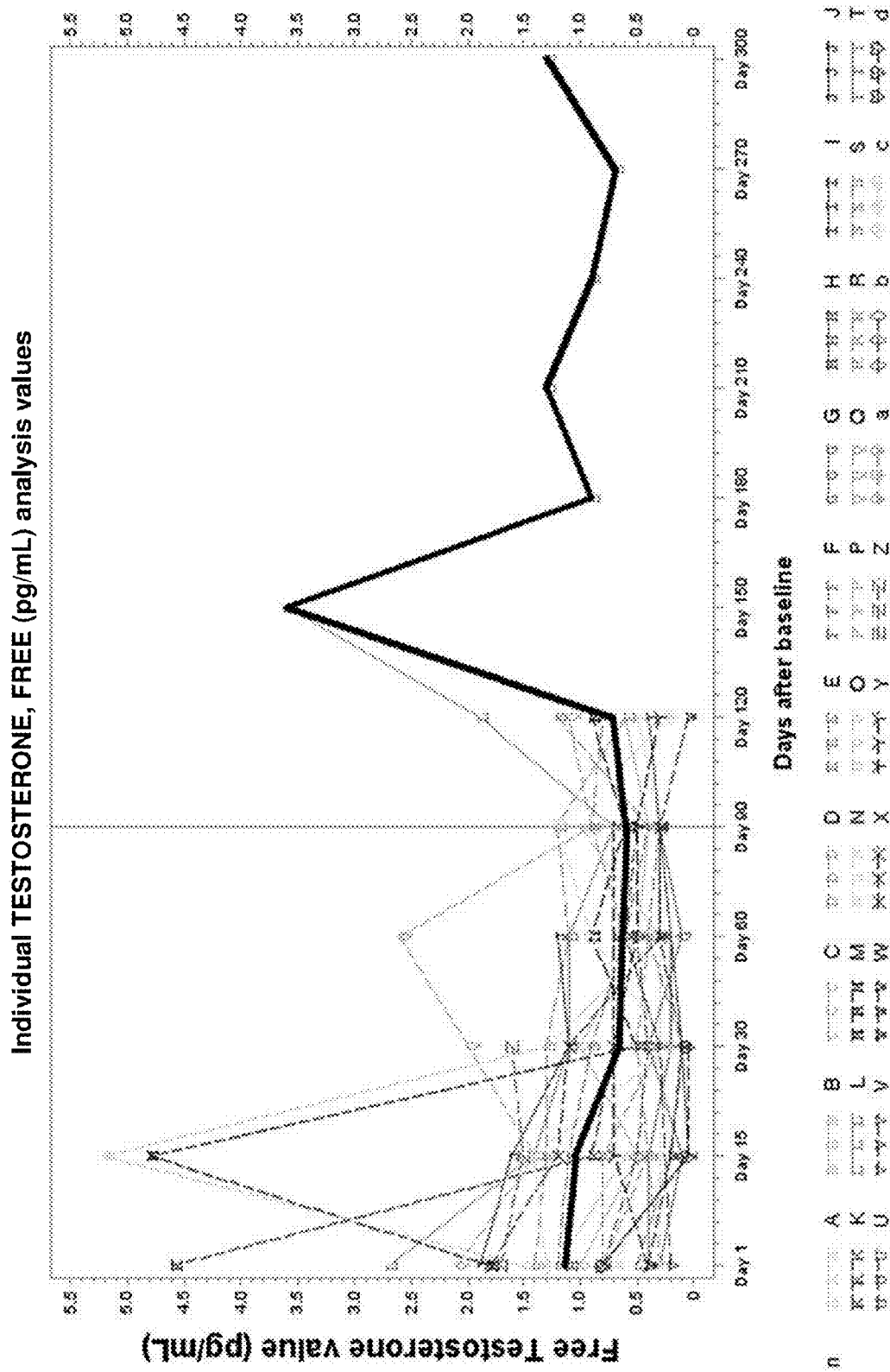

FIG. 45 depicts free testosterone levels (pg/mL) for men with mCRPC treated with Compound IV, 125 mg, for at least 90 days. Eleven of the 15 men began the study with suboptimal castration (free T>0.7 pg/ml) and 91% (10/11) of these men became optimally castrated by day 90. (Example 30, Study 6)

Figure 46:
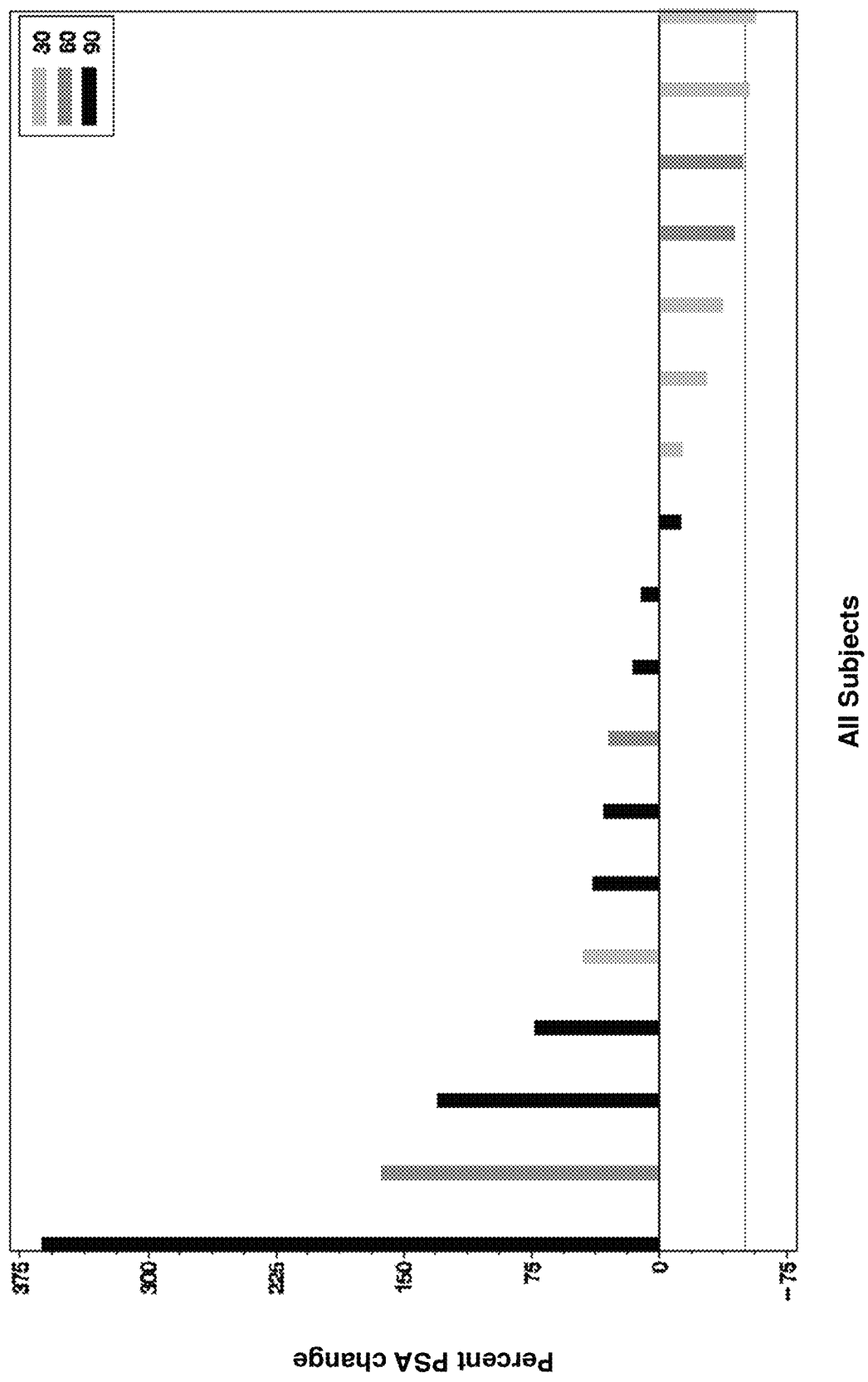

FIG. 46 depicts percentage of PSA, for men with mCRPC treated with Compound IV, 125 mg after 30, 60 and 90 days. 4 patients (from total 15) had >45% decrease in PSA prior to day 90. All patients started the study with PSA progression. (Example 30, Study 6)

Figure 47:
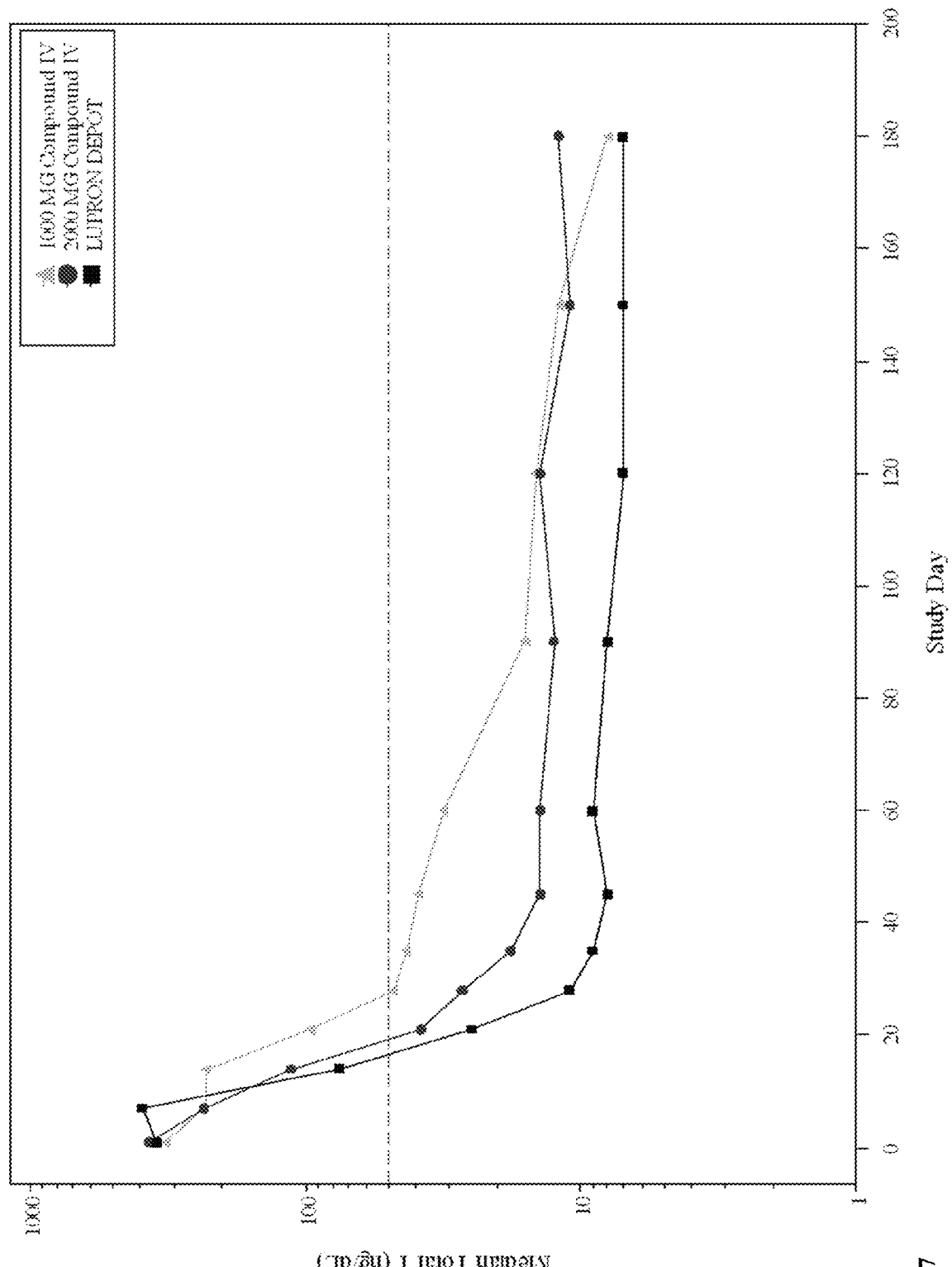

FIG. 47 depicts decline in total serum testosterone in response to treatment with Compound IV over time. Dotted line indicates the cut-off value (50 ng/dL) for castration levels of total serum testosterone (Example 25, Study 2)

Figure 48:
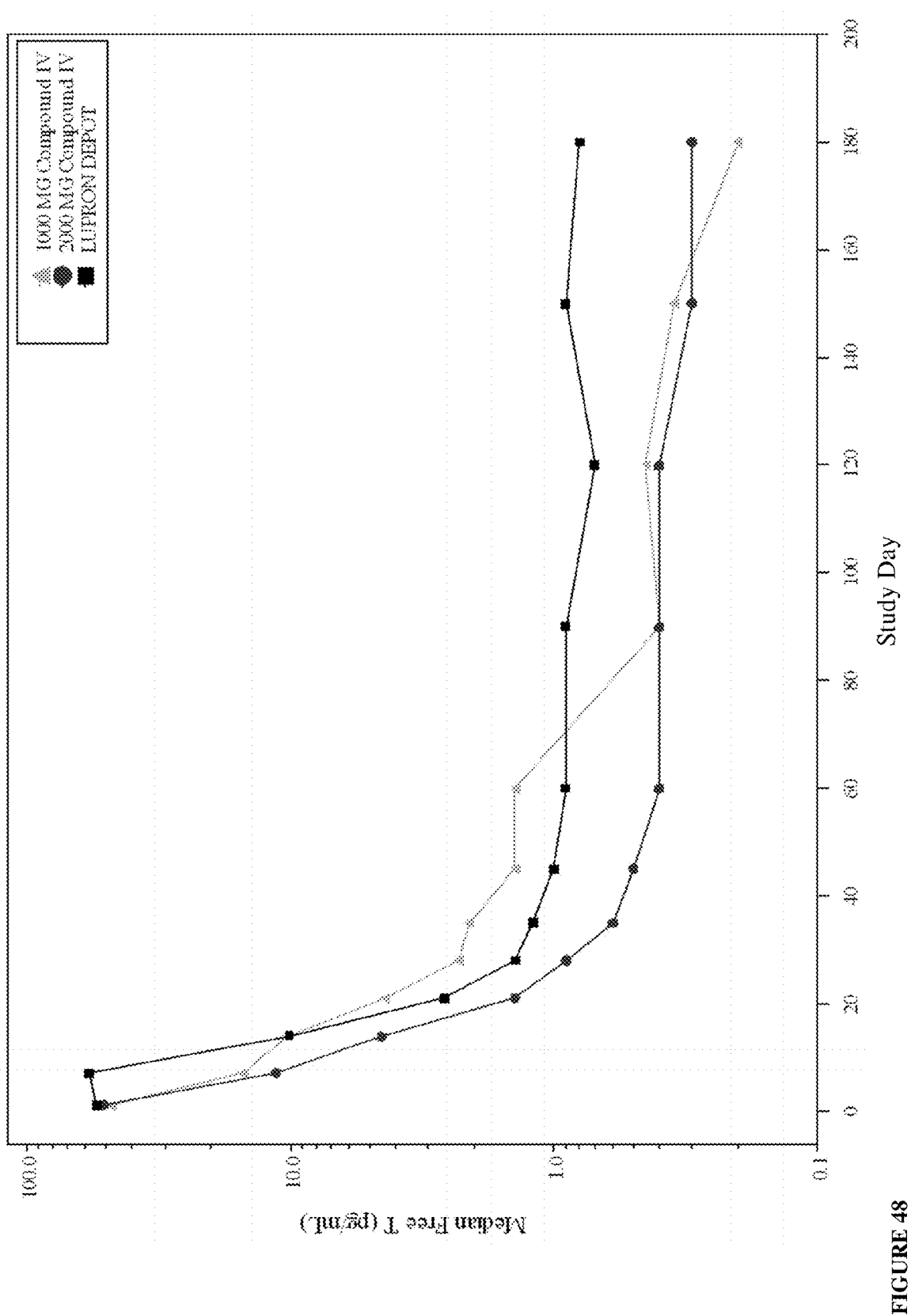

FIG. 48 depicts median free testosterone levels in response to treatment with Compound IV over time. (Example 25, Study 2)

Figure 49A:
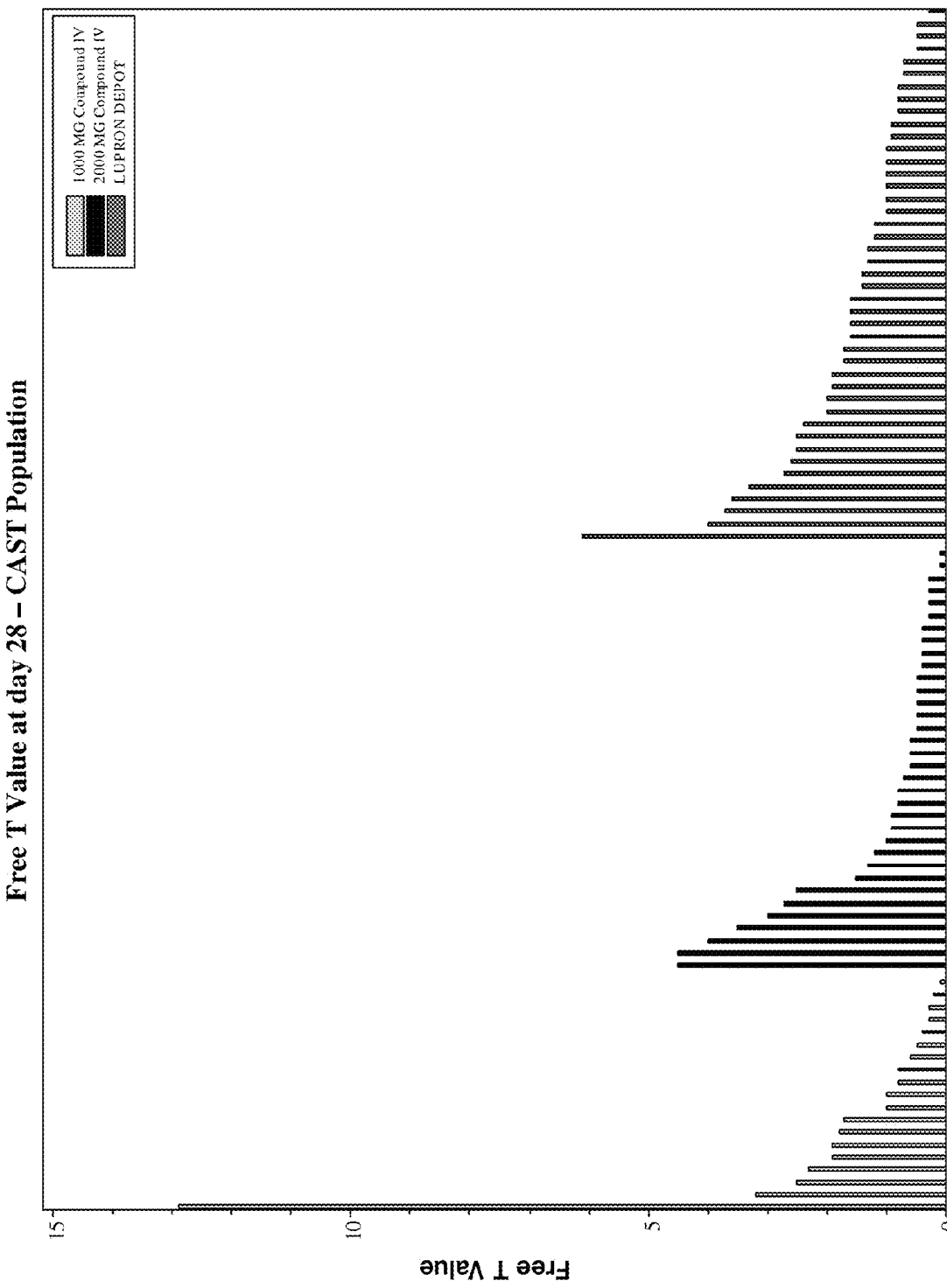
Figure 49B:
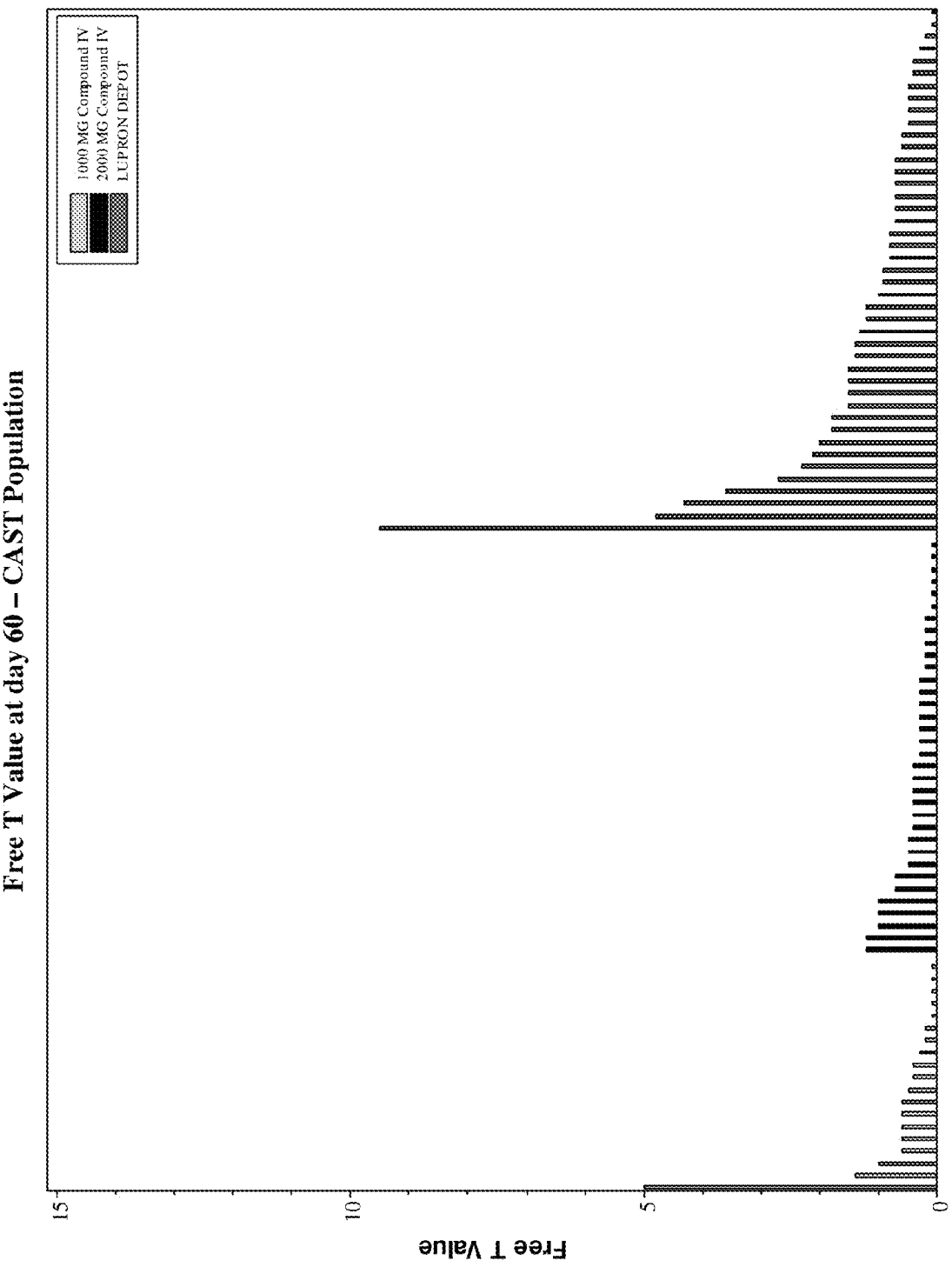
Figure 49C:
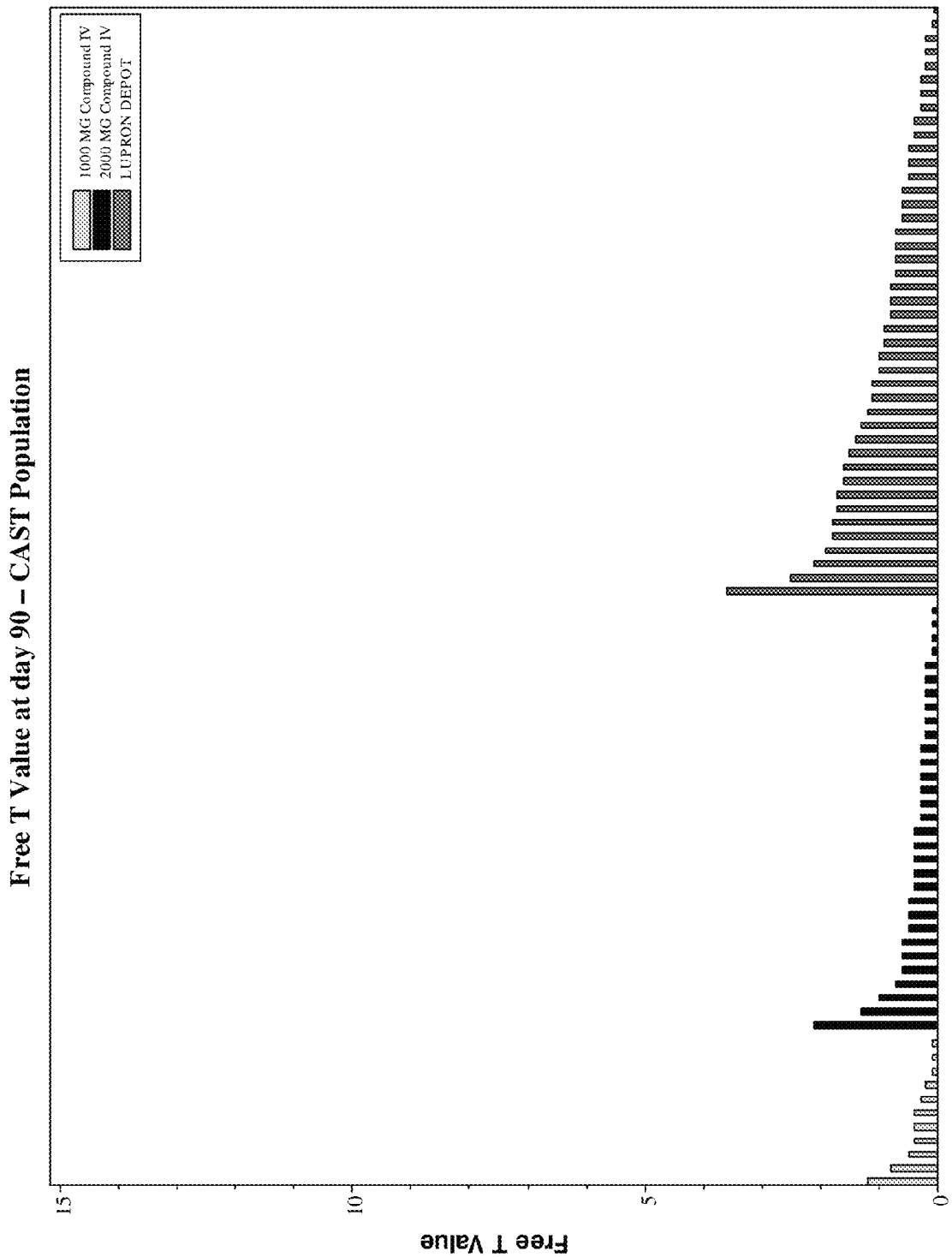

FIGS. 49A-C depicts absolute values of free testosterone (pg/nL) as measured in the population that reached castrate levels by day 60. The results for individual patients are shown at day 28 (FIG. 49A), day 60 (FIG. 49B) and day 90 (FIG. 49C) on study. (Example 25, Study 2)

Figure 50:
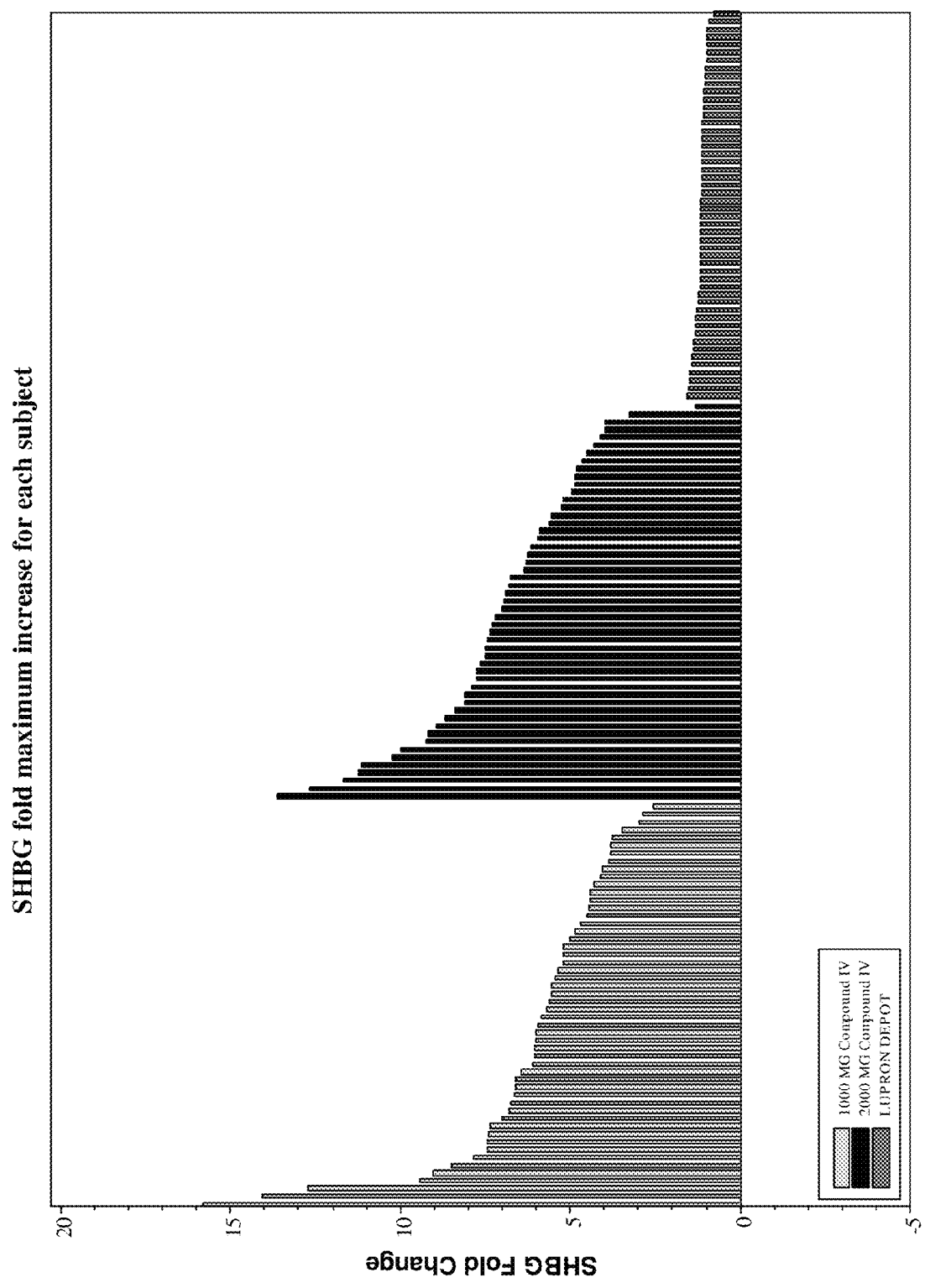

FIG. 50 presents a waterfall plot demonstrating the largest changes in SHBG levels per patient. (Example 25, Study 2)

Figure 51:
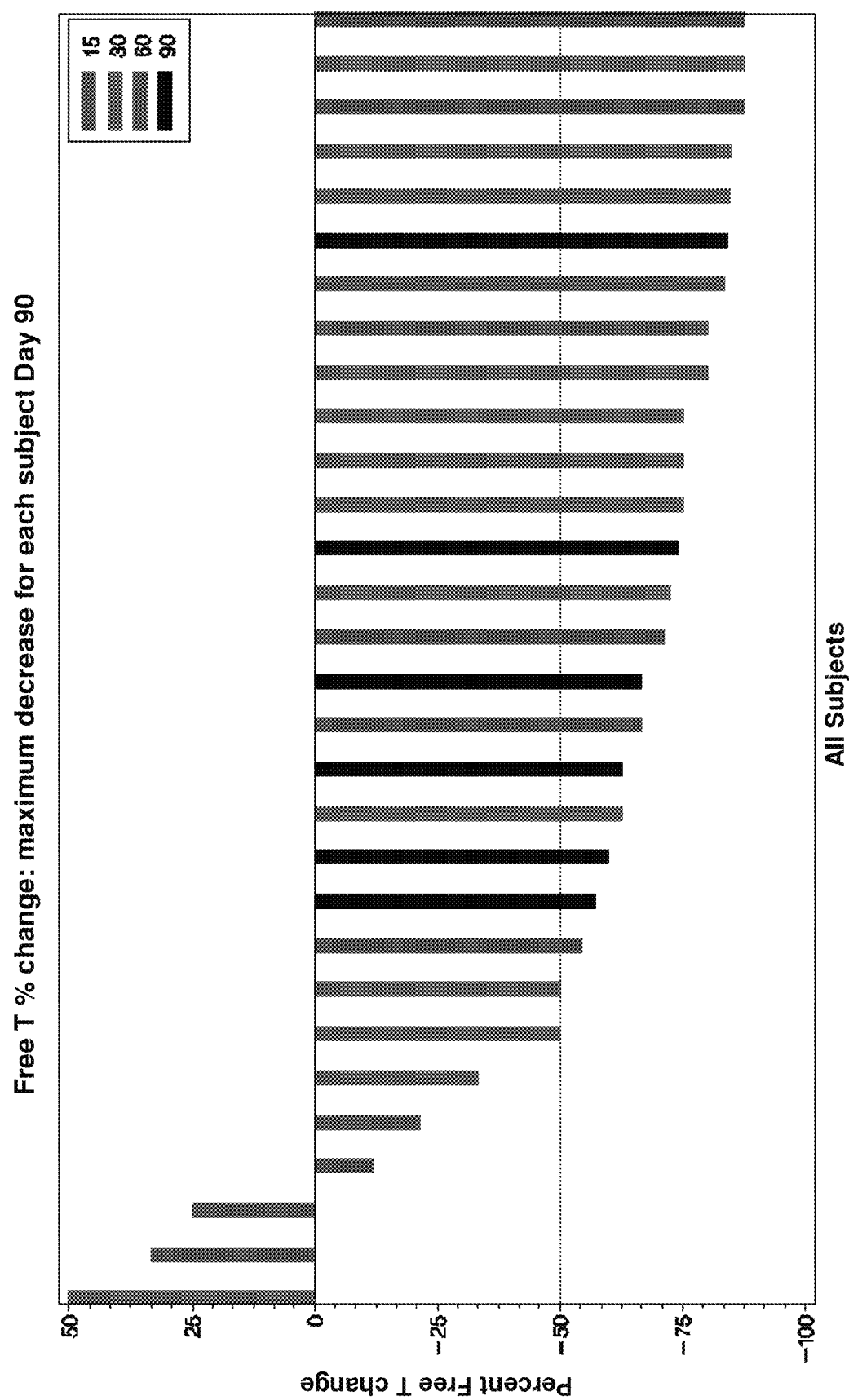

FIG. 51 illustrates that Compound IV treatment lowers free T levels in mCRPC with a maximum decrease by day 90 (Study 6; Example 30).

Figure 52:
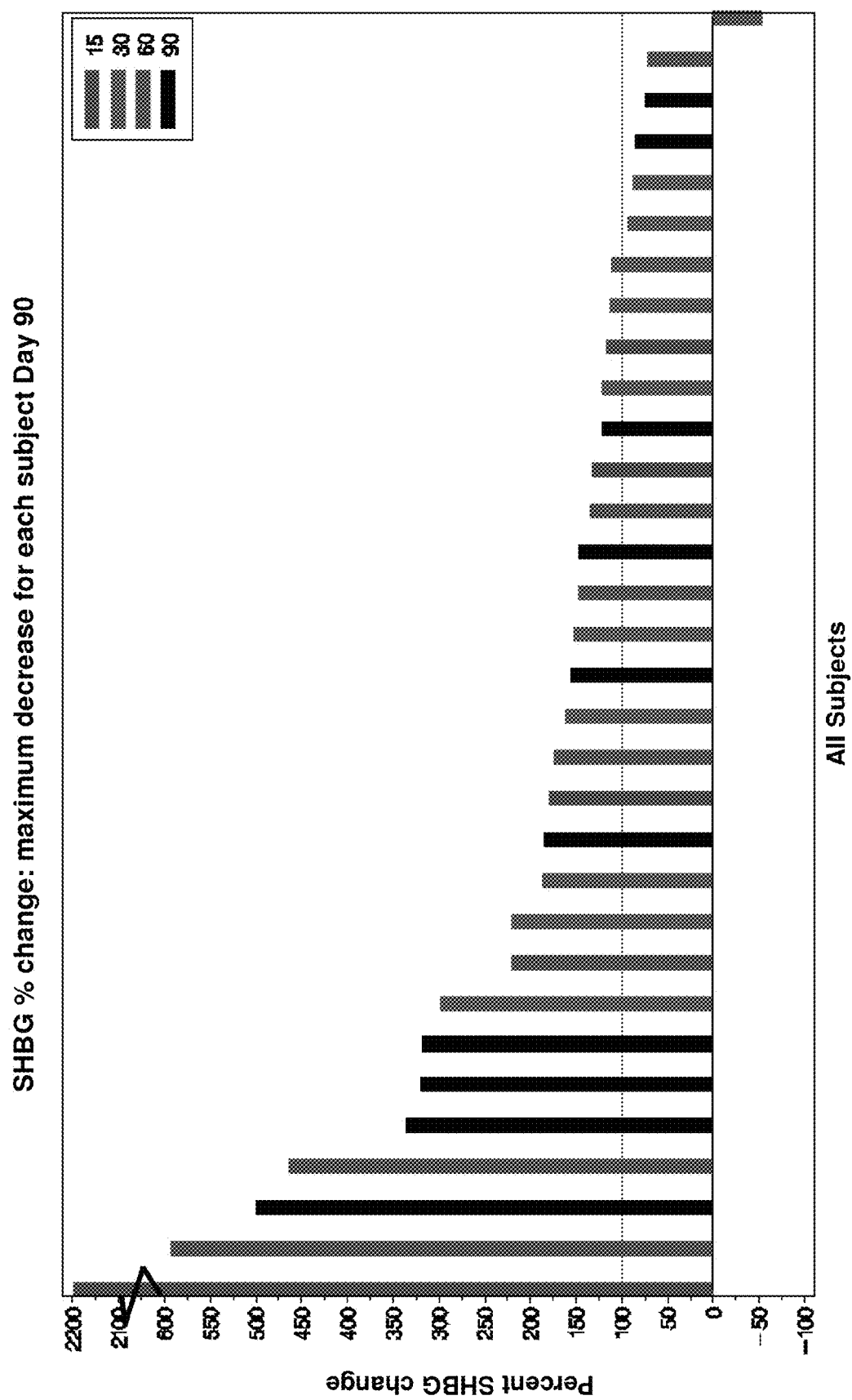

FIG. 52 illustrates that Compound IV treatment increases SHBG levels in mCRPC with a maximum increase by day 90 (Study 6; Example 30).

Figure 53:
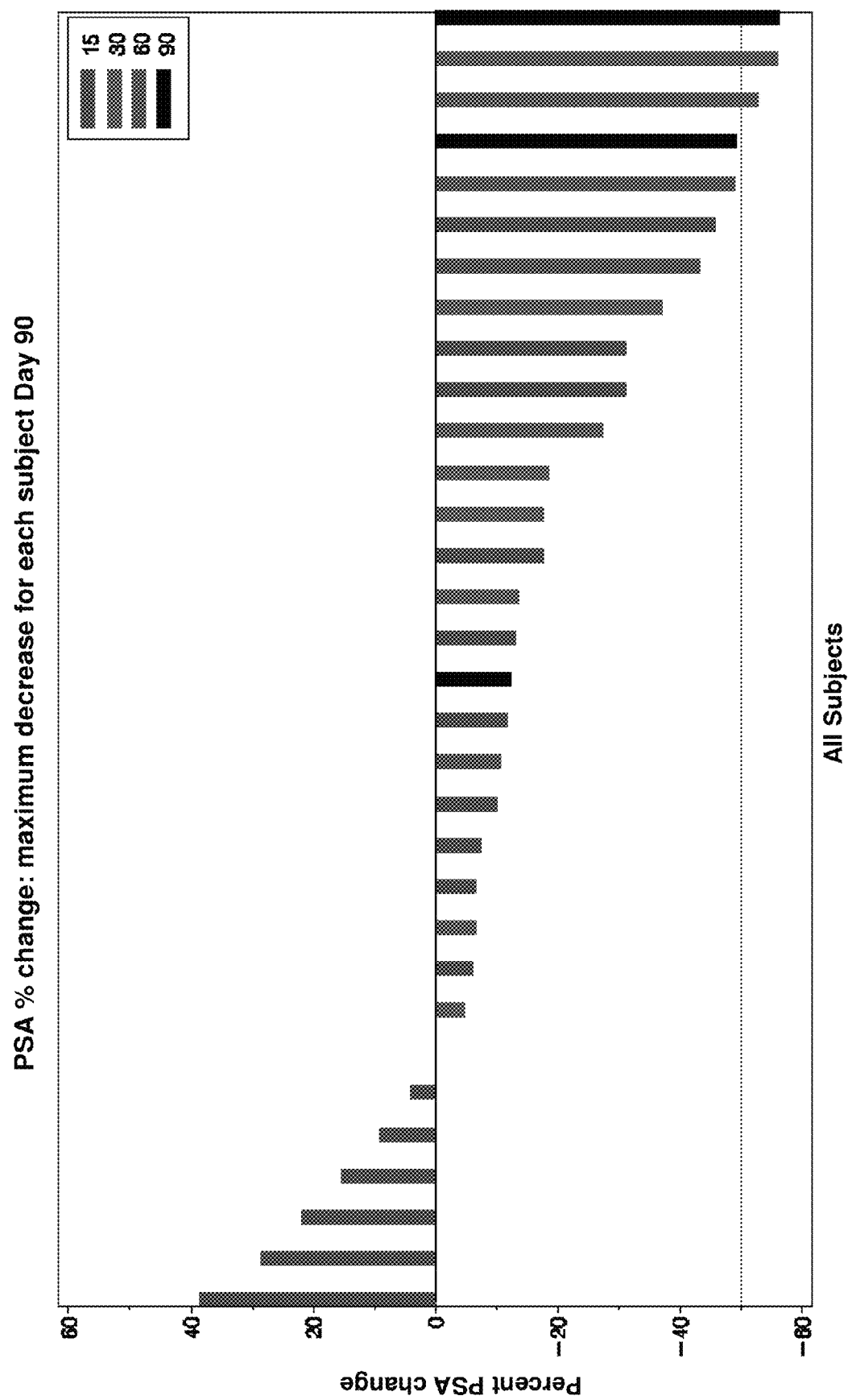

FIG. 53 illustrates that Compound IV treatment lowers PSA levels in mCRPC with a maximum decrease by day 90 (Study 6; Example 30).

Figure 54:
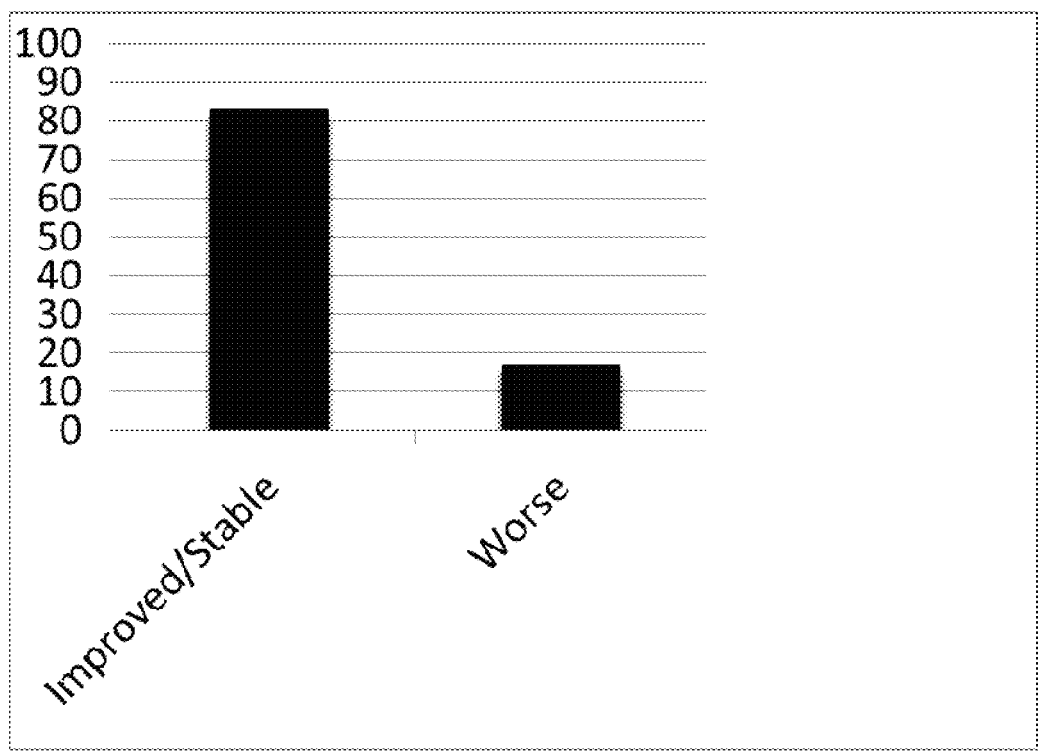

FIG. 54 depicts frequency and severity of hot flashes in a subset of Study 6 patients (Example 30).

Figure 55A:
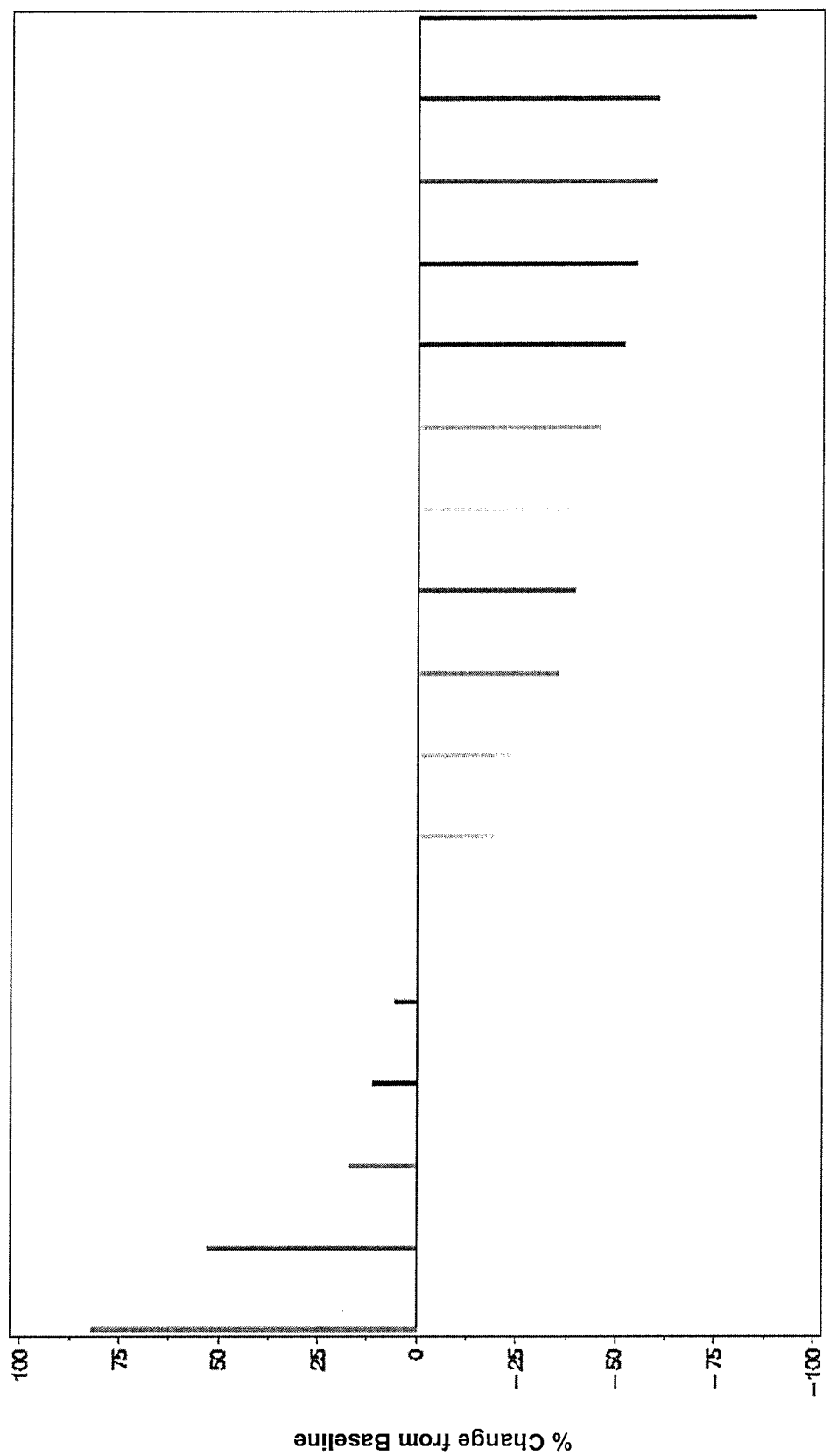
Figure 55B:
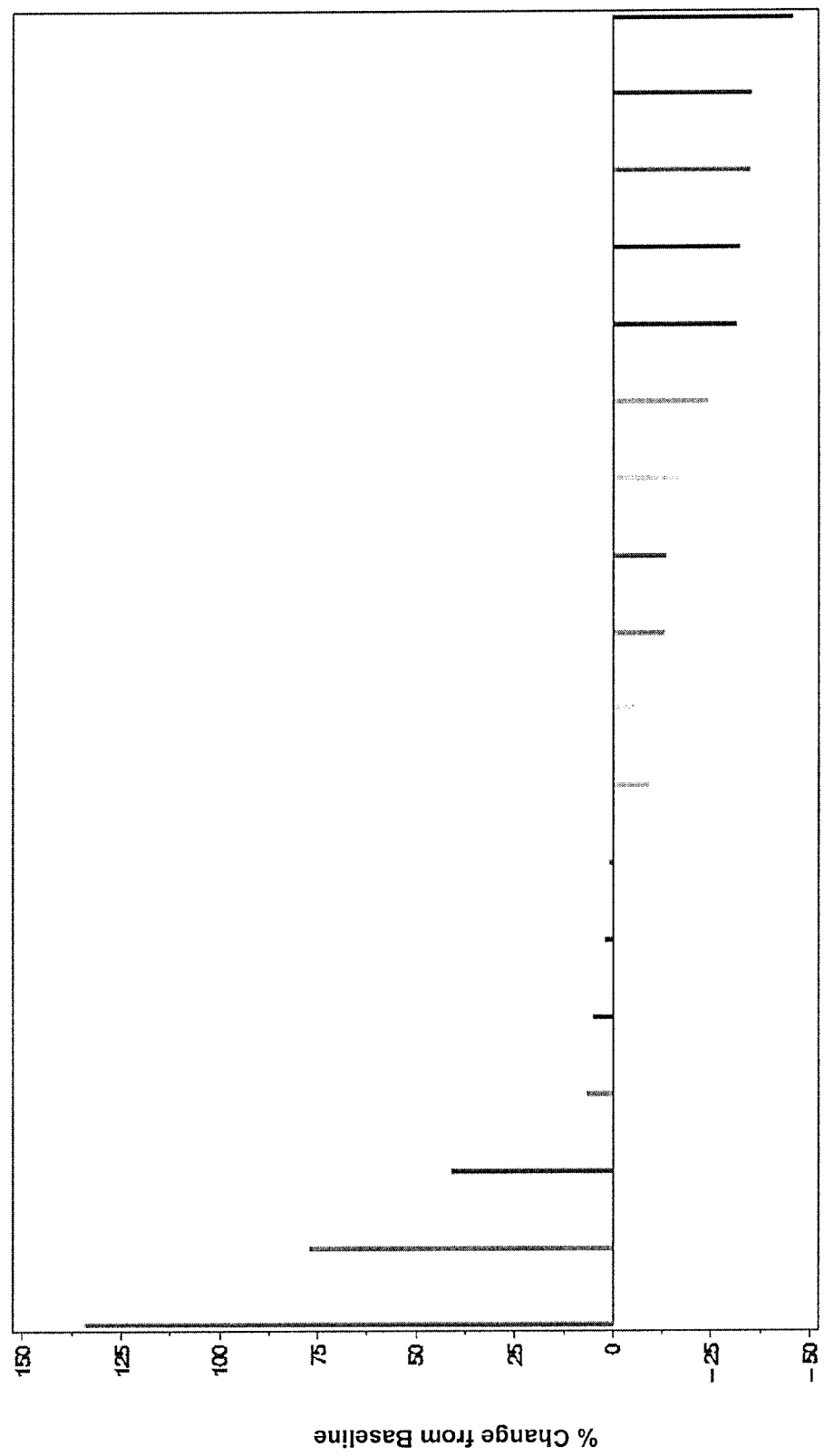

FIGS. 55A and B depict percent (%) changes in bone loss turnover markers collagen C-telopeptides (FIG. 55A) and bone specific alkaline phosphatase (FIG. 55B). (Study 6)

Figure 56:
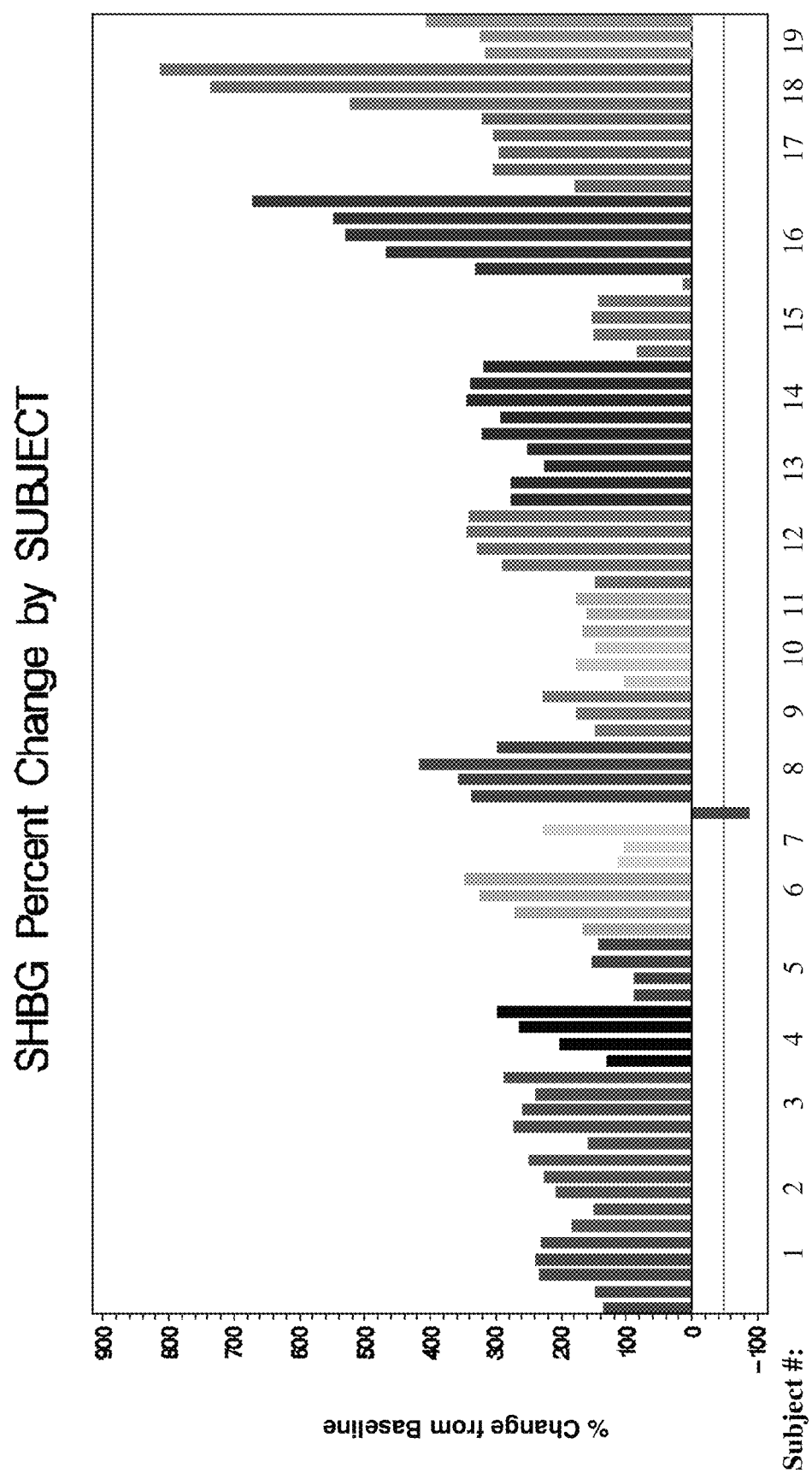

FIG. 56 depicts SHBG percent change by subject (increase in SHBG levels) following 250 mg Compound IV treatment in these patients (19 mCRPC patients and 1 nmCRPC patient) (Study 6; Example 31).

Figure 57:
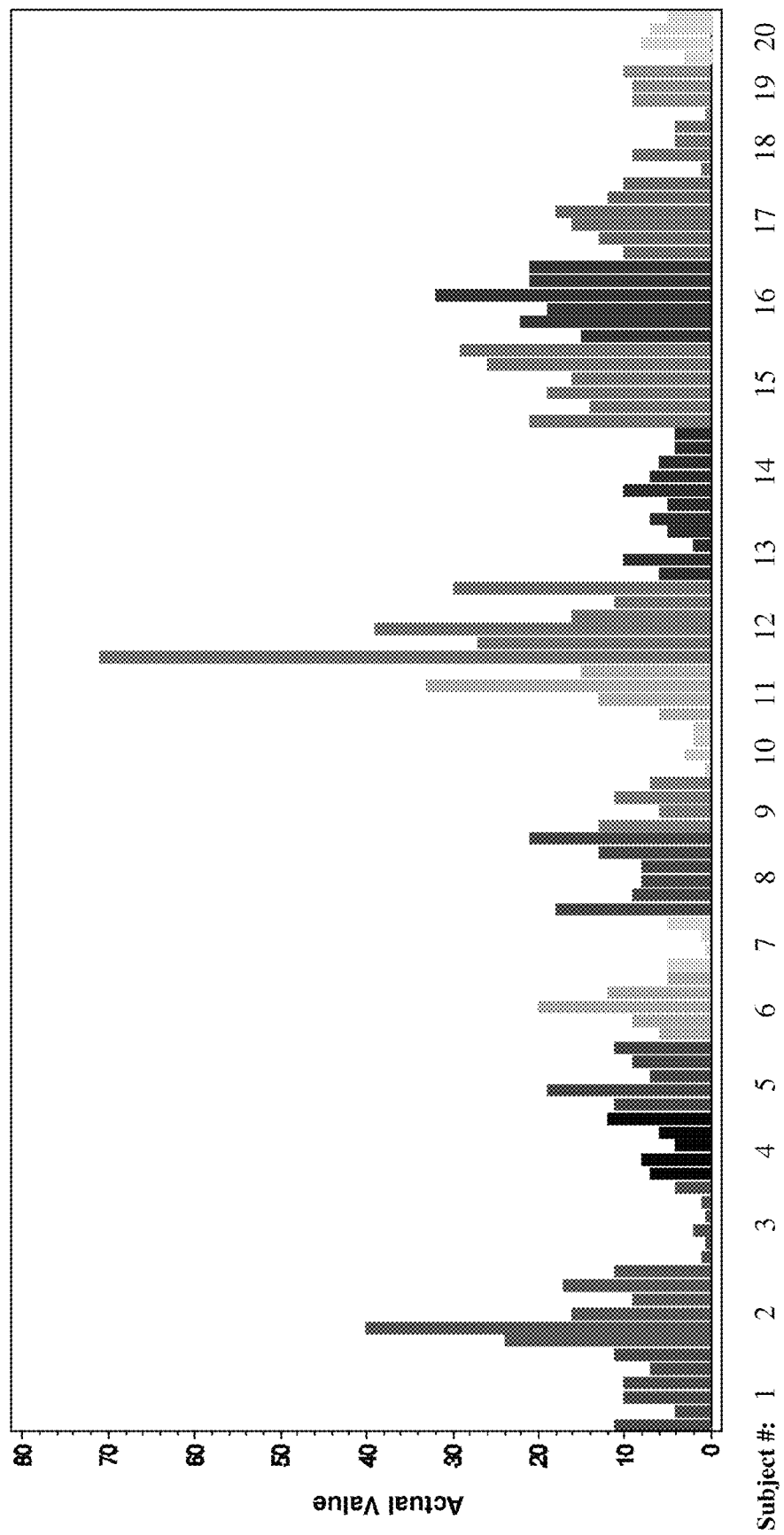

FIG. 57 depicts total testosterone levels by subject (decrease in total testosterone levels) following 250 mg Compound IV treatment in these patients (19 mCRPC patients and 1 nmCRPC patient) (Study 6; Example 31).

Figure 58:
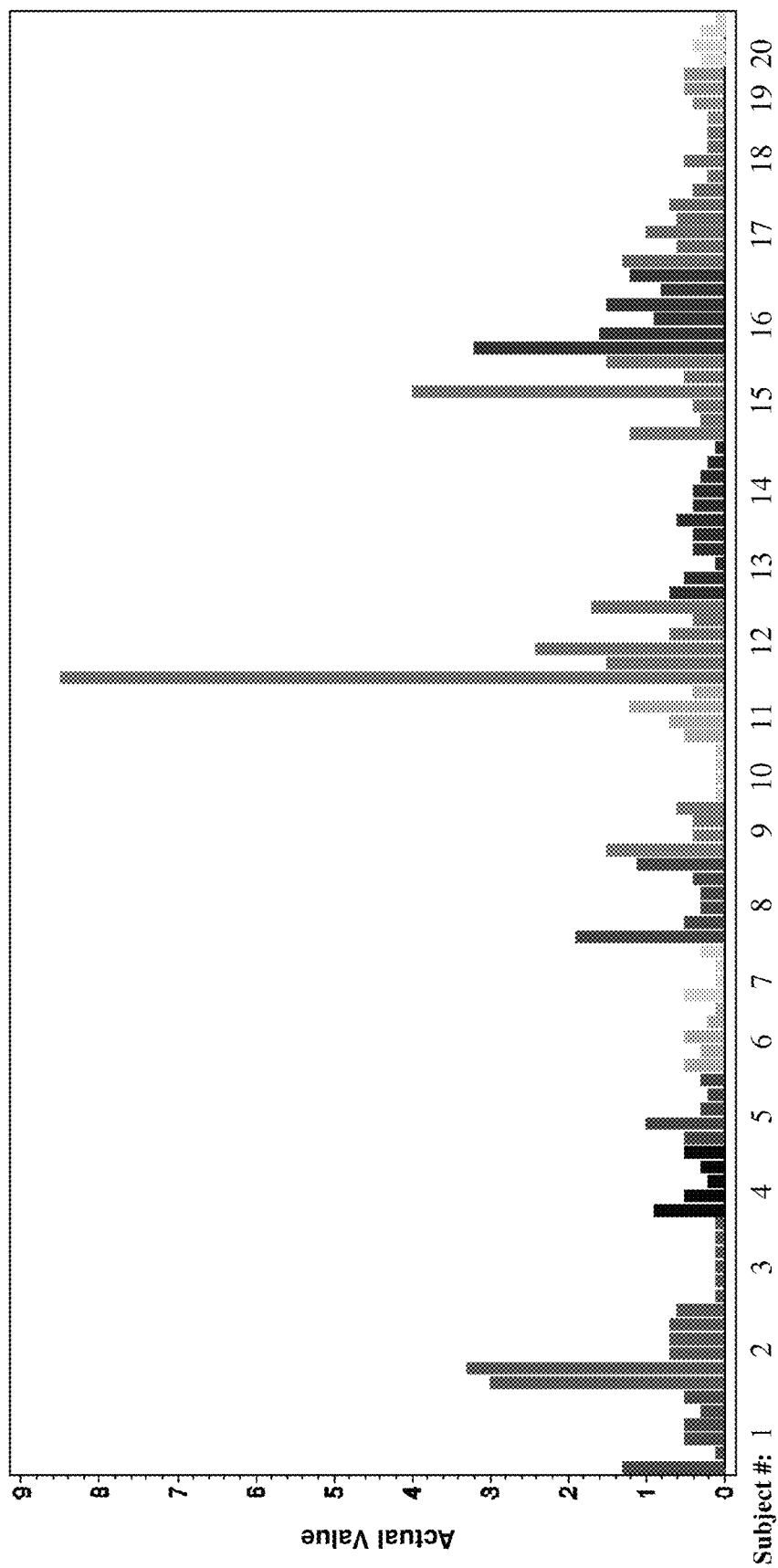

FIG. 58 depicts free testosterone levels by subject (decrease in free testosterone levels) following 250 mg Compound IV treatment in these patients (19 mCRPC patients and 1 nmCRPC patient) (Study 6; Example 31).

Figure 59:
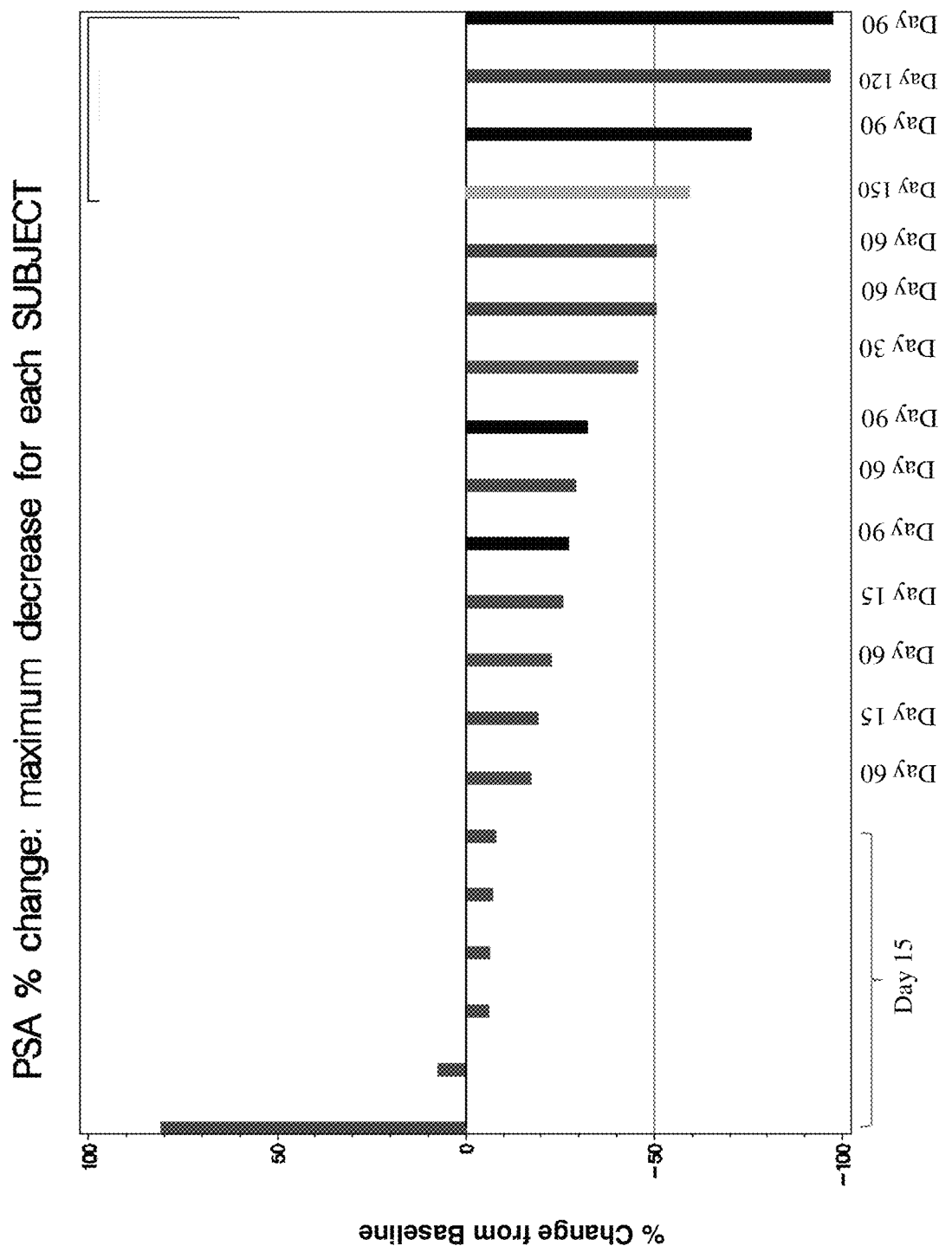

FIG. 59 illustrates that Compound IV treatment (250 mg) lowers PSA levels in these patients (19 mCRPC patients and 1 nmCRPC patient) after 15, 30, 60, 90, 120 and 150 days. (Study 6; Example 31).

Figure 60A:
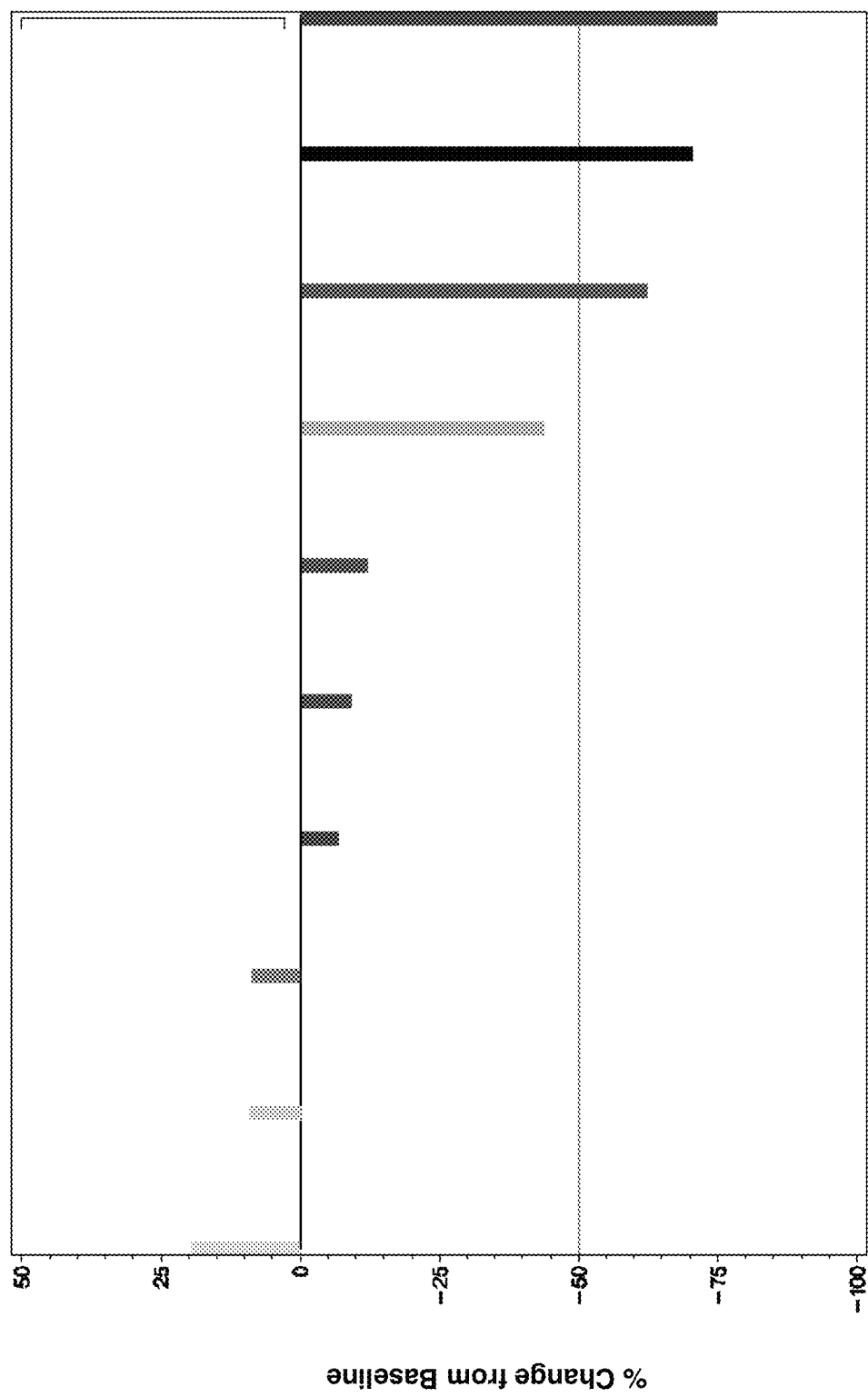
Figure 60B:
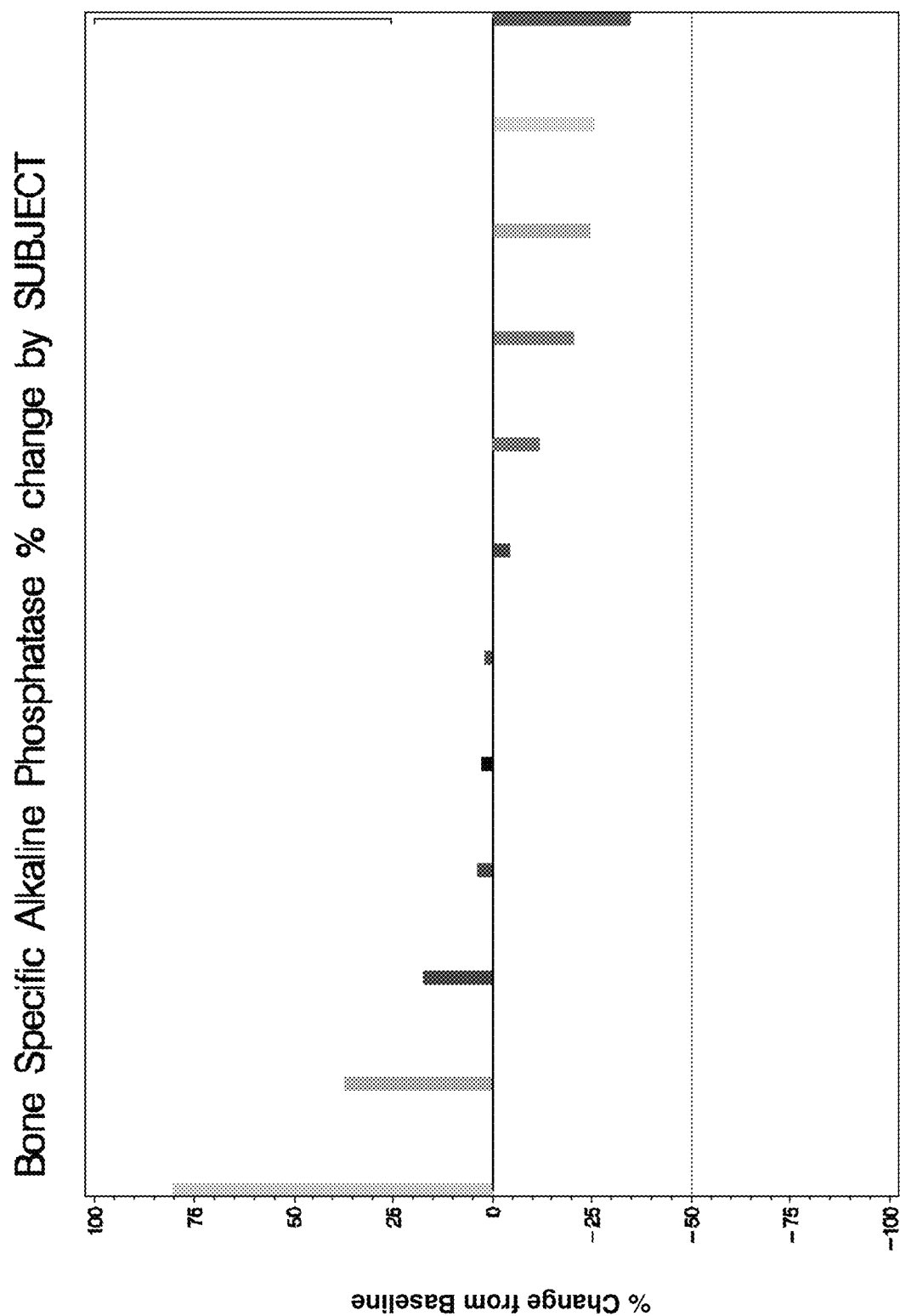

FIGS. 60A and 60B depict percentage change of bone turnover biomarkers using 250 mg Compound IV treatment in these patients (19 mCRPC patients and 1 nmCRPC patient). FIG. 60A depicts change in collagen C-telopeptides (CTX) by subject. FIG. 60B depicts change in bone specific alkaline phosphate by subject.

Figure 61:
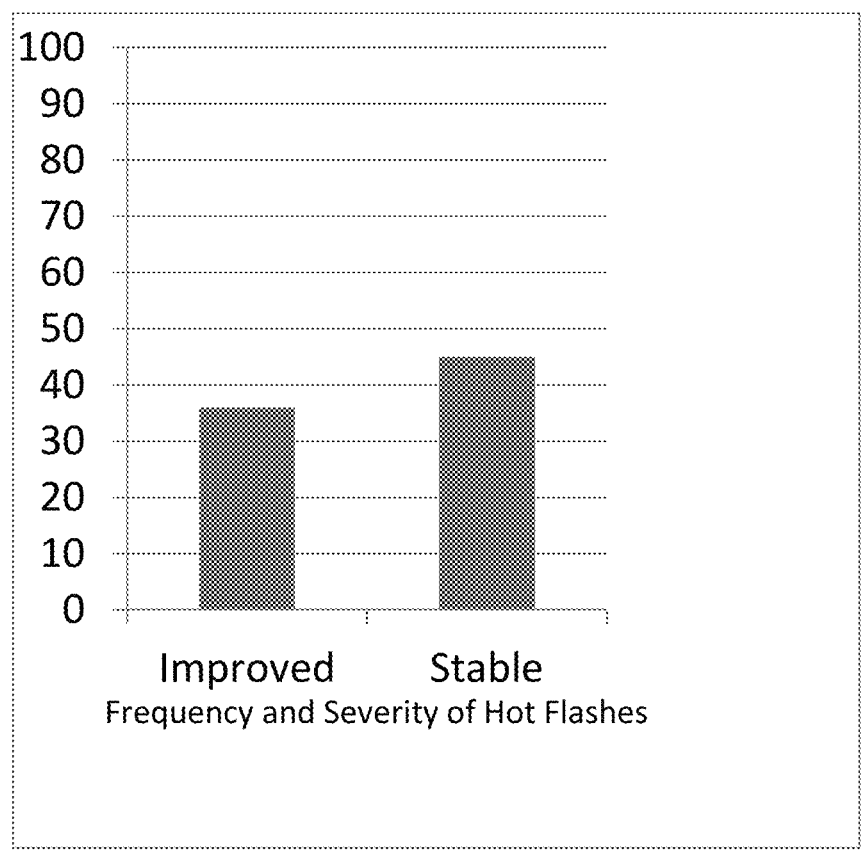

FIG. 61 depicts amelioration of the estrogen deficiency side effect of hot flashes using 250 mg Compound IV in mCRPC patients. Measured using both frequency and severity. There were 11 evaluable patients with hot flashes before starting study. 4/11 (36%) demonstrated improvement in both/either frequency and severity. 5/11 (45%) demonstrated stable in both measurements.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, the compounds as described herein and/or compositions comprising the same may be used for lowering total serum testosterone levels in a male subject.

In one embodiment, the compounds as described herein and/or compositions comprising the same may be used for lowering total serum testosterone levels and lowering prostate specific antigen (PSA) in a male subject. In one embodiment, the lowering of total serum testosterone levels is to below castrate levels. In one embodiment, the lowering of total serum testosterone levels is to castrate levels. In one embodiment, the lowering of total serum testosterone levels does not reach castrate levels. In one embodiment, the lowering of total serum testosterone levels is to below levels attainable with ADT alone.

In one embodiment, the compounds as described herein and/or composition comprising the same may be used for lowering prostate specific antigen, independent of reduction or lack thereof on testosterone levels.

In one embodiment, the compounds as described herein and/or compositions comprising the same may be used for lowering total serum testosterone levels in a male subject wherein the lowering of total serum testosterone occurs by a reduction of serum luteinizing hormone (LH) levels.

In one embodiment, the compounds as described herein and/or compositions comprising the same may be used for lowering total serum testosterone levels in a male subject wherein the lowering of total serum testosterone is independent of a reduction of serum luteinizing hormone levels.

In one embodiment, the compounds as described herein and/or compositions comprising the same may be used for lowering serum free testosterone percent (% FreeT) in a male subject.

In one embodiment, the compounds as described herein and/or compositions comprising the same may be used for treating, suppressing, reducing the incidence, reducing the severity, or inhibiting the progression of castration resistant prostate cancer (CRPC) and its symptoms, or increasing the survival of men with castration resistant prostate cancer. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject further receives Androgen Deprivation Therapy.

In one embodiment, the compounds as described herein and/or compositions comprising the same may be used for increasing radiographic progression free survival (rPFS) in a subject suffering from metastatic prostate cancer. In one embodiment, the metastatic prostate cancer is advanced metastatic prostate cancer. In another embodiment, the metastatic prostate cancer is metastatic CRPC.

As used herein, the terms "increase" and "prolong" may be used interchangeably having all the same meanings and qualities, wherein these terms may in one embodiment refer to a lengthening of time. In another embodiment, as used herein, the terms "increase", increasing" "increased" may be used interchangeably and refer to an entity becoming progressively greater (as in size, amount, number, or intensity), wherein for example the entity is sex hormone-binding globulin (SHBG) or prostate-specific antigen (PSA).

In one embodiment, the compounds as described herein and/or compositions comprising the same may be used for increasing metastasis-free survival (MFS) in a subject suffering from non-metastatic prostate cancer. In one embodiment, the non-metastatic prostate cancer is non-metastatic advanced prostate cancer. In another embodiment, the non-metastatic prostate cancer is non-metastatic CRPC (nmCRPC). In one embodiment, the nmCRPC is high-risk nmCRPC.

In one embodiment, the compounds as described herein and/or compositions comprising the same may be used for providing a secondary hormone therapy. Use of a compound for secondary hormone therapy may be indicated, in one embodiment, in a subject suffering from castration resistant prostate cancers (CRPC) including non-metastatic CRPC (nmCRPC) and high-risk nmCRPC. Use of a compound for secondary hormone therapy may be indicated, in one embodiment, in a subject previously treated with ADT or currently being treated with ADT, wherein serum PSA levels are rising, total serum testosterone levels are greater than 20 ng/dL, or wherein serum free testosterone levels are greater than 0.9 ng/dL, or any combination thereof. Use of a compound for secondary hormone therapy may be indicated, in one embodiment, in a subject previously treated with ADT or currently being treated with ADT, wherein serum free testosterone levels are greater than 0.9 ng/dL, such that chemical castration is suboptimal. Use of a compound as described herein and/or compositions comprising the same in a method of secondary hormonal therapy, may in one embodiment, result in increased metastasis-free survival (MFS). Use of a compound as described herein and/or compositions comprising the same in a method of secondary hormonal therapy, may in one embodiment, result in serum free testosterone reduction to castrate levels observed with orchiectomy. Use of a compound as described herein and/or compositions comprising the same in a method of secondary hormonal therapy, may in one embodiment, result in pro-estrogenic beneficial effects.

In one embodiment, the compounds as described herein and/or compositions comprising the same may be used for decreasing symptomatic bone fractures in a subject suffering from prostate cancer. In one embodiment, the prostate cancer is metastatic prostate cancer. In another embodiment, the prostate cancer is advanced metastatic prostate cancer. In another embodiment, the metastatic prostate cancer is metastatic CRPC. In another embodiment, the prostate cancer is non-metastatic prostate cancer. In another embodiment, the prostate cancer is non-metastatic advanced prostate cancer. In another embodiment, the prostate cancer is non-metastatic CRPC (nmCRPC). In one embodiment, the nmCRPC is high-risk nmCRPC.

In one embodiment, the compounds as described herein and/or compositions comprising the same may be used for providing pro-estrogenic effects. In one embodiment, pro-estrogenic effects include prevention of symptomatic bone fractures, prevention of bone loss, promotion of bone formation, a decrease in bone turnover markers, or resistance to bone metastasis, or any combination thereof.

In one embodiment, the compounds as described herein and/or compositions comprising the same may be used to provide a dual action, for example treating prostate cancer and preventing metastases. In one embodiment, the prostate cancer being treated is advanced prostate cancer. In one embodiment, the prostate cancer being treated is castration resistant prostate cancer (CRPC). In one embodiment, the prostate cancer being treated is metastatic CRPC (mCRPC). In one embodiment, the prostate cancer being treated is non-metastatic CRPC (nmCRPC). In one embodiment, the nmCRPC is high-risk nmCRPC.

Men with advanced prostate cancer who are at high risk for progression to castration resistant prostate cancer (CRPC) may, in one embodiment, be selected from the group comprising men on ADT with serum total testosterone concentrations greater than 20 ng/dL or men with advanced prostate cancer who at the time of starting ADT had either (1) confirmed Gleason pattern 4 or 5 prostate cancer, (2) metastatic prostate cancer, (3) a PSA doubling time <3 months, (4) a PSA ≥20 ng/mL, or (5) a PSA relapse in <3 years after definitive local therapy (radical prostatectomy or radiation therapy).

Men with high risk non-metastatic castration resistant prostate cancer (high-risk nmCRPC) may include those with rapid PSA doubling times, having an expected progression-free survival of approximately 18 months or less (Miller K, Moul J W, Gleave M, et al. 2013. Phase III, randomized, placebo-controlled study of once-daily oral zibotentan (ZD4054) in patients with non-metastatic castration-resistant prostate cancer. *Prostate Canc Prost Dis.* February; 16:187-192). This relatively rapid progression of their disease underscores the importance of novel therapies for these individuals. In one embodiment, the PSA levels are greater than 8 ng/mL in a subject suffering from high-risk nmCRPC. In one embodiment, the PSA doubling time is less than 8 months in a subject suffering from high-risk nmCRPC. In another embodiment, the PSA doubling time is less than 10 months in a subject suffering from high-risk nmCRPC. In one embodiment, the total serum testosterone levels are greater than 20 ng/mL in a subject suffering from high-risk nmCRPC. In one embodiment, the serum free testosterone levels are greater than those observed in an orchiechtomized male in a subject suffering from high-risk nmCRPC.

In one embodiment, the compounds as described herein and/or compositions comprising the same may be used in combination with LHRH agonist or antagonist for increasing the progression free survival or overall survival of a subject suffering from prostate cancer. In another embodiment the prostate cancer is advanced prostate cancer. In another embodiment, the prostate cancer is castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject is surgically castrated. In another embodiment, the subject is chemically castrated.

In certain embodiments treatment of prostate cancer, advanced prostate cancer, CRPC, mCRPC and/or nmCRPC may result in clinically meaningful improvement in prostate cancer related symptoms, function and/or survival. Clinically meaningful improvements include but are not limited to increasing radiographic progression free survival (rPFS) if cancer is metastatic, increasing metastasis-free survival (MFS) if cancer is non-metastatic, and reducing symptomatic bone fractures.

In one embodiment, the compounds as described herein and/or compositions comprising the same may be used for increasing the survival of men with castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject further receives Androgen Deprivation Therapy.

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by the structure of formula I:

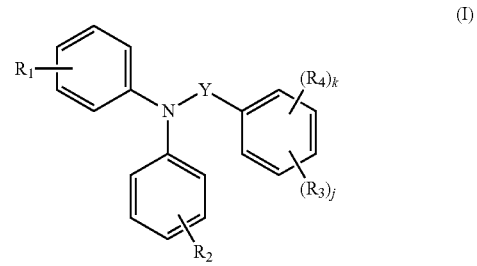

(I)

wherein
Y is C(O) or $CH_2$;
$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;
$R_3$, $R_4$ are independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;
R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;
$R_5$ and $R_6$ are independently hydrogen, phenyl, an alkyl group of 1 to 6 carbon atoms, a 3 to 7 membered cycloalkyl, a 3 to 7 membered heterocycle, a 5 to 7 membered aryl; or $R_5$ and $R_6$ form a 3 to 7 membered ring with the nitrogen atom;
j and k are independently 1-4; and
Alk is linear alkyl of 1-7 carbons, branched alkyl of 1-7 carbons, or cyclic alkyl of 3-8 carbons.

In additional embodiments of the methods described herein, the compound of Formula I is represented by formula IA:

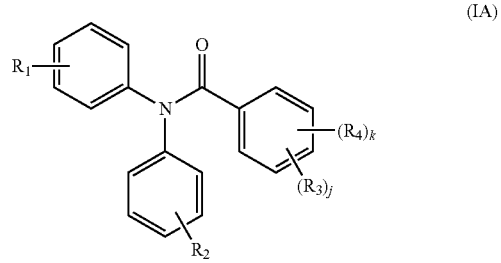

(IA)

wherein $R_1$, $R_2$, $R_3$, $R_4$, j and k are as defined for Formula I.

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula II:

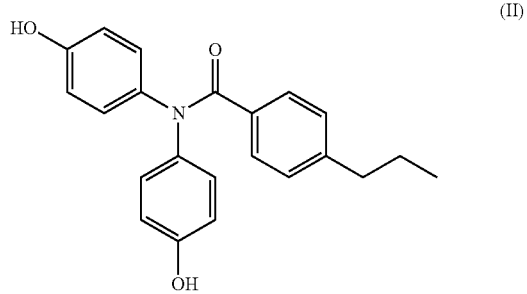 [SMILES: CCCc1ccc(C(=O)N(c2ccc(O)cc2)c2ccc(O)cc2)cc1]

(II)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula III:

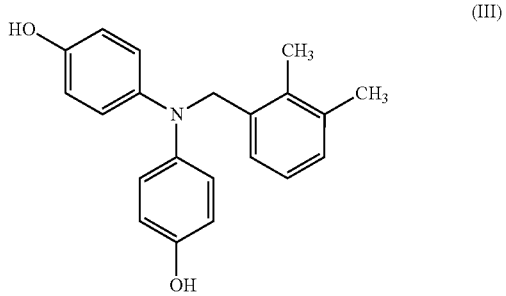 [SMILES: Cc1cccc(CN(c2ccc(O)cc2)c2ccc(O)cc2)c1C]

(III)

In one embodiment, this invention provides a method of lowering total serum testosterone levels in a male subject comprising administering a therapeutically effective amount of a compound or its isomer, pharmaceutical product, pharmaceutical acceptable salt, polymorph, hydrate or any combination thereof, represented by a compound of formula IV:

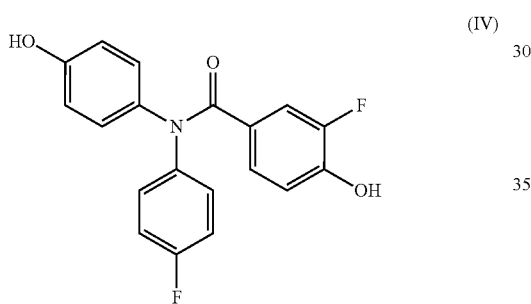

(IV)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula V:

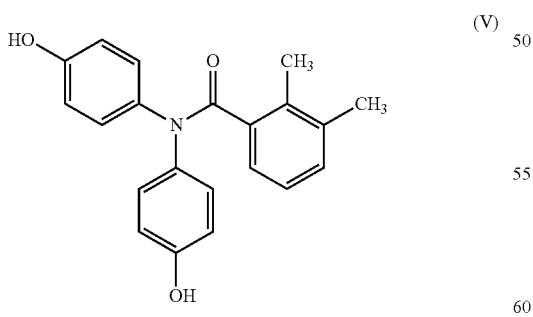

(V)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula VI:

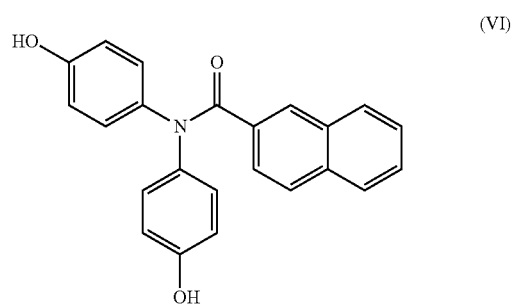 [SMILES: O=C(c1ccc2ccccc2c1)N(c1ccc(O)cc1)c1ccc(O)cc1]

(VI)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula VII:

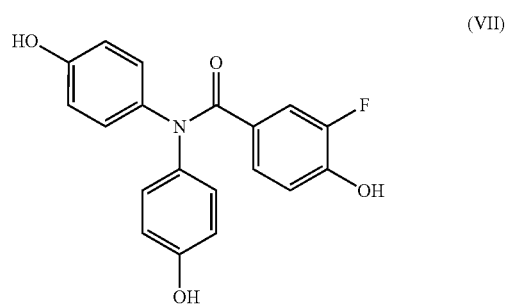 [SMILES: O=C(c1ccc(O)c(F)c1)N(c1ccc(O)cc1)c1ccc(O)cc1]

(VII)

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula VIII:

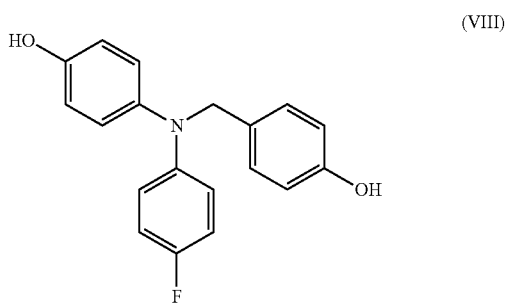 [SMILES: Oc1ccc(CN(c2ccc(O)cc2)c2ccc(F)cc2)cc1]

(VIII)

In one embodiment, this invention provides a method of lowering total serum testosterone levels by reduction of luteinizing hormone (LH) levels in a male subject having prostate cancer, comprising administering a therapeutically effective amount of a compound or its isomer, pharmaceutical acceptable salt, pharmaceutical product, polymorph, hydrate or any combination thereof represented by a compound of formula IX:

(IX)

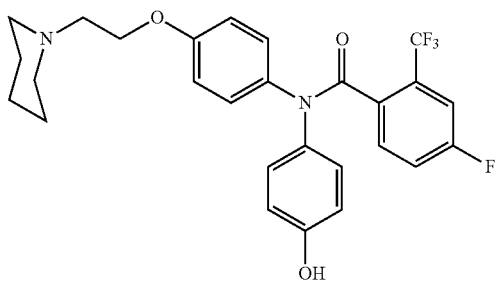

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula X:

(X)

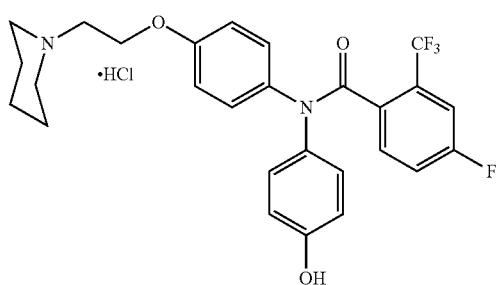

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula XI:

(XI)

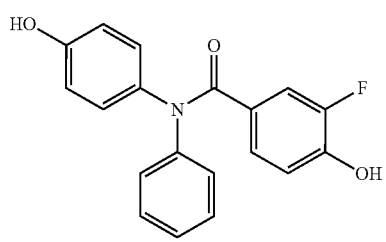

In one embodiment, this invention provides a method of lowering total serum testosterone levels in a male subject comprising administering a therapeutically effective amount of a compound or its isomer, pharmaceutical acceptable salt, pharmaceutical product, polymorph, hydrate or any combination thereof, represented by a compound of formula XII:

(XII)

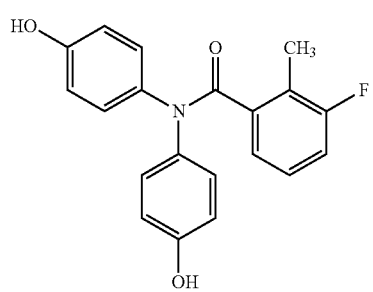

In one embodiment, this invention provides a method of lowering free serum testosterone levels in a male subject comprising administering a therapeutically effective amount of a compound or its isomer, pharmaceutical acceptable salt, pharmaceutical product, polymorph, hydrate or any combination thereof, represented by the structure of formula I:

(I)

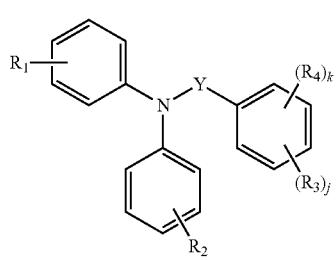

wherein

Y is C(O) or $CH_2$;

$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;

$R_3$, $R_4$ are independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_5$ and $R_6$ are independently hydrogen, phenyl, an alkyl group of 1 to 6 carbon atoms, a 3 to 7 membered cycloalkyl, a 3 to 7 membered heterocycle, a 5 to 7 membered aryl; or $R_5$ and $R_6$ form a 3 to 7 membered ring with the nitrogen atom;

j and k are independently 1-4; and

Alk is linear alkyl of 1-7 carbons, branched alkyl of 1-7 carbons, or cyclic alkyl of 3-8 carbons.

In additional embodiments of the methods described herein, the compound of Formula I is represented by formula IA:

(IA)

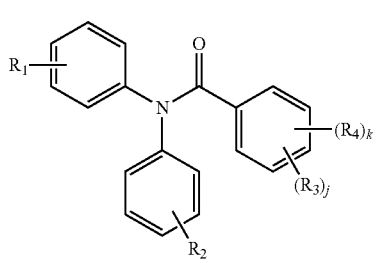

wherein $R_1$, $R_2$, $R_3$, $R_4$, j and k are as defined for Formula I.

In one embodiment, this invention provides a method of lowering free serum testosterone levels in a male subject comprising administering a therapeutically effective amount of a compound or its isomer, pharmaceutical acceptable salt, pharmaceutical product, polymorph, hydrate or any combination thereof, represented by a compound of formula II:

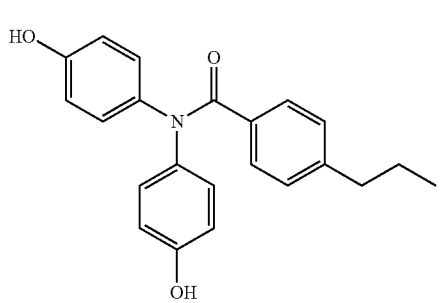
(II)

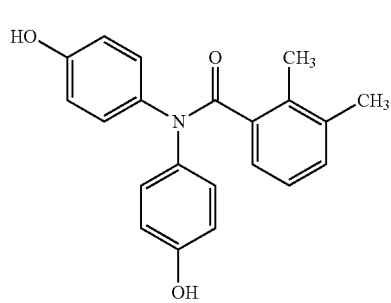
(V)

In one embodiment, this invention provides a method of lowering free serum testosterone levels in a male subject comprising administering a therapeutically effective amount of a compound or its isomer, pharmaceutical acceptable salt, pharmaceutical product, polymorph, hydrate or any combination thereof, represented by a compound of formula III:

In one embodiment, this invention provides a method of lowering free serum testosterone levels in a male subject comprising administering a therapeutically effective amount of a compound or its isomer, pharmaceutical acceptable salt, pharmaceutical product, polymorph, hydrate or any combination thereof, represented by a compound of formula VI:

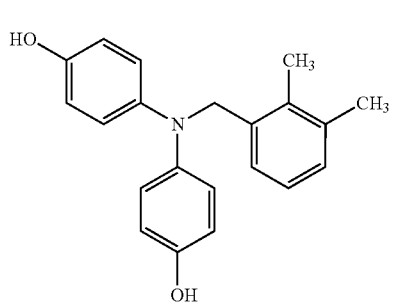
(III)

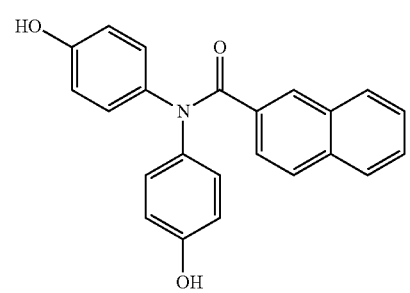
(VI)

In one embodiment, this invention provides a method of lowering free serum testosterone levels in a male subject comprising administering a therapeutically effective amount of a compound or its isomer, pharmaceutical product, pharmaceutical acceptable salt, polymorph, hydrate or any combination thereof, represented by a compound of formula IV:

In one embodiment, this invention provides a method of lowering free serum testosterone levels in a male subject comprising administering a therapeutically effective amount of a compound or its isomer, pharmaceutical acceptable salt, pharmaceutical product, polymorph, hydrate or any combination thereof, represented by a compound of formula VII:

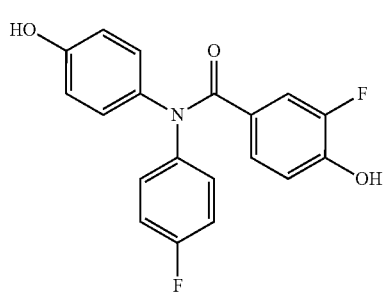
(IV)

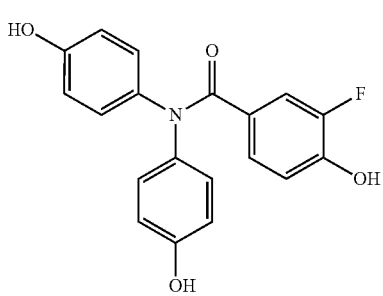
(VII)

In one embodiment, this invention provides a method of lowering free serum testosterone levels in a male subject comprising administering a therapeutically effective amount of a compound or its isomer, pharmaceutical acceptable salt, pharmaceutical product, polymorph, hydrate or any combination thereof, represented by a compound of formula V:

In one embodiment, this invention provides a method of lowering free serum testosterone levels in a male subject comprising administering a therapeutically effective amount of a compound or its isomer, pharmaceutical acceptable salt, pharmaceutical product, polymorph, hydrate or any combination thereof, represented by a compound of formula VIII:

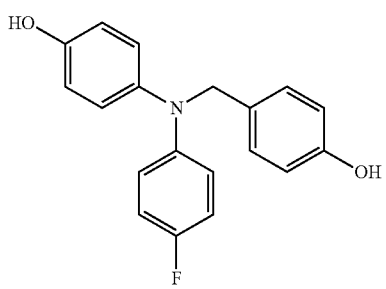

(VIII)

In one embodiment, this invention provides a method of lowering free serum testosterone levels by reduction of luteinizing hormone (LH) levels in a male subject having prostate cancer, comprising administering a therapeutically effective amount of a compound or its isomer, pharmaceutical acceptable salt, pharmaceutical product, polymorph, hydrate or any combination thereof represented by a compound of formula IX:

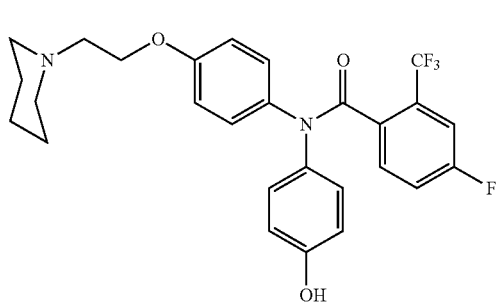

(IX)

In one embodiment, this invention provides a method of lowering free serum testosterone levels in a male subject comprising administering a therapeutically effective amount of a compound or its isomer, pharmaceutical acceptable salt, pharmaceutical product, polymorph, hydrate or any combination thereof, represented by a compound of formula X:

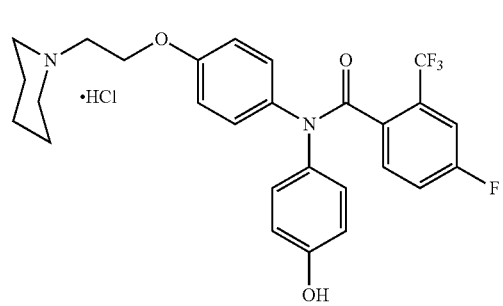

(X)

In one embodiment, this invention provides a method of lowering free serum testosterone levels in a male subject comprising administering a therapeutically effective amount of a compound or its isomer, pharmaceutical acceptable salt, pharmaceutical product, polymorph, hydrate or any combination thereof, represented by a compound of formula XI:

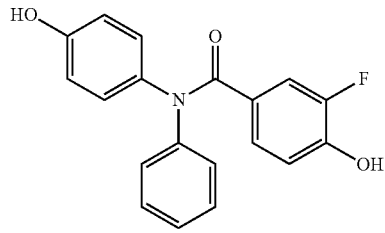

(XI)

In one embodiment, this invention provides a method of lowering free serum testosterone levels in a male subject comprising administering a therapeutically effective amount of a compound or its isomer, pharmaceutical acceptable salt, pharmaceutical product, polymorph, hydrate or any combination thereof, represented by a compound of formula XII:

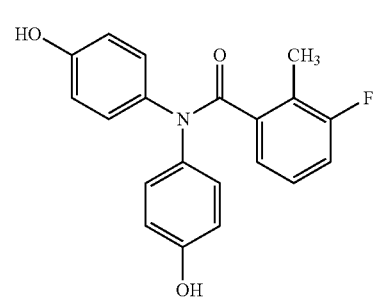

(XII)

In one embodiment, this invention provides a method of lowering free serum testosterone percentage (% FreeT) in a male subject comprising administering a therapeutically effective amount of a compound or its isomer, pharmaceutical acceptable salt, pharmaceutical product, polymorph, hydrate or any combination thereof, represented by the structure of formula I:

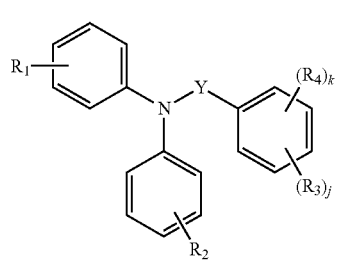

(I)

wherein
Y is C(O) or $CH_2$;
$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;
$R_3$, $R_4$ are independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;
R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_5$ and $R_6$ are independently hydrogen, phenyl, an alkyl group of 1 to 6 carbon atoms, a 3 to 7 membered cycloalkyl, a 3 to 7 membered heterocycle, a 5 to 7 membered aryl; or $R_5$ and $R_6$ form a 3 to 7 membered ring with the nitrogen atom;

j and k are independently 1-4; and

Alk is linear alkyl of 1-7 carbons, branched alkyl of 1-7 carbons, or cyclic alkyl of 3-8 carbons.

In additional embodiments of the methods described herein, the compound of Formula I is represented by formula IA:

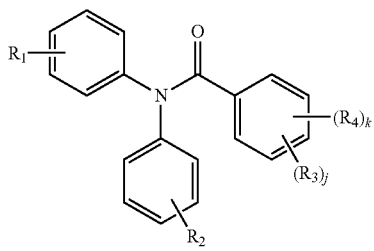

(IA)

wherein $R_1$, $R_2$, $R_3$, $R_4$, j and k are as defined for Formula I.

In one embodiment, this invention provides a method of lowering free serum testosterone percentage (% FreeT) in a male subject comprising administering a therapeutically effective amount of a compound or its isomer, pharmaceutical acceptable salt, pharmaceutical product, polymorph, hydrate or any combination thereof, represented by a compound of formula II:

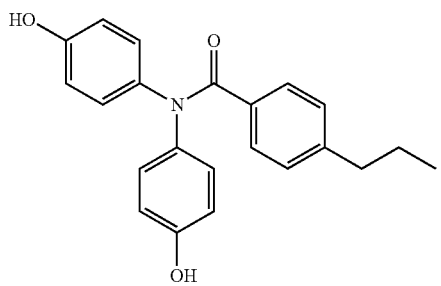

(II)

In one embodiment, this invention provides a method of lowering free serum testosterone percentage (% FreeT) in a male subject comprising administering a therapeutically effective amount of a compound or its isomer, pharmaceutical acceptable salt, pharmaceutical product, polymorph, hydrate or any combination thereof, represented by a compound of formula III:

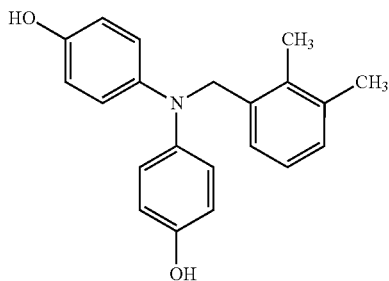

(III)

In one embodiment, this invention provides a method of lowering free serum testosterone percentage (% FreeT) in a male subject comprising administering a therapeutically effective amount of a compound or its isomer, pharmaceutical product, pharmaceutical acceptable salt, polymorph, hydrate or any combination thereof, represented by a compound of formula IV:

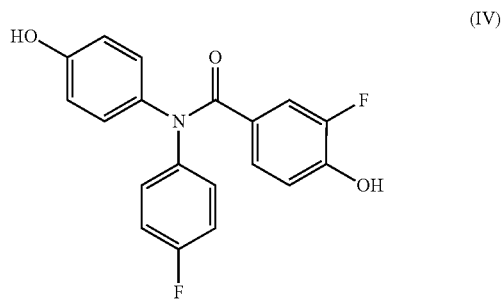 [SMILES: O=C(c1ccc(O)c(F)c1)N(c1ccc(O)cc1)c1ccc(F)cc1]

(IV)

In one embodiment, this invention provides a method of lowering free serum testosterone percentage (% FreeT) in a male subject comprising administering a therapeutically effective amount of a compound or its isomer, pharmaceutical acceptable salt, pharmaceutical product, polymorph, hydrate or any combination thereof, represented by a compound of formula V:

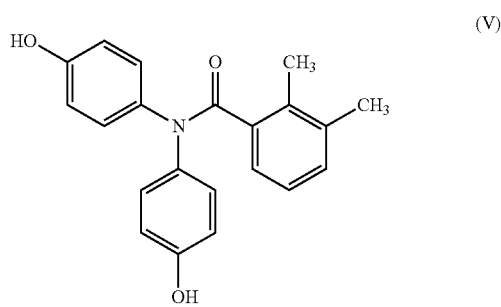 [SMILES: Cc1cccc(C(=O)N(c2ccc(O)cc2)c2ccc(O)cc2)c1C]

(V)

In one embodiment, this invention provides a method of lowering free serum testosterone percentage (% FreeT) in a male subject comprising administering a therapeutically effective amount of a compound or its isomer, pharmaceutical acceptable salt, pharmaceutical product, polymorph, hydrate or any combination thereof, represented by a compound of formula VI:

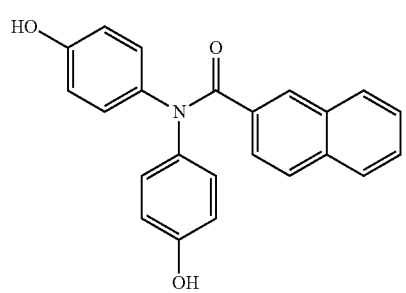

(VI)

In one embodiment, this invention provides a method of lowering free serum testosterone percentage (% FreeT) in a male subject comprising administering a therapeutically effective amount of a compound or its isomer, pharmaceutical acceptable salt, pharmaceutical product, polymorph, hydrate or any combination thereof, represented by a compound of formula VII:

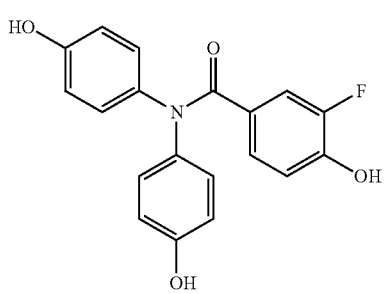

(VII)

In one embodiment, this invention provides a method of lowering free serum testosterone percentage (% FreeT) in a male subject comprising administering a therapeutically effective amount of a compound or its isomer, pharmaceutical acceptable salt, pharmaceutical product, polymorph, hydrate or any combination thereof, represented by a compound of formula VIII:

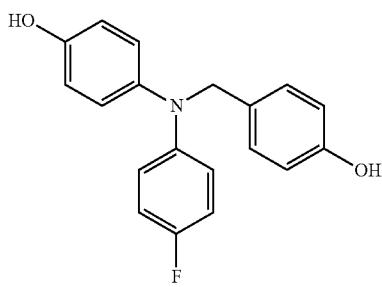

(VIII)

In one embodiment, this invention provides a method of lowering free serum testosterone percentage (% FreeT) by reduction of luteinizing hormone (LH) levels in a male subject having prostate cancer, comprising administering a therapeutically effective amount of a compound or its isomer, pharmaceutical acceptable salt, pharmaceutical product, polymorph, hydrate or any combination thereof represented by a compound of formula IX:

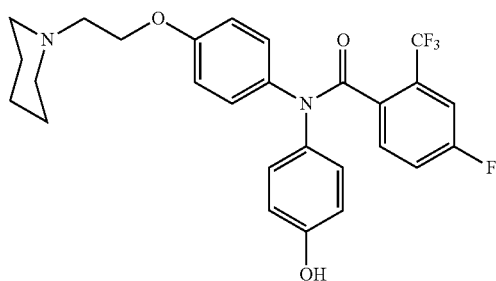

(IX)

In one embodiment, this invention provides a method of lowering free serum testosterone percentage (% FreeT) in a male subject comprising administering a therapeutically effective amount of a compound or its isomer, pharmaceutical acceptable salt, pharmaceutical product, polymorph, hydrate or any combination thereof, represented by a compound of formula X:

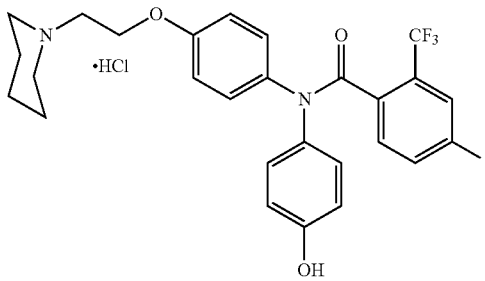

(X)

In one embodiment, this invention provides a method of lowering free serum testosterone percentage (% FreeT) in a male subject comprising administering a therapeutically effective amount of a compound or its isomer, pharmaceutical acceptable salt, pharmaceutical product, polymorph, hydrate or any combination thereof, represented by a compound of formula XI:

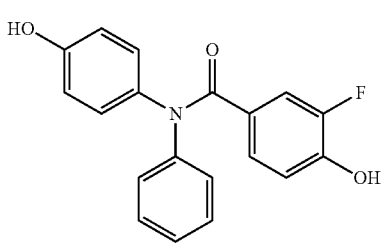

(XI)

In one embodiment, this invention provides a method of lowering free serum testosterone percentage (% FreeT) in a male subject comprising administering a therapeutically effective amount of a compound or its isomer, pharmaceutical acceptable salt, pharmaceutical product, polymorph, hydrate or any combination thereof, represented by a compound of formula XII:

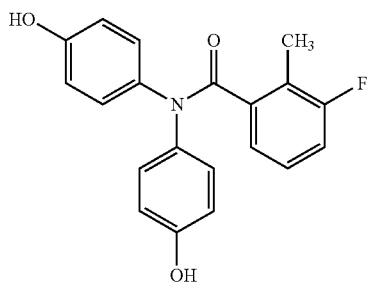

(XII)

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical acceptable salt, pharmaceutical product, polymorph, hydrate or any combination thereof, represented by the structure of formula I:

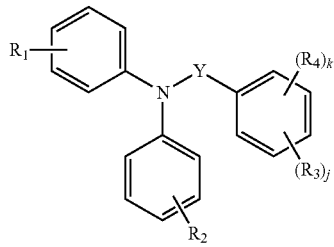

wherein

Y is C(O) or CH$_2$;

R$_1$, R$_2$ are independently hydrogen, halogen, hydroxyl, alkoxy, cyano, nitro, CF$_3$, N(R)$_2$, sulfonamide, SO$_2$R, alkyl, haloalkyl, aryl, O-Alk-NR$_5$R$_6$ or O-Alk-heterocycle in which the heterocycle is a 3-7 membered substituted or unsubstituted heterocyclic ring, optionally aromatic;

R$_3$, R$_4$ are independently hydrogen, halogen, hydroxyalkyl, hydroxyl, alkoxy, cyano, nitro, CF$_3$, NHCOR, N(R)$_2$, sulfonamide, SO$_2$R, alkyl, haloalkyl, aryl or protected hydroxyl;

R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$, or OH;

R$_5$ and R$_6$ are independently hydrogen, phenyl, an alkyl group of 1 to 6 carbon atoms, a 3 to 7 membered cycloalkyl, a 3 to 7 membered heterocycle, a 5 to 7 membered aryl; or R$_5$ and R$_6$ form a 3 to 7 membered ring with the nitrogen atom;

j and k are independently 1-4; and

Alk is linear alkyl of 1-7 carbons, branched alkyl of 1-7 carbons, or cyclic alkyl of 3-8 carbons.

In another embodiment, the CRPC is metastatic CRPC (mCRPC). In another embodiment, the CRPC is non-metastatic CRPC (nmCRPC). In one embodiment, the nmCRPC is high-risk nmCRPC.

In additional embodiments of the methods described herein, the compound of Formula I is represented by formula IA:

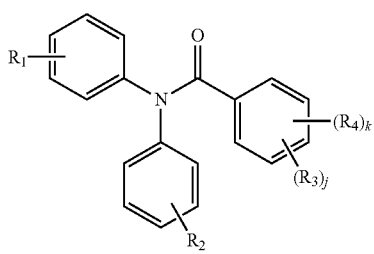

wherein R$_1$, R$_2$, R$_3$, R$_4$, j and k are as defined for Formula I.

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical acceptable salt, pharmaceutical product, polymorph, hydrate or any combination thereof, represented by a compound of formula II:

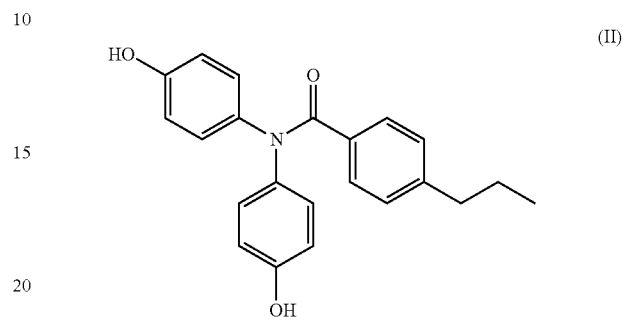

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical acceptable salt, pharmaceutical product, polymorph, hydrate or any combination thereof, represented by a compound of formula III:

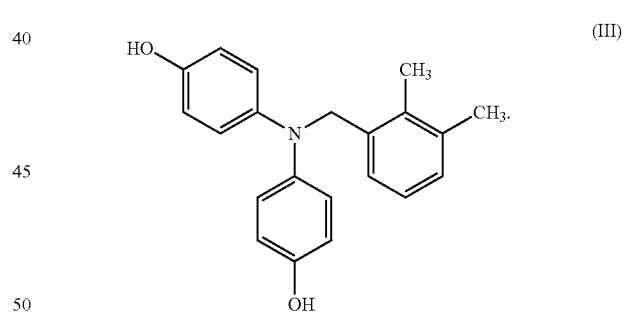

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical product, pharmaceutical acceptable salt, polymorph, hydrate or any combination thereof, represented by a compound of formula IV:

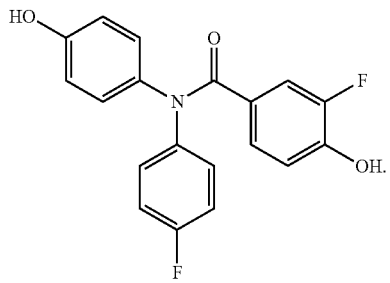

(IV)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical acceptable salt, pharmaceutical product, polymorph, hydrate or any combination thereof, represented by a compound of formula V:

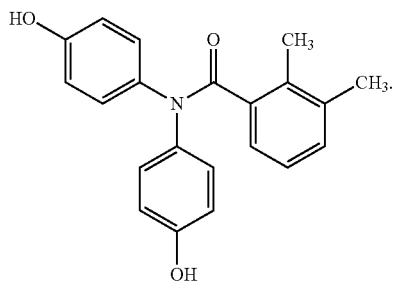

(V)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical acceptable salt, pharmaceutical product, polymorph, hydrate or any combination thereof, represented by a compound of formula VI:

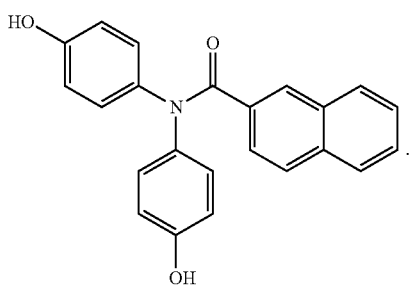

(VI)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical acceptable salt, pharmaceutical product, polymorph, hydrate or any combination thereof, represented by a compound of formula VII:

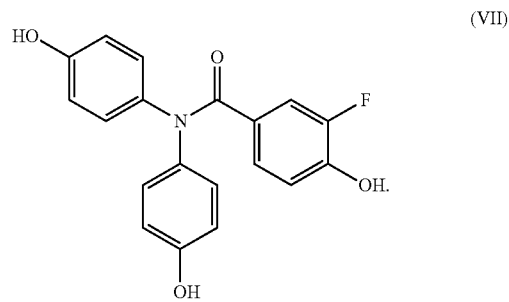 [SMILES: O=C(c1ccc(O)c(F)c1)N(c1ccc(O)cc1)c1ccc(O)cc1]

(VII)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical acceptable salt, pharmaceutical product, polymorph, hydrate or any combination thereof, represented by a compound of formula VIII:

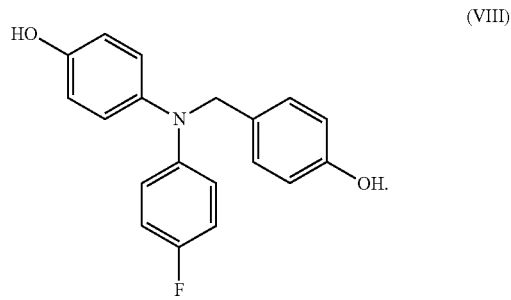 [SMILES: Oc1ccc(CN(c2ccc(O)cc2)c2ccc(F)cc2)cc1]

(VIII)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical acceptable salt, pharmaceutical product, polymorph, hydrate or any combination thereof represented by a compound of formula IX:

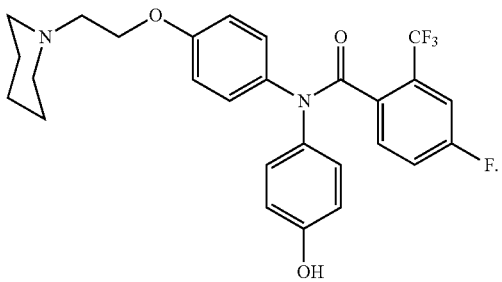

(IX)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical acceptable salt, pharmaceutical product, polymorph, hydrate or any combination thereof, represented by a compound of formula X:

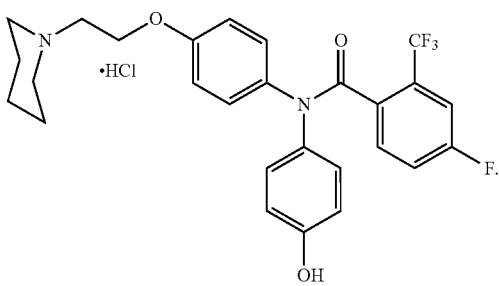

(X)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical acceptable salt, pharmaceutical product, polymorph, hydrate or any combination thereof, represented by a compound of formula XI:

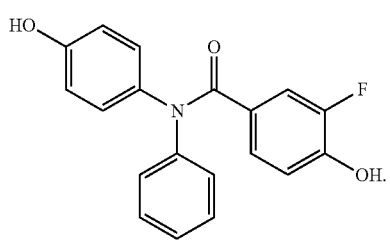

(XI)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound or its isomer, pharmaceutical acceptable salt, pharmaceutical product, polymorph, hydrate or any combination thereof, represented by a compound of formula XII:

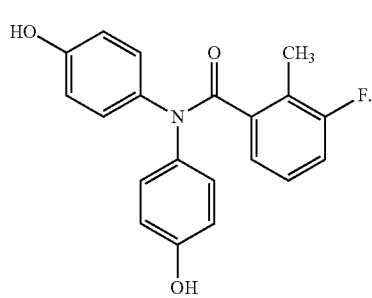

(XII)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of lowering serum prostate specific antigen (PSA) levels in a male subject suffering from castration resistant prostate cancer (CRPC), comprising administering a therapeutically effective amount of a compound or its isomer, pharmaceutical acceptable salt, pharmaceutical product, polymorph, hydrate or any combination thereof, represented by the structure of formula I:

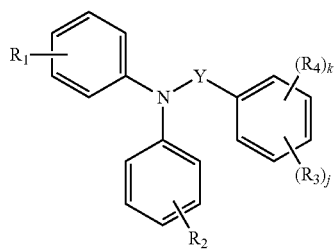

(I)

wherein

Y is C(O) or $CH_2$;

$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;

$R_3$, $R_4$ are independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_5$ and $R_6$ are independently hydrogen, phenyl, an alkyl group of 1 to 6 carbon atoms, a 3 to 7 membered cycloalkyl, a 3 to 7 membered heterocycle, a 5 to 7 membered aryl; or $R_5$ and $R_6$ form a 3 to 7 membered ring with the nitrogen atom;

j and k are independently 1-4; and

Alk is linear alkyl of 1-7 carbons, branched alkyl of 1-7 carbons, or cyclic alkyl of 3-8 carbons.

In another embodiment, the CRPC is metastatic CRPC (mCRPC). In another embodiment, the CRPC is non-metastatic CRPC (nmCRPC). In one embodiment, the nmCRPC is high-risk nmCRPC.

In additional embodiments of the methods described herein, the compound of Formula I is represented by formula IA:

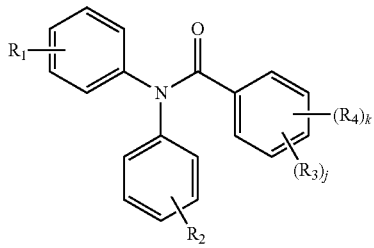

(IA)

wherein $R_1$, $R_2$, $R_3$, $R_4$, j and k are as defined for Formula I.

In one embodiment, this invention provides a method of lowering serum prostate specific antigen (PSA) levels in a male subject suffering from castration resistant prostate cancer (CRPC), comprising administering a therapeutically effective amount of a compound or its isomer, pharmaceutical acceptable salt, pharmaceutical product, polymorph, hydrate or any combination thereof, represented by a compound of formula II:

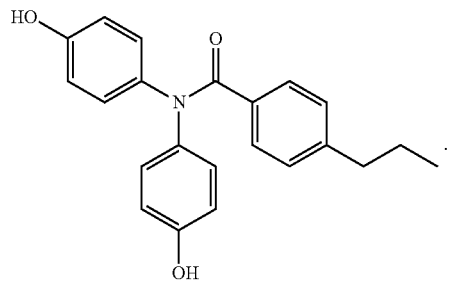

(II)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of lowering serum prostate specific antigen (PSA) levels in a male subject suffering from castration resistant prostate cancer (CRPC), comprising administering a therapeutically effective amount of a compound or its isomer, pharmaceutical acceptable salt, pharmaceutical product, polymorph, hydrate or any combination thereof, represented by a compound of formula III:

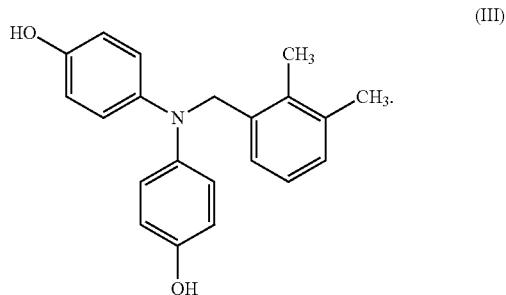 [SMILES: Cc1cccc(CN(c2ccc(O)cc2)c2ccc(O)cc2)c1C]

(III)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of lowering serum prostate specific antigen (PSA) levels in a male subject suffering from castration resistant prostate cancer (CRPC), comprising administering a therapeutically effective amount of a compound or its isomer, pharmaceutical product, pharmaceutical acceptable salt, polymorph, hydrate or any combination thereof, represented by a compound of formula IV:

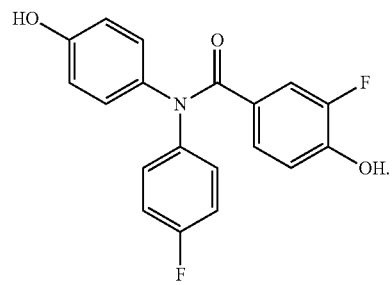

(IV)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of lowering serum prostate specific antigen (PSA) levels in a male subject suffering from castration resistant prostate cancer (CRPC), comprising administering a therapeutically effective amount of a compound or its isomer, pharmaceutical acceptable salt, pharmaceutical product, polymorph, hydrate or any combination thereof, represented by a compound of formula V:

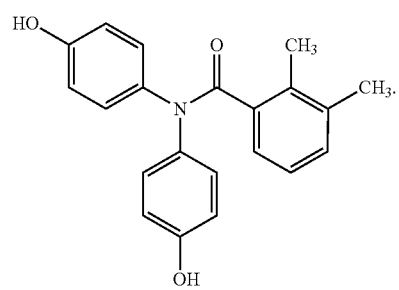

(V)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of lowering serum prostate specific antigen (PSA) levels in a male subject suffering from castration resistant prostate cancer (CRPC), comprising administering a therapeutically effective amount of a compound or its isomer, pharmaceutical acceptable salt, pharmaceutical product, polymorph, hydrate or any combination thereof, represented by a compound of formula VI:

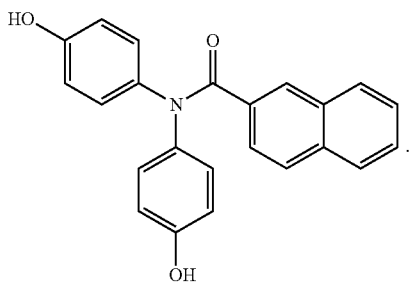

(VI)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of lowering serum prostate specific antigen (PSA) levels in a male subject suffering from castration resistant prostate cancer (CRPC), comprising administering a therapeutically effective amount of a compound or its isomer, pharmaceutical acceptable salt, pharmaceutical product, polymorph, hydrate or any combination thereof, represented by a compound of formula VII:

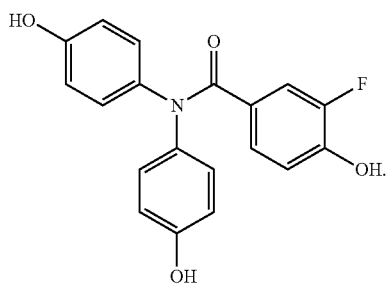

(VII)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of lowering serum prostate specific antigen (PSA) levels in a male subject suffering from castration resistant prostate cancer (CRPC), comprising administering a therapeutically effective amount of a compound or its isomer, pharmaceutical acceptable salt, pharmaceutical product, polymorph, hydrate or any combination thereof, represented by a compound of formula VIII:

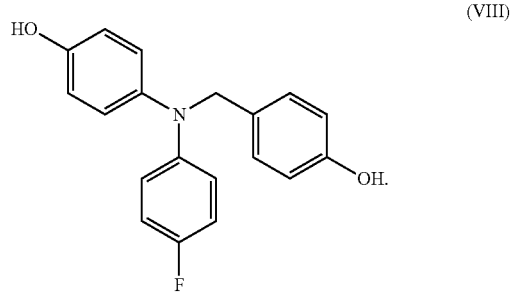 [SMILES: Oc1ccc(CN(c2ccc(O)cc2)c2ccc(F)cc2)cc1]

(VIII)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of lowering serum prostate specific antigen (PSA) levels in a male subject suffering from castration resistant prostate cancer (CRPC), comprising administering a therapeutically effective amount of a compound or its isomer, pharmaceutical acceptable salt, pharmaceutical product, polymorph, hydrate or any combination thereof represented by a compound of formula IX:

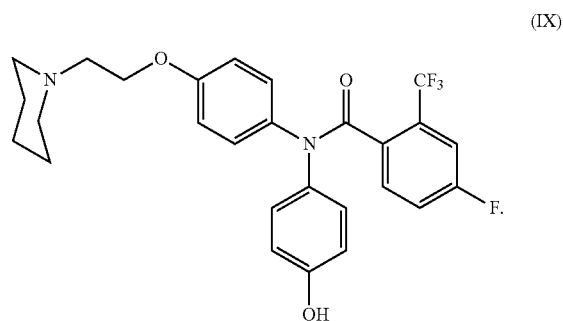 [SMILES: O=C(c1ccc(F)cc1C(F)(F)F)N(c1ccc(O)cc1)c1ccc(OCCN2CCCCC2)cc1]

(IX)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of lowering serum prostate specific antigen (PSA) levels in a male subject suffering from castration resistant prostate cancer (CRPC), comprising administering a therapeutically effective amount of a compound or its isomer, pharmaceutical acceptable salt, pharmaceutical product, polymorph, hydrate or any combination thereof, represented by a compound of formula X:

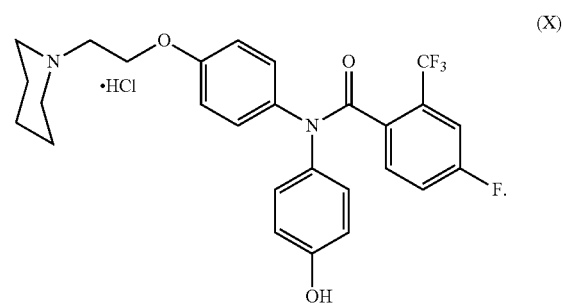 [SMILES: O=C(c1ccc(F)cc1C(F)(F)F)N(c1ccc(O)cc1)c1ccc(OCCN2CCCCC2)cc1 ; Cl]

(X)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of lowering serum prostate specific antigen (PSA) levels in a male subject suffering from castration resistant prostate cancer (CRPC), comprising administering a therapeutically effective amount of a compound or its isomer, pharmaceutical acceptable salt, pharmaceutical product, polymorph, hydrate or any combination thereof, represented by a compound of formula XI:

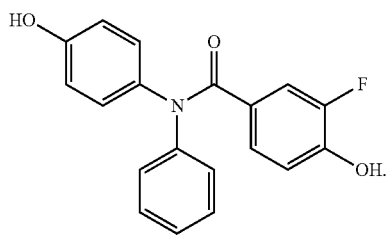

(XI)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of lowering serum prostate specific antigen (PSA) levels in a male subject suffering from castration resistant prostate cancer (CRPC) comprising administering a therapeutically effective amount of a compound or its isomer, pharmaceutical acceptable salt, pharmaceutical product, polymorph, hydrate or any combination thereof, represented by a compound of formula XII:

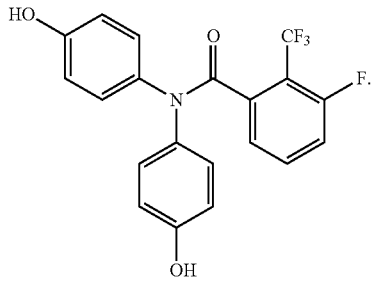

(XII)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by the structure of formula I:

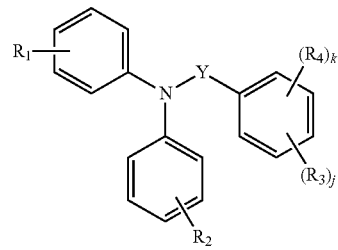

(I)

wherein
Y is C(O) or $CH_2$;
$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;
$R_3$, $R_4$ are independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;
R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;
$R_5$ and $R_6$ are independently hydrogen, phenyl, an alkyl group of 1 to 6 carbon atoms, a 3 to 7 membered cycloalkyl, a 3 to 7 membered heterocycle, a 5 to 7 membered aryl; or $R_5$ and $R_6$ form a 3 to 7 membered ring with the nitrogen atom;
j and k are independently 1-4; and
Alk is linear alkyl of 1-7 carbons, branched alkyl of 1-7 carbons, or cyclic alkyl of 3-8 carbons. In another embodiment, the prostate cancer is advanced prostate cancer.

In one embodiment, this invention provides a method of decreasing serum insulin-like growth factor-1 (IGF-1) levels in a subject suffering from advanced prostate cancer or castration resistant prostate cancer (CRPC) comprising administering a therapeutically effective amount of a compound or its isomer, pharmaceutical acceptable salt, pharmaceutical product, polymorph, hydrate or any combination thereof, represented by the structure of formula I:

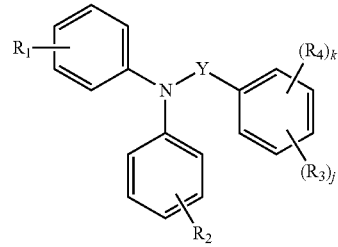

(I)

wherein
Y is C(O) or $CH_2$;
$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;
$R_3$, $R_4$ are independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;

R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_5$ and $R_6$ are independently hydrogen, phenyl, an alkyl group of 1 to 6 carbon atoms, a 3 to 7 membered cycloalkyl, a 3 to 7 membered heterocycle, a 5 to 7 membered aryl; or $R_5$ and $R_6$ form a 3 to 7 membered ring with the nitrogen atom;

j and k are independently 1-4; and

Alk is linear alkyl of 1-7 carbons, branched alkyl of 1-7 carbons, or cyclic alkyl of 3-8 carbons.

In another embodiment, the CRPC is metastatic CRPC (mCRPC). In another embodiment, the CRPC is non-metastatic CRPC (nmCRPC). In one embodiment, the nmCRPC is high-risk nmCRPC.

In additional embodiments of the methods described herein, the compound of Formula I is represented by formula IA:

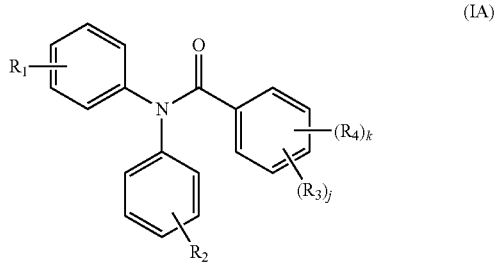

(IA)

wherein $R_1$, $R_2$, $R_3$, $R_4$, j and k are as defined for Formula I.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by a compound of formula II:

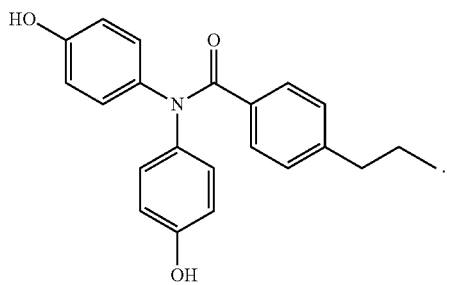

(II)

In another embodiment, the prostate cancer is advanced prostate cancer.

In one embodiment, this invention provides a method of decreasing serum insulin-like growth factor-1 (IGF-1) levels in a subject suffering from castrate-resistant prostate cancer (CRPC) comprising administering a therapeutically effective amount of a compound or its isomer, pharmaceutical acceptable salt, pharmaceutical product, polymorph, hydrate or any combination thereof, represented by a compound of formula II:

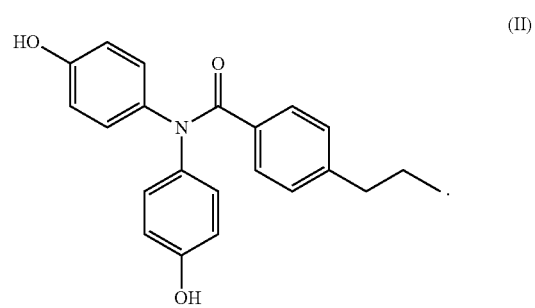 [SMILES: CCCc1ccc(C(=O)N(c2ccc(O)cc2)c2ccc(O)cc2)cc1]

(II)

In another embodiment, the CRPC is metastatic CRPC (mCRPC). In another embodiment, the CRPC is non-metastatic CRPC (nmCRPC). In one embodiment, the nmCRPC is high-risk nmCRPC.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by a compound of formula III:

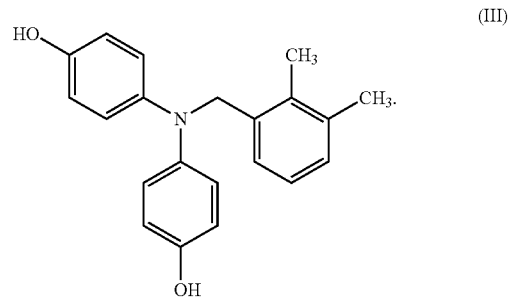 [SMILES: Cc1cccc(CN(c2ccc(O)cc2)c2ccc(O)cc2)c1C]

(III)

In another embodiment, the subject suffers from advanced prostate cancer, castration resistant prostate cancer (CRPC), metastatic CRPC (mCRPC) or non-metastatic CRPC (nmCRPC). In one embodiment, the nmCRPC is high-risk nmCRPC.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by a compound of formula IV:

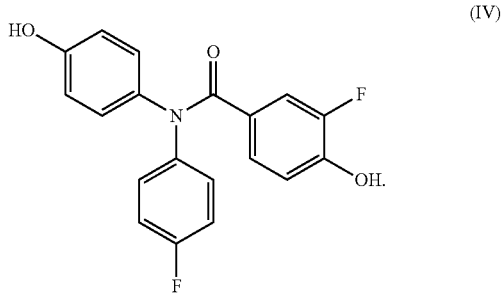 [SMILES: O=C(c1ccc(O)c(F)c1)N(c1ccc(O)cc1)c1ccc(F)cc1]

(IV)

In another embodiment, the subject suffers from advanced prostate cancer, castration resistant prostate cancer (CRPC), metastatic CRPC (mCRPC) or non-metastatic CRPC (nm-CRPC). In one embodiment, the nmCRPC is high-risk nmCRPC.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by a compound of formula V:

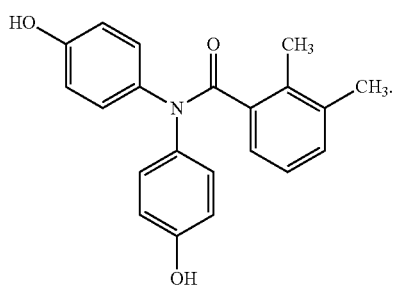

(V)

In another embodiment, the subject suffers from advanced prostate cancer, castration resistant prostate cancer (CRPC), metastatic CRPC (mCRPC) or non-metastatic CRPC (nm-CRPC). In one embodiment, the nmCRPC is high-risk nmCRPC.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by a compound of formula VI:

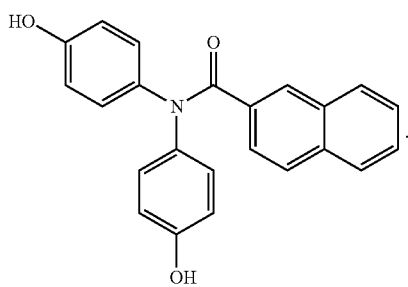

(VI)

In another embodiment, the subject suffers from advanced prostate cancer, castration resistant prostate cancer (CRPC), metastatic CRPC (mCRPC) or non-metastatic CRPC (nm-CRPC). In one embodiment, the nmCRPC is high-risk nmCRPC.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by a compound of formula VII:

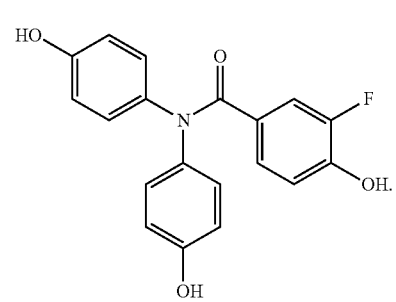

(VII)

In another embodiment, the subject suffers from advanced prostate cancer, castration resistant prostate cancer (CRPC), metastatic CRPC (mCRPC) or non-metastatic CRPC (nm-CRPC). In one embodiment, the nmCRPC is high-risk nmCRPC.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by a compound of formula VIII:

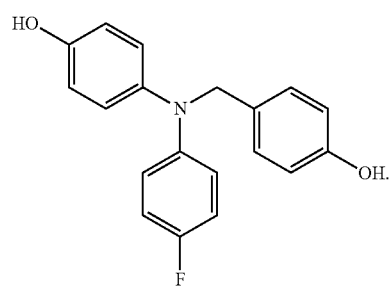

(VIII)

In another embodiment, the subject suffers from advanced prostate cancer, castration resistant prostate cancer (CRPC), metastatic CRPC (mCRPC) or non-metastatic CRPC (nm-CRPC). In one embodiment, the nmCRPC is high-risk nmCRPC.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by a compound of formula IX:

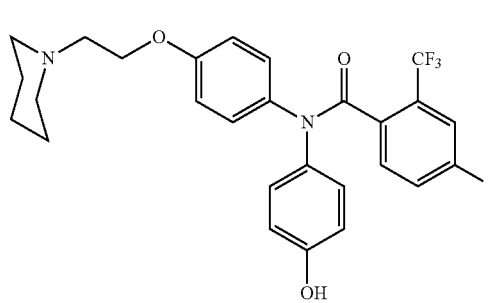

(IX)

In another embodiment, the subject suffers from advanced prostate cancer, castration resistant prostate cancer (CRPC), metastatic CRPC (mCRPC) or non-metastatic CRPC (nm-CRPC). In one embodiment, the nmCRPC is high-risk nmCRPC.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by a compound of formula X:

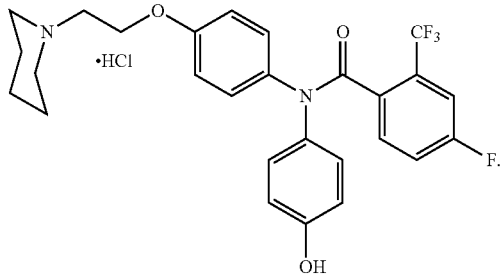

(X)

In another embodiment, the subject suffers from advanced prostate cancer, castration resistant prostate cancer (CRPC), metastatic CRPC (mCRPC) or non-metastatic CRPC (nm-CRPC). In one embodiment, the nmCRPC is high-risk nmCRPC.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by a compound of formula XI:

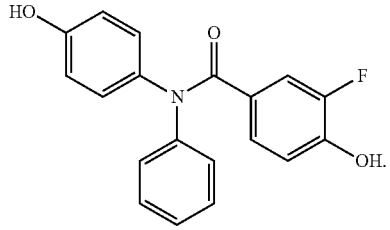

(XI)

In another embodiment, the subject suffers from advanced prostate cancer, castration resistant prostate cancer (CRPC), metastatic CRPC (mCRPC) or non-metastatic CRPC (nm-CRPC). In one embodiment, the nmCRPC is high-risk nmCRPC.

In one embodiment, this invention provides a method of decreasing serum insulin-like growth factor-1 (IGF-1) levels in a subject suffering from prostate cancer comprising administering a therapeutically effective amount of a compound or its isomer, pharmaceutical acceptable salt, pharmaceutical product, polymorph, hydrate or any combination thereof, represented by a compound of formula XII:

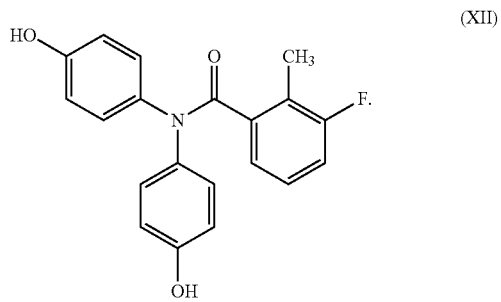

(XII)

In another embodiment, the subject suffers from advanced prostate cancer, castration resistant prostate cancer (CRPC), metastatic CRPC (mCRPC) or non-metastatic CRPC (nm-CRPC). In one embodiment, the nmCRPC is high-risk nmCRPC.

In one embodiment, this invention provides a method of lowering serum free testosterone concentration to levels unattainable by ADT alone in a: i) prostate cancer patient; ii) prostate cancer patient on ADT; iii) prostate cancer patient on ADT with castrate levels of total T; iv) advanced prostate cancer patient; v) advanced prostate cancer patient on ADT; yl) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by the structure of formula I:

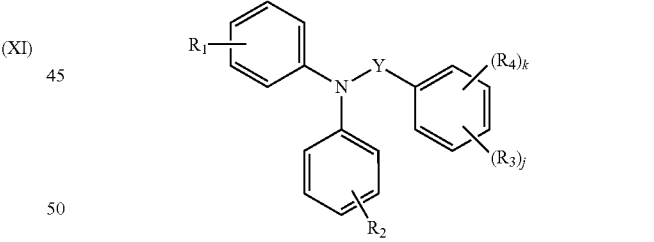

(I)

wherein
Y is C(O) or $CH_2$;
$R_1$, $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;
$R_3$, $R_4$ are independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;
R is alkyl, hydrogen, haloalkyl, dihaloalkyl, trihaloalkyl, $CH_2F$, $CHF_2$, $CF_3$, $CF_2CF_3$, aryl, phenyl, halogen, alkenyl, CN, $NO_2$, or OH;

$R_5$ and $R_6$ are independently hydrogen, phenyl, an alkyl group of 1 to 6 carbon atoms, a 3 to 7 membered cycloalkyl, a 3 to 7 membered heterocycle, a 5 to 7 membered aryl; or $R_5$ and $R_6$ form a 3 to 7 membered ring with the nitrogen atom;

j and k are independently 1-4; and

Alk is linear alkyl of 1-7 carbons, branched alkyl of 1-7 carbons, or cyclic alkyl of 3-8 carbons.

In additional embodiments of the methods described herein, the compound of Formula I is represented by formula IA:

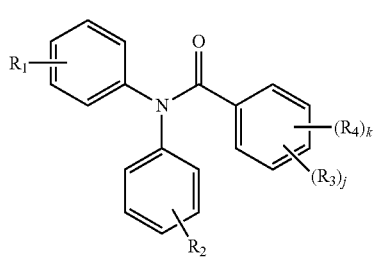

(IA)

wherein $R_1$, $R_2$, $R_3$, $R_4$, j and k are as defined for Formula I.

In one embodiment, this invention provides a method of lowering serum free testosterone concentration to levels unattainable by ADT alone in a: i) prostate cancer patient; ii) prostate cancer patient on ADT; iii) prostate cancer patient on ADT with castrate levels of total T; iv) advanced prostate cancer patient; v) advanced prostate cancer patient on ADT; yl) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula II:

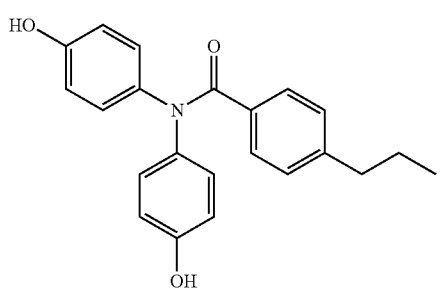

(II)

In one embodiment, this invention provides a method of lowering serum free testosterone concentration to levels unattainable by ADT alone in a i) prostate cancer patient; ii) prostate cancer patient on ADT; iii) prostate cancer patient on ADT with castrate levels of total T; iv) advanced prostate cancer patient; v) advanced prostate cancer patient on ADT; yl) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula III:

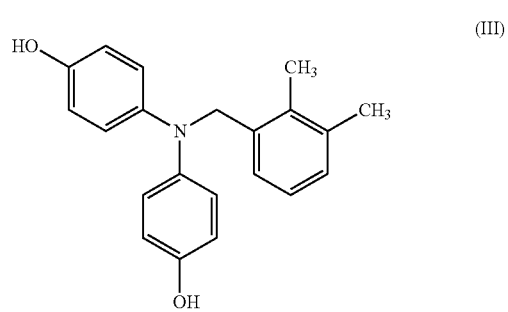 [SMILES: Cc1cccc(CN(c2ccc(O)cc2)c2ccc(O)cc2)c1C]

(III)

In one embodiment, this invention provides a method of lowering serum free testosterone concentration to levels unattainable by ADT alone in a i) prostate cancer patient; ii) prostate cancer patient on ADT; iii) prostate cancer patient on ADT with castrate levels of total T; iv) advanced prostate cancer patient; v) advanced prostate cancer patient on ADT; yl) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical product, pharmaceutical acceptable salt, polymorph, hydrate or any combination thereof, represented by a compound of formula IV:

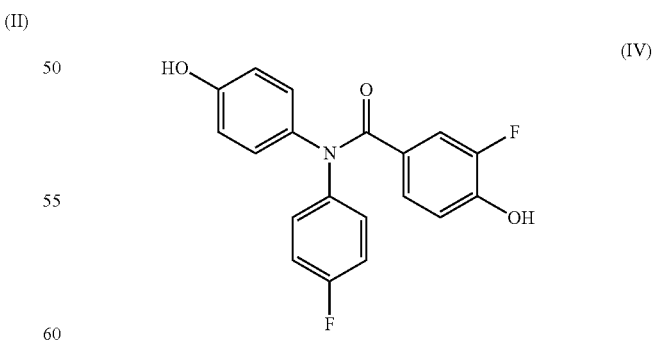

(IV)

In one embodiment, this invention provides a method of lowering serum free testosterone concentration to levels unattainable by ADT alone in a i) prostate cancer patient; ii) prostate cancer patient on ADT; iii) prostate cancer patient on ADT with castrate levels of total T; iv) advanced prostate cancer patient; v) advanced prostate cancer patient on ADT;

yl) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula V:

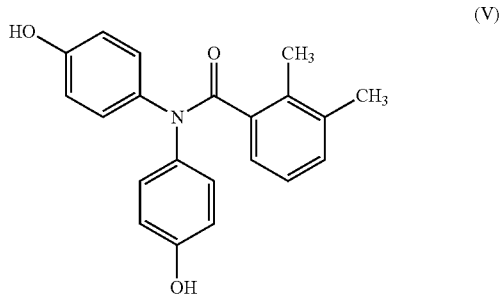 [SMILES: Cc1cccc(C(=O)N(c2ccc(O)cc2)c2ccc(O)cc2)c1C]

(V)

In one embodiment, this invention provides a method of lowering serum free testosterone concentration to levels unattainable by ADT alone in a i) prostate cancer patient; ii) prostate cancer patient on ADT; iii) prostate cancer patient on ADT with castrate levels of total T; iv) advanced prostate cancer patient; v) advanced prostate cancer patient on ADT; yl) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula VI:

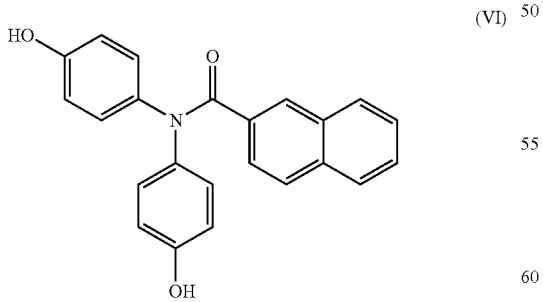

(VI)

In one embodiment, this invention provides a method of lowering serum free testosterone concentration to levels unattainable by ADT alone in a i) prostate cancer patient; ii) prostate cancer patient on ADT; iii) prostate cancer patient on ADT with castrate levels of total T; iv) advanced prostate cancer patient; v) advanced prostate cancer patient on ADT; yl) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula VII:

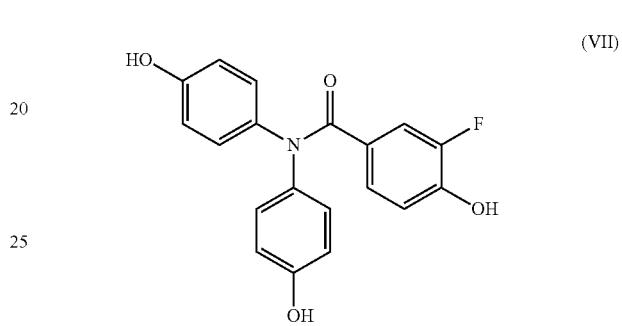

(VII)

In one embodiment, this invention provides a method of lowering serum free testosterone concentration to levels unattainable by ADT alone in a i) prostate cancer patient; ii) prostate cancer patient on ADT; iii) prostate cancer patient on ADT with castrate levels of total T; iv) advanced prostate cancer patient; v) advanced prostate cancer patient on ADT; yl) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula VIII:

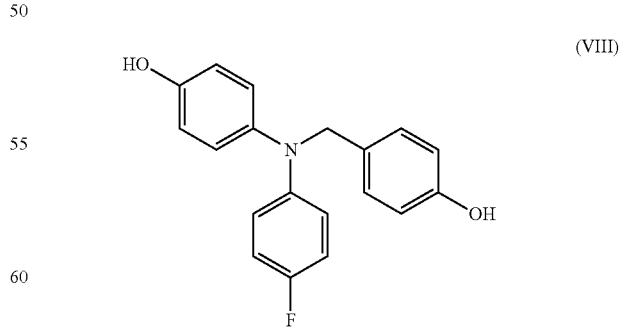

(VIII)

In one embodiment, this invention provides a method of lowering serum free testosterone concentration to levels unattainable by ADT alone in a i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof represented by a compound of formula IX:

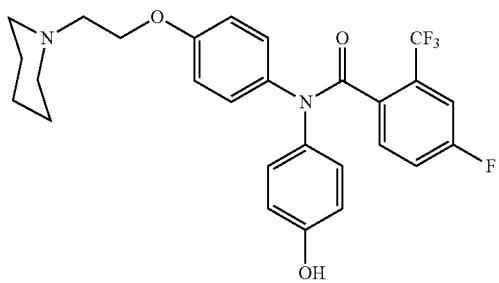

(IX)

In one embodiment, this invention provides a method of lowering serum free testosterone concentration to levels unattainable by ADT alone in a i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula X:

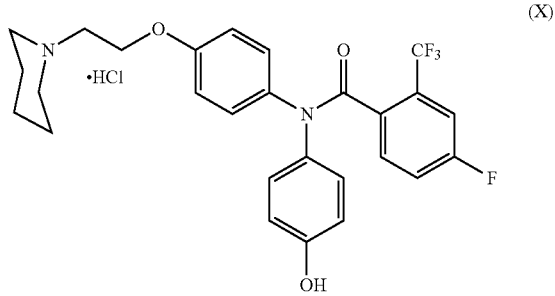 [SMILES: O=C(c1ccc(F)cc1C(F)(F)F)N(c1ccc(O)cc1)c1ccc(OCCN2CCCCC2)cc1 ; Cl]

(X)

In one embodiment, this invention provides a method of lowering serum free testosterone concentration to levels unattainable by ADT alone in a i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula XI:

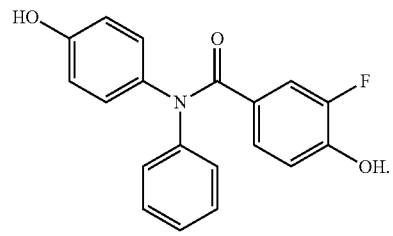

(XI)

In one embodiment, this invention provides a method of lowering serum free testosterone concentration to levels unattainable by ADT alone in a i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula XII:

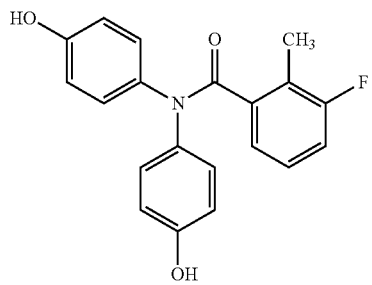

(XII)

In one embodiment, this invention provides a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by the structure of formula I:

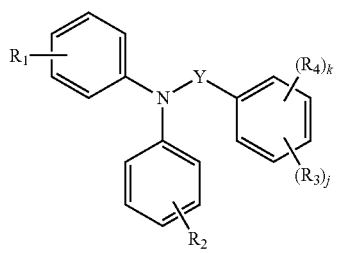

(I)

wherein
Y is C(O) or CH$_2$;

R$_1$, R$_2$ are independently hydrogen, halogen, hydroxyl, alkoxy, cyano, nitro, CF$_3$, N(R)$_2$, sulfonamide, SO$_2$R, alkyl, haloalkyl, aryl, O-Alk-NR$_5$R$_6$ or O-Alk-heterocycle in which the heterocycle is a 3-7 membered substituted or unsubstituted heterocyclic ring, optionally aromatic;

R$_3$, R$_4$ are independently hydrogen, halogen, hydroxyalkyl, hydroxyl, alkoxy, cyano, nitro, CF$_3$, NHCOR, N(R)$_2$, sulfonamide, SO$_2$R, alkyl, haloalkyl, aryl or protected hydroxyl;

R is alkyl, hydrogen, haloalkyl, dihaloalkyl, trihaloalkyl, CH$_2$F, CHF$_2$, CF$_3$, CF$_2$CF$_3$, aryl, phenyl, halogen, alkenyl, CN, NO$_2$, or OH;

R$_5$ and R$_6$ are independently hydrogen, phenyl, an alkyl group of 1 to 6 carbon atoms, a 3 to 7 membered cycloalkyl, a 3 to 7 membered heterocycle, a 5 to 7 membered aryl; or R$_5$ and R$_6$ form a 3 to 7 membered ring with the nitrogen atom;

j and k are independently 1-4; and
Alk is linear alkyl of 1-7 carbons, branched alkyl of 1-7 carbons, or cyclic alkyl of 3-8 carbons.

In additional embodiments of the methods described herein, the compound of Formula I is represented by formula IA:

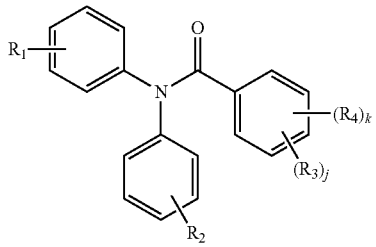

(IA)

wherein R$_1$, R$_2$, R$_3$, R$_4$, j and k are as defined for Formula I.

In one embodiment, this invention provides a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula II:

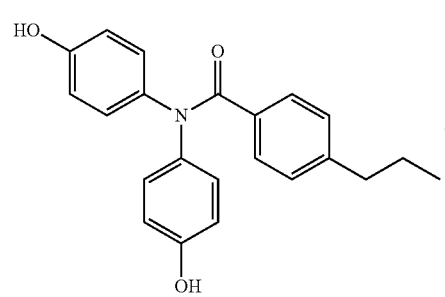

(II)

In one embodiment, this invention provides a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula III:

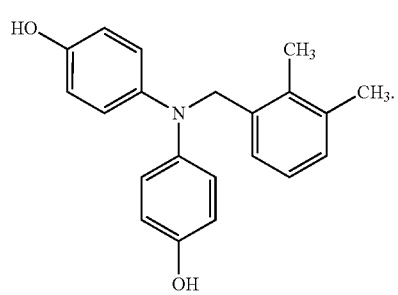

(III)

In one embodiment, this invention provides a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical product, pharmaceutical acceptable salt, polymorph, hydrate or any combination thereof, represented by a compound of formula IV:

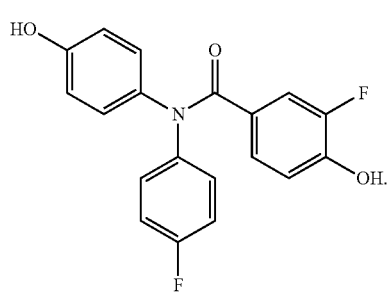

(IV)

In one embodiment, this invention a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula V:

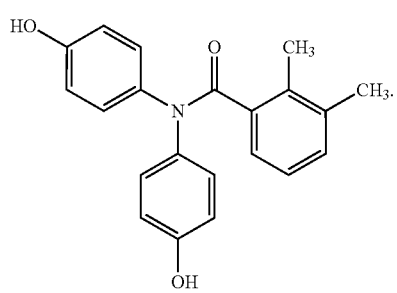

(V)

In one embodiment, this invention provides a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula VI:

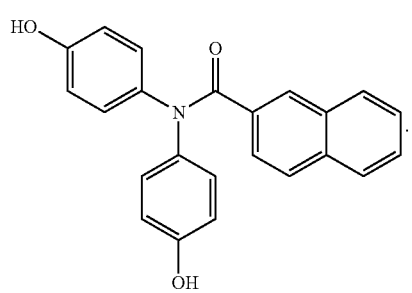

(VI)

In one embodiment, this invention provides a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula VII:

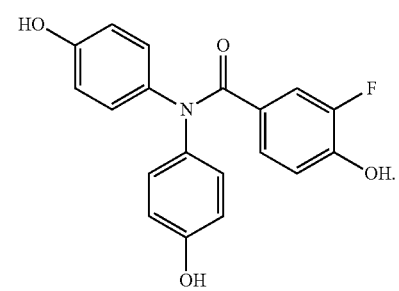

(VII)

In one embodiment, this invention provides a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula VIII:

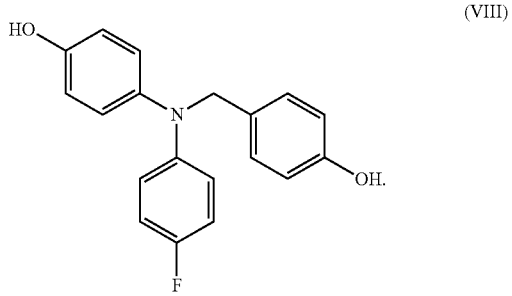 [SMILES: Oc1ccc(CN(c2ccc(O)cc2)c2ccc(F)cc2)cc1]

(VIII)

In one embodiment, this invention provides a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof represented by a compound of formula IX:

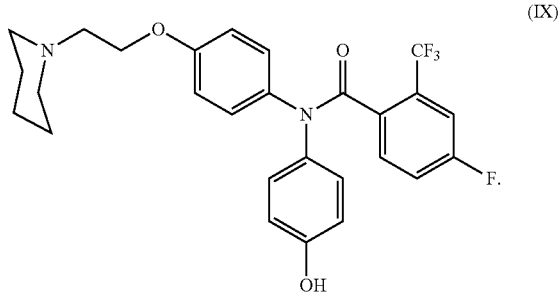 [SMILES: O=C(c1ccc(F)cc1C(F)(F)F)N(c1ccc(O)cc1)c1ccc(OCCN2CCCCC2)cc1]

(IX)

In one embodiment, this invention provides a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula X:

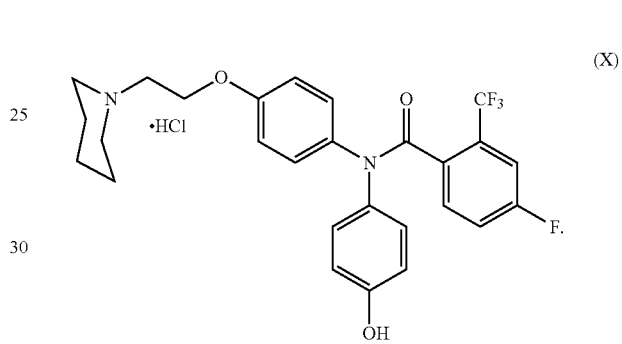

(X)

In one embodiment, this invention provides a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula XI:

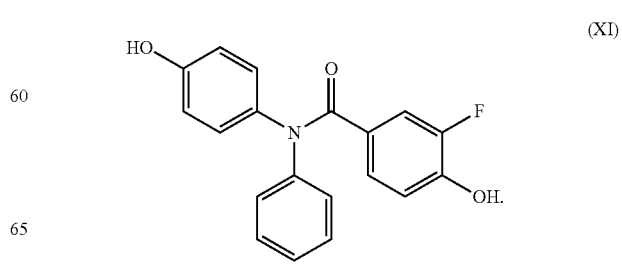

(XI)

In one embodiment, this invention provides a method of lowering serum free testosterone concentration to levels unattainable by ADT alone in a castrated patient, wherein said patient is a: i) prostate cancer patient; ii) prostate cancer patient on ADT; iii) prostate cancer patient on ADT with castrate levels of total T; iv) advanced prostate cancer patient; v) advanced prostate cancer patient on ADT; vi) advanced prostate cancer patient on ADT with castrate levels of total T; vii) CRPC patient; viii) CRPC patient maintained on ADT; ix) CRPC patient maintained on ADT with castrate levels of total T; x) mCRPC patient; xi) mCRPC patient maintained on ADT; xii) mCRPC patient maintained on ADT with castrate levels of total T; xiii) nmCRPC patient; xiv) nmCRPC patient maintained on ADT; or xv) nmCRPC patient maintained on ADT with castrate levels of total T, comprising administering a therapeutically effective amount of a compound or its isomer, pharmaceutical acceptable salt, pharmaceutical product, polymorph, hydrate or any combination thereof, represented by a compound of formula XII:

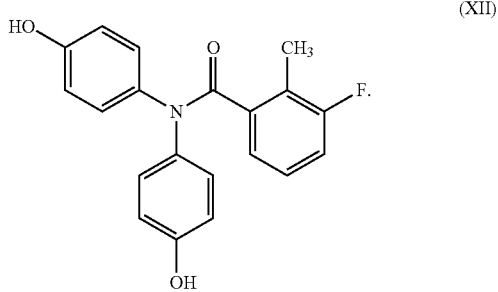 [SMILES: Cc1c(F)cccc1C(=O)N(c1ccc(O)cc1)c1ccc(O)cc1]

(XII)

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound of formula IA, I-XII or its isomer, pharmaceutical acceptable salt, pharmaceutical product, polymorph, hydrate or any combination thereof. In another embodiment, the castration is surgical castration. In another embodiment, the castration is chemical castration. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the method further treats, suppresses, reduces the incidence, reduces the severity, or inhibits new bone metastasis. In another embodiment, the method further treats, suppresses, reduces the incidence, reduces the severity, or inhibits new or worsening soft tissue metastases (visceral and lymph nodes). In another embodiment, the method further treats, suppresses, reduces the incidence, reduces the severity, or inhibits symptomatic bone fractures. In another embodiment, the method further increases radiographic progression free survival (rPFS) in a subject suffering from a metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy, or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the subject has failed Androgen Deprivation Therapy (ADT). In another embodiment the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing prostate specific antigen (PSA) levels. In another embodiment, the subject is a prostate cancer patient. In another embodiment, the subject is a prostate cancer patient on ADT. In another embodiment, the subject is a prostate cancer patient on ADT with castrate levels of total T. In another embodiment, the subject is an advanced prostate cancer patient. In another embodiment, the subject is an advanced prostate cancer patient on ADT. In another embodiment, the subject is an advanced prostate cancer patient on ADT with castrate levels of total T. In another embodiment, the subject is a CRPC patient. In another embodiment, the subject is a CRPC patient on ADT. In another embodiment, the subject is a CRPC patient on ADT with castrate levels of total T. In another embodiment, the subject is a metastatic castration resistant prostate cancer (mCRPC) patient. In another embodiment, the subject is a mCRPC patient maintained on ADT. In another embodiment, the subject is a mCRPC patient maintained on ADT with castrate levels of total T. In another embodiment, the subject is a non-metastatic castration resistant prostate cancer (nmCRPC) patient. In another embodiment, the subject is an nmCRPC patient maintained on ADT. In another embodiment, the subject is an nmCRPC patient maintained on ADT with castrate levels of total T. In one embodiment, the nmCRPC is high-risk nmCRPC.

In another embodiment, administering of the compound of this invention reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method of treating, suppressing, reducing the incidence, reducing the severity, or inhibiting the progression of castration resistant prostate cancer (CRPC) or metastatic castration resistant prostate cancer (mCRPC) or non-metastatic castration resistant prostate cancer (nmCRPC) and its symptoms, or increasing the survival of men with castration resistant prostate cancer comprising administering a therapeutically effective amount of estradiol, ethynyl estradiol, steroidal estrogen agonists, nonsteroidal estrogen agonist or combination thereof. In one embodiment, the nmCRPC is high-risk nmCRPC.

In one embodiment, this invention provides a method of lowering total serum testosterone levels/concentration in a male subject suffering from castration resistant prostate cancer (CRPC) or metastatic castration resistant prostate cancer (mCRPC) or non-metastatic castration resistant prostate cancer (nmCRPC), comprising administering a therapeutically effective amount of a compound of formula IA, I-XII or its isomer, pharmaceutical acceptable salt, pharmaceutical product, polymorph, hydrate or any combination thereof. In one embodiment, the nmCRPC is high-risk nmCRPC. In another embodiment, the castration is surgical castration. In another embodiment, the castration is chemical castration. In another embodiment, the CRPC is metastatic CRPC (mCRPC). In another embodiment, CRPC is non-metastatic castration resistant prostate cancer (nmCRPC). In another embodiment, CRPC is high-risk non-metastatic castration resistant prostate cancer (high-risk nmCRPC). In another embodiment, the method further treats, suppresses, reduces the incidence, reduces the severity, or inhibits new bone metastasis. In another embodiment, the method further treats, suppresses, reduces the incidence, reduces the severity, or inhibits new or worsening soft tissue metastasis (visceral and lymph nodes). In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy, or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the subject has failed Androgen Deprivation Therapy (ADT). In another embodiment the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing prostate specific antigen (PSA) levels. In another embodiment, the subject is a prostate cancer patient. In another embodiment, the subject is a prostate cancer patient on ADT. In another embodiment, the subject is a prostate cancer patient on ADT with castrate levels of total T. In another embodiment, the subject is an advanced prostate cancer patient. In another embodiment, the subject is an advanced prostate cancer patient on ADT. In another embodiment, the subject is an advanced prostate cancer patient on ADT with castrate levels of total T. In another embodiment, the subject is a CRPC patient. In another embodiment, the subject is a CRPC patient maintained on ADT. In another embodiment, the subject is a CRPC patient maintained on ADT with castrate levels of total T. In another embodiment, the subject is a mCRPC patient. In another embodiment, the subject is a mCRPC patient maintained on ADT. In another embodiment, the subject is a mCRPC patient maintained on ADT with castrate levels of total T. In another embodiment, the subject is a nmCRPC patient. In another embodiment, the subject is a nmCRPC patient maintained on ADT. In another embodiment, the subject is a nmCRPC patient maintained on ADT with castrate levels of total T. In one embodiment the nmCRPC patient is a high-risk nmCRPC patient. In another embodiment, administering of the compound reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment, the compound is administered at a dosage of 500 mg per day. In another embodiment, the total serum testosterone is lowered below about 100 ng/dL. In another embodiment, the total serum testosterone is lowered below about 50 ng/dL. In another embodiment, the total serum testosterone concentration is lowered below about 25 ng/dL. In another embodiment, the total serum testosterone is lowered below about 20 ng/dL. In another embodiment, the total serum testosterone concentration is lowered below about 10 ng/dL. In another embodiment, the total serum testosterone concentration is lowered below about 5 ng/dL. In another embodiment, the total serum testosterone concentration is lowered below about 1 ng/dL.

In one embodiment, this invention provides a method of lowering total serum testosterone levels in a male subject suffering from castration resistant prostate cancer (CRPC) or metastatic castration resistant prostate cancer (mCRPC) or non-metastatic castration resistant prostate cancer (nmCRPC) or high-risk nmCRPC, comprising administering a therapeutically effective amount of estradiol, ethynyl estradiol, steroidal estrogen agonists, nonsteroidal estrogen agonist or combination thereof.

In one embodiment, this invention provides a method of lowering serum free testosterone levels/concentration in a male subject suffering from castration resistant prostate cancer (CRPC) or metastatic castration resistant prostate cancer (mCRPC) or non-metastatic castration resistant prostate cancer (nmCRPC) or high-risk nmCRPC, comprising administering a therapeutically effective amount of a compound of formula IA, I-XII or its isomer, pharmaceutical acceptable salt, pharmaceutical product, polymorph, hydrate or any combination thereof. In another embodiment, the castration is surgical castration. In another embodiment, the castration is chemical castration. In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC. In another embodiment, the method further treats, suppresses, reduces the incidence, reduces the severity, or inhibits new bone metastasis. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the method further treats, suppresses, reduces the incidence, reduces the severity, or inhibits new or worsening soft tissue metastasis (visceral and lymph nodes). In another embodiment, the subject has failed Androgen Deprivation Therapy (ADT). In another embodiment the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing prostate specific antigen (PSA) levels. In another embodiment, the subject is a prostate cancer patient. In another embodiment, the subject is a prostate cancer patient on ADT. In another embodiment, the subject is a prostate cancer patient on ADT with castrate levels of total T. In another embodiment, the subject is an advanced prostate cancer patient. In another embodiment, the subject is an advanced prostate cancer patient on ADT. In another embodiment, the subject is an advanced prostate cancer patient on ADT with castrate levels of total T. In another embodiment, the subject is a CRPC patient. In another embodiment, the subject is a CRPC patient maintained on ADT. In another embodiment, the subject is a CRPC patient maintained on ADT with castrate levels of total T. In another embodiment, the subject is a metastatic CRPC (mCRPC) patient. In another embodiment, the subject is an mCRPC patient maintained on ADT. In another embodiment, the subject is an mCRPC patient maintained on ADT with castrate levels of total T. In another embodiment, the subject is a non-metastatic CRPC (nmCRPC) patient. In another embodiment, the subject is an nmCRPC patient maintained on ADT. In another embodiment, the subject is an nmCRPC patient maintained on ADT with castrate levels of total T. In one embodiment, the nmCRPC is high-risk nmCRPC. In another embodiment, administering of the compound reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment, the free serum testosterone is lowered to levels below castration. In another embodiment, the free serum testosterone is lowered to levels below what has been observed with LHRH agonists or antagonists or surgical castration. In one embodiment, the free testosterone concentration is lowered below about 1.5 pg/mL. In another embodiment, the free testosterone concentration is lowered below about 1 pg/mL. In another embodiment, the free testosterone concentration is lowered below about 0.8 pg/mL. In another embodiment, the free testosterone concentration is lowered below about 0.6 pg/mL. In another embodiment, the free testosterone concentration is lowered below about 0.4 pg/mL. In another embodiment, the free testosterone concentration is lowered below about 0.2 pg/mL. In another embodiment, the free testosterone concentration is lowered below about 0.1 pg/mL.

In one embodiment, this invention provides a method of lowering serum free testosterone levels in a male subject suffering from castration resistant prostate cancer (CRPC) or metastatic castration resistant prostate cancer (mCRPC) comprising administering a therapeutically effective amount of estradiol, ethynyl estradiol, steroidal estrogen agonists, nonsteroidal estrogen agonist or combination thereof.

In one embodiment, this invention provides a method of lowering serum free testosterone percentage (% FreeT) in a male subject suffering from castration resistant prostate cancer (CRPC) or metastatic castration resistant prostate cancer (mCRPC) or non-metastatic castration resistant prostate cancer (nmCRPC) or high-risk nmCRPC, comprising administering a therapeutically effective amount of a compound of formula IA, I-XII or its isomer, pharmaceutical acceptable salt, pharmaceutical product, polymorph, hydrate or any combination thereof. In another embodiment, the castration is surgical castration. In another embodiment, the castration is chemical castration. In another embodiment, the method further treats, suppresses, reduces the incidence, reduces the severity, or inhibits new bone metastasis. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the method further treats, suppresses, reduces the incidence, reduces the severity, or inhibits new or worsening soft tissue metastasis (visceral and lymph nodes). In another embodiment, the subject has failed Androgen Deprivation Therapy (ADT). In another embodiment the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing Prostate specific antigen (PSA) levels. In one embodiment, the free testosterone concentration is lowered below about 1.5 pg/mL. In another embodiment, the free testosterone concentration is lowered below about 1 pg/mL. In another embodiment, the free testosterone concentration is lowered below about 0.8 pg/mL. In another embodiment, the free testosterone concentration is lowered below about 0.6 pg/mL. In another embodiment, the free testosterone concentration is lowered below about 0.4 pg/mL. In another embodiment, the free testosterone concentration is lowered below about 0.2 pg/mL. In another embodiment, the free testosterone concentration is lowered below about 0.1 pg/mL. In another embodiment, administering of the compound reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment, the free serum testosterone is lowered to levels below castration. In another embodiment, the free serum testosterone is lowered to levels below what has been observed with LHRH agonists or antagonists or surgical castration.

In one embodiment, this invention provides a method of lowering serum free testosterone percentage (% FreeT) in a male subject suffering from castration resistant prostate cancer (CRPC) or metastatic castration resistant prostate cancer (mCRPC) or non-metastatic castration resistant prostate cancer (nmCRPC) or high-risk nmCRPC, comprising administering a therapeutically effective amount of estradiol, ethynyl estradiol, steroidal estrogen agonists, non-steroidal estrogen agonist or combination thereof.

In one embodiment, this invention provides a method of lowering serum PSA levels in a male subject suffering from castration resistant prostate cancer (CRPC) or metastatic castration resistant prostate cancer (mCRPC) or non-metastatic castration resistant prostate cancer (nmCRPC) or high-risk nmCRPC, comprising administering a therapeutically effective amount of a compound of formula IA, I-XII or its isomer, pharmaceutical acceptable salt, pharmaceutical product, polymorph, hydrate or any combination thereof. In another embodiment, the castration is surgical castration. In another embodiment, the castration is chemical castration. In another embodiment, the method further treats, suppresses, reduces the incidence, reduces the severity, or inhibits new bone metastasis. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the method further treats, suppresses, reduces the incidence, reduces the severity, or inhibits new or worsening soft tissue metastasis (visceral and lymph nodes). In another embodiment, the subject has failed Androgen Deprivation Therapy (ADT). In another embodiment the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing Prostate specific antigen (PSA) levels. In another embodiment, administering of the compound reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment the serum PSA levels are decreased by at least 10% from baseline. In another embodiment the serum PSA levels are decreased by at least 30% from baseline. In another embodiment the serum PSA levels are decreased by at least 50% from baseline. In another embodiment the serum PSA levels are decreased by at least 70% from baseline. In another embodiment the serum PSA levels are decreased by at least 90% from baseline.

In one embodiment, this invention provides a method of lowering serum PSA levels in a male subject suffering from castration resistant prostate cancer (CRPC) or metastatic castration resistant prostate cancer (mCRPC) comprising administering a therapeutically effective amount of estradiol, ethynyl estradiol, steroidal estrogen agonists, non-steroidal estrogen agonist or combination thereof.

In one embodiment, this invention provides a method of increasing sex hormone binding globulin (SHBG) levels in a male subject suffering from castration resistant prostate cancer (CRPC) or metastatic castration resistant prostate cancer (mCRPC) metastatic castration resistant prostate cancer (mCRPC) or non-metastatic castration resistant prostate cancer (nmCRPC) or high-risk nmCRPC, comprising administering a therapeutically effective amount of a compound of formula IA, I-XII or its isomer, pharmaceutical acceptable salt, pharmaceutical product, polymorph, hydrate or any combination thereof. In another embodiment, the castration is surgical castration. In another embodiment, the castration is chemical castration. In another embodiment, the method further treats, suppresses, reduces the incidence, reduces the severity, or inhibits new bone metastasis. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the method further treats, suppresses, reduces the incidence, reduces the severity, or inhibits new or worsening soft tissue metastasis (visceral and lymph nodes). In another embodiment, the subject has failed Androgen Deprivation Therapy (ADT). In another embodiment the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing Prostate specific antigen (PSA) levels. In another embodiment, administering of the compound reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method of increasing sex hormone binding globulin (SHBG) levels in a male subject suffering from castration resistant prostate cancer (CRPC) or metastatic castration resistant prostate cancer (mCRPC) or non-metastatic castration resistant prostate cancer (nmCRPC) or high-risk nmCRPC, comprising administering a therapeutically effective amount of estradiol, ethynyl estradiol, steroidal estrogen agonists, non-steroidal estrogen agonist or combination thereof.

In one embodiment, this invention provides a method of decreasing serum insulin-like growth factor-1 (IGF-1) levels in a subject suffering from advanced prostate cancer comprising administering a therapeutically effective amount of a compound of formula IA, I-XII or its isomer, pharmaceutical acceptable salt, pharmaceutical product, polymorph, hydrate or any combination thereof. In another embodiment, the advanced prostate cancer is castration resistant prostate cancer (CRPC). In another embodiment, the castration is surgical castration. In another embodiment, the castration is chemical castration. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the method further treats, suppresses, reduces the incidence, reduces the severity, or inhibits new bone metastasis. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the method further treats, suppresses, reduces the incidence, reduces the severity, or inhibits new or worsening soft tissue metastasis (visceral and lymph nodes). In another embodiment, the subject has failed Androgen Deprivation Therapy (ADT). In another embodiment the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing serum insulin-like growth factor-1 (IGF-1) levels. In another embodiment, administering of the compound reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment the serum insulin-like growth factor-1 (IGF-1) levels are decreased by at least 10% from baseline. In another embodiment the serum insulin-like growth factor-1 (IGF-1) levels are decreased by at least 30% from baseline. In another embodiment the serum PSA levels are decreased by at least 50% from baseline. In another embodiment the serum insulin-like growth factor-1 (IGF-1) levels are decreased by at least 70% from baseline. In another embodiment the serum insulin-like growth factor-1 (IGF-1) levels are decreased by at least 90% from baseline. In one embodiment, this invention provides a method of decreasing serum insulin-like growth factor-1 (IGF-1) levels in a male subject suffering from advanced prostate cancer (CRPC) comprising administering a therapeutically effective amount of estradiol, ethynyl estradiol, steroidal estrogen agonists, nonsteroidal estrogen agonist or combination thereof. In another embodiment, the advanced prostate cancer is castration resistant prostate cancer (CRPC). In another embodiment, the CRPC is metastatic CRPC (mCRPC). In another embodiment, the CRPC is non-metastatic castration resistant prostate cancer (nmCRPC). In one embodiment, the nmCRPC is high-risk nmCRPC.

In one embodiment, this invention provides a method of lowering serum free testosterone levels/concentration and/or serum free testosterone percent (% FreeT) in a male subject suffering from advanced prostate cancer comprising administering a therapeutically effective amount of a compound of formula IA, I-XII or its isomer, pharmaceutical acceptable salt, pharmaceutical product, polymorph, hydrate or any combination thereof, in combination with other forms of ADT. In another embodiment, the subject has failed Androgen Deprivation Therapy (ADT). In another embodiment other forms of ADT refers to LHRH agonist. In another embodiment the LHRH agonist is leuprolide acetate. In another embodiment other forms of ADT refers to LHRH antagonist. In another embodiment the LHRH antagonist is degarelix. In another embodiment, the subject had undergone orchidectomy. In another embodiment, the subject has high or increasing prostate specific antigen (PSA) levels. In another embodiment, the subject is a prostate cancer patient. In another embodiment, the subject is a prostate cancer patient on ADT. In another embodiment, the subject is a prostate cancer patient on ADT with castrate levels of total T. In another embodiment, the subject is an advanced prostate cancer patient. In another embodiment, the subject is an advanced prostate cancer patient on ADT. In another embodiment, the subject is an advanced prostate cancer patient on ADT with castrate levels of total T. In another embodiment, the subject is a CRPC patient. In another embodiment, the subject is a mCRPC patient. In another embodiment, the subject is an nmCRPC patient. In another embodiment, the subject is a CRPC patient maintained on ADT. In another embodiment, the subject is a CRPC patient maintained on ADT with castrate levels of total T. In another embodiment, administering of the compound reduces or ameliorates side effects associated with androgen deprivation therapy (ADT). In another embodiment, the method further provides palliative treatment of advanced prostate cancer. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment, the free serum testosterone is lowered to levels below castration. In another embodiment, the free serum testosterone is lowered to levels below what has been observed with LHRH agonists or antagonists or surgical castration. In one embodiment, the free testosterone concentration is lowered below about 1.5 pg/mL. In another embodiment, the free testosterone concentration is lowered below about 1 pg/mL. In another embodiment, the free testosterone concentration is lowered below about 0.8 pg/mL. In another embodiment, the free testosterone concentration is lowered below about 0.6 pg/mL. In another embodiment, the free testosterone concentration is lowered below about 0.4 pg/mL. In another embodiment, the free testosterone concentration is lowered below about 0.2 pg/mL. In another embodiment, the free testosterone concentration is lowered below about 0.1 pg/mL.

In one embodiment, this invention provides a method of lowering serum free testosterone levels/concentration and/or serum free testosterone percent (% FreeT) in a male subject suffering from prostate cancer comprising administering a therapeutically effective amount of a compound of formula IA, I-XII or its isomer, pharmaceutical acceptable salt, pharmaceutical product, polymorph, hydrate or any combination thereof, in combination with a selective estrogen receptor modulator (SERM). In another embodiment, the prostate cancer is advanced prostate cancer. In another embodiment, the prostate cancer is castration resistant prostate cancer (CRPC). In another embodiment, the prostate cancer is metastatic castration resistant prostate cancer (mCRPC). In another embodiment, the prostate cancer is non-metastatic castration resistant prostate cancer (nmCRPC). In one embodiment, the nmCRPC is high-risk nmCRPC. In another embodiment, the SERM is selected from a group consisting of: tamoxifen, toremifene, raloxifene, clomifene, femarelle, ormeloxifene and lasofoxifene. In another embodiment, the SERM is tamoxifen. In another embodiment, the SERM is raloxifene. In another embodiment, the SERM is toremifene. In another embodiment, the SERM is ormeloxifene. In another embodiment, the subject had undergone orchidectomy. In another embodiment, the subject has failed Androgen Deprivation Therapy (ADT). In another embodiment, the subject has high or increasing Prostate specific antigen (PSA) levels. In another embodiment, administering of the compound reduces or ameliorates side effects associated with androgen deprivation therapy (ADT). In another embodiment, the method further provides palliative treatment of advanced prostate cancer. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment, the compound is administered at a dosage of 500 mg per day. In one embodiment, the free testosterone concentration is lowered below about 1.5 pg/mL. In another embodiment, the free testosterone concentration is lowered below about 1 pg/mL. In another embodiment, the free testosterone concentration is lowered below about 0.8 pg/mL. In another embodiment, the free testosterone concentration is lowered below about 0.6 pg/mL. In another embodiment, the free testosterone concentration is lowered below about 0.4 pg/mL. In another embodiment, the free testosterone concentration is lowered below about 0.2 pg/mL. In another embodiment, the free testosterone concentration is lowered below about 0.1 pg/mL In another embodiment, the free serum testosterone percent is lowered to levels below castration. In another embodiment, the free serum testosterone percent is lowered to levels below what has been observed with LHRH agonists or antagonists or surgical castration.

In one embodiment, this invention provides a method of lowering serum free testosterone levels and/or serum free testosterone percent (% FreeT) in a male subject suffering from prostate cancer comprising administering a therapeutically effective amount of estradiol, ethynyl estradiol, steroidal estrogen agonists, nonsteroidal estrogen agonist or combination thereof.

In one embodiment, this invention provides a method of secondary hormonal therapy that reduces serum PSA and serum free testosterone levels in a male subject suffering from castration resistant prostate cancer (CRPC) comprising administering a therapeutically effective amount of a compound of formula IA, I-XII or its isomer, pharmaceutical acceptable salt, pharmaceutical product, polymorph, hydrate or any combination thereof. In another embodiment, the castration is surgical castration. In another embodiment, the castration is chemical castration. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the method further treats, suppresses, reduces the incidence, reduces the severity, or inhibits new bone metastasis. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the method further treats, suppresses, reduces the incidence, reduces the severity, or inhibits new or worsening soft tissue metastasis (visceral and lymph nodes). In another embodiment, the subject has failed Androgen Deprivation Therapy (ADT). In another embodiment, the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing Prostate specific antigen (PSA) levels. In another embodiment, administering of the compound reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method of treating, suppressing, reducing the incidence, reducing the severity, or inhibiting skeletal related events (SRE) in a male subject suffering from castration resistant prostate cancer (CRPC) comprising administering a therapeutically effective amount of a compound of formula IA, I-XII or its isomer, pharmaceutical acceptable salt, pharmaceutical product, polymorph, hydrate or any combination thereof. In another embodiment, the castration is surgical castration. In another embodiment, the castration is chemical castration. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the method further treats, suppresses, reduces the incidence, reduces the severity, or inhibits new bone metastasis. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the method further treats, suppresses, reduces the incidence, reduces the severity, or inhibits new or worsening soft tissue metastasis (visceral and lymph nodes). In another embodiment, the subject has failed Androgen Deprivation Therapy (ADT). In another embodiment, the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing Prostate specific antigen (PSA) levels. In another embodiment, administering of the compound reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

The term "Skeletal Related Events (SREs)" refer to a composite endpoint which includes bone fractures, pathologic fracture, spinal cord compression, radiation or surgery to bone, new bone metastasis, bone loss, or a combination thereof.

In one embodiment, the skeletal-related events treated using the methods provided herein and/or utilizing the compositions provided herein, are fractures, which in one embodiment, are pathological fractures, non-traumatic fractures, vertebral fracture, non-vertebral fractures, morphometric fractures, or a combination thereof. In some embodiments, fractures may be simple, compound, transverse, greenstick, or comminuted fractures. In one embodiment, fractures may be to any bone in the body, which in one embodiment, is a fracture in any one or more bones of the arm, wrist, hand, finger, leg, ankle, foot, toe, hip, collar bone, or a combination thereof.

In another embodiment, the methods and/or compositions provided herein, are effective in treatment, prevention, suppression, inhibition or reduction of the risk of skeletal-related events such as pathologic fractures, spinal cord compression, hypercalcemia, bone-related pain, or their combination.

In another embodiment, the skeletal-related events sought to be treated using the methods provided herein and/or utilizing the compositions provided herein, comprise the necessity for bone surgery and/or bone radiation, which in some embodiments, is for the treatment of pain resulting in one embodiment from bone damage, or nerve compression. In another embodiment, the skeletal-related events sought to be treated using the methods provided herein and/or utilizing the compositions provided herein, comprise spinal cord compression, or the necessity for changes in antineoplastic therapy, including changes in hormonal therapy, in a subject. In some embodiments, skeletal-related events sought to be treated using the methods provided herein and/or utilizing the compositions provided herein, comprise treating, suppressing, preventing, reducing the incidence of, or delaying progression or severity of bone metastases, or bone loss. In one embodiment, bone loss may comprise osteoporosis, osteopenia, or a combination thereof. In one embodiment, skeletal-related events may comprise any combination of the embodiments listed herein.

In one embodiment, this invention provides a method of (i) reducing the levels of bone turnover markers in a male subject suffering from advanced prostate cancer, castration resistant prostate cancer (CRPC) or metastatic castration resistant prostate cancer (mCRPC) or non-metastatic castration resistant prostate cancer (nmCRPC) or high-risk nmCRPC; (ii) treating bone loss, osteoporosis or fractures in men on ADT suffering from advanced prostate cancer, castration resistant prostate cancer (CRPC) or metastatic castration resistant prostate cancer (mCRPC) or non-metastatic castration resistant prostate cancer (nmCRPC) or high-risk nmCRPC; or (iii) inhibiting or preventing bone loss, osteoporosis or fractures in men on ADT suffering from advanced prostate cancer, advanced prostate cancer at high risk for progressing to CRPC, castration resistant prostate cancer (CRPC) or metastatic castration resistant prostate cancer (mCRPC) or non-metastatic castration resistant prostate cancer (nmCRPC) or high-risk nmCRPC; comprising administering a therapeutically effective amount of a compound of formula IA, I-XII or its isomer, pharmaceutical acceptable salt, pharmaceutical product, polymorph, hydrate or any combination thereof. In another embodiment, the castration is surgical castration. In another embodiment, the castration is chemical castration. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the method further treats, suppresses, reduces the incidence, reduces the severity, or inhibits new bone metastasis. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the method further treats, suppresses, reduces the incidence, reduces the severity, or inhibits new or worsening soft tissue metastasis (visceral and lymph nodes). In another embodiment, the subject has failed Androgen Deprivation Therapy (ADT). In another embodiment, the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing Prostate specific antigen (PSA) levels. In another embodiment, administering of the compound reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is administered at a dosage of 40 mg per day. In another embodiment, the compound is administered at a dosage of 80 mg per day. In another embodiment, the compound is Compound IV. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment, the bone turnover markers are C-telopeptide (CTX) and/or bone specific alkaline phosphatase.

In one embodiment, this invention provides a method of treating, suppressing, reducing the incidence, reducing the severity, reducing the frequency, or inhibiting hot flashes in a male subject suffering from advanced prostate cancer or castration resistant prostate cancer (CRPC) comprising administering a therapeutically effective amount of a compound of formula IA, I-XII or its isomer, pharmaceutical acceptable salt, pharmaceutical product, polymorph, hydrate or any combination thereof. In another embodiment, the castration is surgical castration. In another embodiment, the castration is chemical castration. In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC.

In one embodiment, this invention provides a method of reducing estrogen deficiency related side effects (hot flash, bone loss, insulin resistance, body composition change, fat gain) in a male subject suffering from advanced prostate cancer or castration resistant prostate cancer comprising administering a compound of formula IA, I-XII or its isomer, pharmaceutical acceptable salt, pharmaceutical product, polymorph, hydrate or any combination thereof. In another embodiment, the subject further receives Androgen Deprivation Therapy (ADT). In another embodiment the subject further receives LHRH agonist or antagonist. In another embodiment the LHRH agonist is leuprolide acetate. In another embodiment, the castration is surgical castration. In another embodiment, the castration is chemical castration. In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC. In another embodiment, the men are surgically castrated men with advanced prostate cancer or castration resistant prostate cancer.

In another embodiment, the method further treats, suppresses, reduces the incidence, reduces the severity, or inhibits new bone metastasis. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the method further treats, suppresses, reduces the incidence, reduces the severity, or inhibits new or worsening soft tissue metastasis (visceral and lymph nodes). In another embodiment, the subject has failed Androgen Deprivation Therapy (ADT). In another embodiment, the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing Prostate specific antigen (PSA) levels. In another embodiment, administering of the compound reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method of reducing the levels of adrenal gland production of androgen precursors in a male subject suffering from castration resistant prostate cancer (CRPC) comprising administering a therapeutically effective amount of a compound of formula IA, I-XII or its isomer, pharmaceutical acceptable salt, pharmaceutical product, polymorph, hydrate or any combination thereof. In another embodiment, the castration is surgical castration. In another embodiment, the castration is chemical castration. In another embodiment, the CRPC is metastatic CRPC (mCRPC). In one embodiment, the CRPC is non-metastatic castration resistant prostate cancer (nm-CRPC). In one embodiment, the nmCRPC is high-risk nmCRPC. In another embodiment, the method further treats, suppresses, reduces the incidence, reduces the severity, or inhibits new bone metastasis. In another embodiment, the method further treats, suppresses, reduces the incidence, reduces the severity, or inhibits symptomatic bone fractures. In another embodiment, the method further increases radiographic progression free survival (rPFS) in subjects suffering from metastatic cancer. In another embodiment, the method further increases metastasis-free survival (MFS) in a subject suffering from non-metastatic cancer. In one embodiment, the method may be used for providing a secondary hormone therapy. Secondary hormonal therapy, may in one embodiment, result in increased metastasis-free survival, serum free testosterone reduction to castrate levels observed with orchiectomy or pro-estrogenic beneficial effects, or any combination thereof. In one embodiment, the method may be used for providing pro-estrogenic effects. In one embodiment, pro-estrogenic effects include prevention of symptomatic bone fractures, prevention of bone loss, promotion of bone formation, a decrease in bone turnover markers or resistance to bone metastasis, or any combination thereof. In one embodiment, the method may be used to provide a dual action, for example treating prostate cancer and preventing metastases. In another embodiment, the method further treats, suppresses, reduces the incidence, reduces the severity, or inhibits new or worsening soft tissue metastasis (visceral and lymph nodes). In another embodiment, the subject has failed Androgen Deprivation Therapy (ADT). In another embodiment, the subject further receives Androgen Deprivation Therapy (ADT). In another embodiment the subject further receives LHRH agonist or antagonist. In another embodiment the LHRH agonist is leuprolide acetate. In another embodiment, the subject had undergone orchidectomy. In another embodiment, the subject has high or increasing Prostate specific antigen (PSA) levels. In another embodiment, administering of the compound reduces or ameliorates side effects associated with androgen deprivation therapy (ADT). In another embodiment, the method further treats, suppresses, reduces the incidence, reduces the severity, or inhibits advanced prostate cancer. In another embodiment, the method further provides palliative treatment of advanced prostate cancer. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment, the androgen precursors are utilized by prostate cancer cells to produce testosterone or dihydrotestosterone (DHT). In another embodiment, the androgen precursors are Dehydroepiandrosterone Sulfate (DHEAS) and/or Dehydroepiandrosterone (DHEA).

In one embodiment "a subject suffering from castration resistant prostate cancer" refers to a subject which has been previously treated with androgen deprivation therapy (ADT), has responded to the ADT and currently has a serum PSA >2 ng/mL or >2 ng/mL and representing a 25% increase above the nadir achieved on the ADT. In another embodiment, the term refers to a subject which despite being maintained on Androgen Deprivation Therapy is diagnosed to have serum PSA progression. In another embodiment, the subject has a castrate level of serum total testosterone (<50 ng/dL). In another embodiment, the subject has a castrate level of serum total testosterone (<20 ng/dL). In another embodiment, the subject has rising serum PSA on two successive assessments at least 2 weeks apart. In another embodiment, the subject had been effectively treated with ADT. In another embodiment, the subject has a history of serum PSA response after initiation of ADT. In another embodiment, the subject has been treated with ADT and had an initial serum PSA response, but now has a serum PSA >2 ng/mL and a 25% increase above the nadir observed on ADT. In one embodiment, the CRPC is metastatic CRPC (mCRPC). In another embodiment, the CRPC is non-metastatic CRPC (nmCRPC). In one embodiment, the nmCRPC is high-risk nmCRPC.

The term "serum PSA response" refers to in one embodiment to at least 90% reduction in serum PSA value prior to the initiation of ADT, to <10 ng/mL OR undetectable level of serum PSA (<0.2 ng/mL) at any time, or in another embodiment to at least 50% decline from baseline in serum PSA, or in another embodiment to at least 90% decline from baseline in serum PSA, or in another embodiment to at least 30% decline from baseline in serum PSA, or in another embodiment to at least 10% decline from baseline in serum PSA.

The term "serum PSA progression" refers to in one embodiment, a 25% or greater increase in serum PSA and an absolute increase of 2 ng/ml or more from the nadir; or in another embodiment, to serum PSA >2 ng/mL, or >2 ng/mL and a 25% increase above the nadir after the initiation of androgen deprivation therapy (ADT).

In another embodiment the term "nadir" refers to the lowest PSA level while a patient is undergoing ADT.

In one embodiment, this invention provides a method of lowering total serum testosterone levels in a male subject comprising administering a therapeutically effective amount of a compound of formula IA, I-XII or its isomer, pharmaceutical acceptable salt, pharmaceutical product, polymorph, hydrate or any combination thereof. In another embodiment the male subject has prostate cancer. In another embodiment, the total serum testosterone is lowered below about 100 ng/dL. In another embodiment, the total serum testosterone is lowered below about 50 ng/dL. In another embodiment, the total serum testosterone concentration is lowered below about 25 ng/dL. In another embodiment, the total serum testosterone is lowered below about 20 ng/dL. In another embodiment, the total serum testosterone concentration is lowered below about 10 ng/dL. In another embodiment, the total serum testosterone concentration is lowered below about 5 ng/dL. In another embodiment, the total serum testosterone concentration is lowered below about 1 ng/dL.

In another embodiment, the subject suffers from castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method of lowering total serum testosterone levels in a male subject comprising administering a therapeutically effective amount of a compound of formula IA, I-XII or its isomer, pharmaceutical acceptable salt, pharmaceutical product, polymorph, hydrate or any combination thereof, wherein the lowering of total serum testosterone occurs by a reduction of serum luteinizing hormone (LH) levels. In another embodiment the male subject has prostate cancer. In another embodiment, the total serum testosterone is lowered below about 100 ng/dL. In another embodiment, the total serum testosterone is lowered below about 50 ng/dL. In another embodiment, the total serum testosterone concentration is lowered below about 25 ng/dL. In another embodiment, the total serum testosterone is lowered below about 20 ng/dL.

In another embodiment, the subject suffers from castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method of lowering free serum testosterone levels in a male subject comprising administering a therapeutically effective amount of a compound of formula IA, I-XII or its isomer, pharmaceutical acceptable salt, pharmaceutical product, polymorph, hydrate or any combination thereof, wherein the lowering of free serum testosterone occurs by a reduction of serum luteinizing hormone (LH) levels. In another embodiment, the subject is a prostate cancer patient. In another embodiment, the subject is a prostate cancer patient on ADT. In another embodiment, the subject is a prostate cancer patient on ADT with castrate levels of total T. In another embodiment, the subject is an advanced prostate cancer patient. In another embodiment, the subject is an advanced prostate cancer patient on ADT. In another embodiment, the subject is an advanced prostate cancer patient on ADT with castrate levels of total T. In another embodiment, the subject is a CRPC patient. In another embodiment, the subject is a mCRPC patient. In one embodiment, the subject is a non-metastatic castration resistant prostate cancer (nmCRPC) patient. In one embodiment, the nmCRPC is high-risk nmCRPC. In another embodiment, the subject is a CRPC patient maintained on ADT. In another embodiment, the subject is a CRPC patient maintained on ADT with castrate levels of total T. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In one embodiment, the free testosterone concentration is lowered below about 1.5 pg/mL. In another embodiment, the free testosterone concentration is lowered below about 1 pg/mL. In another embodiment, the free testosterone concentration is lowered below about 0.8 pg/mL. In another embodiment, the free testosterone concentration is lowered below about 0.6 pg/mL. In another embodiment, the free testosterone concentration is lowered below about 0.4 pg/mL. In another embodiment, the free testosterone concentration is lowered below about 0.2 pg/mL. In another embodiment, the free testosterone concentration is lowered below about 0.1 pg/mL In one embodiment, this invention provides a method of lowering total serum testosterone levels in a male subject comprising administering a therapeutically effective amount of a compound of formula IA, I-XII or its isomer, pharmaceutical acceptable salt, pharmaceutical product, polymorph, hydrate or any combination thereof, wherein the lowering of total serum testosterone is independent of a reduction of serum luteinizing hormone (LH) levels. In another embodiment the male subject has prostate cancer. In another embodiment, the total serum testosterone is lowered below about 100 ng/dL. In another embodiment, the total serum testosterone is lowered below about 50 ng/dL. In another embodiment, the total serum testosterone concentration is lowered below about 25 ng/dL. In another embodiment, the total serum testosterone is lowered below about 20 ng/dL.

In another embodiment, the subject suffers from castration resistant prostate cancer (CRPC). In another embodiment, the CRPC is metastatic CRPC (mCRPC). In another embodiment, the CRPC is a non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method of lowering free serum testosterone levels in a male subject comprising administering a therapeutically effective amount of a compound of formula IA, I-XII or its isomer, pharmaceutical acceptable salt, pharmaceutical product, polymorph, hydrate or any combination thereof, wherein the lowering of free serum testosterone levels is independent of a reduction of serum luteinizing hormone levels. In another embodiment, the subject is a prostate cancer patient. In another embodiment, the subject is a prostate cancer patient on ADT. In another embodiment, the subject is a prostate cancer patient on ADT with castrate levels of total T. In another embodiment, the subject is an advanced prostate cancer patient. In another embodiment, the subject is an advanced prostate cancer patient on ADT. In another embodiment, the subject is an advanced prostate cancer patient on ADT with castrate levels of total T. In another embodiment, the subject is a CRPC patient. In another embodiment, the subject is a CRPC patient maintained on ADT. In another embodiment, the subject is a CRPC patient maintained on ADT with castrate levels of total T. In another embodiment, the CRPC is metastatic CRPC (mCRPC). In another embodiment, the CRPC is mCRPC. In another embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment, the free testosterone concentration is lowered below about 1.5 pg/mL. In another embodiment, the free testosterone concentration is lowered below about 1.0 pg/mL. In another embodiment, the free testosterone concentration is lowered below about 0.8 pg/mL. In another embodiment, the free testosterone concentration is lowered below about 0.6 pg/mL. In another embodiment, the free testosterone concentration is lowered below about 0.4 pg/mL. In another embodiment, the free testosterone concentration is lowered below about 0.2 pg/mL. In another embodiment, the free testosterone concentration is lowered below about 0.1 pg/mL.

In one embodiment, this invention provides methods of lowering total serum testosterone, free serum testosterone levels or free serum testosterone percentage (% FreeT) in a male subject. In another embodiment, the subject is a prostate cancer patient. In another embodiment, the subject is a prostate cancer patient on ADT. In another embodiment, the subject is a prostate cancer patient on ADT with castrate levels of total T. In another embodiment, the subject is an advanced prostate cancer patient. In another embodiment, the subject is an advanced prostate cancer patient on ADT. In another embodiment, the subject is an advanced prostate cancer patient on ADT with castrate levels of total T. In another embodiment, the subject is a CRPC patient. In another embodiment, the subject is a mCRPC patient. In another embodiment, the subject is an nmCRPC patient. In one embodiment, the nmCRPC is high-risk nmCRPC. In another embodiment, the subject is a CRPC patient maintained on ADT. In another embodiment, the subject is a CRPC patient maintained on ADT with castrate levels of total T. In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

The term "free serum testosterone percentage (% FreeT)" refers to in one embodiment to the free serum testosterone level (pg/mL) divided by the total serum testosterone level (pg/mL) multiplied by a hundred [Free T (pg/mL)/Total T (pg/mL)*100]. In another embodiment, castration levels refer to free serum testosterone concentration that can be achieved with ADT. In another embodiment, the free testosterone concentration is lowered below about 1.5 pg/mL. In another embodiment, the free testosterone concentration is lowered below about 1.0 pg/mL. In another embodiment, the free testosterone concentration is lowered below about 0.8 pg/mL. In another embodiment, the free testosterone concentration is lowered below about 0.6 pg/mL. In another embodiment, the free testosterone concentration is lowered below about 0.4 pg/mL. In another embodiment, the free testosterone concentration is lowered below about 0.2 pg/mL. In another embodiment, the free testosterone concentration is lowered below about 0.1 pg/mL.

In one embodiment, the reduction in serum concentrations of testosterone is reversible and return to base line levels after treatment with the compounds of this invention.

In another embodiment, serum concentrations of testosterone are reversible after treatment with Compound IV according to FIG. 23 and Example 10.

In one embodiment, this invention provides methods of lowering total serum testosterone levels in a male subject comprising administering a therapeutically effective amount of a compound of formula IA, I-XII or its isomer, pharmaceutical acceptable salt, pharmaceutical product, polymorph, hydrate or any combination thereof. In another embodiment, the total serum testosterone is lowered below about 100 ng/dL. In another embodiment, the total serum testosterone is lowered below about 50 ng/dL. In another embodiment, the total serum testosterone is lowered below about 25 ng/dL. In another embodiment, the total serum testosterone is lowered below about 20 ng/dL.

In another embodiment, the total serum testosterone is lowered below about 75 ng/dL. In another embodiment, the total serum testosterone is lowered to about between 75 ng/dL-100 ng/dL. In another embodiment, the total serum testosterone is lowered to about between 50 ng/dL-75 ng/dL. In another embodiment, the total serum testosterone is lowered to about between 40 ng/dL-50 ng/dL. In another embodiment, the total serum testosterone is lowered below about 20 ng/dL. In another embodiment, the total serum testosterone concentration is lowered to about between 25 ng/dL-50 ng/dL. In another embodiment, the total serum testosterone is lowered to about 20 ng/dL-50 ng/dL. In another embodiment, the total serum testosterone is lowered to about between 40 ng/dL-60 ng/dL. In another embodiment, the total serum testosterone is lowered to about between 10 ng/dL-50 ng/dL. In another embodiment, the total serum testosterone is lowered to about between 10 ng/dL-25 ng/dL. In another embodiment, the total serum testosterone is lowered to about between 1 ng/dL-25 ng/dL. In another embodiment, the total serum testosterone is lowered to about between 1 ng/dL-10 ng/dL. In another embodiment, the total serum testosterone is lowered to about between 0.1 ng/dL-1 ng/dL. In another embodiment, the total serum testosterone is lowered to about between 0.1 ng/dL-10 ng/dL.

In another embodiment, the subject suffers from castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides methods of lowering serum free testosterone percent (% FreeT) in a male subject comprising administering a therapeutically effective amount of a compound of formula IA, I-XII or its isomer, pharmaceutical acceptable salt, pharmaceutical product, polymorph, hydrate or any combination thereof. In another embodiment, the free testosterone concentration is lowered below about 1.5 pg/mL. In another embodiment, the free testosterone concentration is lowered below about 1.0 pg/mL. In another embodiment, the free testosterone concentration is lowered below about 0.8 pg/mL. In another embodiment, the free testosterone concentration is lowered below about 0.6 pg/mL. In another embodiment, the free testosterone concentration is lowered below about 0.4 pg/mL. In another embodiment, the free testosterone concentration is lowered below about 0.2 pg/mL. In another embodiment, the free testosterone concentration is lowered below about 0.1 pg/mL. In another embodiment, the free testosterone is lowered to about between 1.0 pg/mL-1.5 pg/mL. In another embodiment, the free testosterone is lowered to about between 0.5 pg/mL-1.0 pg/mL. In another embodiment, the free testosterone is lowered to about between 0.2 pg/mL-0.8 pg/mL. In another embodiment, the free testosterone is lowered to about between 0.1 pg/mL-0.5 pg/mL. In another embodiment, the free testosterone is lowered to about between 0.1 pg/mL-1.5 pg/mL. In another embodiment, the subject suffers from castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

Testosterone can be measured as "free" (that is, bioavailable and unbound) or as "total" (including the percentage which is protein bound and unavailable) serum levels. In one embodiment, total serum testosterone comprises free testosterone and bound testosterone.

Men, without prostate cancer, older than 40 years demonstrate low testosterone levels having total testosterone level of less than 250 ng/dL (<8.7 nmol/L) or a free testosterone level of less than 0.75 ng/dL (<0.03 nmol/L). Methods of this invention provide a method of lowering serum free testosterone levels. In one embodiment, methods provided lower total serum testosterone. In another embodiment, methods provided lower free serum testosterone.

In one embodiment, the methods of this invention provides a method of lowering total serum and/or free testosterone levels independent from reduction of luteinizing hormone (LH) levels or by reduction of LH levels in a male subject having prostate cancer. In another embodiment changes in testosterone levels should be a reduction from the level prior to treatment. In another embodiment, the total serum testosterone level is lowered below 100 ng/dL. In another embodiment, the total serum testosterone is lowered below 50 ng/dL. In another embodiment, the total serum testosterone is lowered below 25 ng/dL. In another embodiment, the total serum testosterone is lowered below about 20 ng/dL. In another embodiment, the free testosterone level is lowered below 2 ng/dL. In another embodiment, the free testosterone concentration is lowered below about 1.5 pg/mL. In another embodiment, the free testosterone concentration is lowered below about 1.0 pg/mL. In another embodiment, the free testosterone concentration is lowered below about 0.8 pg/mL. In another embodiment, the free testosterone concentration is lowered below about 0.6 pg/mL. In another embodiment, the free testosterone concentration is lowered below about 0.4 pg/mL. In another embodiment, the free testosterone concentration is lowered below about 0.2 pg/mL. In another embodiment, the free testosterone concentration is lowered below about 0.1 pg/mL.

In another embodiment, the subject suffers from castration resistant prostate cancer (CRPC). In another embodiment, the CRPC is metastatic CRPC (mCRPC). In another embodiment, the subject suffers from non-metastatic CRPC (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

Methods of determining the free serum testosterone levels and total serum testosterone levels include monitoring the testosterone levels during the course of the treatment period by a blood test. Total testosterone is a combination of circulating testosterone bound to carrier proteins (albumin, SHBG, transcortin, transferrin) and the free/unbound hormone. Total testosterone levels may be affected by several factors including the level of protein in the blood that transports the hormone in the body, age, obesity and interferences associated with commonly used test methods.

Methods available to measure free testosterone (FT) can be complex (equilibrium dialysis and calculated free testosterone (CFT)) or simple (the commercial FT kit "Coat-A-Count") using an analog tracer. In another embodiment the measurement of total testosterone and free testosterone serum levels can be achieved by simultaneous measurement of total testosterone and SHBG (e.g., Irma-Count, DPC) and then a calculated free testosterone (CFT). In another embodiment the measurement of total testosterone and free testosterone is according to the knowledge of one skilled in the art.

In one embodiment, this invention provides a method of lowering total serum testosterone levels, free serum testosterone levels or free serum testosterone percentage (% FreeT) in a male subject comprising administering a therapeutically effective amount of a combination of one or more other forms of ADT and a compound of formula IA, I-XII or its isomer, pharmaceutical acceptable salt, pharmaceutical product, polymorph, hydrate or any combination thereof. In another embodiment, lowering of total or free serum testosterone occurs by a reduction of serum luteinizing hormone (LH) level. In another embodiment, lowering total or free serum testosterone levels is independent of a reduction of serum luteinizing hormone levels. In another embodiment, the subject suffers from castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject has failed Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method of lowering total serum testosterone levels, free serum testosterone levels or free serum testosterone percentage (% FreeT) in a male subject comprising administering a therapeutically effective amount of a combination of one or more Selective Estrogen Receptor Modulator (SERM) and a compound of formula IA, I-XII or its isomer, pharmaceutical acceptable salt, pharmaceutical product, polymorph, hydrate or any combination thereof. In another embodiment, the subject suffers from advanced prostate cancer. In another embodiment, the subject suffers from castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the SERM is selected from a group consisting of: tamoxifen, toremifene, raloxifene, clomifene, femarelle, ormeloxifene and lasofoxifene. In another embodiment, the SERM is tamoxifen. In another embodiment, the SERM is raloxifene. In another embodiment, the SERM is toremifene. In another embodiment, the SERM is ormeloxifene. In another embodiment, the subject has failed Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a combination of one or more other forms of ADT and a compound of formula IA, I-XII or its isomer, pharmaceutical acceptable salt, pharmaceutical product, polymorph, hydrate or any combination thereof. In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method of lowering serum PSA levels in a male subject suffering from castration resistant prostate cancer (CRPC) comprising administering a therapeutically effective amount of a combination of one or more other forms of ADT and a compound of formula IA, I-XII or its isomer, pharmaceutical acceptable salt, pharmaceutical product, polymorph, hydrate or any combination thereof. In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method of reducing free testosterone levels, the percentage of serum free testosterone and/or serum PSA in a male subject suffering from advanced prostate cancer comprising administering a therapeutically effective amount of a combination of one or more other forms of ADT and a compound of formula IA, I-XII or its isomer, pharmaceutical acceptable salt, pharmaceutical product, polymorph, hydrate or any combination thereof. In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

The methods of this invention comprise administering a combination of Estrogen Receptor ligand and a compound of this invention. In one embodiment, Estrogen Receptor ligands include but not limited to Selective Estrogen Receptor Modulators (SERMs). Examples of SERM include, but are not limited to: tamoxifen, toremifene, Raloxifene, clomifene, femarelle, ormeloxifene and lasofoxifene.

The methods of this invention comprise administering a combination of other forms of ADT and a compound of this invention. In one embodiment, other forms of ADT include a LHRH agonist. In another embodiment the LHRH agonist includes leuprolide acetate (Lupron®) (U.S. Pat. No. 5,480,656; U.S. Pat. Nos. 5,575,987; 5,631,020; 5,643,607; 5,716,640; 5,814,342; 6,036,976 which are all incorporated by reference herein) or goserelin acetate (Zoladex®) (U.S. Pat. Nos. 7,118,552; 7,220,247; 7,500,964 which are all incorporated by reference herein). In one embodiment, other forms of ADT include an LHRH antagonist. In another embodiment, the LHRH antagonist includes degarelix. In one embodiment, other forms of ADT include anti-androgens. In another embodiment the anti-androgens include bicalutamide, flutamide, finasteride, dutasteride, enzalutamide, nilutamide, chlormadinone, or any combination thereof. In one embodiment, other forms of ADT include bilateral orchidectomy.

In one embodiment, the methods of this invention comprise administering a therapeutically effective amount of an anti-androgen and a compound of this invention. In one embodiment, the methods of this invention comprise administering a therapeutically effective amount of an LHRH agonist and a compound of this invention. In one embodiment, the methods of this invention comprise administering a therapeutically effective amount of an anti-androgen, LHRH agonist and a compound of this invention. In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides a method for lowering total serum testosterone levels, free serum testosterone levels and/or free serum testosterone percentage (% FreeT) by reduction of luteinizing hormone (LH) levels or independent of reduction of luteinizing hormone levels in a male subject having prostate cancer for the purpose of producing androgen deprivation therapy (ADT) comprising administering a therapeutically effective amount of a compound of formula IA, I-XII. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment, the prostate cancer is castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT).

In another embodiment, this invention provides a method for androgen deprivation therapy (ADT) in a subject, comprising administering a therapeutically effective amount of a compound of formula IA, I-XII or its isomer, pharmaceutical acceptable salt, pharmaceutical product, polymorph, hydrate or any combination thereof. In another embodiment, said subject has prostate cancer. In another embodiment, the prostate cancer is castration resistant prostate cancer (CRPC). In another embodiment, the CRPC is metastatic CRPC (mCRPC). In another embodiment, the CRPC is non-metastatic castration resistant prostate cancer (nmCRPC). In one embodiment, the nmCRPC is high-risk nmCRPC. In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment, the subject has failed Androgen Deprivation Therapy (ADT). In another embodiment, the subject further receives Androgen Deprivation Therapy (ADT).

In another embodiment, ADT is used for treating prostate cancer, for delaying the progression of prostate cancer, or for preventing and/or treating the recurrence of prostate cancer. In another embodiment, the prostate cancer is castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC.

In one embodiment, this invention provides a method of treating prostate cancer or delaying the progression of prostate cancer comprising administering a compound of this invention. In one embodiment, this invention provides a method of preventing and/or treating the recurrence of prostate cancer comprising administering a compound of this invention. In another embodiment, the prostate cancer is castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC.

In one embodiment, this invention provides a method of increasing the survival of a subject having prostate cancer, advanced prostate cancer, castration resistant prostate cancer or metastatic castration resistant prostate cancer or non-metastatic castration resistant prostate cancer or high-risk non metastatic castration resistant prostate cancer, comprising administering a compound of this invention. In another embodiment, administering a compound of this invention in combination with LHRH analogs, reversible anti-androgens (such as bicalutamide, flutamide, or enzalutamide), antiestrogens, anticancer drugs, 5-alpha reductase inhibitors, aromatase inhibitors, progestins, selective androgen receptor modulators (SARMs) or agents acting through other nuclear hormone receptors. In another embodiment, the subject has failed Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the present invention provides a method of treating prostate cancer and reducing of total serum testosterone and/or free serum testosterone levels, by reducing LH levels or independent of reduction of LH levels, comprising administering a compound of formula IA, I-XII. In another embodiment, administering Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In another embodiment, the prostate cancer is castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC.

Androgen deprivation therapy not only reduces testosterone, but estrogen levels are also lower as estrogen is derived from the aromatization of testosterone. Androgen deprivation therapy-induced estrogen deficiency causes significant side effects which include hot flashes, gynecomastia and mastalgia, bone loss, decreases in bone quality and strength, osteoporosis, osteopenia, and life-threatening fractures, adverse lipid changes and higher cardiovascular disease and myocardial infarction, loss of libido, impotence, loss of muscle mass (sarcopenia), fatigue, cognitive dysfunction, and depression and other mood changes.

In other embodiments, the present invention provides a method of treating any disease, disorder, or symptom associated with ADT. In other embodiments, the present invention provides a method of treating any disease, disorder, or symptom associated with testosterone deprivation. Each disease, disorder, or symptom represents a separate embodiment of the present invention.

In one embodiment, this invention provides a method of lowering total serum testosterone levels, free serum testosterone levels and/or free serum testosterone percentage (% FreeT) in a male subject comprising administering a therapeutically effective amount of a compound of formulas IA, I-XII or its isomer, pharmaceutical acceptable salt, pharmaceutical product, polymorph, hydrate or any combination thereof, wherein said administering said compounds of formulas IA, I-XII or its isomer, pharmaceutical acceptable salt, pharmaceutical product, polymorph, hydrate or any combination thereof, treats, prevents, suppresses, reduces the incidence or inhibits side effects associated with androgen deprivation therapy (ADT) from occurring, wherein said subject has prostate cancer. In another embodiment the lowering of the total or free serum testosterone levels is by reducing LH levels or is independent of reduction of LH levels. In another embodiment, the subject suffers from castration resistant prostate cancer (CRPC). In another embodiment, the CRPC is metastatic CRPC (mCRPC). In another embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, administering the compounds of this invention suppresses, reduces the incidence, inhibits or treats typical side effects associated with traditional androgen deprivation therapy (ADT) from occurring. In another embodiment, the subject has prostate cancer. In another embodiment, the prostate cancer is castration resistant prostate cancer (CRPC). In another embodiment, the CRPC is metastatic CRPC (mCRPC). In another embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

Such prevention and/or reduction of side effects are relative to placebo or control group. In one embodiment, the typical side effects associated with traditional androgen deprivation therapy (ADT) include hot flashes, gynecomastia, decreased bone mineral density and increased bone fracture. In another embodiment, administering the compounds of this invention prevents hot flashes from occurring as would be found using traditional forms of androgen deprivation therapy (ADT). In another embodiment, administering the compounds of this invention prevents gynecomastia from occurring as would be found using traditional forms of androgen deprivation therapy (ADT). In another embodiment, administering the compounds of this invention prevents decreased bone mineral density (BMD) from occurring as would be found using traditional forms of androgen deprivation therapy (ADT). In another embodiment, administering the compounds of this invention prevents increased bone fracture from occurring as would be found using traditional forms of androgen deprivation therapy (ADT). In another embodiment, bone fracture refers to pathological fracture, non-traumatic fracture, vertebral fracture, non-vertebral fracture, new morphometric fracture, clinical fracture or a combination thereof.

In one embodiment, administering the compounds of this invention lowers total serum testosterone without causing typical side effects associated with traditional androgen deprivation therapy (ADT) from occurring. In another embodiment, the subject has prostate cancer. In yet another embodiment, the subject has advanced prostate cancer. In another embodiment, the subject has castration resistant prostate cancer (CRPC). In another embodiment, the CRPC is metastatic CRPC (mCRPC). In another embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the typical side effects associated with traditional androgen deprivation therapy (ADT) include hot flashes, gynecomastia, decreased bone mineral density and increased bone fracture. In another embodiment, the typical side effect associated with traditional ADT includes increased body fat. In another embodiment, administering the compounds of this invention reduces or ameliorates hot flashes to occur as would be found using traditional forms of androgen deprivation therapy (ADT). In another embodiment, administering the compounds of this invention reduces or ameliorates gynecomastia to occur as would be found using traditional forms of androgen deprivation therapy (ADT). In another embodiment, administering the compounds of this invention reduces or ameliorates decreased bone mineral density (BMD) to occur as would be found using traditional forms of androgen deprivation therapy (ADT). In another embodiment, administering the compounds of this invention reduces or ameliorates increased bone fracture to occur as would be found using traditional forms of androgen deprivation therapy (ADT). In another embodiment, increased bone fracture is pathological fractures, non-traumatic fractures, vertebral fracture, non-vertebral fractures, new morphometric fractures, clinical fracture or a combination thereof. In yet another embodiment, administering the compounds of this invention reduces or ameliorates increased body fat to occur as would be found using traditional forms of androgen deprivation therapy (ADT). In another embodiment, the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, administering the compounds of this invention lowers free testosterone levels without causing typical side effects associated with traditional androgen deprivation therapy (ADT) from occurring. In another embodiment, the subject has prostate cancer. In yet another embodiment, the subject has advanced prostate cancer. In another embodiment, the subject has castration resistant prostate cancer (CRPC). In another embodiment, the CRPC is metastatic CRPC (mCRPC). In another embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, administering the compounds of this invention lowers free testosterone percentage (% FreeT) without causing typical side effects associated with traditional androgen deprivation therapy (ADT) from occurring. In another embodiment, the subject has prostate cancer. In yet another embodiment, the subject has advanced prostate cancer. In another embodiment, the subject has castration resistant prostate cancer (CRPC). In another embodiment, the CRPC is metastatic CRPC (mCRPC). In another embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the subject further receives Androgen Deprivation Therapy (ADT). In another embodiment the compound is Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the term "hot flashes" refers to sudden feeling of heat in the upper part or all of the body, face and neck flush, red blotches appearing on the chest, back and arms, heavy sweating, cold shivering, etc.

In one embodiment, the term "gynecomastia" refers to a benign enlargement of the male breast resulting from a proliferation of the glandular component of the breast, which may or may not be associated with pain. Gynecomastia is defined clinically by the presence of a rubbery or firm mass extending concentrically from the nipples. The condition known as pseudogynecomastia, or lipomastia, is characterized by fat deposition without glandular proliferation. Although gynecomastia is usually bilateral, it can be unilateral.

In one embodiment, the methods of this invention are directed to treating men with prostate cancer or advanced prostate cancer or castration resistant prostate cancer (CRPC) or metastatic castration resistant prostate cancer (mCRPC) or non-metastatic castration resistant prostate cancer (nmCRPC) or high-risk nmCRPC, by reduction of testosterone without also causing bone loss, symptomatic fractures and hot flashes. In one embodiment, the methods of this invention are directed to treating men with prostate cancer or advanced prostate cancer or castration resistant prostate cancer (CRPC) or metastatic castration resistant prostate cancer (mCRPC) or non-metastatic castration resistant prostate cancer (nmCRPC) or high-risk nmCRPC, without also causing bone loss, symptomatic fractures, gynecomastia and hot flashes.

Compound IV does not increase proliferation of prostate epithelial cancer cells in vitro. Mechanistically, Compound IV offers several key advantages over existing therapies such as gonadotropin releasing hormone (GnRH) agonists and GnRH antagonists. Compound IV is specific for the estrogen receptor, and is orally bioavailable in rats, dogs, monkeys and man. In contrast to GnRH agonists and GnRH antagonists which cause hot flashes and significant bone loss and increase the risk of fractures, Compound IV attenuates morphine withdrawal-induced hot flashes (Example 14) in rats and fully maintains trabecular bone mass and bone mineral density in the distal femur of rats even at doses which maximally suppress LH and serum testosterone. (Example 11)

In another embodiment, the methods of this invention make use of compounds IA, I-XII, wherein the compounds have the potential to reduce testosterone, a primary stimulus for prostate cancer, without also causing certain side effects such as bone loss, symptomatic fractures and hot flashes which are common with current androgen deprivation therapies (ADT) for prostate cancer.

In another embodiment, Table 8 (Example 11) hereinbelow demonstrate reduction of testosterone without also causing bone loss by administering Compound IV.

In one embodiment, the methods of this invention are directed to reduction of testosterone levels which further treats advanced prostate cancer by administering a compound of formula IA, I-XII. In another embodiment, by administering Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the methods of this invention are directed to reduction of testosterone levels which further treats castration resistant prostate cancer by administering a compound of formulas IA, I-XII. In another embodiment, by administering Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In one embodiment the castration resistant prostate cancer is mCRPC. In another embodiment, the castration resistant prostate cancer is nmCRPC. In another embodiment, the castration resistant prostate cancer is high-risk nmCRPC.

In one embodiment, the methods of this invention are directed to reduction of testosterone levels which further treats metastatic castration resistant prostate cancer (mCRPC) by administering a compound of formulas IA, I-XII. In another embodiment, by administering Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the methods of this invention are directed to reduction of testosterone levels which further treats non-metastatic castration resistant prostate cancer (nmCRPC) by administering a compound of formulas IA, I-XII. In another embodiment, by administering Compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day. In one embodiment, the nmCRPC is high-risk nmCRPC.

In one embodiment, the methods of this invention are directed to reduction of testosterone levels which further suppresses, reduces the incidence, reduces the severity, or inhibits advanced prostate cancer by administering a compound of formulas IA, I-XII. In another embodiment, the methods of this invention are directed to reduction of testosterone levels which further suppresses, reduces the incidence, reduces the severity, or inhibits advanced prostate cancer by administering compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the methods of this invention are directed to reduction of testosterone levels which further increases the radiographic progression free survival (rPFS) in a subject suffering from metastatic CRPC by administering a compound of formulas IA, I-XII. In another embodiment, the methods of this invention are directed to reduction of testosterone levels which further increases the radiographic progression free survival (rPFS) in a subject suffering from metastatic CRPC by administering compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the methods of this invention are directed to reduction of testosterone levels which further increases the metastasis free survival (MFS) in a subject suffering from non-metastatic CRPC by administering a compound of formulas IA, I-XII. In another embodiment, the methods of this invention are directed to reduction of testosterone levels which further increases the metastasis-free survival (MFS) in a subject suffering from non-metastatic CRPC by administering compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the methods of this invention are directed to reduction of testosterone levels which further results in increased metastasis-free survival, serum free testosterone reduction to castrate levels observed with orchiectomy or pro-estrogenic beneficial effects, or any combination thereof, in a subject suffering from metastatic CRPC by administering a compound of formulas IA, I-XII. In another embodiment, the methods of this invention are directed to reduction of testosterone levels which further result in increased metastasis-free survival, serum free testosterone reduction to castrate levels observed with orchiectomy or pro-estrogenic beneficial effects, or any combination thereof, in a subject suffering from metastatic CRPC by administering compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the methods of this invention provide a dual action treating prostate cancer and preventing metastases, in a subject suffering from metastatic CRPC by administering a compound of formulas IA, I-XII. In another embodiment, the methods of this invention provide a dual action treating prostate cancer and preventing metastases, in a subject suffering from metastatic CRPC by administering compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the methods of this invention are directed to reduction of testosterone levels which further provides palliative treatment of advanced prostate cancer, CRPC or mCRPC or nmCRPC or high-risk nmCRPC by administering a compound of formulas IA, I-XII. In another embodiment, the methods of this invention are directed to reduction of testosterone levels which further provides palliative treatment of advanced prostate cancer by administering compound IV. In another embodiment, the compound is administered at a dosage of 40 mg per day. In another embodiment, the compound is administered at a dosage of 80 mg per day. In another embodiment, the compound is administered at a dosage of 125 mg per day. In another embodiment, the compound is administered at a dosage of 250 mg per day. In another embodiment, the compound is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the methods of this invention are directed to treating advanced prostate cancer. In another embodiment, the methods of this invention are directed to suppressing, reducing the incidence, reducing the severity, or inhibiting advanced prostate cancer. In one embodiment, the methods of this invention are directed to palliative treatment of advanced prostate cancer. In another embodiment, this invention is directed to suppressing advanced prostate cancer. In another embodiment, this invention is directed to reducing the incidence of advanced prostate cancer. In another embodiment, this invention is directed to reducing the severity of advanced prostate cancer. In another embodiment, this invention is directed to inhibiting advanced prostate cancer comprising administering a compound of this invention.

In one embodiment, the methods of this invention are directed to treating castration resistant prostate cancer. In one embodiment, the methods of this invention are directed to suppressing, reducing the incidence, reducing the severity, or inhibiting castration resistant prostate cancer. In one embodiment, the methods of this invention are directed to palliative treatment of castration resistant prostate cancer. In another embodiment, this invention is directed to suppressing castration resistant prostate cancer. In another embodiment, this invention is directed to reducing the incidence of castration resistant prostate cancer. In another embodiment, this invention is directed to reducing the severity of castration resistant prostate cancer. In another embodiment, this invention is directed to inhibiting castration resistant prostate cancer. In another embodiment, this invention is directed to increase the survival of a subject with castration resistant prostate cancer. In one embodiment, the CRPC is mCRPC. In another embodiment, the CRPC is nmCRPC. In another embodiment, the nmCRPC is high-risk nmCRPC. In another embodiment, the methods of this invention make use of a compound of formulas IA, I-XII. In another embodiment, the methods of this invention make use of a compound IV. In another embodiment, the methods of this invention make use of a compound of formulas IA, I-XII in combination with LHRH agonist. In another embodiment, the methods of this invention make use of compound IV in combination with LHRH agonist. In another embodiment, the methods of this invention make use of compound IV in combination with leuprolide acetate (Lupron®). In another embodiment, the methods of this invention make use of a compound of formulas IA, I-XII in combination with leuprolide acetate (Lupron®). In another embodiment, the methods of this invention make use of a compound of formulas IA, I-XII in combination with LHRH antagonist. In another embodiment, the methods of this invention make use of compound IV in combination with LHRH antagonist. In another embodiment, the methods of this invention make use of compound IV in combination with degarelix. In another embodiment, the methods of this invention make use of a compound of formulas IA, I-XII in combination with degarelix. In another embodiment, the methods of this invention make use of a compound of formulas IA, I-XII in combination with an anti-androgen. In another embodiment, the methods of this invention make use of compound IV in combination with an anti-androgen.

In one embodiment, the methods of this invention are directed to treating metastatic castration resistant prostate cancer (mCRPC). In one embodiment, the methods of this invention are directed to suppressing, reducing the incidence, reducing the severity, or inhibiting metastatic castration resistant prostate cancer (mCRPC). In one embodiment, the methods of this invention are directed to palliative treatment of metastatic castration resistant prostate cancer (mCRPC). In another embodiment, this invention is directed to suppressing metastatic castration resistant prostate cancer (mCRPC). In another embodiment, this invention is directed to reducing the incidence of metastatic castration resistant prostate cancer (mCRPC). In another embodiment, this invention is directed to reducing the severity of metastatic castration resistant prostate cancer (mCRPC). In another embodiment, this invention is directed to inhibiting metastatic castration resistant prostate cancer (mCRPC). In another embodiment, this invention is directed to increase the survival of a subject with metastatic castration resistant prostate cancer (mCRPC). In another embodiment, this invention is directed to increase radiographic progression free survival (rPFS) of a subject with metastatic castration resistant prostate cancer (mCRPC). In another embodiment, the methods of this invention make use of a compound of formulas IA, I-XII. In another embodiment, the methods of this invention make use of a compound IV. In another embodiment, the methods of this invention make use of a compound of formulas IA, I-XII in combination with LHRH agonist. In another embodiment, the methods of this invention make use of compound IV in combination with LHRH agonist. In another embodiment, the methods of this invention make use of compound IV in combination with leuprolide acetate (Lupron®). In another embodiment, the methods of this invention make use of a compound of formulas IA, I-XII in combination with leuprolide acetate (Lupron®). In another embodiment, the methods of this invention make use of a compound of formulas IA, I-XII in combination with LHRH antagonist. In another embodiment, the methods of this invention make use of compound IV in combination with LHRH antagonist. In another embodiment, the methods of this invention make use of compound IV in combination with degarelix. In another embodiment, the methods of this invention make use of a compound of formulas IA, I-XII in combination with degarelix. In another embodiment, the methods of this invention make use of a compound of formulas IA, I-XII in combination with an anti-androgen. In another embodiment, the methods of this invention make use of compound IV in combination with an anti-androgen. In one embodiment, the methods of this invention are directed to treating non-metastatic castration resistant prostate cancer (nmCRPC). In one embodiment, the methods of this invention are directed to suppressing, reducing the incidence, reducing the severity, or inhibiting non-metastatic castration resistant prostate cancer (nmCRPC). In one embodiment, the methods of this invention are directed to palliative treatment of non-metastatic castration resistant prostate cancer (nmCRPC). In another embodiment, this invention is directed to suppressing non-metastatic castration resistant prostate cancer (nmCRPC). In another embodiment, this invention is directed to reducing the incidence of non-metastatic castration resistant prostate cancer (nmCRPC). In another embodiment, this invention is directed to reducing the severity of non-metastatic castration resistant prostate cancer (nmCRPC). In another embodiment, this invention is directed to inhibiting non-metastatic castration resistant prostate cancer (nmCRPC). In another embodiment, this invention is directed to increase the survival of a subject with non-metastatic castration resistant prostate cancer (nmCRPC). In another embodiment, this invention is directed to increase metastasis-free survival (MFS) of a subject with non-metastatic castration resistant prostate cancer (nmCRPC). In one embodiment, the nmCRPC is high-risk nmCRPC. In another embodiment, the methods of this invention make use of a compound of formulas IA, I-XII. In another embodiment, the methods of this invention make use of a compound IV. In another embodiment, the methods of this invention make use of a compound of formulas IA, I-XII in combination with LHRH agonist. In another embodiment, the methods of this invention make use of compound IV in combination with LHRH agonist. In another embodiment, the methods of this invention make use of compound IV in combination with leuprolide acetate (Lupron®). In another embodiment, the methods of this invention make use of a compound of formulas IA, I-XII in combination with leuprolide acetate (Lupron®). In another embodiment, the methods of this invention make use of a compound of formulas IA, I-XII in combination with LHRH antagonist. In another embodiment, the methods of this invention make use of compound IV in combination with LHRH antagonist. In another embodiment, the methods of this invention make use of compound IV in combination with degarelix. In another embodiment, the methods of this invention make use of a compound of formulas IA, I-XII in combination with degarelix. In another embodiment, the methods of this invention make use of a compound of formulas IA, I-XII in combination with an anti-androgen. In another embodiment, the methods of this invention make use of compound IV in combination with an anti-androgen.

In another embodiment, this invention is directed to increase the survival of a subject with advanced prostate cancer, CRPC, mCRPC, nmCRPC or high-risk nmCRPC. In another embodiment, the methods of this invention make use of a compound of formulas IA, I-XII. In another embodiment, the methods of this invention make use of a compound of formulas IA, I-XII in combination with LHRH agonist. In another embodiment, the methods of this invention make use of a compound of formulas IA, I-XII in combination with leuprolide acetate (Lupron®). In another embodiment, the methods of this invention make use of a compound of formulas IA, I-XII in combination with LHRH antagonist. In another embodiment, the methods of this invention make use of compound IV in combination with LHRH antagonist. In another embodiment, the methods of this invention make use of compound IV in combination with degarelix. In another embodiment, the methods of this invention make use of a compound of formulas IA, I-XII in combination with degarelix. In another embodiment, the methods of this invention make use of a compound of formulas IA, I-XII in combination with an anti-androgen. In another embodiment, the methods of this invention make use of compound IV in combination with an anti-androgen.

In another embodiment, this invention is directed to increase the survival of a subject with advanced prostate cancer, CRPC, mCRPC, nmCRPC or high-risk nmCRPC. In another embodiment, the methods of this invention make use of compound IV. In another embodiment, the methods of this invention make use of compound IV in combination with LHRH agonist. In another embodiment, the methods of this invention make use of compound IV in combination with leuprolide acetate (Lupron®). In another embodiment, the methods of this invention make use of compound IV in combination with LHRH antagonist. In another embodiment, the methods of this invention make use of compound IV in combination with degarelix.

The term "advanced prostate cancer" refers to metastatic cancer having originated in the prostate, and having widely metastasized to beyond the prostate such as the surrounding tissues to include the seminal vesicles the pelvic lymph nodes or bone, or to other parts of the body. Prostate cancer pathologies are graded with a Gleason grading from 1 to 5 in order of increasing malignancy. In another embodiment, patients with significant risk of progressive disease and/or death from prostate cancer should be included in the definition and that any patient with cancer outside the prostate capsule with disease stages as low as IIB clearly has "advanced" disease.

Men with advanced prostate cancer often receive treatment to block the production of androgens, which are male sex hormones that may help prostate tumors grow. However, prostate cancers that initially respond to anti-androgen therapy eventually develop the ability to grow without androgens. Such cancers are often referred to as hormone refractory, androgen independent, or castration resistant.

In one embodiment, the advanced prostate cancer is castration resistant prostate cancer.

The term "castration resistant prostate cancer" (CRPC) refers to advanced prostate cancer that is worsening or progressing while the patient remains on ADT or other therapies to reduce testosterone, or prostate cancer which is considered hormone refractory, hormone naïve, androgen independent or chemical or surgical castration resistant.

In another embodiment, castration resistant prostate cancer (CRPC) is an advanced prostate cancer which developed despite ongoing ADT and/or surgical castration. In another embodiment, ADT refers to treatment consisting leuprolide acetate (Lupron®).

In one embodiment, castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix), antiandrogens (e.g., bicalutamide, flutamide, enzalutamide, ketoconazole, aminoglutethamide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa®), Cabozantinib (Comtriq™, also known as XL184)) or other prostate cancer therapies (e.g., vaccines (sipuleucel-T (Provenge®), GVAX, etc.), herbal (PC-SPES) and lyase inhibitor (abiraterone)) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition. In another embodiment, castration resistant prostate cancer is defined as hormone naïve prostate cancer.

Many early prostate cancers require androgens for growth, but advanced prostate cancers are often androgen-independent, or hormone naïve. In men with castration resistant prostate cancer, the tumor cells may have the ability to grow in the absence of androgens (hormones that promote the development and maintenance of male sex characteristics).

In one embodiment, the term "androgen deprivation therapy" (ADT) or "traditional androgen deprivation therapy" is directed to orchiectomy (surgical castration) wherein the surgeon removes the testicles. In another embodiment, the term "androgen deprivation therapy" or "traditional androgen deprivation therapy" is directed to administering luteinizing hormone-releasing hormone (LHRH) analogs: These drugs lower the amount of testosterone made by the testicles. Examples of LHRH analogs available in the United States include leuprolide (Lupron®, Viadur®, Eligard®), goserelin (Zoladex®), triptorelin (Trelstar®), and histrelin (Vantas®). In another embodiment, the term "androgen deprivation therapy" or "traditional androgen deprivation therapy" is directed to administering anti-androgens: Anti-androgens block the body's ability to use any androgens. Even after orchiectomy or during treatment with LHRH analogs, a small amount of androgens is still made by the adrenal glands. Examples of anti-androgens drugs include enzalutamide, flutamide (Eulexin®), bicalutamide (Casodex®), and nilutamide (Nilandron®). In another embodiment, the term "androgen deprivation therapy" or "traditional androgen deprivation therapy" is directed to administering luteinizing hormone-releasing hormone (LHRH) antagonists such as abarelix (Plenaxis®) or degarelix (Firmagon®) (approved for use by the FDA in 2008 to treat advanced prostate cancer). In another embodiment, the term "androgen deprivation therapy" or "traditional androgen deprivation therapy" is directed to administering 5α-reductase inhibitors such as finasteride (Proscar®) and dutasteride (Avodart®): 5α-reductase inhibitors block the body's ability to convert testosterone to the more active androgen, 5α-dihydrotestosterone (DHT). In another embodiment, the term "androgen deprivation therapy" or "traditional androgen deprivation therapy" is directed to administering inhibitors of testosterone biosynthesis such as ketoconazole (Nizoral®). In another embodiment, the term "androgen deprivation therapy" or "traditional androgen deprivation therapy" is directed to administering estrogens such as diethylstilbestrol or 17β-estradiol. In another embodiment, the term "androgen deprivation therapy" or "traditional androgen deprivation therapy" is directed to administering 17α-hydroxylase/C17, 20 lyase (CYP17A1) inhibitors such as abiraterone (Zytiga®).

In one embodiment, the methods of this invention are directed to treating, suppressing, reducing the incidence, reducing the severity, inhibiting, providing palliative care, or increasing the survival of a subject suffering from prostate cancer. In one embodiment, the methods of this invention are directed to methods of treating, suppressing, reducing the incidence, reducing the severity, inhibiting, providing palliative care, or increasing the survival of advanced prostate cancer in a subject. In one embodiment, the methods of this invention are directed to treating, suppressing, reducing the incidence, reducing the severity, inhibiting, providing palliative care, or increasing the survival of a subject suffering from castration resistant prostate cancer. In one embodiment, the methods of this invention are directed to treating, suppressing, reducing the incidence, reducing the severity, inhibiting, providing palliative care, or increasing the survival of a subject suffering from metastatic castration resistant prostate cancer (mCRPC). In one embodiment, the methods of this invention are directed to treating, suppressing, reducing the incidence, reducing the severity, inhibiting, providing palliative care, or increasing the survival of a subject suffering from non-metastatic castration resistant prostate cancer (nmCRPC). In one embodiment, the nmCRPC is high-risk nmCRPC. In another embodiment, the subject has high or increasing prostate specific antigen (PSA) levels.

In one embodiment, levels of prostate specific antigen (PSA) considered normal are age dependent. In one embodiment, levels of prostate specific antigen (PSA) considered normal are dependent on the size of a male subject's prostate. In one embodiment, PSA levels in the range between 2.5-10 ng/mL are considered "borderline high". In another embodiment, PSA levels above 10 ng/mL are considered "high".

In one embodiment, the rate of change or "PSA velocity" is high. In one embodiment, a rate of change or "PSA velocity" greater than 0.75/year is considered high.

In one embodiment, this invention is directed to treatment of a subject with high or increasing PSA levels comprising administering a compound of this invention. In one embodiment, this invention is directed to treatment of a subject with high or increasing PSA levels despite ongoing ADT or a history of ADT, surgical castration or despite treatment with anti-androgens and/or LHRH agonist. In another embodiment, the treatment makes use of compounds of this invention. In another embodiment, the treatment makes use of compound IV.

In one embodiment, this invention is directed to a method of reducing the prostate specific antigen (PSA) levels in a subject, comprising administering a compound of this invention. In one embodiment, this invention is directed to a method of reducing the prostate specific antigen (PSA) levels in a subject, comprising administering a compound of formulas IA, I-XII. In another embodiment, by administering compound IV. In one embodiment, this invention is directed to a method of reducing the prostate specific antigen (PSA) levels in a subject, comprising administering a compound of formulas IA, I-XII in combination with LHRH agonist. In another embodiment, administering compound IV in combination with LHRH agonist. In one embodiment, this invention is directed to a method of reducing the prostate specific antigen (PSA) levels in a subject, comprising administering a compound of formulas IA, I-XII in combination with LHRH antagonist. In another embodiment, administering compound IV in combination with LHRH antagonist. In one embodiment, this invention is directed to a method of reducing the prostate specific antigen (PSA) levels in a subject, comprising administering a compound of formulas IA, I-XII in combination with leuprolide acetate (Lupron®). In another embodiment, administering compound IV in combination with leuprolide acetate (Lupron®). In one embodiment, this invention is directed to a method of reducing the prostate specific antigen (PSA) levels in a subject, comprising administering a compound of formulas IA, I-XII in combination with degarelix. In another embodiment, administering compound IV in combination with degarelix. In another embodiment, the subject suffers from advanced prostate cancer. In another embodiment, the subject suffers from castration resistant prostate cancer (CRPC). In another embodiment, the CRPC is metastatic CRPC (mCRPC). In another embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the compound is administered at a dosage of 40 mg per day. In another embodiment, the compound is administered at a dosage of 80 mg per day. In another embodiment, compound IV is administered at a dosage of 125 mg per day. In another embodiment, compound IV is administered at a dosage of 250 mg per day. In another embodiment, compound IV is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, the term "Insulin-like growth factor-1 (IGF-1) levels" refers to a concentration of IGF-1 obtained in whole blood or in a fluid obtained from blood, such as plasma or serum.

The reduced IGF-1 is beneficial in advanced prostate cancer patient from the metabolic and oncologic perspectives. A common side effect of androgen deprivation therapy (ADT) is the worsening of insulin resistance and the consequent development of metabolic diseases among ADT patients. As prostate cancer patients live longer, the metabolic consequences of the therapy becomes an issue that should be addressed, and there is a need to find hormonal therapies that do not have the intrinsic deleterious metabolic effects of anti-androgens and GnRH agonists and antagonists.

The compounds of this invention decrease IGF-1 and improve insulin sensitivity. And do not cause long-term metabolic disorders (non limiting examples of metabolic disorders include obesity, metabolic syndrome, insulin resistance, diabetes (e.g., Type I diabetes, Type II diabetes, diabetes mellitus), atherosclerosis, hyperlipidemia, fatty liver, osteoporosis and/or leptin related disorders).

IGF-1 has been observed to promote growth through the agonism of IGF-1R of a wide variety of cancers including prostate, breast, etc. and non-hormone dependent cancers such as multiple myeloma and leukemia. Hence, IGF-1 is an ancillary mechanism, unrelated to the androgen deprivation that may inhibit growth of tumors in prostate cancers and other cancers. (IGF-1R antagonists have been widely investigated as therapeutics in a wide variety of cancer.)

In one embodiment, this invention is directed to treatment of a subject with high or increasing serum insulin-like growth factor-1 (IGF-1) levels comprising administering a compound of this invention. In one embodiment, this invention is directed to treatment of a subject with high or increasing IGF-1 levels despite ongoing ADT or a history of ADT, surgical castration or despite treatment with anti-androgens and/or LHRH agonist. In another embodiment, the treatment makes use of compounds of this invention. In another embodiment, the treatment makes use of compound IV.

In one embodiment, this invention is directed to a method of decreasing serum insulin-like growth factor-1 (IGF-1) levels in a subject, comprising administering a compound of this invention. In one embodiment, this invention is directed to a method of reducing the IGF-1 levels in a subject, comprising administering a compound of formulas IA, I-XII. In another embodiment, by administering compound IV. In one embodiment, this invention is directed to a method of decreasing serum insulin-like growth factor-1 (IGF-1) levels in a subject, comprising administering a compound of formulas IA, I-XII in combination with LHRH agonist. In another embodiment, administering compound IV in combination with LHRH agonist. In one embodiment, this invention is directed to a method of decreasing the serum insulin-like growth factor-1 (IGF-1) levels in a subject, comprising administering a compound of formulas IA, I-XII in combination with LHRH antagonist. In another embodiment, administering compound IV in combination with LHRH antagonist. In one embodiment, this invention is directed to a method of decreasing the serum insulin-like growth factor-1 (IGF-1) levels in a subject, comprising administering a compound of formulas IA, I-XII in combination with leuprolide acetate (Lupron®). In another embodiment, administering compound IV in combination with leuprolide acetate (Lupron®). In one embodiment, this invention is directed to a method of decreasing the serum insulin-like growth factor-1 (IGF-1) levels in a subject, comprising administering a compound of formulas IA, I-XII in combination with degarelix. In another embodiment, administering compound IV in combination with degarelix. In another embodiment, the subject suffers from advanced prostate cancer. In another embodiment, the subject suffers from castration resistant prostate cancer (CRPC). In another embodiment, the CRPC is metastatic CRPC (mCRPC). In another embodiment, the CRPC is non-metastatic castration resistant prostate cancer (nmCRPC). In one embodiment, the nmCRPC is high-risk nmCRPC. In another embodiment, the subject has failed Androgen Deprivation Therapy (ADT). In another embodiment, the compound is administered at a dosage of 40 mg per day. In another embodiment, the compound is administered at a dosage of 80 mg per day. In another embodiment, compound IV is administered at a dosage of 125 mg per day. In another embodiment, compound IV is administered at a dosage of 250 mg per day. In another embodiment, compound IV is administered at a dosage of 500 mg per day. In another embodiment, the compound is administered at a dosage of 1000 mg per day. In another embodiment, the compound is administered at a dosage of 1500 mg per day. In another embodiment, the compound is administered at a dosage of 2000 mg per day. In another embodiment, the compound is administered at a dosage of 2500 mg per day.

In one embodiment, this invention provides methods of treating castration resistant prostate cancer using the compounds of this invention, thereby requiring reduced chemotherapy.

In one embodiment, this invention provides a method of treating, suppressing, reducing the incidence, reducing the severity, increasing the survival, or inhibiting a chemotherapy-resistant prostate cancer. In another embodiment, the chemotherapy comprises treatment with docetaxel or paclitaxel.

In one embodiment, this invention provides a method of treating, suppressing, reducing the incidence, reducing the severity, increasing the survival, or inhibiting a GnRH agonist-resistant prostate cancer. In another embodiment, GnRH agonist is leuprolide.

In one embodiment, this invention provides a method of treating, suppressing, reducing the incidence, reducing the severity, increasing the survival, or inhibiting a GnRH antagonist (GRHA)-resistant prostate cancer. In another embodiment, GRHA agonist is degarelix.

In one embodiment, this invention provides a method of treating, suppressing, reducing the incidence, reducing the severity, increasing the survival, or inhibiting an antiandrogen-resistant prostate cancer. In another embodiment, the antiandrogen is bicalutamide flutamide, or enzalutamide.

In one embodiment, this invention provides a method of treating, suppressing, reducing the incidence, reducing the severity, increasing the survival, or inhibiting a vaccines-resistant prostate cancer.

In one embodiment, this invention provides a method of treating, suppressing, reducing the incidence, reducing the severity, increasing the survival, or inhibiting an abiraterone-resistant prostate cancer.

In one embodiment, the methods provided herein and/or utilising the compounds provided herein, are effective in providing feedback on the hypothalamus-pituitary-testicular axis (HPT axis). Feedback refers to the ability of a substance produced in one organ or tissue to regulate the activity of another organ or tissue that affects its own activity. In one embodiment, feedback on the hypothalamus-pituitary-testicular axis (HPT axis) results in reduction of LH levels. In one embodiment, feedback on the hypothalamus-pituitary-testicular axis (HPT axis) results in reduction of total serum testosterone levels. In one embodiment, feedback on the hypothalamus-pituitary-testicular axis (HPT axis) results in reduction of free serum testosterone levels. In one embodiment, feedback on the hypothalamus-pituitary-testicular axis (HPT axis) results in reduction of serum, tissue or tumor levels of androgens.

The hypothalamic-pituitary-testicular (HPT) axis refers to the endocrine physiologic system that regulates hormone levels in the Hypothalmus, the Pituitary gland and the Testes. LHRH (luteinizing hormone releasing hormone) is released by the hypothalamus and stimulates the pituitary to synthesize and secrete LH and FSH (gonadotropins). LH and FSH then act on the testes to stimulate testosterone and sperm production. Testosterone then has a direct negative feedback effect on hypothalamic LHRH secretion and an indirect negative feedback effect on pituitary LH and FSH production. Estrogens, androgens and serum proteins (e.g., inhibin) also have a negative effect on LHRH secretion and secretion of LH and FSH.

The pituitary gland is one gland that controls the level of testosterone in the body. When the testosterone level is low, the pituitary gland releases the luteinizing hormone (LH). This hormone induces the testes to make more testosterone. The level of testosterone increases during puberty. The level of testosterone is the highest around age 20 to 40, and then gradually becomes less in older men. Women have a much smaller amount of testosterone in their bodies compared to men. But testosterone plays an important role throughout the body in both men and women. It affects the brain, bone and muscle mass, fat distribution, the vascular system, energy levels, genital tissues, and sexual function. Most of the testosterone in the blood is bound to a protein called sex hormone binding globulin (SHBG) or to another serum protein called albumin. Testosterone that is not bound (or "free") can also be clinically determined.

In another embodiment, lowering total serum testosterone, free serum testosterone levels or free serum testosterone percentage (% FreeT) independent of a reduction of serum luteinizing hormone levels is due to increase of sex hormone-binding globulin (SHBG). In another embodiment, lowering free testosterone levels independent of a reduction of serum luteinizing hormone levels is due to increase of sex hormone-binding globulin (SHBG). In another embodiment, lowering free testosterone percentage (% FreeT) independent of a reduction of serum luteinizing hormone levels is due to increase of sex hormone-binding globulin (SHBG). In another embodiment, lowering total serum or free serum testosterone levels independent of a reduction of serum luteinizing hormone (LH) levels is due to inhibition of testosterone production or secretion by Leydig cells in testes. In another embodiment, lowering total serum or free serum testosterone levels independent of a reduction of serum luteinizing hormone (LH) levels is due to decrease of adrenal steroidogenesis.

In one embodiment, the compounds as described herein and/or compositions comprising the same may be used for reduction of luteinizing hormone (LH) levels. In another embodiment, the compounds and/or compositions of this invention may be used to reduce endogenous sex hormones.

Hydroxysteroid dehydrogenase (HSD) family members are involved in the conversion of circulating steroids. 17β-HSD5 converts androstenedione to testosterone and estrone to estradiol. In addition, it is also involved in prostaglandin synthesis. In one embodiment the compounds of this invention inhibit HSD specifically 17β-hydroxysteroid dehydrogenase 5 (17β-HSD5) inhibition. Such inhibition may be useful in ADT, by preventing the peripheral/extragonadal testosterone synthesis which may escape the HPT axis control and cause incomplete reduction of total or free serum testosterone or allow locally elevated intracellular testosterone levels, either of which could be detrimental in ADT.

Androgen deprivation therapy (ADT) achieved by LHRH agonist therapy, i.e., administering luteinizing hormone releasing hormone agonists (LHRH) or analogues thereof, results in an initial stimulation of gonadotropin release from the pituitary and testosterone production from the testes (termed "flare reaction"), followed by decrease of gonadotropin release and decrease of both testosterone and estrogen levels. The "flare reaction" caused by LHRH agonist therapy has a negative impact on treatment of prostate cancer, due to the increase of androgen/testosterone levels. In addition, LHRH therapy has been associated with increased risk of diabetes and cardiovascular disease (Smith (2008) *Current Prostate Reports*. 6:149-154).

In an effort to overcome the flare effects of LHRH therapy, antiandrogen monotherapy (e.g., bicalutamide, flutamide, enzalutamide, chlormadinone), combined LHRH/antiandrogen therapy approaches, and LHRH antagonists (e.g., degarelix) have been suggested (Suzuki et al., (2008) *Int. J. Clin. Oncol*. 13: 401-410; Sharifi, N. et al., (2005) *JAMA*. 294(2): 238-244). Antiandrogen monotherapy does not reduce androgen levels in a subject. Bicalutamide antiandrogen monotherapy was shown to be less effective than ADT in prostate cancer patients with bone metastases. In addition, adverse effects observed with bicalutamide therapy include breast tenderness and breast enlargement (gynecomastia and mastodynia). (Suzuki et al., ibid) Additional risk with antiandrogen therapy includes increased liver transaminases. (Sharifi et al. ibid).

In one embodiment, the present invention provides a reduction of LH levels and thereby a reduction of total serum testosterone and/or free serum testosterone levels, without production of the "flare" effect, and while overcoming the adverse effects associated with estrogen deficit caused by testosterone reduction using traditional ADT methods. Methods/uses of the subject compounds provide tissue-selective estrogen activities that provide maintenance of bone tissue (agonist effect on bone tissue), decreased thrombic potential and/or hot flashes and/or lesser or neutral effects on breast tissue than estradiol or diethylstilbestrol.

In one embodiment compound IV shows agonist but no antagonistic effects (Examples 6 and 7) so compound IV would not cause increase in gonadotropins and testosterone.

In one embodiment, compound IV shows agonist activity (Examples 8-11) demonstrating a robust pharmacologic response for the reduction of serum hormones, testosterone and total androgens.

In one embodiment, compound IV is a nonsteroidal selective estrogen receptor alpha (ERα) agonist that binds to the estrogen receptor (ER) with nanomolar affinity for both ERα and ERβ. Although many estrogenic ligands cross-react with other nuclear hormone receptors, the actions of Compound IV are specific for ERα and ERβ. Compound IV has 16-fold selectivity in relative transactivation potency for ERα and ERβ, and ~1400-fold less potency in its ability to stimulate ERβ-mediated transcription as compared to estradiol.

In one embodiment, the methods provided herein utilizing the compounds and/or compositions provided herein, are effective in reducing or eliminating bone resorptive effects caused by reduction of LH using traditional forms of ADT. In one embodiment, the methods provided herein and/or utilizing the compositions provided herein, are effective in reducing or eliminating bone resorptive effects caused by reduction of testosterone levels using traditional forms of ADT. In one embodiment, the methods provided herein utilizing the compositions provided herein, are effective in reducing or eliminating bone resorptive effects caused by reduction of estrogen as a result of LH level reduction. In one embodiment, the methods provided herein utilizing the compounds and/or compositions provided herein, prevent bone resorptive effects associated with LH level reduction using traditional forms of ADT. In one embodiment, the methods provided herein utilizing the compounds and/or compositions provided herein, prevent bone loss associated with endogenous LH, testosterone and/or estradiol reduction using traditional forms of ADT. In one embodiment, the methods provided herein utilizing the compounds and/or compositions provided herein, increase bone mass density (BMD) while providing LH level reduction. In one embodiment, the methods provided herein utilizing the compounds and/or compositions provided herein, increase percent bone volume while providing endogenous LH, testosterone and/or estradiol level reduction.

In some embodiments, this invention provides a method of avoiding and/or reducing thromboembolism by administering a compound of this invention or its isomer, pharmaceutical product, polymorph, hydrate or any combination thereof.

In one embodiment, the methods provided herein utilizing the compounds and/or compositions provided herein, are effective in breast tissue. In one embodiment, the methods provided herein utilizing the compounds and/or compositions provided herein, provide LH level reduction while preventing gynecomastia associated with LH level reduction achieved by traditional ADT.

In one embodiment, Example 13 discloses special toxicity studies wherein in vitro studies with human platelets showed that Compound IV had much lower procoagulatory activity than DES. Thus, Compound IV, an ER-selective agonist, should deliver the prostate cancer benefits of DES with lesser risk of thrombotic events than DES, and also deliver the benefits of an LHRH agonist or antagonist without causing bone loss, hot flash or adverse lipid profiles.

Diethylstilbestrol (DES) therapy alone or combined with other ADT showed DES prevented bone resorption in patients with prostate cancer. Although use of DES has been promoted as a therapy for prostate cancer, effects of DES on angiogenesis and malignancy are thought to be mediated by DES metabolites and are not thought to act through the estrogen receptor. In addition, dosage levels of DES administered for therapeutic uses present numerous adverse side effects including vascular disease, cardiovascular morbidity, thrombotic toxicity, gynecomastia, erectile dysfunction and decreased libido (Scherr and Pitts, ibid and Presti, J. C. Jr. (1996) JAMA. 275(15): 1153-6).

In one embodiment, the present invention overcomes the negative side effects of LHRH agonist or antagonist therapy, alone or in combination with anti-androgens or DES. In another embodiment, methods of the subject invention provide androgen deprivation therapy without adverse estrogen deprivation side-effects, such as adverse bone related conditions, and without adverse estrogen stimulation side-effects, such as gynecomastia. In another embodiment, methods of the current invention provide for a reduction of LH levels and thereby a reduction of total and/or free serum testosterone levels, without production of the "flare" effect, while overcoming the adverse effects associated with estrogen deficit caused by LH reduction and overcoming the adverse effects associated with a general estrogen agonist increase observed with DES therapy. Methods/uses of the subject compounds provide tissue-selective estrogen activities thereby providing maintenance of bone tissue (agonist effect on bone tissue), decreased thrombic potential and neutral effects on breast tissue.

Antiestrogenic effects of traditional selective estrogen receptor modulators (SERMs) such as tamoxifen, toremifene and raloxifene at the hypothalamic level result in an increase of gonadotropin levels or an increase of LH levels in men, and thereby potentially resulting in an increase in the testosterone serum levels. (Tsouri et al., 2008, *Fertility and Sterility* doi: 10.1016) In contrast, the methods of this invention provide reduction of LH in a male subject comprising administering a compound of formula IA, I-XII.

Additional Embodiments for Compound of Formula I:

In one embodiment of the methods of this invention, Y of compound of formula I is C(O). In another embodiment Y is CH$_2$. In another embodiment R$_1$ and R$_2$ of the compound of formula I or IA are independently O-Alk-NR$_5$R$_6$ or O-Alk-heterocycle. In another embodiment the Alk of said O-Alk-heterocycle, O-Alk-NR$_5$R$_6$, -Alk-heterocycle and Alk-NR$_5$R$_6$ as described herein above are linear alkyl of 1-7 carbons, branched alkyl of 1-7 carbons, or cyclic alkyl of 3-8 carbons. In another embodiment, the alkyl is ethylene (—CH$_2$CH$_2$—). In another embodiment the Alk is methylene (—CH$_2$—). In another embodiment the Alk is propylene (—CH$_2$CH$_2$CH$_2$—). In another embodiment the Alk is 2-methylpropylene (—CH$_2$CH(CH$_3$)CH$_2$—).

In one embodiment of the methods of this invention R$_1$ of the compound of formula I or IA is in the para position. In one embodiment of the methods of this invention R$_1$ and R$_2$ of the compound of formula I or IA are different. In another embodiment of the methods of this invention R$_1$ and R$_2$ of the compound of formula I or IA are the same. In another embodiment of the methods of this invention R$_1$ of the compound of formula I or IA is

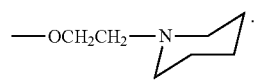

In another embodiment of the methods, $R_1$ of the compound of formula I or IA is hydroxyl. In another embodiment of the methods, $R_1$ of the compound of formula I or IA is alkoxy. In another embodiment of the methods, $R_1$ and $R_2$ are independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic. In another embodiment of the methods, $R_1$ and $R_2$ of the compound of formula I or IA are independently halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic. In another embodiment of the methods, $R_2$ of the compound of formula I or IA is halogen. In another embodiment of the methods, $R_2$ of the compound of formula I or IA is F. In another embodiment of the methods, $R_2$ of the compound of formula I is Cl. In another embodiment of the methods, $R_2$ of the compound of formula I or IA is Br. In another embodiment of the methods, $R_2$ of the compound of formula I or IA is I. In another embodiment of the methods, $R_2$ of the compound of formula I or IA is hydroxyl. In another embodiment of the methods, $R_1$ and/or $R_2$ is $CF_3$. In another embodiment, $R_1$ and/or $R_2$ is $CH_3$. In another embodiment, $R_1$ and/or $R_2$ is halogen. In another embodiment, $R_1$ and/or $R_2$ is F. In another embodiment, $R_1$ and/or $R_2$ is Cl. In another embodiment, $R_1$ and/or $R_2$ is Br. In another embodiment, $R_1$ and/or $R_2$ is I. In another embodiment, $R_2$ of compound of formula I is in the para position.

In one embodiment of the methods of this invention, $R_3$ and $R_4$ of the compound of formula I or IA are the same. In another embodiment of the methods of this invention, $R_3$ and $R_4$ of the compound of formula I or IA are different. In another embodiment of the methods, j and k of the compound of formula I or IA are independently 1. In another embodiment of the methods, $R_3$ and $R_4$ of the compound of formula I or IA are independently halogen, haloalkyl, hydroxyl or alkyl. In another embodiment of the methods, $R_3$ and $R_4$ of the compound of formula I or IA are independently F. In another embodiment of the methods, $R_3$ and $R_4$ of the compound of formula I or IA are independently Br. In another embodiment of the methods, $R_3$ and $R_4$ of the compound of formula I or IA are independently Cl. In another embodiment, $R_4$ is in the para position. In another embodiment, $R_3$ is in the ortho position. In another embodiment, $R_3$ is in the meta position. In another embodiment, $R_3$ and/or $R_4$ is $CF_3$. In another embodiment, $R_3$ and/or $R_4$ is $CH_3$.

In one embodiment of the methods of this invention, $R_5$ and $R_6$ of the compound of formula I or IA form a 3 to 7 membered ring with the nitrogen atom. In another embodiment the ring is saturated or unsaturated ring. In another embodiment the ring substituted or unsubstituted ring. In another embodiment of the methods of this invention, $R_5$ and $R_6$ of the compound of formula I or IA form a piperidine ring with the nitrogen. In another embodiment of the methods, $R_5$ and $R_6$ of the compound of formula I or IA form a pyrazine ring with the nitrogen. In another embodiment of the methods, $R_5$ and $R_6$ of the compound of formula I or IA form a piperazine ring with the nitrogen. In another embodiment of the methods, $R_5$ and $R_6$ of the compound of formula I or IA form a morpholine ring with the nitrogen. In another embodiment of the methods, $R_5$ and $R_6$ of the compound of formula I or IA form a pyrrole ring with the nitrogen. In another embodiment of the methods, $R_5$ and $R_6$ of the compound of formula I or IA form a pyrrolidine. In another embodiment of the methods, $R_5$ and $R_6$ of the compound of formula I or IA form a pyridine ring with the nitrogen. In another embodiment the ring is substituted by halogen, alkyl, alkoxy, alkylene, hydroxyl, cyano, nitro, amino, amide, COOH or an aldehyde.

In another embodiment of the methods of this invention, $R_1$ of the compound of formula I or IA and $R_2$ of compound of the compound of formula I or IA are independently O-Alk-heterocycle or $OCH_2CH_2$-heterocycle. In another embodiment, the term "heterocycle" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 4-8 membered ring. In another embodiment, the heterocycle group may be unsubstituted or substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. In another embodiment, the heterocycle is piperidine. In another embodiment, the heterocycle is pyridine. In another embodiment, the heterocycle is piperidine, pyridine, furan, thiophene, pyrrole, pyrrolidine, pyrazine, piperazine or pyrimidine.

The term "cycloalkyl" refers to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, (C3-C7) cycloalkyl groups, such as cyclopropyl, cyclobutyl, cyclopentyl, cyclohexyl, and cycloheptyl, and saturated cyclic and bicyclic terpenes and (C3-C7) cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two substituents. Preferably, the cycloalkyl group is a monocyclic ring or bicyclic ring.

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. In another embodiment, the cyclic alkyl group has 3-8 carbons. In another embodiment, the cyclic alkyl group has 3-12 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, alkoxy carbonyl, amido, alkylamido, dialkylamido, nitro, amino, alkylamino, dialkylamino, carboxyl, thio and/or thioalkyl.

An "alkenyl" group refers, in another embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. Examples of alkenyl groups are ethenyl, propenyl, butenyl, cyclohexenyl, etc. The alkenyl group may be unsubstituted or substituted by a halogen, hydroxy, alkoxy carbonyl, amido, alkylamido, dialkylamido, nitro, amino, alkylamino, dialkylamino, carboxyl, thio and/or thioalkyl.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 6 membered ring. In another embodiment, the aryl group is a 5 membered ring. In another embodiment, the aryl group is 2-4 fused ring system.

A "aldehyde" group refers, in one embodiment to an alkyl, or alkenyl substituted by a formyl group, wherein the alkyl or alkenyl are as defined hereinabove. In another embodiment, the aldehyde group is an aryl, or phenyl group substituted by a formyl group, wherein the aryl is as defined hereinabove. Examples of aldehydes are: formyl, acetal, propanal, butanal, pentanal, benzaldehyde. In another embodiment, the aldehyde group is a formyl group.

A "haloalkyl" group refers, in another embodiment, to an alkyl group as defined above, which is substituted by one or more halogen atoms, e.g. by F, Cl, Br or I.

A "hydroxyl" group refers, in another embodiment, to an OH group. It is understood by a person skilled in the art that when $R_1$, $R_2$ or $R_3$ in the compounds of the present invention is OR, then R is not OH.

In one embodiment, the term "halogen" or "halo" refers to a halogen, such as F, Cl, Br or I.

In another embodiment, the phrase "phenol" refers to an alcohol (OH) derivative of benzene.

Reference to protected hydroxyl, in some embodiments, includes the incorporation of a substituent bonded to the oxygen moiety of the benzene ring, wherein the substituent may be readily removed. In some embodiments, phenolic protecting groups may comprise a: methyl ether (methoxy), alkyl ether (alkoxy), benzyl ether (Bn), methoxymethyl (MOM) ether, benzoyloxymethyl (BOM) ether, benzyl, carbobenzoxy, methoxyethoxymethyl (MEM) ether, 2-(trimethylsilyl)ethoxymethyl (SEM) ether, methylthiomethyl (MTM) ether, phenylthiomethyl (PTM) ether, azidomethyl ether, cyanomethyl ether, 2,2-dichloro-1,1-difluoroethyl ether, 2-chloroethyl ether, 2-bromoethyl ether, tetrahydropyranyl (THP) ether, 1-ethoxyethyl (EE) ether, phenacyl ether, 4-bromophenacyl ether, cyclopropylmethyl ether, allyl ether, propargyl ether, isopropyl ether, cyclohexyl ether, t-butyl ether, 2,6-dimethylbenzyl ether, 4-methoxybenzyl ether, o-nitrobenzyl ether, 2,6-dichlorobenzyl ether, 3,4-dichlorobenzyl ether, 4-(dimethylamino)carbonylbenzyl ether, 4-methylsulfinylbenzyl ether, 4-anthrylmethyl ether, 4-picolyl ether, heptafluoro-p-tolyl, tetrafluoro-4-pyridyl ether, trimethylsilyl (TMS) ether, t-butyldimethylsilyl (TBDMS) ether, t-butyldiphenylsilyl (TBDPS) ether, triisopropylsilyl (TIPS) ether, aryl formate, arylacetate, aryl levulinate, arylpivaloate, aryl benzoate, aryl 9-fluorencarboxylate, aryl methyl carbonate, 1-adamantyl carbonate, t-butyl carbonate, 4-methylsulfinylbenzyl carbonate, 2,4-dimethylpent-3-yl carbonate, aryl 2,2,2-trichloroethyl carbonate, aryl benzyl carbonate, aryl carbamate, dimethylphosphinyl ester (Dmp-OAr), dimethylphosphinothionyl ester (Mpt-OAr), diphenylphosphinothionyl ester (Dpt-OAr), aryl methanesulfonate, aryl toluenesulfonate or aryl 2-formylbenzenesulfonate.

In one embodiment, the methods of this invention make use of N,N-bis(4-hydroxyphenyl)-4-propylbenzamide (II) or its isomer, pharmaceutically acceptable salt, pharmaceutical product, polymorph, hydrate or any combination thereof. In another embodiment the methods of this invention make use of 4,4'-(2,3-dimethyl-benzylazanediyl)diphenol (III) or its isomer, pharmaceutically acceptable salt, pharmaceutical product, polymorph, hydrate or any combination thereof. In another embodiment the methods of this invention make use of 3-fluoro-N-(4-fluorophenyl)-4-hydroxy-N-(4-hydroxyphenyl)benzamide (IV) or its isomer, pharmaceutically acceptable salt, pharmaceutical product, polymorph, hydrate or any combination thereof. In another embodiment the methods of this invention make use of N,N-bis(4-hydroxyphenyl)-2,3-dimethylbenzamide (V) or its isomer, pharmaceutically acceptable salt, pharmaceutical product, polymorph, hydrate or any combination thereof. In another embodiment the methods of this invention make use of N,N-bis(4-hydroxyphenyl)-2-naphthylamide (VI) or its isomer, pharmaceutically acceptable salt, pharmaceutical product, polymorph, hydrate or any combination thereof. In another embodiment the methods of this invention make use of 3-fluoro-4-hydroxy-N,N-bis(4-hydroxyphenyl)-benzamide (VII) or its isomer, pharmaceutically acceptable salt, pharmaceutical product, polymorph, hydrate or any combination thereof. In another embodiment the methods of this invention make use of a 4-((4-fluorophenyl)(4-hydroxybenzyl)amino)phenol (VIII) or its isomer, pharmaceutically acceptable salt, pharmaceutical product, polymorph, hydrate or any combination thereof. In another embodiment the methods of this invention make use of a 4-fluoro-N-(4-hydroxy-phenyl)-N-[4-(2-piperidin-1-yl-ethoxy)-phenyl]-2-trifluoromethyl-benzamide (IX) or its isomer, pharmaceutically acceptable salt, pharmaceutical product, polymorph, hydrate or any combination thereof. In another embodiment the methods of this invention make use of a hydrochloride salt of IX (HCl salt of IX) or 4-fluoro-N-(4-hydroxyphenyl)-N-[4-(2-piperidin-1-yl-ethoxy)-phenyl]-2-trifluoromethyl-benzamide hydrochloride (X) or its isomer, pharmaceutically acceptable salt, pharmaceutical product, polymorph, hydrate or any combination thereof. In another embodiment the methods of this invention make use of a 3-fluoro-4-hydroxy-N-(4-hydroxyphenyl)-N-phenylbenzamide (XI) or its isomer, pharmaceutically acceptable salt, pharmaceutical product, polymorph, hydrate or any combination thereof. In another embodiment the methods of this invention make use of a 3-fluoro-N,N-bis-(4-hydroxy-phenyl)-2-methyl-benzamide (XII) or its isomer, pharmaceutically acceptable salt, pharmaceutical product, polymorph, hydrate or any combination thereof.

In one embodiment the methods of this invention make use of "pharmaceutically acceptable salts" of the compounds, which may be produced, by reaction of a compound of this invention with an acid or base.

Suitable pharmaceutically-acceptable salts of amines of the compounds of the methods of this invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrate, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, carboxylates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorates, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, nitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, pectinates, phenylpropionates, palmitates, pantothenates, polygalacturates, pyruvates, quinates, salicylates, succinates, stearates, sulfanilates, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or phenols may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment, the methods of this invention make use of a pharmaceutically acceptable salt of the compounds of this invention. In one embodiment the methods of this invention make use of a pharmaceutically acceptable salt of compounds of formulas IA, I-XII. In one embodiment, the methods of this invention make use of a salt of an amine of the compounds of formulas IA, I-XII of this invention. In one embodiment, the methods of this invention make use of a salt of a phenol of the compounds of formulas IA, I-XII of this invention.

In one embodiment the methods of this invention make use of a free base, free acid, non charged or non-complexed compounds of formulas IA, I-XII and/or its isomer, pharmaceutical product, hydrate, polymorph, or combinations thereof.

In some embodiments of this invention, the compounds of this invention comprise three phenyl groups which are held together by an amide bond. In one embodiment, the compounds of this invention are non-charged structures. In another embodiment, the compounds of this invention are free base structures. In another embodiment, the compounds of this invention are free acid structures. In another embodiment, the compounds of this invention are non-complexed structures. In another embodiment, the compounds of this invention are non-ionized structures. In another embodiment, the compounds of this invention are pharmaceutically acceptable salts. In another embodiment, some compounds of this invention include hydrochloride (HCl) salts.

In one embodiment, the methods of this invention make use of an isomer of a compound of formulas IA, I-XII. In one embodiment, the methods of this invention make use of a pharmaceutical product of a compound of formulas IA, I-XII. In one embodiment, the methods of this invention make use of a hydrate of a compound of formulas IA, I-XII. In one embodiment the methods of this invention make use of a polymorph of a compound of formulas IA, I-XII. In one embodiment the methods of this invention make use of a metabolite of a compound of formulas IA, I-XII. In another embodiment the methods of this invention make use of a composition comprising a compound of formulas IA, I-XII, as described herein, or, in another embodiment, a combination of isomer, metabolite, pharmaceutical product, hydrate, polymorph of a compound of formulas IA, I-XII.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the compound. In one embodiment, the term "isomer" is meant to encompass stereoisomers of the compound. The compounds of this invention possess an amide bond which may be in its cis or trans isomerization. It is to be understood that the present invention encompasses any optically-active, or stereroisomeric form, or mixtures thereof, and use of these for any application is to be considered within the scope of this invention.

In another embodiment, this invention further includes hydrates of the compounds. In one embodiment, the term "hydrate" refers to hemihydrate, monohydrate, dihydrate, trihydrate or others, as known in the art.

Synthetic Processes

Compounds of Formula I or IA may readily be prepared, for example, by reacting a substituted diphenyl amine with benzoic acid or benzoyl halide in the presence of a base to yield a benzamide. In one embodiment, the base is pyridine. In another embodiment, the benzoyl halide is benzoyl chloride. In another embodiment, a hydroxyl substituent is protected during the reaction between the diphenylamine and the benzoic acid or benzoyl halide. In another embodiment, the protecting group for the hydroxyl, optionally is removed in the last step. See also U.S. Publication No. 2009/00624231 and U.S. Pat. No. 8,158,828, which are incorporated by reference in their entirety.

For example, a compound of formula IA:

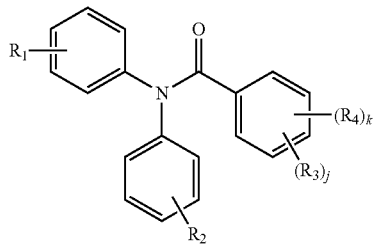
(IA)

wherein $R_1$, $R_2$, $R_3$ and $R_4$, j and k are as described above; may be prepared by a process that comprises reacting

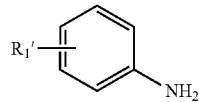
(1)

together with

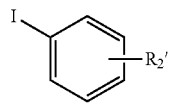
(2)

to yield

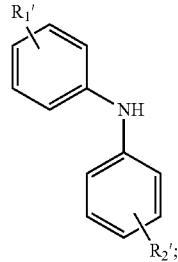
(3)

and
the diphenyl amine (3) is reacted with

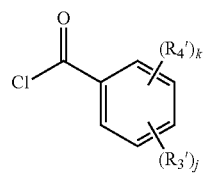
(4)

in the presence of a base to yield

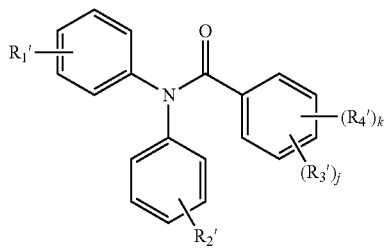
(5)

wherein if $R_1$, $R_2$, $R_3$ and $R_4$ are independently OH, O-Alk-$R_5R_6$ or O-Alk-heterocycle, then $R_1'$, $R_2'$, $R_3'$, $R_4'$ are protected hydroxyl group, wherein the protecting group is removed to obtain the free hydroxyl or optionally followed by reacting with Cl-Alk-heterocycle or Cl-Alk-$NR_5R_6$ to yield a compound of formula IA:

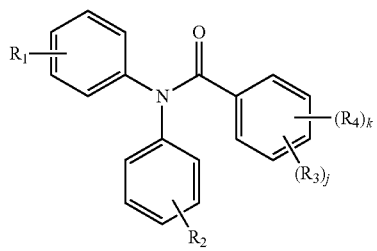
(IA)

wherein, if $R_1$, $R_2$, $R_3$ and $R_4$ are independently different than OH, O-Alk-$NR_5R_6$ or O-Alk-heterocycle then $R_1'$, $R_2'$, $R_3'$ and $R_4'$ are $R_1$, $R_2$, $R_3$ and $R_4$, respectively.

As another example, a process for the preparation of compound of Formula IA:

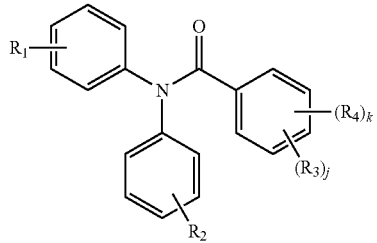
(IA)

wherein $R_1$, $R_2$, $R_3$ and $R_4$ are as described above, comprises reacting

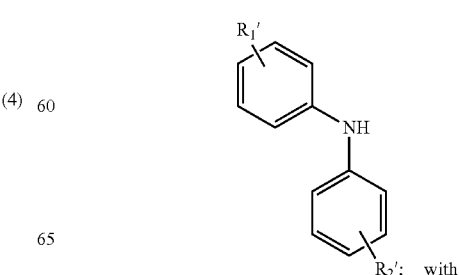
(3)

with (4)

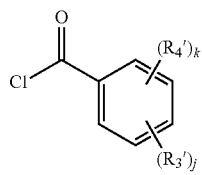

in the presence of a base to yield (5)

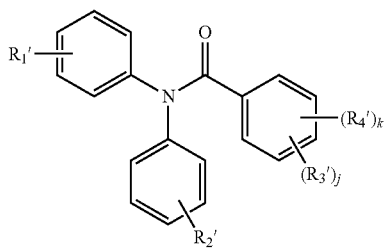

wherein if $R_1$, $R_2$, $R_3$ and $R_4$ are independently OH, O-Alk-$R_5R_6$ or O-Alk-heterocycle, then $R_1'$, $R_2'$, $R_3'$, $R_4'$ are protected hydroxyl group, wherein the protecting group is removed to obtain the free hydroxyl or optionally followed by reacting with Cl-Alk-heterocycle or Cl-Alk-$NR_5R_6$ to yield a compound of formula IA:

(IA)

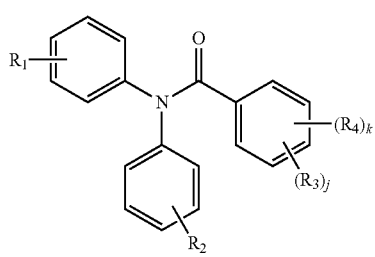

wherein, if $R_1$, $R_2$, $R_3$ and $R_4$ are independently different than OH, O-Alk-$NR_5R_6$ or O-Alk-heterocycle then $R_1'$, $R_2'$, $R_3'$ and $R_4'$ are $R_1$, $R_2$, $R_3$ and $R_4$, respectively.

In one example, Compound II is prepared according to Example 1, and FIG. 5.

In another example Compound III is prepared according to Example 1, and FIG. 5.

In a further example a compound of formula IV (Compound IV):

(IV)

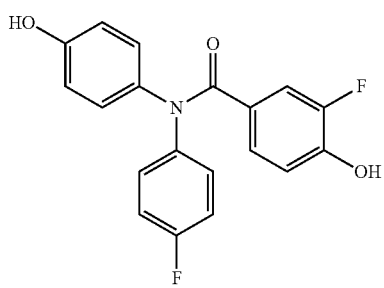

may be prepared by reacting (11)

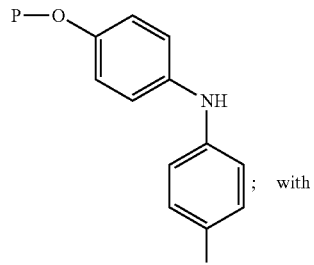

; with (12)

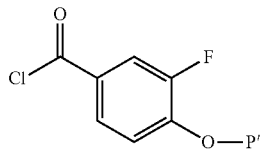

in the presence of a base to yield (13)

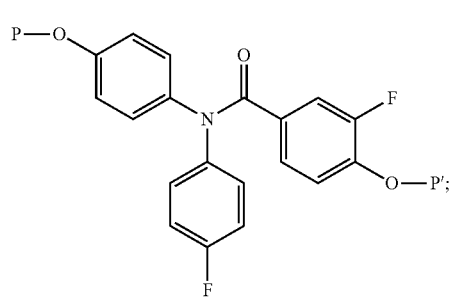

followed by deprotection of the protecting groups to yield Compound IV:

(IV)

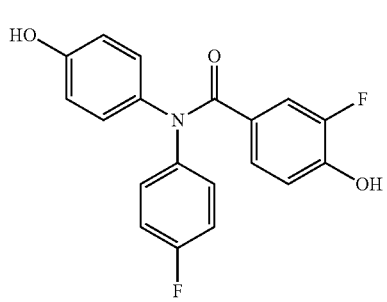

wherein P and P' are the same or different protecting groups.

In one example, Compound IV is prepared according to Example 2, and FIG. 6.

In another example, Compound V is prepared according to Example 1, and FIG. 5.

In a further example, Compound VI is prepared according to Example 3, and FIG. 7.

In another example, Compound VII is prepared according to Example 1, and FIG. 5.

In another example, Compound VIII is prepared according to Example 4, and FIG. 5.

In another example, Compound IX is prepared according to Example 5 and FIG. 8.

In another example, Compound X hydrochloride is prepared according to Example 5 and FIG. 8.

In another example, Compound XI is prepared according to Example 1, and FIG. 5.

In another example, Compound XII is prepared according to Example 1, and FIG. 5.

Suitable hydroxyl protecting groups include, for example, a methyl ether (methoxy), benzyl ether (benzyloxy) methoxymethyl (MOM) ether, benzoyloxymethyl (BOM) ether, benzyl, carbobenzoxy, methoxyethoxymethyl (MEM) ether, 2-(trimethylsilyl)ethoxymethyl (SEM) ether, methylthiomethyl (MTM) ether, phenylthiomethyl (PTM) ether, azidomethyl ether, cyanomethyl ether, 2,2-dichloro-1,1-difluoroethyl ether, 2-chloroethyl ether, 2-bromoethyl ether, tetrahydropyranyl (THP) ether, 1-ethoxyethyl (EE) ether, phenacyl ether, 4-bromophenacyl ether, cyclopropylmethyl ether, allyl ether, propargyl ether, isopropyl ether, cyclohexyl ether, t-butyl ether, benzyl ether, 2,6-dimethylbenzyl ether, 4-methoxybenzyl ether, o-nitrobenzyl ether, 2,6-dichlorobenzyl ether, 3,4-dichlorobenzyl ether, 4-(dimethylamino)carbonylbenzyl ether, 4-methylsulfinylbenzyl ether, 4-anthrylmethyl ether, 4-picolyl ether, heptafluoro-p-tolyl, tetrafluoro-4-pyridyl ether, trimethylsilyl (TMS) ether, t-butyldimethylsilyl (TBDMS) ether, t-butyldiphenylsilyl (TBDPS) ether, triisopropylsilyl (TIPS) ether, aryl formate, arylacetate, aryl levulinate, arylpivaloate, aryl benzoate, aryl 9-fluorencarboxylate, aryl methyl carbonate, 1-adamantyl carbonate, t-butyl carbonate, 4-methylsulfinylbenzyl carbonate, 2,4-dimethylpent-3-yl carbonate, aryl 2,2,2-trichloroethyl carbonate, aryl benzyl carbonate, aryl carbamate, dimethylphosphinyl ester (Dmp-OAr), dimethylphosphinothionyl ester (Mpt-OAr), diphenylphosphinothionyl ester (Dpt-OAr), aryl methanesulfonate, aryl toluenesulfonate or aryl 2-formylbenzenesulfonate.

The methods of this invention comprise the use of compounds of formula IA or I-XII, wherein the process for the preparation of the compounds of this invention comprise reaction of a diphenyl amine with a benzoyl chloride in the presence of a base. Suitable bases include, for example, pyridine, triethylamine, $K_2CO_3$, $Cs_2CO_3$, $Na_2CO_3$, methylamine, imidazole, benzimidazole, histidine, tributylamine or any combination thereof. In one embodiment, the base is pyridine.

The methods of this invention comprise the use of compounds of formula IA or I-XII, wherein the process for the preparation of the compounds of this invention comprises deprotection of a protected hydroxyl. In another embodiment, the deprotection conditions depend on the protecting group. In some embodiment, the deprotection step comprises hydrogenation in the presence of Pd/C. In another embodiment, the deprotection comprises reaction with $BBr_3$. In another embodiment, the deprotection step comprises reaction with an acid.

In further examples, Compounds of formula IA or I-XII are prepared according to FIGS. 5-8 and Examples 1-5.

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compound of this invention, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a male subject.

This invention provides, in other embodiments, pharmaceutical products of the compounds described herein. The term "pharmaceutical product" refers, in other embodiments, to a composition suitable for pharmaceutical use (pharmaceutical composition), for example, as described herein.

The compounds of the invention can be administered alone or as an active ingredient of a formulation. Thus, the present invention also includes pharmaceutical compositions of compounds of Formula I, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and dosage forms is closely related to the therapeutic amounts of the compounds or compositions which are desirable and efficacious for the given treatment application.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterile administration, and other dosage forms for systemic delivery of active ingredients. Formulations suitable for oral administration are preferred.

To prepare such pharmaceutical dosage forms, the active ingredient may be mixed with a pharmaceutical carrier according to conventional pharmaceutical compounding techniques. The carrier may take a wide variety of forms depending on the form of preparation desired for administration.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients, for example, ingredients that aid solubility or for preservation, may be included. Injectable solutions may also be prepared in which case appropriate stabilising agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Treatment methods of the present invention using formulations suitable for oral administration may be presented as discrete units such as capsules, cachets, tablets, or lozenges, each containing a predetermined amount of the active ingredient as, for example, a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration may comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from, for example, diluents, buffers, flavoring agents, binders, disintegrants, surface active agents, thickeners, lubricants, preservatives (including antioxidants), and the like.

The formulations of the present invention can have immediate release, sustained release, delayed-onset release or any other release profile known to one skilled in the art.

In one embodiment, this invention provides methods of a) lowering total serum testosterone levels; b) lowering free serum testosterone levels by reduction of luteinizing hormone (LH) or independent of reduction of LH hormone in a male subject having prostate cancer; c) secondary hormonal therapy that reduces serum PSA and serum free testosterone levels in a male subject having prostate cancer; d) treating, suppressing, reducing the incidence, reducing the severity, or inhibiting the progression of castration resistant prostate cancer (CRPC) and its symptoms, or increasing the survival of men with castration resistant prostate cancer; e) lowering serum PSA levels in a male subject having prostate cancer; f) increasing sex hormone binding globulin (SHBG) levels in a male subject having prostate cancer; g) inhibiting skeletal related events (SRE) in a male subject having prostate cancer; h) reducing the levels of bone turnover markers in a male subject having prostate cancer; i) inhibiting hot flashes in a male subject having prostate cancer; and/or j) reducing the levels of adrenal gland production of androgen precursors in a male subject having prostate cancer; k) treating, suppressing, reducing the incidence, reducing the severity, or inhibiting the progression of metastatic castration resistant prostate cancer (mCRPC) and its symptoms, or increasing the survival of men with metastatic castration resistant prostate cancer; 1) treating, suppressing, reducing the incidence, reducing the severity, or inhibiting the progression of non-metastatic castration resistant prostate cancer (nmCRPC) and its symptoms, or increasing the survival of men with non-metastatic castration resistant prostate cancer; m) increasing the radiographic progression free survival of men with metastatic castration resistant prostate cancer (mCRPC); n) increasing the metastasis-free survival of men with non-metastatic castration resistant prostate cancer (nmCRPC) comprising administering an oral composition comprising a compound of formulas IA, I-XII. In another embodiment, the subject suffers from castration resistant prostate cancer (CRPC). In one embodiment, the nmCRPC is high-risk nmCRPC. In additional embodiments, the methods of this invention make use of an oral composition comprising a compound of formula II, formula III, formula IV, formula V, formula VI, formula VII, formula VIII, formula IX, formula X, formula XI or formula XII.

In one embodiment, this invention provides a method of treating prostate cancer by reducing LH levels or independent of reduction of LH levels in a male subject having prostate cancer comprising administering an oral composition comprising a compound of formulas IA, I-XII. In additional embodiments, this invention provides methods of treating prostate cancer by reducing LH levels or independent of reduction of LH levels in a male subject having prostate cancer comprising administering an oral composition comprising a compound of formula II, formula III, formula IV, formula V, formula VI, formula VII, formula VIII, formula IX, formula X, formula XI or formula XII. In another embodiment, the subject suffers from castration resistant prostate cancer (CRPC). In another embodiment, the subject suffers from metastatic castration resistant prostate cancer (mCRPC). In another embodiment, the CRPC is non-metastatic castration resistant prostate cancer (nmCRPC). In one embodiment, the nmCRPC is high-risk nmCRPC.

It is to be understood that this invention encompasses any embodiment of a compound as described herein, which in some embodiments is referred to as "a compound of this invention".

In one embodiment, the methods of this invention may comprise administration of a compound of this invention at various dosages. In one embodiment, a compound of this invention is administered at a dosage of 1-3000 mg per day. In additional embodiments, a compound of this invention is administered at a dose of 1-10 mg per day, 3-26 mg per day, 3-60 mg per day, 3-16 mg per day, 3-30 mg per day, 10-26 mg per day, 15-60 mg, 50-100 mg per day, 50-200 mg per day, 100-250 mg per day, 125-300 mg per day, 20-50 mg per day, 5-50 mg per day, 200-500 mg per day, 125-500 mg per day, 500-1000 mg per day, 200-1000 mg per day, 1000-2000 mg per day, 1000-3000 mg per day, 125-3000 mg per day, 2000-3000 mg per day, 300-1500 mg per day or 100-1000 mg per day. In one embodiment, a compound of this invention is administered at a dosage of 25 mg per day. In one embodiment, a compound of this invention is administered at a dosage of 40 mg per day. In one embodiment, a compound of this invention is administered at a dosage of 50 mg per day. In one embodiment, a compound of this invention is administered at a dosage of 67.5 mg per day. In one embodiment, a compound of this invention is administered at a dosage of 75 mg per day. In one embodiment, a compound of this invention is administered at a dosage of 80 mg per day. In one embodiment, a compound of this invention is administered at a dosage of 100 mg per day. In one embodiment, a compound of this invention is administered at a dosage of 125 mg per day. In one embodiment, a compound of this invention is administered at a dosage of 250 mg per day. In one embodiment, a compound of this invention is administered at a dosage of 300 mg per day. In one embodiment, a compound of this invention is administered at a dosage of 500 mg per day. In one embodiment, a compound of this invention is administered at a dosage of 600 mg per day. In one embodiment, a compound of this invention is administered at a dosage of 1000 mg per day. In one embodiment, a compound of this invention is administered at a dosage of 1500 mg per day. In one embodiment, a compound of this invention is administered at a dosage of 2000 mg per day. In one embodiment, a compound of this invention is administered at a dosage of 2500 mg per day. In one embodiment, a compound of this invention is administered at a dosage of 3000 mg per day. In another embodiment, the compound is Compound IV.

In one embodiment, the methods of this invention may comprise administration of a compound of this invention at various dosages. In one embodiment, a compound of this invention is administered at a dosage of 3 mg. In additional embodiments, a compound of this invention is administered at a dosage of 10 mg, 30 mg, 40 mg, 50 mg, 80 mg, 100 mg, 120 mg, 125 mg, 200 mg, 250 mg, 300 mg, 450 mg, 500 mg, 600 mg, 900 mg, 1000 mg, 1500 mg, 2000 mg, 2500 mg or 3000 mg. In another embodiment, the compound is Compound IV.

In one embodiment, the methods of this invention may comprise administration of a compound of this invention at various dosages. In one embodiment, a compound of this invention is administered at a dosage of 0.1 mg/kg/day. In additional embodiments, a compound of this invention is administered at a dosage between 0.2 to 30 mg/kg/day, or 0.2 mg/kg/day, 0.3 mg/kg/day, 1 mg/kg/day, 3 mg/kg/day, 5 mg/kg/day, 10 mg/kg/day, 20 mg/kg/day or 30 mg/kg/day.

In one embodiment of the methods of this invention are provided for use of a pharmaceutical composition comprising a compound of formulas IA, I-XII. In additional embodiments, the methods of this invention are provided for use of a pharmaceutical composition comprising a compound of formula II, formula III, formula IV, formula V, formula VI, formula VII, formula VIII, formula IX, formula X, formula XI or formula XII.

In certain embodiment, the pharmaceutical composition is a solid dosage form. In another embodiment, the pharmaceutical composition is a tablet. In another embodiment, the pharmaceutical composition is a capsule. In another embodiment, the pharmaceutical composition is a solution. In another embodiment, the pharmaceutical composition is a transdermal patch.

In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

For administration to mammals, and particularly humans, it is expected that the physician will determine the actual dosage and duration of treatment, which will be most suitable for an individual and can vary with the age, weight, genetics and/or response of the particular individual.

In some embodiments, any of the compositions of this invention will comprise a compound of this invention, in any form or embodiment as described herein. In some embodiments, any of the compositions of this invention will consist of a compound of this invention, in any form or embodiment as described herein. In some embodiments, of the compositions of this invention will consist essentially of a compound of this invention, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

It is to be understood that any use of any of the compounds as herein described may be used in the treatment of any disease, disorder or condition as described herein, and represents an embodiment of this invention. In one embodiment, the compounds are a free base, free acid, non charged or non-complexed compound.

The following examples are presented in order to more fully illustrate the preferred embodiments of the invention. They should in no way, however, be construed as limiting the broad scope of the invention.

EXAMPLES

Example 1

General Synthesis Procedures for Compounds of Formulas II-XII and Synthetic Intermediates The organic solvents, surfactants and antioxidants, etc., they may be used in the compositions described herein are typically readily available from commercial sources. For example, PEG-300, polysorbate 80, Captex™ 200, Capmul™ MCM C8 may be purchased, for example, from Dow Chemical Company (Midland, Mich.), ICI Americas, Inc (Wilmington, Del.) or Abitec Corporation (Janesville, Wis.).

The estrogen receptor ligands described herein may be prepared in a number of ways well known to those skilled in the art. For example, the estrogen receptor ligands described herein may be prepared by the synthetic methods described in U.S. Patent Application Publication No. 2009/0062341 and U.S. Pat. No. 8,158,828, the disclosures of each of which are hereby incorporated by reference in their entireties.

General Synthesis of N,N-bis Aryl Benzamide Derivatives

General Synthesis of Diarylanilines (FIG. 5)

A mixture of arylamine (1.5 equivalent), aryl iodide (1 equivalent), $K_2CO_3$ (2 equivalents), CuI (0.1 equivalent) and L-proline (0.2 equivalent) were mixed together and dissolved in anhydrous DMSO at room temperature. Then, the reaction mixture was stirred and heated to 90° C. for 28 hours. The mixture was cooled to room temperature and hydrolyzed with water. EtOAc was added to partition the solution. The EtOAc layer was separated, washed with brine, and dried over anhydrous $MgSO_4$. The solvent was removed under reduced pressure. The solid residue was purified by flash column chromatography (silica gel) using 5% EtOAc/hexanes as eluent to afford the corresponding diarylaniline.

Bis-(4-methoxyphenyl)amine (1a)

pale-yellow solid, 73% yield. M.p. 98.6-99.0° C. $^1$H NMR ($CDCl_3$, 300 MHz) δ 6.93-6.81 (m, 8H), 5.37 (s, br, 1H), 3.78 (s, 6H). MS m/z 228.4 (M–H)$^+$

N-(4-Methoxyphenyl)-phenylamine (1b)

pale-yellow solid, 70% yield. M.p. 106.3-106.5° C. $^1$H NMR ($CDCl_3$, 300 MHz) δ 7.24-7.18 (m, 3H), 7.08-7.06 (m, 2H), 6.92-6.84 (m, 4H), 5.61 (s, br, 1H), 3.79 (s, 3H). MS m/z 200.1 (M+H)$^+$.

N-(4-Fluorophenyl)-N-4-methoxyphenylamine (1c)

pale-yellow solid, 54% yield. M.p. 60.6-61.0° C. $^1$H NMR ($CDCl_3$, 300 MHz) δ 7.01-6.83 (m, 8H), 3.78 (s, 3H). MS m/z 217 (M)$^+$.

N-(4-Benzyloxyphenyl)-N-4-methoxyphenylamine (1d)

pale-yellow solid, 54% yield. M.p. 108.0-108.4° C. $^1$H NMR ($CDCl_3$, 300 MHz) δ 7.34-7.08 (m, 5H), 6.90-6.81 (s, 3H), 3.78 (s, 3H). MS m/z 306 (M+H)$^+$.

General Synthesis of Benzamides

A mixture of arylaniline (1 equivalent), benzoyl chlorides (1.3 equivalents), and pyridine (6 equivalents) was mixed together and dissolved in anhydrous THF at room temperature. The mixture was stirred and refluxed for 24 hours. The reaction solution was cooled to room temperature, and hydrolyzed by addition of 2 N HCl solution. The solution was extracted with ethyl acetate. The organic layer was washed with a saturated aqueous $NaHCO_3$ solution to remove excess acid, dried over anhydrous $MgSO_4$, filtered and concentrated under reduced pressure. The residue was purified by flash column chromatography using EtOAc/hexanes (3/7 v/v) to afford the corresponding benzamide compounds.

3-Fluoro-N-(4-fluorophenyl)-4-methoxy-N-(4-methoxyphenyl)benzamide (2a)

yellow solid, M.p. 54-56° C., $^1$H NMR ($CDCl_3$/TMS) δ 7.24-7.11 (m, 4H), 7.05-6.97 (m, 4H), 6.85-6.78 (m, 3H), 3.86 (s, 3H), 3.79 (s, 3H). MS (ESI) m/z 370.1 [M+H]$^+$

4-Fluoro-N,N-bis(4-methoxyphenyl)-2-(trifluoromethyl)benzamide (2b)

colorless oil, 84.2% yield. $^1$H NMR ($CDCl_3$, 300 MHz) δ 7.34-7.26 (m, 4H), 7.09-7.01 (m, 3H), 6.91 (d, 2H, J=8.7 Hz), 6.87 (d, 2H, J=8.7 Hz), 3.80 (s, 3H), 3.71 (s, 3H). MS m/z 442.1 (M+Na)$^+$.

4-Methoxy-N-(4-methoxyphenyl)-N-(4-fluorophenyl)-benzamide (2c)

white solid, 97% yield, M.p. 133.5.0-134.5° C. $^1$H NMR ($CDCl_3$, 300 MHz) δ 8.11-6.66 (m, 15H), 3.74 (s, 3H), 3.73 (s, 3H). MS m/z 384 (M+H)$^+$.

N-(4-Methoxyphenyl)-N-(4-benzyloxyphenyl)-2-naphthylamide (2d)

white solid, 58% yield. M.p. 174.9-175.5° C. $^1$H NMR ($CDCl_3$, 300 MHz) δ 8.04 (s, 1H), 7.77-7.74 (m, 2H), 7.64-7.61 (m, 1H), 7.51-7.43 (m, 4H), 7.40-7.31 (m, 4H), 7.13-7.10 m, 4H), 6.88-6.78 (m, 4H), 4.99 (s, 2H), 3.74 (s, 3H). MS m/z 460 (M+H)$^+$.

4-Fluoro-N,N-bis(4-methoxyphenyl)-2-(trifluoromethyl)benzamide (2e)

colorless oil, 84.2% yield. $^1$H NMR ($CDCl_3$, 300 MHz) δ 7.34-7.26 (m, 4H), 7.09-7.01 (m, 3H), 6.91 (d, 2H, J=8.7 Hz), 6.87 (d, 2H, J=8.7 Hz), 3.80 (s, 3H), 3.71 (s, 3H). MS m/z 442.1 (M+Na)$^+$.

General Procedure for Demethylation of Benzamide Derivatives Using BBr₃

A methoxybenzamide compound was dissolved in dry CH₂Cl₂. BBr₃ (1.0 M CH₂Cl₂ solution) was added dropwise at 0° C. The reaction solution was slowly warmed to room temperature and allowed to stir overnight at room temperature. The mixture was cooled to 0° C. in an ice bath and hydrolyzed by adding water. EtOAc was added to partition the solution. The organic layer was separated; the aqueous layer was extracted with EtOAc. The organic layer was washed with brine and dried over anhydrous MgSO₄. The solvent was removed under reduced pressure. The residue was purified by flash column chromatography using CH₃OH/CH₂Cl₂ (1/9 v/v) to afford the corresponding phenolic compounds.

4-Fluoro-N,N-bis(4-hydroxyphenyl)-2-(trifluoromethyl)benzamide (3a)

white solid, 92.5% yield. ¹H NMR (DMSO-d₆, 300 MHz) δ 9.55 (s, 1H), 9.53 (s, 1H), 7.69-7.58 (m, 2H), 7.46-7.39 (m, 1H), 7.18 (d, 2H, J=8.7 Hz), 6.93 (d, 4H, J=8.7 Hz), 7.03 (d, 2H, J=8.4 Hz), 6.78 (d, 2H, J=8.7 Hz), 6.57 (d, 2H, J=8.7 Hz). MS m/z 392.1 (M+H)⁺.

The following compounds where synthesized as described herein above and characterized and summarized in Table 1: N,N-bis(4-hydroxyphenyl)-4-propylbenzamide (II); 3-fluoro-N-(4-fluorophenyl)-4-hydroxy-N-(4-hydroxyphenyl)benzamide (IV); N,N-bis(4-hydroxyphenyl)-2,3-dimethylbenzamide (V); 3-fluoro-4-hydroxy-N,N-bis(4-hydroxyphenyl)-benzamide (VII); 3-fluoro-4-hydroxy-N-(4-hydroxyphenyl)-N-phenylbenzamide (XI); and 3-fluoro-N,N-bis(4-hydroxyphenyl)-2-methylbenzamide (XII).

General Procedures for Debenzylation of Benzyloxyphenyl-Benzamides

A benzyloxyphenyl-benzamides compound was dissolved in EtOH in a 250 mL hydrogenation bottle. Pd/C powder (5% mol) was added to the solution. The reaction vessel was mounted to a hydrogenation apparatus under 20 psi pressure hydrogen gas. The reaction was monitored by TLC until the disappearance of starting material. Then, the solvent was removed under reduced pressure. The residue was purified by flash column chromatography with hexanes/EtOAc=3/2 v/v to afford the desired product.

The following compounds where synthesized as described herein above and characterized and summarized in Table 1: N,N-bis(4-hydroxyphenyl)-2-naphthylamide (VI).

General Procedures for Reduction of Deprotected Benzamides

Benzamide compounds were dissolved in 20 mL anhydrous THF at room temperature. H₃B(SMe₂) was added via a syringe at room temperature under argon. The reaction solution was stirred and heated to reflux for 6 hours. Then, the reaction was quenched by adding 10 mL of MeOH at 0° C. The solvent was removed under reduced pressure. The residue was subjected to flash column chromatography (silica-gel, CH₂Cl₂/MeOH=9/1 v/v) to afford the desired product.

The following compounds where synthesized as described herein above and characterized and summarized in Table 1: 4,4'-(2,3-dimethylbenzylazanediyl)diphenol (III); 4-((4-fluorophenyl)(4-hydroxybenzyl)amino)phenol (VIII).

General synthesis of O-(2-piperidin-1-ylethoxy)-benzamides and analogues

To a solution of hydroxyphenyl containing benzamide analogue (1 equivalent) in acetone, K₂CO₃ (3 equivalents) and N-chloroethyl-piperidine hydrochloride salt (1.2 equivalents) were added. The solution was heated to reflux for 6 hours. The solution was evaporated to dryness. The residue was hydrolyzed by adding water, and then extracted with ethyl acetate. The organic layers were separated and dried over anhydrous MgSO₄. The solvent was removed under reduced pressure. The residue was purified by flash chromatography with methylene chloride/methanol=9/1 v/v to give the desired compound. The hydrochloride salts were prepared by adding HCl in Et₂O to the methanol solution of the compounds followed by evaporation of solvents.

The following compounds where synthesized as described herein above and characterized and summarized in Table 1: 4-fluoro-N-(4-hydroxyphenyl)-N-(4-(2-(piperidin-1-yl)ethoxy)phenyl)-2-(trifluoromethyl)benzamide (IX); and 4-fluoro-N-(4-hydroxyphenyl)-N-(4-(2-(piperidin-1-yl)ethoxy)phenyl)-2-(trifluoromethyl)benzamide hydrochloride (X) which is the HCl salt of TX.

TABLE 1

Physical Characterization of Compounds of Formulas II-XII

| Cmpd # | Structure | PHYSICAL CHARACTERIZATION |
|---|---|---|
| II. | 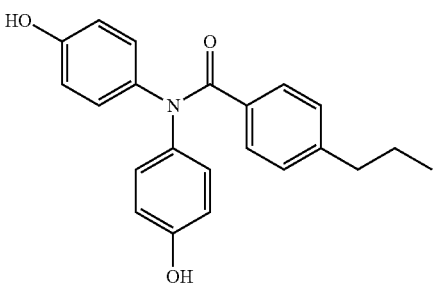 | ¹H NMR (DMSO-d₆, 300 MHz) δ 9.46 (s, 2H, 2 X OH), 7.27-7.26 (m, 2H, ArH), 7.06-7.04 (m, 2H, ArH), 6.99-6.97 (m, 4H, ArH), 6.66-6.65 (m, 4H, ArH), 2.50 (s, 2H, CH₂, overlapped with DMSO peak), 1.53-1.52 (m, 2H, CH₂), 0.82 (t, J = 7.33 Hz, 3H, CH₃). m/z 346.0 (M − H)⁻ |

TABLE 1-continued

Physical Characterization of Compounds of Formulas II-XII

| Cmpd # | Structure | PHYSICAL CHARACTERIZATION |
| --- | --- | --- |
| III. | 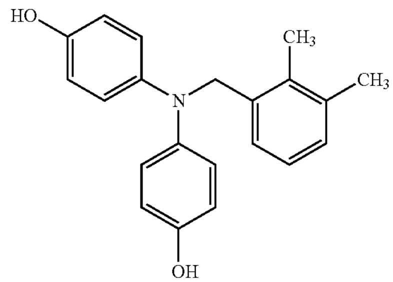 [SMILES: Cc1cccc(CN(c2ccc(O)cc2)c2ccc(O)cc2)c1C] | Tan foam, 41% yield. M.p. 147-150° C. $^1$H NMR (DMSO-$d_6$, 300 MHz) δ 8.92 (s, 2H), 7.07 (d, J = 7.33 Hz, 1H), 7.00-6.94 (m, 2H), 6.76-6.72 (m, 4H), 6.63-6.59 (m, 4H), 4.72 (s, 2H), 2.23 (s, 3H), 2.16 (s, 3H). m/z 320.2 (M + H)$^+$ |
| IV. | 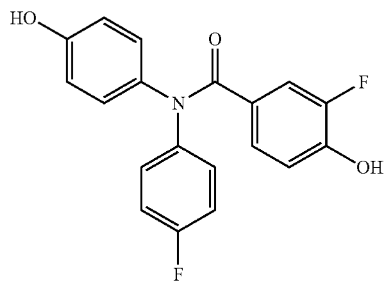 [SMILES: O=C(c1ccc(O)c(F)c1)N(c1ccc(O)cc1)c1ccc(F)cc1] | Tan solid, 92% yield. M.p. 110-112° C. $^1$H NMR (DMSO-$d_6$, 300 MHz) δ 10.14 (bs, 1H), 9.71 (bs, 1H), 7.26-7.11 (m, 5H), 7.05-6.99 (m, 3H), 6.78 (t, J = 6.81 Hz, 2H), 6.68 (d, J = 8.68 Hz, 2H). m/z 364.1 (M + Na)$^+$ |
| V. | 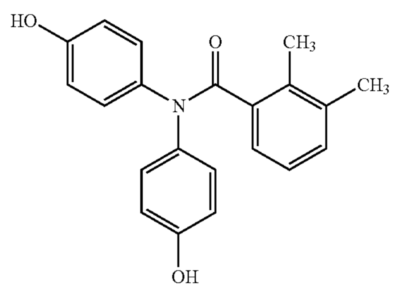 [SMILES: Cc1cccc(C(=O)N(c2ccc(O)cc2)c2ccc(O)cc2)c1C] | $^1$H NMR (DMSO-$d_6$, 300 MHz) δ 9.47 (bs, 2H, 2 X OH), 7.18 (d, J = 8.30 Hz, 2H, ArH), 7.06 (d, J = 7.08 Hz, 1H, ArH), 7.00-6.92 (m, 4H, ArH), 6.78 (d, J = 8.30 Hz, 2H, ArH), 6.51 (d, J = 8.06 Hz, 2H, ArH), 2.22 (s, 3H, CH$_3$), 2.15 (s, 3H, CH$_3$). m/z 334.3 (M + H)$^+$ |
| VI. | 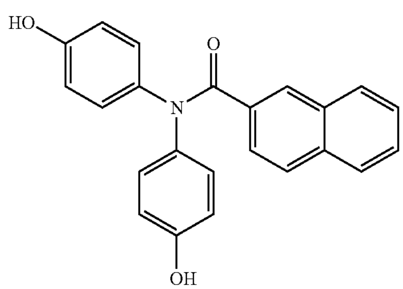 [SMILES: O=C(c1ccc2ccccc2c1)N(c1ccc(O)cc1)c1ccc(O)cc1] | white solid, 70% yield. M.p. 264.3-265.2° C. (decomposed). $^1$H NMR (DMSO-$d_6$, 500 MHz) δ 9.46 (s, 2H), 7.98 (s, 1H), 7.85-7.75 (m, 2H), 7.75-7.73 (m, 2H), 7.54-7.48 (m, 2H), 7.45-7.43 (m, 1H), 7.05 (s, 4H), 6.66 (s, 4H). m/z 356 (M + H)$^+$ |
| VII. | 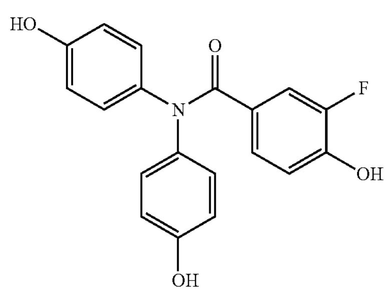 [SMILES: O=C(c1ccc(O)c(F)c1)N(c1ccc(O)cc1)c1ccc(O)cc1] | $^1$H NMR (DMSO-$d_6$, 300 MHz) δ 10.25 (bs, 1H, OH), 9.48 (bs, 2H, 2 X OH), 7.12-6.95 (m, 6H, ArH), 6.80-6.65 (m, 5H, ArH). m/z 338.0 (M − H)$^-$ |

TABLE 1-continued

Physical Characterization of Compounds of Formulas II-XII

| Cmpd # | Structure | PHYSICAL CHARACTERIZATION |
|---|---|---|
| VIII. | 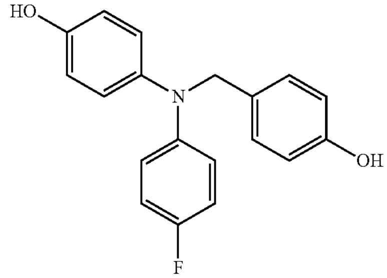 [SMILES: Oc1ccc(CN(c2ccc(O)cc2)c2ccc(F)cc2)cc1] | yellow oil, 92% yield. $^1$H NMR (DMSO-$d_6$, 500 MHz) δ 9.29 (s, 1H), 9.24 (s, 1H), 7.09 (d, 2H, J = 8.3 Hz), 6.98 (d, 2H, J = 9.0 Hz), 6.94-6.91 (m, 2H), 6.73 (d, 2H, J = 9.0 Hz), 6.68-6.64 (m, 4H), 4.70 (s, 2H). m/z 307.8 (M − H)$^-$ |
| IX. and X. (HCl salt of IX.) | 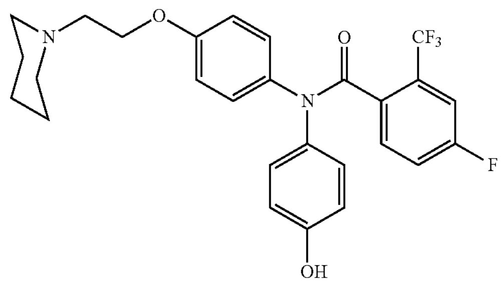 [SMILES: O=C(c1ccc(F)cc1C(F)(F)F)N(c1ccc(O)cc1)c1ccc(OCCN2CCCCC2)cc1] | white solid, 57.7% yield. $^1$H NMR (DMSO-$d_6$, 300 MHz) δ 9.57 (s, 1H), 7.71-7.68 (m, 2H), 7.47-7.44 (m, 1H), 7.28 (d, 1H, J = 9.0 Hz), 7.18 (d, 1H, J = 8.7 Hz), 7.13 (d, 1H, J = 8.7 Hz), 7.05 (d, 1H, J = 8.4 Hz), 6.97 (d, 1H, J = 9.0 Hz), 6.80-6.76 (m, 2H), 6.57 (d, 1H, J = 87. Hz), 4.06 (t, 1H, J = 6.0 Hz), 3.93 (t, 1H, J = 6.0 Hz), 2.66 (t, 1H, J = 5.7 Hz), 2.55 (t, 1H, J = 5.4 Hz), 2.44 (s, 2H), 2.36 (s, 2H), 1.49-1.37 (m, 6H). m/z 501.0 (M − H)$^-$ |
| XI. | 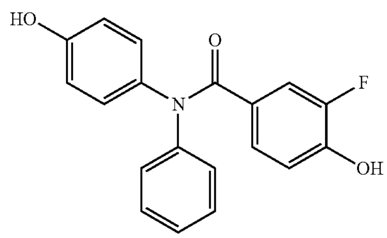 [SMILES: O=C(c1ccc(O)c(F)c1)N(c1ccccc1)c1ccc(O)cc1] | $^1$H NMR (DMSO-$d_6$, 300 MHz) δ 9.95 (bs, 1H, OH), 9.47 (bs, 2H, 2 X OH), 7.02-6.95 (m, 6H, ArH), 6.75-6.72 (m, 1H, ArH), 6.68-6.66 (m, 4H, ArH). m/z 324.0 (M + H)$^+$ |
| XII. | 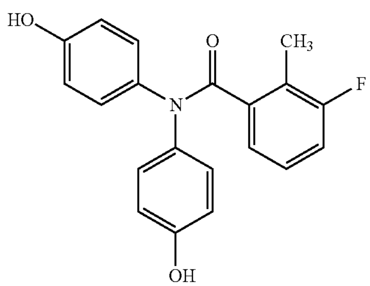 [SMILES: Cc1c(F)cccc1C(=O)N(c1ccc(O)cc1)c1ccc(O)cc1] | Pale-red solid. 72.0% yield. M.p. >240° C. $^1$H NMR (DMSO-$d_6$, 300 MHz) δ 9.50 (bs, 2H), 7.19-6.79 (m, 7H), 6.61 (d, J = 8.93 Hz, 2H), 6.53 (d, J = 7.79 Hz, 2H), 2.23 (s, 3H). m/z 336.0 (M − H)$^-$. |

Example 2

Synthesis of the Compound of Formula IV (FIG. 6)

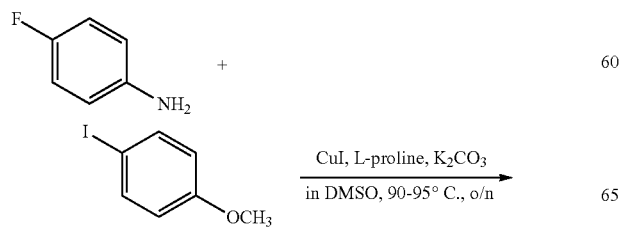

-continued

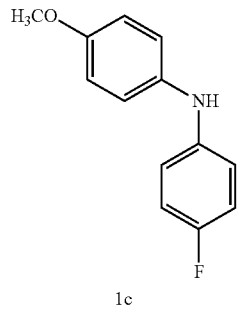

Step 1: Synthesis of 4-fluoro-N-(4-methoxyphenyl)aniline (1c)

A mixture of 4-fluoroaniline (78.63 g, 0.708 mol), 4-iodoanisole (138.00 g, 0.590 mol), anhydrous $K_2CO_3$ (122.23 g, 0.884 mol), CuI (11.23 g, 58.96 mmol) and L-proline (13.58 g, 0.118 mol) was mixed together in a dry 1 L three-necked round-bottomed flask fitted with a stirring bar, a reflux condenser and an argon inlet. Anhydrous DMSO (300 mL) was added at room temperature. The reaction mixture was stirred and heated to 90° C. for 20 hours under argon. Then, the mixture was cooled to room temperature and hydrolyzed with water (300 mL). EtOAc (200 mL) was added to partition the solution. The EtOAc layer was separated. The aqueous layer was extracted with 100 mL of EtOAc. The EtOAc layers were combined, washed with brine (2×100 mL) and dried over anhydrous $MgSO_4$ (50 g). The solvent was removed under reduced pressure. The brown oil residue was purified by flash column chromatography (silica gel, hexanes/EtOAc=9/1 v/v) to afford 4-fluoro-N-(4-methoxyphenyl)aniline (1c) as a yellow solid product, 99.70 g, 77.8% yield. M.p. 46-48° C. MS (ESI) m/z 218.1 [M+H]$^+$, $^1$H NMR (DMSO-d$_6$, 300 MHz) δ 7.77 (bs, 1H), 7.03-6.98 (m, 4H), 6.93-6.82 (m, 4H), 3.70 (s, 3H).

Step 2: Synthesis of 3-fluoro-N-(4-fluorophenyl)-4-methoxy-N-(4-methoxyphenyl)benzamide (2a)

4-Fluoro-N-(4-methoxyphenyl)aniline (1c) (90.78 g, 0.418 mol) and 3-fluoro-4-methoxybenzoyl chloride (94.55 g, 0.501 mol) were mixed together and dissolved in anhydrous THF (200 mL) in a dry 1 L three-necked round-bottomed flask fitted with a stirring bar, a reflux condenser and an argon inlet. Anhydrous pyridine (132.22 g, 1.672 mol) was added via a syringe at room temperature under argon. The reaction mixture was stirred and heated to reflux overnight. Then, the reaction mixture was cooled to room temperature and filtered to remove pyridine salt. The solution was concentrated to remove THF solvent. The residue oil was washed with 200 mL of 2N HCl solution and extracted with ethyl acetate (2×200 mL). The combined organic layer was washed with a saturated aqueous $Na_2CO_3$ solution (150 mL) to remove excess benzoyl chloride and acid, dried over $MgSO_4$ (50 g), filtered, and concentrated under reduced pressure to give an oil. The residue was purified by flash column chromatography using silica-gel with $CH_2Cl_2$/acetone (50/1 v/v) to afford the pure corresponding benzamide compound as a yellow solid. M.p. 54-56° C. MS (ESI) m/z 370.1 [M+H]$^+$, $^1$H NMR (CDCl$_3$/TMS) δ 7.24-7.11 (m, 4H), 7.05-6.97 (m, 4H), 6.85-6.78 (m, 3H), 3.86 (s, 3H), 3.79 (s, 3H).

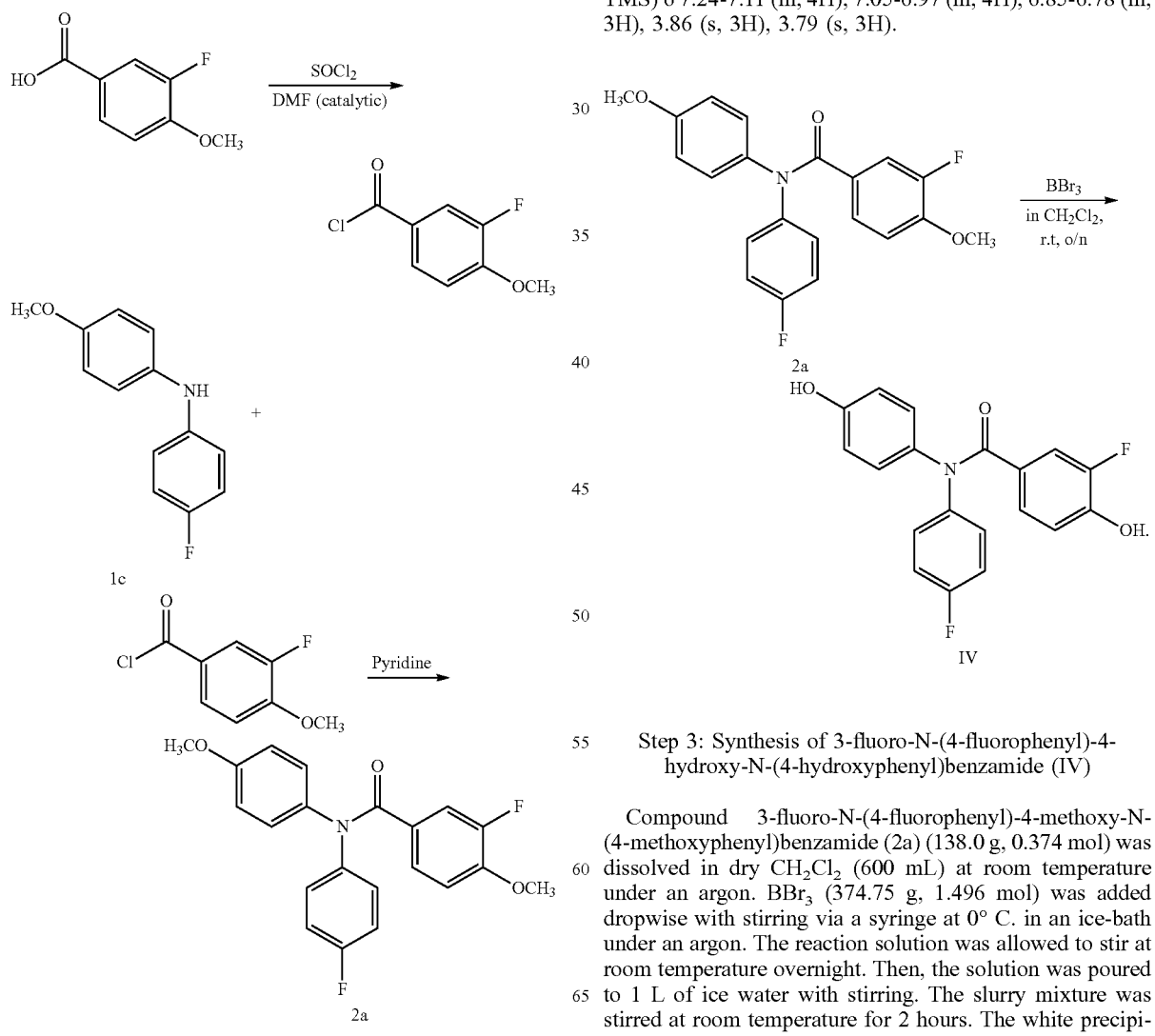

Step 3: Synthesis of 3-fluoro-N-(4-fluorophenyl)-4-hydroxy-N-(4-hydroxyphenyl)benzamide (IV)

Compound 3-fluoro-N-(4-fluorophenyl)-4-methoxy-N-(4-methoxyphenyl)benzamide (2a) (138.0 g, 0.374 mol) was dissolved in dry $CH_2Cl_2$ (600 mL) at room temperature under an argon. BBr$_3$ (374.75 g, 1.496 mol) was added dropwise with stirring via a syringe at 0° C. in an ice-bath under an argon. The reaction solution was allowed to stir at room temperature overnight. Then, the solution was poured to 1 L of ice water with stirring. The slurry mixture was stirred at room temperature for 2 hours. The white precipitate was filtered, washed with water (2×100 mL) and dried under vacuum. The CH$_2$Cl$_2$ layer was separated, dried over anhydrous MgSO$_4$ (50 g), filtered and concentrated under reduced pressure to dryness. The white precipitate and residue from CH$_2$Cl$_2$ solution were combined and purified by flash column chromatography (silica gel, CH$_2$Cl$_2$/acetone/MeOH=90/7/3 v/v/v) to give a light tan solid which was recrystallized from hot EtOAc/hexanes solution twice to afford a white crystalline solid, 104.0 g, 81.6% yield. M.p. 110-112° C. MS (ESI) m/z 364.1 [M+Na]$^+$, $^1$H NMR (DMSO-d$_6$) δ 10.14 (bs, 1H), 9.71 (bs, 1H), 7.25-7.11 (m, 5H), 7.05-6.99 (m, 3H), 6.78 (t, J=8.6 Hz, 1H), 6.68 (d, J=8.7 Hz, 2H).

Example 3

Synthesis of the Compound of Formula VI (FIG. 7)

Synthesis of 4-(benzyloxy)-N-(4-methoxyphenyl)aniline (1d)

A mixture of 4-benzyloxyaniline (16.6 g, 83.31 mmol), 4-iodoanisole (15.0 g, 64.09 mmol), K$_2$CO$_3$ (17.72 g, 128.18 mmol), CuI (1.22 g, 6.41 mmol) and L-proline (1.48 g, 12.82 mmol) were mixed together and dissolved in anhydrous DMSO (120 mL) at room temperature. Then, the reaction mixture was stirred and heated to 90° C. for 48 hours. The mixture was cooled to room temperature and hydrolyzed with water. EtOAc was added to partition the solution. The EtOAc layer was separated washed with brine, dried over anhydrous MgSO$_4$. The solvent was removed under reduced pressure. The solid residue was purified by flash column chromatography (silica gel) using EtOAc/hexanes (1/9 v/v) to afford the corresponding diarylaniline as a yellow solid, 9.8 g, 50% yield. M.p. 108.0-108.4° C. $^1$H NMR (CDCl$_3$, 300 MHz) δ 7.34-7.25 (m, 5H), 6.90-6.81 (m, 8H), 5.02 (s, 2H), 3.78 (s, 3H). MS m/z 306 (M+H)$^+$.

Synthesis of N-(4-benzyloxyphenyl)-N-(4-methoxyphenyl)-2-naphthamide (2d)

One equivalent of 4-(benzyloxy)-N-(4-methoxyphenyl)aniline (0.80 g, 2.62 mmol) was mixed with 1.5 equivalents of 2-naphthoyl chloride (0.75 g, 3.93 mmol) and 4 equivalents of pyridine (0.83 g, 10.48 mmol) in a dry three-necked round-bottomed flask equipped with a magnetic stirring bar and a reflux condenser. The mixture was dissolved in anhydrous THF (30 mL) and heated to reflux for 20 hours. The reaction solution was cooled to room temperature and filtered. The solvent was removed under reduced pressure. The residue was purified by flash column chromatography using silica-gel with EtOAc/hexanes (3/7 v/v) to afford the pure corresponding naphthamide compound as a white solid, 0.70 g, 58% yield. M.p. 174.9-175.5° C. $^1$H NMR (CDCl$_3$, 300 MHz) δ 8.04 (s, 1H), 7.77-7.74 (m, 2H), 7.64-7.61 (m, 1H), 7.51-7.43 (m, 4H), 7.40-7.31 (m, 4H), 7.13-7.10 (m, 4H), 6.88-6.78 (m, 4H), 4.99 (s, 2H), 3.74 (s, 3H). MS m/z 460 (M+H)$^+$.

Synthesis of N,N-Bis(4-hydroxyphenyl)-2-naphthylamide (VI)

Compound N-(4-benzyloxyphenyl)-N-(4-methoxyphenyl)-2-naphthamide (2d) (0.50 g, 1.09 mmol) was dissolved in dry CH$_2$Cl$_2$ (30 mL) at room temperature. BBr$_3$ (3.26 mL of 1.0 M CH$_2$Cl$_2$ solution, 3.26 mmol) was added dropwise with stirring via a syringe at room temperature. The reaction solution was allowed to stir overnight at room temperature. The mixture was cooled to 0° C. in an ice bath and hydrolyzed by adding water. EtOAc was added to partition the solution. The organic layer was separated; the aqueous layer was extracted with EtOAc twice. The organic layers were combined, washed with brine and dried over anhydrous MgSO$_4$. The solvent was removed under vacuum. The residue was purified by flash column chromatography using silica-gel with CH$_3$OH/CH$_2$Cl$_2$ (1/9 v/v) to afford the pure desired phenolic compound as a white solid, 0.27 g, white solid, 70% yield. M.p. 264.3-265.2° C. (decomposed). $^1$H NMR (DMSO-d$_6$, 500 MHz) δ 9.46 (s, 2H), 7.98 (s, 1H), 7.85-7.75 (m, 2H), 7.75-7.73 (m, 2H), 7.54-7.48 (m, 2H), 7.45-7.43 (m, 1H), 7.05 (s, 4H), 6.66 (s, 4H). MS m/z 356 (M+H)$^+$.

Example 4

Synthesis of the Compound of Formula VIII

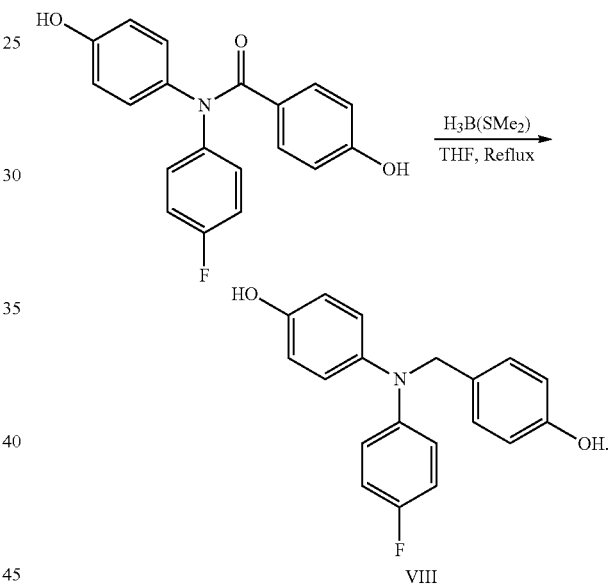

Synthesis of 4-((4-fluorophenyl)(4-hydroxybenzyl)amino)phenol (VIII)

Compound N-(4-fluorophenyl)-4-hydroxy-N-(hydroxyphenyl)benzamide (0.30 g, 0.93 mmol) was dissolved in 20 mL anhydrous THF at room temperature. H$_3$B(SMe$_2$) (1.86 mL of 2M THF solution, 3.71 mmol) was added via a syringe at room temperature under argon. The reaction solution was stirred and heated to reflux for 6 hours. Then, the reaction was quenched by adding 10 mL of MeOH at 0° C. The solvent was removed under reduced pressure. The residue was subjected to flash column chromatography (silica-gel, CH$_2$Cl$_2$/MeOH=9/1 v/v) to give a yellow oil, 0.26 g, 92% yield. $^1$H NMR (DMSO-d$_6$, 500 MHz) δ 9.29 (s, 1H), 9.24 (s, 1H), 7.09 (d, 2H, J=8.3 Hz), 6.98 (d, 2H, J=9.0 Hz), 6.94-6.91 (m, 2H), 6.73 (d, 2H, J=9.0 Hz), 6.68-6.64 (m, 4H), 4.70 (s, 2H). MS m/z 307.8 (M−H)$^−$.

Example 5

Synthesis of the Compound of Formulas IX and X (FIG. 8)

Synthesis of Diarylanilines

A mixture of arylamine (1.5 equivalent), aryl iodide (1 equivalent), $K_2CO_3$ (2 equivalents), CuI (0.1 equivalent) and L-proline (0.2 equivalent) were mixed together and dissolved in anhydrous DMSO at room temperature. Then, the reaction mixture was stirred and heated to 90° C. for 28 hours. The mixture was cooled to room temperature and hydrolyzed with water. EtOAc was added to partition the solution. The EtOAc layer was separated, washed with brine, dried over anhydrous $MgSO_4$. The solvent was removed under reduced pressure. The solid residue was purified by flash column chromatography (silica gel) using EtOAc/hexanes (3/7 v/v) as solvent to afford the corresponding diarylaniline. Bis-(4-methoxyphenyl)amine (1a): pale-yellow solid, 73% yield. $^1$H NMR ($CDCl_3$, 300 MHz) δ 6.93-6.81 (m, 8H), 5.37 (s, br, 1H), 3.78 (s, 6H). MS m/z 228.4 (M−H)$^+$.

Synthesis of 4-fluoro-N,N-bis(4-methoxyphenyl)-2-(trifluoromethyl)benzamide (2e)

1 equivalent of bis-(4-methoxyphenyl)amine (1a) (0.73 g, 3.18 mmol) was mixed with 1.2 equivalents of 4-fluoro-2-trifluoromethylbenzoyl chloride (0.87 g, 3.82 mmol) and 6 equivalents of pyridine (1.51 g, 19.08 mmol) in a dry three-necked round-bottomed flask equipped with a magnetic stirring bar and a reflux condenser. The mixture was dissolved in anhydrous THF (20 mL) and heated to 90° C. for 20 hours. The reaction solution was cooled to room temperature and filtered. The solvent was removed under reduced pressure. The residue was purified by flash column chromatography using silica-gel with EtOAc/hexanes (3/7 v/v) to afford the pure corresponding benzamide compound as a colorless oil, 1.12 g, 84.2% yield. $^1$H NMR ($CDCl_3$, 300 MHz) δ 7.34-7.26 (m, 4H), 7.09-7.01 (m, 3H), 6.91 (d, 2H, J=8.7 Hz), 6.87 (d, 2H, J=8.7 Hz), 3.80 (s, 3H), 3.71 (s, 3H). MS m/z 442.1 (M+Na)$^+$.

Synthesis of 4-fluoro-N,N-bis(4-hydroxyphenyl)-2-(trifluoromethyl)benzamide (3a)

Compound 4-fluoro-N,N-bis(4-methoxyphenyl)-2-(trifluoromethyl)benzamide (2e) (1.00 g, 2.38 mmol) was dissolved in dry $CH_2Cl_2$ (30 mL) at room temperature. $BBr_3$ (10 mL of 1.0 M $CH_2Cl_2$ solution, 10.0 mmol) was added dropwise with stirring via a syringe at room temperature. The reaction solution was allowed to stir overnight at room temperature. The mixture was cooled to 0° C. in an ice bath and hydrolyzed by adding water. EtOAc was added to partition the solution. The organic layer was separated; the aqueous layer was extracted with EtOAc twice. The organic layers were combined, washed with brine and dried over anhydrous $MgSO_4$. The solvent was removed under vacuum. The residue was purified by flash column chromatography using silica-gel with $CH_3OH/CH_2Cl_2$ (1/9 v/v) to afford the pure desired phenolic compound as a white solid, 0.86 g, 92.5% yield. $^1$H NMR (DMSO-$d_6$, 300 MHz) δ 9.55 (s, 1H), 9.53 (s, 1H), 7.69-7.58 (m, 2H), 7.46-7.39 (m, 1H), 7.18 (d, 2H, J=8.7 Hz), 6.93 (d, 4H, J=8.7 Hz), 7.03 (d, 2H, J=8.4 Hz), 6.78 (d, 2H, J=8.7 Hz), 6.57 (d, 2H, J=8.7 Hz). MS m/z 392.1 (M+H)$^+$.

Synthesis of 4-fluoro-N-(4-hydroxyphenyl)-N-[4-(2-piperidin-1-yl)-ethoxy)phenyl]-2-(trifluoromethyl)benzamide. (IX)

To a solution of 4-fluoro-N,N-bis(4-hydroxyphenyl)-2-(trifluoromethyl)benzamide (3a) (0.61 g, 1.56 mmol) in acetone, $K_2CO_3$ (1.29 g, 9.36 mmol) and N-chloroethyl-piperidine hydrochloride salt (0.34 g, 1.87 mmol) were added. The solution was heated to reflux for 20 hours. The solution was evaporated to dryness. The residue was purified by flash chromatography (silica-gel; methylene chloride/methanol=9/1 v/v) to give the desired compound as a white solid, 0.45 g, 57.7% yield. $^1$H NMR (DMSO-$d_6$, 300 MHz) δ 9.57 (s, 1H), 7.71-7.68 (m, 2H), 7.47-7.44 (m, 1H), 7.28 (d, 1H, J=9.0 Hz), 7.18 (d, 1H, J=8.7 Hz), 7.13 (d, 1H, J=8.7 Hz), 7.05 (d, 1H, J=8.4 Hz), 6.97 (d, 1H, J=9.0 Hz), 6.80-6.76 (m, 2H), 6.57 (d, 1H, J=87. Hz), 4.06 (t, 1H, J=6.0 Hz), 3.93 (t, 1H, J=6.0 Hz), 2.66 (t, 1H, J=5.7 Hz), 2.55 (t, 1H, J=5.4 Hz), 2.44 (s, 2H), 2.36 (s, 2H), 1.49-1.37 (m, 6H). MS m/z 501.0 (M−H)$^-$.

The hydrochloride salt (X) was prepared by adding HCl in $Et_2O$ to the methanol solution of the compounds followed by evaporation of solvents.

Example 6

Estrogen Receptor Binding Affinities, Agonist and Antagonist Activity

The ER binding affinity of the compounds was determined using an in vitro competitive radioligand binding assay with [2,4,6,7-$^3$H(N)]-Estradiol ([$^3$H]E2), a natural high affinity ER ligand, and bacterially expressed GST fusion ER-α or ER-β ligand binding domain (LBD) protein.
Method
Recombinant ER-α or ER-β was combined with [$^3$H]E$_2$ to determine the equilibrium dissociation constant ($K_d$) of [$^3$H]E$_2$. Protein was incubated with increasing concentrations of [$^3$H]E$_2$ with and without a high concentration of unlabeled E$_2$ at 4° C. for 18 h in order to determine total and non-specific binding. Non-specific binding was subtracted and the $K_d$ of E$_2$ (ERα: 0.71 nM; ERβ: 1.13 nM) was determined using non-linear regression. In addition, the concentration of [$^3$H]E$_2$ required to saturate ER-α and ER-β LBD was determined to be 4-6 nM.

Increasing concentrations of the compounds (range: $10^{-11}$ to $10^{-6}$ M) were incubated with [$^3$H]E$_2$ (5.7 nM) and ER LBD using the conditions described above. Following incubation, plates were harvested with GF/B filters on the Unifilter-96 Harvester (PerkinElmer) and washed three times with ice-cold buffer B (50 mM Tris, pH 7.2). The filter plates were dried at room temperature, then 35 Microscint-O cocktail was added to each well and the filter plates were sealed with TopSeal-A. Radioactivity was counted in a TopCount® NXT Microplate Scintillation Counter using the settings for $^3$H in Microscint cocktail (PerkinElmer).

The specific binding of [$^3$H]E$_2$ at each concentration of the compounds was determined by subtracting the nonspecific binding of [$^3$H]E$_2$ (determined by incubating with $10^{-6}$ M unlabeled E$_2$) and expressing it as a percentage of the specific binding in the absence of test compound. The concentration of the compounds that reduced the specific binding of [$^3$H]E$_2$ by 50% (IC$_{50}$) was determined. The equilibrium binding constant (K$_i$) of the compounds was then calculated by: $K_i=K_d \times IC_{50}/(K_d+L)$, where $K_d$ is the equilibrium dissociation constant of [$^3$H]E$_2$ (ER-α=0.71 nM; ER-β=1.13 nM), and L is the concentration of [³H]E₂ (ER-α: 5.7 nM; ER-β: 5.7 nM).

Results

Binding assays revealed that ligands bound ER-α and ER-β at various concentrations ranging from 3.75 nM to greater than 1000 nM and selectivity ranges from the compound being isoform selective to being non-isoform selective. Results from representative compounds are listed in Table 2.

TABLE 2

Binding results for selected compounds.

| COMPOUNDS | ER-α $K_i$ (nM) | ER-β $K_i$ (nM) |
|---|---|---|
| II | 3.75 | 81.6 |
| III | 3.81 | 6.44 |
| IV | 21.7 | 15.2 |
| V | 7.13 | 35.9 |
| VI | 9 | 72 |
| VII | 6.06 | 76.92 |
| VIII | 13 | 19 |
| IX (or X) | 14.79 | 646.32 |
| XI | 15 | 57 |

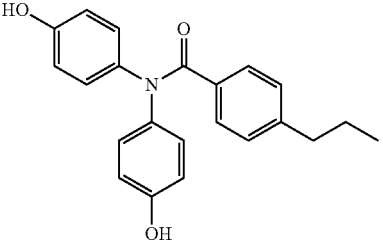 [SMILES: CCCc1ccc(C(=O)N(c2ccc(O)cc2)c2ccc(O)cc2)cc1]
II

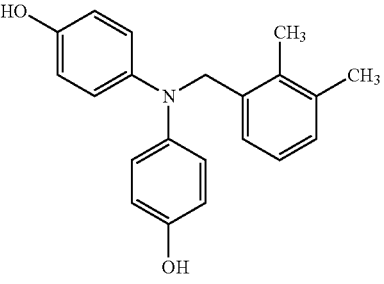
III

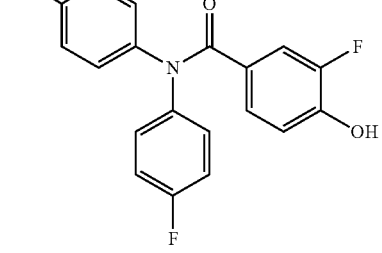
IV

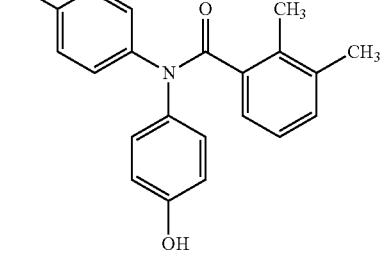
V

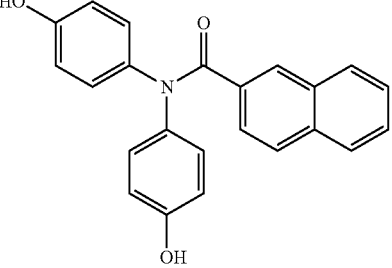
VI

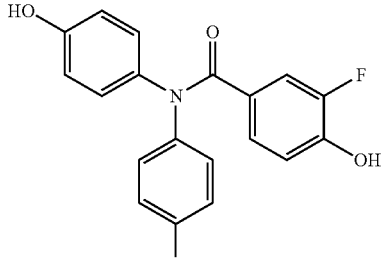
VII

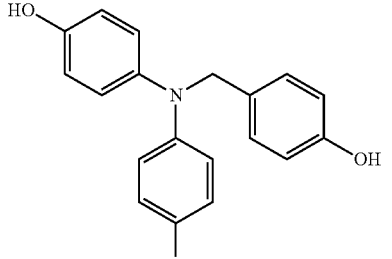
VIII

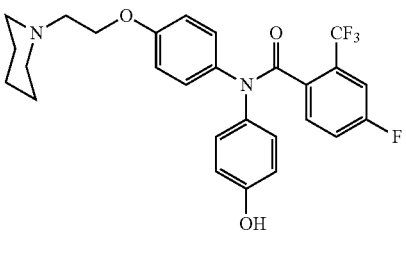 [SMILES: O=C(c1ccc(F)cc1C(F)(F)F)N(c1ccc(O)cc1)c1ccc(OCCN2CCCCC2)cc1]
IX (or X)

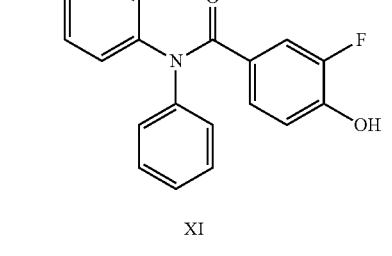
XI

TABLE 2-continued

Binding results for selected compounds.

| COMPOUNDS | ER-α $K_i$ (nM) | ER-β $K_i$ (nM) |
|---|---|---|
| XII (HO-C6H4)-N(-C6H4-OH)-C(=O)-C6H3(CH3)(F) | 15.12 | 25.02 |

Compound IV binds to ERα and ERβ with nanomolar affinity. The ER binding affinity of Compound IV was determined using an in vitro competitive radioligand binding assay with [2,4,6,7-$^3$H(N)]-Estradiol ([$^3$H]E$_2$), a natural high affinity ER ligand, and bacterially expressed GST fusion ERα or ERβ ligand binding domain (LBD) protein. In this assay, the ERα and ERβ binding affinities ($K_i$ values) of Compound IV were 21.7±1.7 nM (n=3) and 15.2±4.1 nM (n=3), respectively. Upon binding to ER, Compound IV initiates a complex series of molecular events that lead to the expression or repression of target genes involved with pharmacologic response in a tissue-selective manner. In transient transfection assays, Compound IV is an ERα and ERβ agonist, with greater demonstrated potency to stimulate ERα-mediated transcriptional activation as compared to that of ERβ. Whereas estradiol activates ERα and ERβ with a 5.1-fold greater selectivity for ERα, Compound IV shows a 49.0-fold selectivity for ERα. Thus, Compound IV has a relative 9.7-fold selectivity in relative transactivation potency (normalized to estradiol values) for ERα over ERβ. Additionally, no antagonist effects were observed in estradiol (1 nM)-stimulated transcriptional activation by Compound IV at concentrations up to 10 μM. Although many steroidal ligands cross-react with other nuclear hormone receptors, the actions of Compound IV are specific for ERα and ERβ. Compound IV was screened for cross-reactivity against rat isoforms of glucocorticoid receptor (GR), mineralocorticoids receptor (MR), progesterone receptor (PR), androgen receptor (AR) and human isoforms of farnesoid X receptor (FXR), liver X receptor (LXR), peroxisome proliferator-activated receptors (PPAR-α and PPAR-γ), and retinoid X receptor (RXR-α) in both agonist and antagonist modes in transcriptional activation assays. Compound IV did not display any agonist or antagonist activity in any of these assays, supporting the conclusion that Compound IV does not functionally cross-react with these nuclear hormone receptor superfamily members.

Example 7

Transactivation of Selected Compounds

Transactivation assays in agonist and antagonist modes were performed to identify whether the compound is an agonist, antagonist or a partial.

Method

Rat estrogen receptors (ER-α and ER-β) were cloned from rat ovarian cDNA into a pCR3.1 plasmid vector backbone. Sequencing was performed to determine the absence of any mutations. HEK-293 cells were plated at 100,000 cells per well of a 24 well plate in Dulbecco's Minimal Essential Media (DMEM)+5% charcoal-stripped fetal bovine serum (csFBS). The cells were transfected using Lipofectamine (Invitrogen, Carlsbad, Calif.) with 0.25 μg ERE-LUC, 0.02 μg CMV-LUC (renilla luciferase) and 12.5 ng of rat ER-α or 25 ng rat ER-β. The cells were treated 24 hrs after transfection with various concentrations of compounds or a combination of compounds and estradiol to determine the antagonistic activity. Luciferase assays were performed 48 hrs after transfection.

Results

Screening of compounds of this invention in the transactivation system revealed that the compounds belonged to all the three classes i.e. agonists, antagonists and partial agonist. An example of an agonist and an antagonist is given in Table-3. Transactivation results matched extremely well with the binding results for isoform selectivity.

Table 3 provides the $EC_{50}$ and $IC_{50}$ transactivation values for some selected compounds of this invention.

TABLE 3

Transactivation (both agonist and antagonist) of selective compounds of this invention.

| COMPOUND | ER-α $EC_{50}$ (nM) | ER-β $EC_{50}$ (nM) | ER-α $IC_{50}$ (nM) | ER-β $IC_{50}$ (nM) |
|---|---|---|---|---|
| IV (HO-C6H4)-N(-C6H4-F)-C(=O)-C6H3(F)(OH) | 0.65 | 40.4 | >1000 | >1000 |

TABLE 3-continued

Transactivation (both agonist and antagonist) of selective compounds of this invention.

| COMPOUND | ER-α EC$_{50}$ (nM) | ER-β EC$_{50}$ (nM) | ER-α IC$_{50}$ (nM) | ER-β IC$_{50}$ (nM) |
|---|---|---|---|---|
| 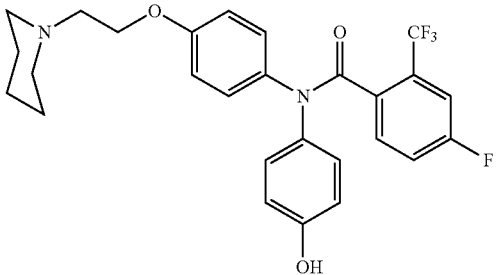 [SMILES: O=C(c1ccc(F)cc1C(F)(F)F)N(c1ccc(O)cc1)c1ccc(OCCN2CCCCC2)cc1]<br>IX (or X) | >1000 | >1000 | 2.207 | 145 |

Example 8

Testosterone Suppression in Cynomolgus Monkeys

Figure 1:
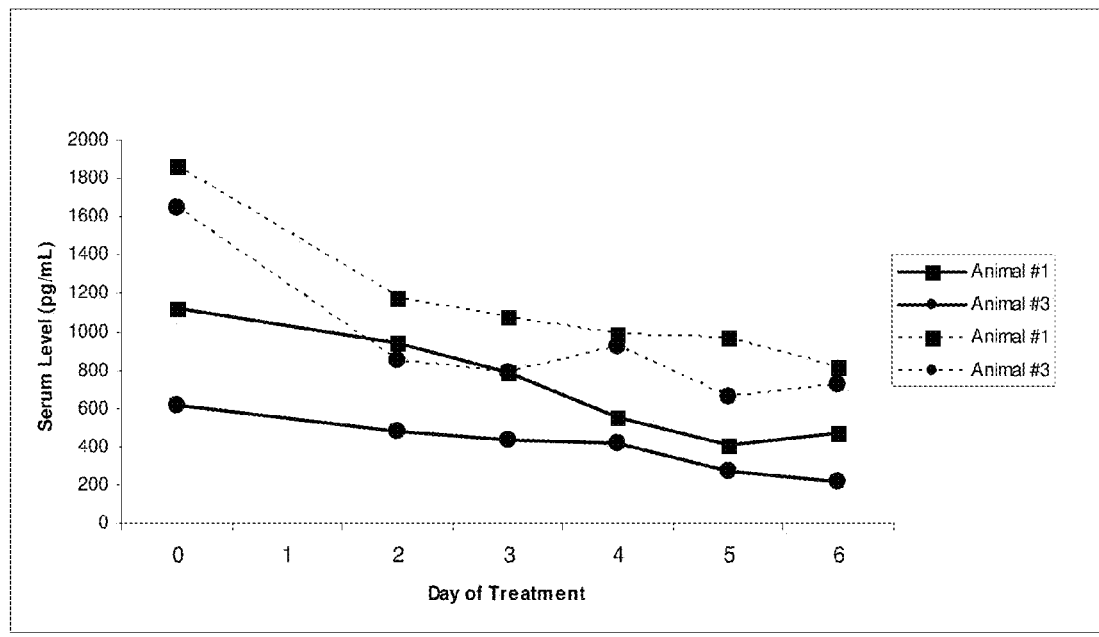
FIG. 1 depicts serum testosterone (solid line) and total androgen (dotted line) levels in intact male monkeys after daily 30 mg/kg oral administration of Compound IV (first dose on Day 0). (See Example 8.)

Two-year old gonadally-intact male Cynomolgus monkeys (n=2) were housed during the study in compliance with USDA Guidelines with free access to primate diet and water (except fasted prior to oral dose administration). Animals were given a once-daily oral gavage dose of 30 mg/kg of compound of formula IV in a microemulsion vehicle of Tween 80/deionized water for 7 consecutive days. Serum samples were withdrawn by venipuncture prior to the oral dose administration on days 1 (baseline), 3, 4, 5, 6, and 7. Testosterone and total androgens were quantified using an enzyme immunoassay (EIA) method combined with or without an HPLC method respectively. After 6-days of treatment with compound of formula IV, time-dependent decreases were apparent for testosterone and total androgens (testosterone/dihydrotestosterone). Compound of formula IV suppressed the levels of testosterone by 58% and 64% in animal #1 and animal #3, respectively, relative to baseline values (see solid lines in FIG. 1; Table 4). Similarly, total androgen levels were suppressed by 56% in both animals #1 and #3 (see dashed lines in FIG. 1; Table 4) compared to baseline values.

Consistent with estrogen feedback of the pituitary-testicular axis in males, these results demonstrate a robust pharmacologic response for the suppression of serum hormones (testosterone and total androgens) in intact non human primates (Cynomolgus monkeys) after repeated oral doses (30 mg/kg) of compound of formula IV.

TABLE 4

Testosterone and total androgen levels in serum of intact male monkeys with daily 30 mg/kg oral administration compound of formula IV (first dose on Day 0).

| | Testosterone Serum level (pg/mL) | | Total Androgens Serum level (pg/mL) | |
|---|---|---|---|---|
| Day | Animal 1 | Animal 3 | Animal 1 | Animal 3 |
| 0 (baseline) | 1120 | 617 | 1868 | 1643 |
| 2 | 937 | 479 | 1178 | 847 |
| 3 | 784 | 437 | 1078 | 786 |
| 4 | 552 | 415 | 988 | 924 |
| 5 | 403 | 276 | 966 | 664 |
| 6 | 474 | 221 | 819 | 726 |

| | Percent reduction from baseline | | Percent reduction from baseline | |
|---|---|---|---|---|
| Day | Animal 1 | Animal 3 | Animal 1 | Animal 3 |
| 0 (baseline) | 100 | 100 | 100 | 100 |
| 2 | 16 | 22 | 37 | 48 |
| 3 | 30 | 29 | 42 | 52 |
| 4 | 51 | 33 | 47 | 44 |
| 5 | 64 | 55 | 48 | 60 |
| 6 | 58 | 64 | 56 | 56 |

Example 9

Suppression of LH and Testosterone Hormone Levels in Rats

An in vivo dose-response study was conducted to evaluate the effect of Compound IV on LH suppression in intact and orchiectomized (ORX) male rats. In intact and ORX animals, Compound IV at doses ≥10 mg/kg per day significantly suppressed LH levels when compared to respective controls. (The same pattern of suppression was observed in FSH levels.) LH suppression resulted in robustly decreased testosterone levels to below the limit of quantitation (BLOQ) which is 0.08 ng/mL and decreased weights of prostate, seminal vesicles, and levator ani weights muscle since these are highly androgen-dependent organs. In intact animals, dose-dependent decreases in the weights of these target organs were noted with the seminal vesicles and levator ani muscle weights to the level of castrated controls. Although prostate weights were significantly reduced in intact animals, these values did not reach the level of castrated controls. Results are summarized in Table 6 hereinbelow.

Materials and Methods:

Male Sprague-Dawley rats weighing approximately 200 g were maintained on a 12-h light/dark cycle with food (2016 Teklad Global 16% Protein Rodent Diet, Harlan, Madison, Wis.) and water available ad libitum. The animal protocol was reviewed and approved by the Institutional Animal Care and Use Committee of the University of Tennessee.

The test article for this study was weighed and dissolved in 10% DMSO (Fisher) diluted with PEG 300 (Acros Organics, NJ) to prepare the appropriate dose formulations. For this study, sixty (60) male Sprague-Dawley rats were randomized by body weight, and assigned to one of the twelve treatment groups (n=5 animals/group). Treatment groups are listed in Table 5. The animals were housed in groups of 2 to 3 animals per cage. Control groups (intact and orchidectomized (ORX)) were administered vehicle daily. Compound IV was administered via subcutaneous injection (200 µL) at doses of 0.3, 1, 3, 10, and 30 mg/kg/day to both intact and ORX groups.

After a 14-day dosing regimen, the animals were sacrificed under anesthesia (ketamine/xylazine, 87:13 mg/kg) and body weights were recorded. In addition, ventral prostate, seminal vesicles, and levator ani muscle were removed, cleaned of extraneous tissue, and individually weighed. Organ weight were normalized to body weight and expressed as a percentage of intact control. Blood was collected from the abdominal aorta under isoflurane anesthesia and allowed to clot. Serum was separated by centrifugation and stored at −80° C. prior to determination of serum hormone levels. Serum luteinizing hormone (LH) and follicle stimulating hormone (FSH) concentrations were determined by the Rat Pituitary Luminex Assay (Millipore, Billerica, Mass.) according to manufacturer's directions. The lower limit of quantitation for this assay was 3.2 pg/mL for LH and 32 pg/mL for FSH. Testosterone was measured by a Testosterone EIA (Alpco Diagnostics, Salem, N.H.) with a LLOQ of 0.08 ng/mL. Serum hormone values below the lower limit of quantitation (BLOQ) were omitted from analysis of group means. Therefore, the reported value for LH and T in the groups with samples BLOQ is higher than the actual value. This method of analysis provided the most conservative estimate of LH and T suppression. Fisher's Least Significant Difference test was used to compare individual dose groups to the intact and ORX vehicle control groups. Significance was defined a priori as a P-value <0.05.

TABLE 5

Treatment groups

| Group | Gonadal Status | Dose (mg/kg/day) | Test Article |
|---|---|---|---|
| 1 | Intact | — | Vehicle |
| 2 | ORX | — | Vehicle |
| 3 | Intact | 0.3 | Compound IV |
| 4 | Intact | 1 | Compound IV |
| 5 | Intact | 3 | Compound IV |
| 6 | Intact | 10 | Compound IV |
| 7 | Intact | 30 | Compound IV |
| 8 | ORX | 0.3 | Compound IV |
| 9 | ORX | 1 | Compound IV |
| 10 | ORX | 3 | Compound IV |
| 11 | ORX | 10 | Compound IV |
| 12 | ORX | 30 | Compound IV |

Luteinizing Hormone Levels in Intact and ORX Rats (Table 6)

LH levels (mean±SD) in intact and ORX vehicle control groups were 1.46±0.64 and 11.1±3.9 ng/mL, respectively. Compound IV dose-dependently reduced LH levels in intact animals, reaching statistically significant reductions with daily doses ≥3 mg/kg. LH levels in intact Compound IV treated animals were 0.863±0.384, 0.704±0.530, 0.395±0.302, 0.226±0.165, and 0.236±0.176 ng/mL, following doses of 0.3, 1, 3, 10, and 30 mg/kg/day, respectively. LH levels in ORX males were also significantly decreased by Compound IV treatment. In ORX animals the LH levels were 15.4±2.9, 13.5±2.2, 6.5±5.6, 0.425±0.135, and 0.368±0.119 ng/mL, following doses of 0.3, 1, 3, 10, and 30 mg/kg/d, respectively. The results are presented graphically in FIG. 10A.

In intact and orchiectomized rats, Compound IV at doses of 10 mg/kg/day significantly suppressed luteinizing hormone (LH) levels resulting in castrate serum levels of endogenous testosterone.

Follicle Stimulating Hormone Levels in Intact and ORX Rats (Table 6)

Serum FSH levels in intact and ORX vehicle control groups were 20.9±8.5 and 93.5±13.8 ng/mL, respectively. In intact animals, Compound IV dose-dependently reduced FSH levels with significant reductions observed at doses ≥10 mg/kg/day. FSH levels in intact Compound IV treated animals were 17.3±6.4, 15.7±7.3, 18.4±7.7, 9.2±4.0, and 6.3±1.8 ng/mL, following doses of 0.3, 1, 3, 10, and 30 mg/kg/day, respectively. In ORX animals the LH levels were 115±17, 114±22, 65.2±31.9, 27.6±8.2, and 15.1±4.1 ng/mL, following doses of 0.3, 1, 3, 10, and 30 mg/kg/day, respectively. The results are presented graphically in FIG. 10B.

Testosterone Levels in Intact and ORX Rats

Figure 2:
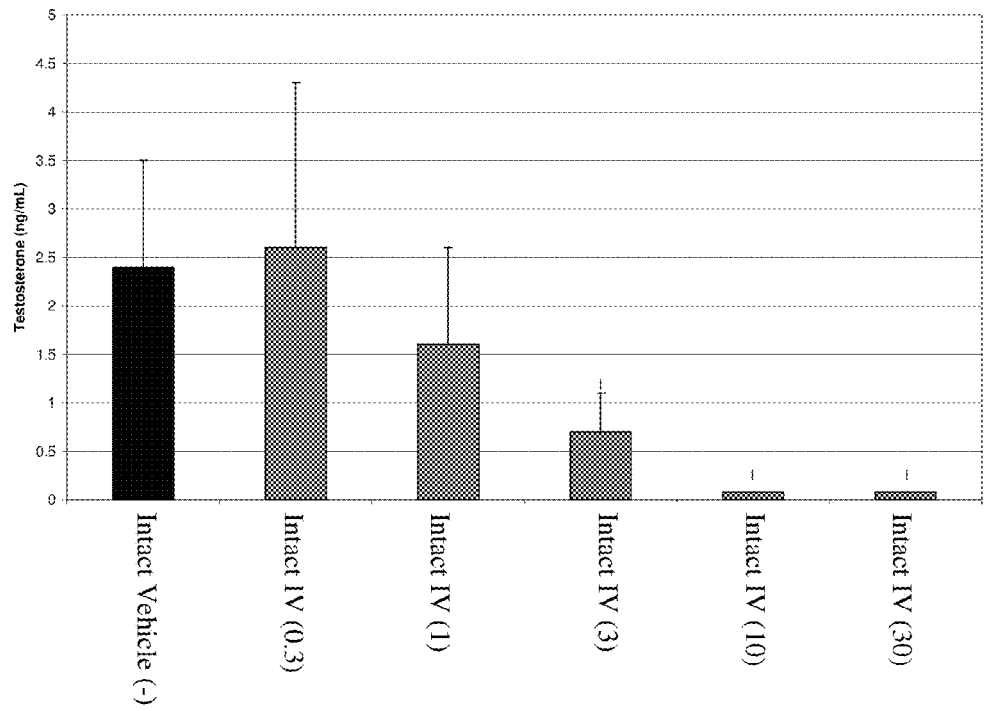
FIG. 2 depicts testosterone levels in intact rats treated with Compound IV (0.3, 1, 10, 30 mg/kg). $^{I}$denotes P<0.05 vs. intact vehicle controls. BLOQ values are represented graphically at the limit of quantitation 0.08 ng/mL. (See Example 9.)

Serum testosterone levels in intact vehicle control groups were 2.4±1.1 ng/mL. The lower limit of quantitation for T was 0.08 ng/mL. Values less than 0.08 ng/mL are designated as Below the Limit Of Quantitation (BLOQ). In intact animals, compound of formula IV dose-dependently reduced T levels with significant reductions observed at doses ≥3 mg/kg per day. Testosterone levels in intact animals treated with compound of formula IV were 2.6±1.7, 1.6±1.0, 0.7±0.4, BLOQ, and BLOQ ng/mL, following doses of 0.3, 1, 3, 10, and 30 mg/kg per day, respectively. In ORX animals the T levels were BLOQ for all groups treated with compound IV and the vehicle treated group. The results are for the intact animals are presented graphically in FIG. 10C (and FIG. 2) (BLOQ values are represented at the limit of quantitation for graphical purposes).

Rapid and potent suppression of serum testosterone in intact male rats was measured by administering Compound IV with dosages of 3 mg/kg, 10 mg/kg and 300 mg/kg after 24 h, 72 h and 168 h as presented in FIG. 9.

Organ Weights (Table 6)

Prostate, seminal vesicles, and levator ani muscle weights were measured to confirm the suppression of T. The organ weights (mean±SD) are presented in FIGS. 10D, 10E and 10F respectfully. Dose-dependant decreases in prostate, seminal vesicles, and levator ani muscle weight were observed in intact animals treated with Compound IV. Prostate weights in intact animals were 84.0±19.2, 75.2±20.7, 68.2±8.1, 45.1±20.0, and 43.6±8.8, following doses of 0.3, 1, 3, 10, and 30 mg/kg/day, respectively. Prostate weights in ORX animals were 19.0±4.2, 17.4±3.4, 19.6±6.7, 22.9±5.4, and 20.6±2.1, following doses of 0.3, 1, 3, 10, and 30 mg/kg/day, respectively. Seminal vesicle weights in intact animals were 76.2±7.8, 66.3±27.2, 51.8±28.5, 19.1±7.0, and 17.9±3.3, following doses of 0.3, 1, 3, 10, and 30 mg/kg/day, respectively. Seminal vesicle weights in ORX animals were 12.2±1.3, 16.6±5.4, 16.5±4.8, 13.3±1.9, and 12.9±2.1, following doses of 0.3, 1, 3, 10, and 30 mg/kg/day, respectively. Levator ani weights in intact animals were 86.9±10.0, 82.1±12.1, 65.2±4.4, 57.8±11.2, and 58.1±4.7, following doses of 0.3, 1, 3, 10, and 30 mg/kg/day, respectively. Levator ani weights in ORX animals were 54.5±6.6, 49.6±7.0, 53.6±10.0, 51.1±4.9, and 49.2±4.2, following doses of 0.3, 1, 3, 10, and 30 mg/kg/day, respectively.

The LH suppression and organ weights data are summarized in Table 6.

TABLE 6

In vivo effects of the compound of formula IV on serum hormones and organ weight

| Gonadal Status | Compound | Dose (mg/kg per day) | | LH (ng/mL) | FSH (ng/mL) | Prostate (% of Intact) | Seminal Vesicles (% of Intact) | Levator Ani Muscle (% of Intact) |
|---|---|---|---|---|---|---|---|---|
| Intact | Vehicle | — | Mean | $1.46^b$ | $20.9^b$ | $100.0^b$ | $100.0^b$ | $100.0^b$ |
| | | | S.D. | 0.642 | 8.49 | 28.6 | 13.4 | 4.97 |
| ORX | Vehicle | — | Mean | $11.1^a$ | $93.5^a$ | $13.7^a$ | $14.0^a$ | $58.8^a$ |
| | | | S.D. | 3.87 | 13.8 | 2.56 | 2.93 | 6.62 |
| Intact | Compound IV | 0.3 | Mean | $0.863^b$ | $17.3^b$ | $84.0^b$ | $76.2^{a,b}$ | $86.9^{a,b}$ |
| | | | S.D. | 0.384 | 6.44 | 19.2 | 7.83 | 10 |
| Intact | Compound IV | 1 | Mean | $0.704^b$ | $15.7^b$ | $75.2^b$ | $66.3^{a,b}$ | $82.1^{a,b}$ |
| | | | S.D. | 0.53 | 7.26 | 20.7 | 27.2 | 12.1 |
| Intact | Compound IV | 3 | Mean | $0.395^{a,b}$ | $18.4^b$ | $68.2^{a,b}$ | $51.8^{a,b}$ | $65.2^a$ |
| | | | S.D. | 0.302 | 7.72 | 8.12 | 28.5 | 4.35 |
| Intact | Compound IV | 10 | Mean | $0.226^{a,b}$ | $9.25^{a,b}$ | $45.1^{a,b}$ | $19.1^a$ | $57.8^a$ |
| | | | S.D. | 0.165 | 3.97 | 20 | 6.98 | 11.2 |
| Intact | Compound IV | 30 | Mean | $0.236^{a,b}$ | $6.25^{a,b}$ | $43.6^{a,b}$ | $17.9^a$ | $58.1^a$ |
| | | | S.D. | 0.176 | 1.82 | 8.75 | 3.33 | 4.71 |
| ORX | Compound IV | 0.3 | Mean | $15.4^a$ | $116^a$ | $19.0^{a,b}$ | $12.2^a$ | $54.5^a$ |
| | | | S.D. | 2.94 | 17.2 | 4.19 | 1.31 | 6.56 |
| ORX | Compound IV | 1 | Mean | $13.5^a$ | $114^a$ | $17.4^a$ | $16.6^a$ | $49.6^a$ |
| | | | S.D. | 2.18 | 22.3 | 3.4 | 5.36 | 7.04 |
| ORX | Compound IV | 3 | Mean | $6.5$ | $65.2^a$ | $19.6^a$ | $16.5^a$ | $53.6^a$ |
| | | | S.D. | 5.63 | 31.9 | 6.67 | 4.82 | 10 |
| ORX | Compound IV | 10 | Mean | $0.425^{a,b}$ | $27.6^b$ | $22.9^{a,b}$ | $13.3^a$ | $51.1^a$ |
| | | | S.D. | 0.135 | 8.16 | 5.44 | 1.91 | 4.88 |
| ORX | Compound IV | 30 | Mean | $0.368^{a,b}$ | $15.1^b$ | $20.6^{a,b}$ | $12.9^a$ | $49.2^{a,b}$ |
| | | | S.D. | 0.119 | 4.11 | 2.08 | 2.14 | 4.21 |

[a] $P < 0.05$ versus Intact Vehicle.
[b] $P < 0.05$ versus ORX Vehicle

In intact and orchiectomized rats, Compound IV at doses of 10 mg/kg/day significantly suppressed luteinizing hormone (LH) levels resulting in castrate serum levels of endogenous testosterone.

Compound IV did not increase proliferation of prostate epithelial cancer cells in vitro. Mechanistically, Compound IV offers several key advantages over existing therapies such as gonadotropin releasing hormone (GnRH) agonists and GnRH antagonists. Compound IV is specific for the estrogen receptor, and is orally bioavailable in rats, dogs, monkeys and man. In contrast to GnRH agonists and GnRH antagonists which cause hot flashes and significant bone loss and increase the risk of fractures, Compound IV attenuates morphine withdrawal-induced hot flashes in rats and fully maintains trabecular bone mass and bone mineral density in the distal femur of rats even at doses which maximally suppress LH and serum testosterone.

Example 10

Recovery of Testosterone Levels Following Suppression by Compound IV in Rats and Monkeys The reversibility of chemical castration with Compound IV was studied.

Materials and Methods:

Thirty-five (35) male Sprague-Dawley rats weighing approximately 200 g were maintained on a 12-h light/dark cycle with food (2016 Teklad Global 16% Protein Rodent Diet, Harlan, Madison, Wis.) and water available ad libitum. The animal protocol was reviewed and approved by the Institutional Animal Care and Use Committee of the University of Tennessee.

The test article for this study was weighed and dissolved in PEG 300 (100%) (Acros Organics, NJ) to prepare the appropriate dose formulations. Animals were randomly assigned to one of the ten treatment groups (n=5 animals/group). Treatment groups are listed in Table 7. The animals were housed in groups of 2 to 3 animals per cage. Group 1 was sacrificed at the initiation of the study (Day 1) for determination of baseline testosterone levels in intact animals. Groups 2-7 received daily doses of 1, 3, or 30 mg/kg via oral gavage (~200 uL) for three days. Groups 2, 3, and 4 were sacrificed on Day 4 to measure maximal testosterone suppression. Groups 5, 6, and 7 were allowed to recover for 14 days with a drug free washout period.

TABLE 7

Treatment groups

| Group | Compound IV P.O. Dose | Treatment |
|---|---|---|
| Group 1 | — | Baseline |
| Group 2 | 1 mg/kg for 3 days | No Recovery |
| Group 3 | 3 mg/kg for 3 days | No Recovery |
| Group 4 | 30 mg/kg for 3 days | No Recovery |
| Group 5 | 1 mg/kg for 3 days | 14 day recovery |
| Group 6 | 3 mg/kg for 3 days | 14 day recovery |
| Group 7 | 30 mg/kg for 3 days | 14 day recovery |

Results:

Serum testosterone levels in intact rats were 6.4±3.1 ng/mL (mean±S.D) at baseline. Compound IV administered at doses of 3 and 30 mg/kg for three days significantly suppressed serum testosterone levels to 1.47±0.26 and 1.62±0.49 ng/mL, respectively. No significant suppression was observed in animals that received 1 mg/kg of Compound IV for three days. Most importantly, serum testosterone levels were 3.3±1.92, 3.00±1.06 and 3.8±1.72 in animals that received 1, 3, or 30 mg/kg, respectively, of Compound IV for three days when measured after a 14 day recovery period, and were not statistically significantly differences from baseline serum testosterone concentrations in intact rats as depicted in FIG. 23.

This study confirms previous results showing that Compound IV quickly suppresses serum testosterone levels in intact male rats. We observed suppression of serum testosterone levels in dose groups receiving ≥3 mg/kg/day for 3 days. A significant decrease in serum testosterone was not observed with the 1 mg/kg dose group. However, within 14 days of recovery, serum testosterone levels had returned back to the level of intact controls. This study shows that pharmacologic castration by Compound IV is reversible in rats.

The effect of Compound IV on suppression and recovery of testosterone levels in intact male monkeys was evaluated in conjunction with an oral pharmacokinetic study. Three treatment naïve male Cynomolgus monkeys (2 to 3 years old) were administered Compound IV at 30 mg/kg daily by oral gavage for 7 consecutive days. Blood samples were collected and divided into serum and plasma for testosterone and Compound IV quantitative measurements, respectively. Results show that daily oral doses of Compound IV significantly decreased circulating androgen (primarily testosterone and dihydrotestosterone) levels in all three male monkeys by up to 47% compared to baseline levels (levels of 1591±72.5, 997±104, and 852±136 ng/mL, respectively for baseline, Day 2 and Day 6 of treatment [mean±SEM]). Following a 18-day drug-free recovery period, androgen levels returned to normal, and were not significantly different from pre-treatment baseline levels (1757.7±369.5 ng/mL after recovery).

Example 11

Bone Preservation Despite Reduction of LH and Testosterone in Rats (Table 8)

The effect of compound of formula IV on treatment on bone was studied. Orally administered compound of formula IV completely prevented the bone loss associated with LH suppression in intact male rats. Significant reduction of LH was induced by the compound of formula IV in intact animals at dose levels ≥10 mg/kg per day. Although at 1 mg/kg per day, compound of formula IV did not significantly reduce LH, significant reductions in prostate, seminal vesicles, and levator ani muscle were apparent at this dose indicating that the reduction in circulating testosterone was physiologically relevant to these androgen responsive organs. However, 1 mg/kg per day compound of formula IV maintained trabecular bone volume (measured in the distal femur) at the level of intact controls. When administered at doses of 10 and 30 mg/kg per day, compound of formula IV increased bone volume in the distal femur significantly above that of intact controls. These data show that compound IV increased trabecular bone mineral density (BMD) and percent bone volume at a dose level that reduces LH levels in intact rats. Data from this study are presented in Table 8.

TABLE 8

In vivo effects of Compound IV on rat bone, organ weight, and serum hormone parameters.

| Gonadal Status | Compound | Dose (mg/kg per day) | | Bone Mineral Density (g/cm$^3$) | Percent Bone Volume (BV/TV) (%) | Prostate (% of Intact) | Seminal Vesicles (% of Intact) | Levator Ani Muscle (% of Intact) | FSH (ng/mL) | LH (ng/mL) |
|---|---|---|---|---|---|---|---|---|---|---|
| Intact | Vehicle | — | Mean | 0.274$^b$ | 20.2$^b$ | 100.0$^b$ | 100.0$^b$ | 100.0$^b$ | 9.93$^b$ | 0.781$^b$ |
| | | | S.D. | 0.033 | 3.57 | 11.1 | 15.9 | 11.6 | 2.94 | 0.263 |
| ORX | Vehicle | — | Mean | 0.224$^a$ | 15.4$^a$ | 14.8$^a$ | 10.3$^a$ | 59.4$^a$ | 117$^a$ | 22.0$^a$ |
| | | | S.D. | 0.025 | 2.6 | 4.08 | 0.767 | 7.26 | 40.2 | 5.81 |
| Intact | Compound IV | 1 | Mean | 0.273$^b$ | 20.0$^b$ | 69.2$^{a,b}$ | 44.6$^{a,b}$ | 80.0$^{a,b}$ | 14.1$^{a,b}$ | 0.820$^b$ |
| | | | S.D. | 0.04 | 4.08 | 13.5 | 15.7 | 6.69 | 4.07 | 0.392 |
| Intact | Compound IV | 10 | Mean | 0.326$^{a,b}$ | 25.9$^{a,b}$ | 30.7$^{a,b}$ | 12.8$^{a,b}$ | 58.1$^a$ | 5.48$^{a,b}$ | 0.060$^{a,b}$ |
| | | | S.D. | 0.048 | 4.76 | 12.4 | 0.886 | 9.68 | 1.97 | 0.092 |
| Intact | Compound IV | 30 | Mean | 0.326$^{a,b}$ | 25.5$^{a,b}$ | 30.1$^{a,b}$ | 14.4$^{a,b}$ | 56.1$^a$ | 6.32$^{a,b}$ | 0.078$^{a,b}$ |
| | | | S.D. | 0.046 | 4.49 | 17.4 | 1.45 | 4.67 | 3.4 | 0.114 |

$^a$P < 0.05 versus Intact Vehicle.
$^b$P < 0.05 versus ORX Vehicle

Example 12

Effects on 17β Hydroxysteroid Dehydrogenase 5 (17β-HSD5) Enzyme Activity

HSD family members are involved in the conversion of circulating steroids. 17β-HSD5 converts androstenedione to testosterone and estrone to estradiol. In addition, it is also involved in prostaglandin synthesis. Here the ability of some select compounds of this invention to inhibit 17β-HSD5 activity was demonstrated.

Method

Human 17β-HSD5 was cloned in pGEX 4t1 vector and purified protein was prepared. The purified protein was incubated with the representative compound of this invention, $^{14}$C androstenedione and NADPH in an appropriate buffer. The synthesized testosterone was extracted using ethyl acetate, air dried, spotted and run on a thin layer chromatography (TLC) plate. The TLC was exposed to phosphorimager and the intensity of testosterone band was quantified. Indomethcin was used as a positive control (LHRH agonist).

Results

Compound IV was tested and had partial inhibitory effect on 17β-HSD5 enzyme activity. The positive control (LHRH agonist), indomethacin as expected exhibited strong inhibition of this enzyme, as presented in FIG. 3.

Example 13

Toxicity Studies

A study was conducted to compare the thrombotic potential of Compound IV and diethylstilbestrol (DES, positive control) using the in vitro human platelet aggregation assay. Blood from healthy male donors was used in the study since males are the intended treatment population for Compound IV (LH suppression). Platelet rich plasma was preincubated with either estradiol (E2), DES, Compound IV or vehicle for 30 seconds, and then thrombin (0.3 units) was added to induce platelet aggregation. Results of the study show that preincubation with DES increased the thrombin-induced platelet aggregation by approximately 10-fold. However, Compound IV and estradiol decreased aggregation in the platelet rich plasma. These data demonstrate that Compound IV reduced the reactivity of human platelets in vitro compared to DES, and suggest that Compound IV may have lower thromboembolic potential than DES (FIG. 4).

Example 14

Effect of Compound IV on Hot Flashes

A study was conducted to investigate the effect of Compound IV on hot flashes using the morphine dependent rat model (MD model) which was developed by Simpkins et. al (1983) and was shown to have several similarities to the menopausal hot flush. In addition to the similarities to the human condition, this experimental animal model has a short turn around time which makes it a useful high throughput screening tool for identifying compounds that can alleviate vasomotor symptoms using the tail skin temperature (TST). TST probes TA-40 (Data Sciences International, MN) were taped to the base of the tails and baseline temperatures were obtained for 15 minutes. After 15 minutes the animals were treated with naloxone (1 mg/kg, SQ) to reverse the effects of the morphine. Tail skin temperature (TST) was measured for one hour post-naloxone treatment with a sampling frequency of 5 secs throughout the course of the experiment. Following the data acquisition, the moving average of the temperature recorded every 60 seconds for each animal was calculated and further analyzed. Baseline temperature was computed as the average temperature acquired over the 15 minutes preceding naloxone administration. The area under the curve (AUC) was calculated by subtracting all the values post-naloxone administration from the baseline using a linear trapezoid method.

Compound IV attenuated hot flashes in the morphine withdrawal model (see FIG. 13) with the best results at 10 mg Compound IV. 17β E2 was used at 5 mg/kg in 100% DMSO.

Example 15

Compound IV Versus DES in Rats

Prior to the introduction of LHRH agonists, castrate testosterone levels were achieved by increasing estrogen activity in the pituitary via estrogens, primarily diethylstilbestrol (DES). DES was equally effective as LHRH agonists at suppressing testosterone to castrate levels. Patients treated with DES did not have hot flashes or bone loss, but did have gynecomastia at higher rates than ADT with LHRH agonists. Unfortunately, highly potent, pure estrogens, like DES and estradiol, are often associated with a high risk of severe cardiovascular and thromboembolic complications which have limited their clinical use. It has been hypothesized, but not proven, that the increased risk of venous thromboembolic complications with DES is due to its cross-reactivity with other hormone receptors. In vitro studies with human platelets showed that Compound IV had much lower procoagulatory activity than DES. Thus, Compound IV, an ER-alpha selective agonist, may deliver the prostate cancer benefits of DES and also deliver the benefits of an LHRH agonist without causing osteoporosis or adverse lipid profiles.

Compound IV is as effective as DES in reducing prostate size in rats and presenting moderate increase in prostate size of ORX rats (FIG. 11).

Differences between DES and Compound IV are presented in FIGS. 12A-12C, where DES crossreacted with glucocorticoid receptor (GR) (FIG. 12A) and androgen receptor (AR) (FIG. 12B) while Compound IV did not. In addition, DES antagonized estrogen related receptor (ERR) transactivation while Compound IV did not. Compound IV failed to crossreact with any of the three ERR isoforms (ERR-α, ERR-β and ERR-γ) as depicted in FIG. 12C.

Example 16

Monkey Toxicity Study—90 Days

Colony-bred cynomolgus macaques of Mauritius origin were obtained. The prospective study was designed as a 39-week oral pharmacology and toxicology evaluation of Compound IV and positive control (LHRH agonist) in the male cynomolgus monkey with a 13-week interim period. A total of 39 sexually mature male monkeys, 5 to 8 years of age, were randomly assigned to five groups prior to treatment initiation. Groups included: 1) vehicle control, 2) 1 mg/kg Compound IV, 3) 10 mg/kg Compound IV, 4) 100 mg/kg Compound IV, and 5) positive control (LHRH agonist). Drug was delivered orally by cage-side administration once daily for 39 weeks with vehicle control article (Tween 80/PRANG™) for Groups 1 and 5, or Compound IV in vehicle for Groups 2, 3, and 4. Dose levels of Compound IV were 1, 10, and 100 mg/kg/day for Groups 2, 3, and 4, respectively. Oral doses were delivered in a 10 mL/kg dose volume as calculated based on most recent available body weight for each animal (FIG. 14). Animals in Group 5 also received a once-daily subcutaneous injection of positive control (LHRH agonist) (0.02 mL constant volume) for the 39 week study period. General appearance and clinical signs were observed and recorded daily. Routine evaluations and select other study investigations were performed as indicated in the study protocol. Select parameters include, but are not limited to, testosterone, prostate specific antigen (PSA), and prostate volume and weight.

Testosterone and total PSA levels were quantified in serum samples (following standard procedure) using an enzyme immunoassay (EIA) method and chemiluminescence immunoassay (LIA, ALPCO Diagnostics, Salem N.H.), respectively. Blood samples for testosterone evaluations were collected from all animals (in fasted state) at baseline (i.e., prior to commencement of treatment) and on Days 1, 3, 7, 14, 28, 64, and 90. Blood samples for PSA determinations were collected from all animals (in fasted state) at baseline and during Week 6. For the purpose of discussion, results for samples with concentrations below the limit of quantitation (BLQ) for the testosterone and PSA assays are calculated as ½ of the lower limit of quantitation (LLOQ) of the assay, and are considered as "Estimated final concentrations". Data in Tables 9 through 16 are presented as "Quantifiable concentrations only" (i.e., excludes BLQ values) in addition to "Estimated final concentrations" (i.e., samples with BLQ result included as ½ LLOQ of assay).

animal treated with Compound IV even at the highest dose level (i.e., 100 mg/kg/day). Dose and treatment duration were important to the pharmacologic action of Compound IV, where doses of 100 mg/kg/day suppressed the serum testosterone by 60%, 51%, 42%, 79% and 92% on Days 3, 7, 14, 28 and 64, respectively, relative to the baseline value (see FIG. 15 and Tables 9 and 10). After 90 days of treatment with 100 mg/kg/day Compound IV, the testosterone level in 6 of 10 Group 4 monkeys was reduced to concentrations below the limit of quantification of the assay (refer to Table 11). The mean serum testosterone level in Group 4 monkeys was reduced by 96% compared to respective baseline values ("Estimated final concentrations", i.e., testosterone levels for 6/10 monkeys with BLQ values are calculated as 50% of the LLOQ concentration, see Table 10). It is important to note that by Day 90, Compound IV at 100 mg/kg/day reduced serum testosterone to levels significantly lower than the positive control (LHRH agonist) (p=0.013).

TABLE 9

Mean serum testosterone levels (ng/mL) in intact male monkeys after daily oral administration of Compound IV; @Estimated final concentrations.

| Day | Vehicle Control | | | Compound IV 1 mg/kg | | | Compound IV 10 mg/kg | | | Compound IV 100 mg/kg | | | Positive control (LHRH agonist) | | |
|---|---|---|---|---|---|---|---|---|---|---|---|---|---|---|---|
| | Mean | SEM | N | Mean | SEM | N | Mean | SEM | N | Mean | SEM | N | Mean | SEM | N |
| 0 baseline | 6.1 | 1.2 | 10 | 7.3 | 1.0 | 6 | 4.9 | 0.6 | 6 | 4.4 | 0.6 | 10 | 4.9 | 0.9 | 7 |
| 1 | 8.0 | 1.7 | 10 | 11 | 1.6 | 6 | 7.6 | 1.1 | 6 | 8.0 | 2.2 | 10 | 7.2 | 0.8 | 7 |
| 3 | 8.2 | 2.3 | 10 | 7.4 | 1.2 | 6 | 5.1 | 1.1 | 6 | 1.8* | 0.5 | 10 | 32#$ | 3.8 | 7 |
| 7 | 5.9 | 1.2 | 10 | 6.7 | 0.8 | 6 | 7.7 | 1.9 | 6 | 2.2* | 0.7 | 9 | 4.7 | 2.6 | 7 |
| 14 | 3.4 | 0.5 | 10 | 3.8 | 0.4 | 6 | 7.1 | 1.6 | 6 | 2.6 | 0.9 | 9 | 1.6# | 0.2 | 7 |
| 28 | 3.8 | 0.6 | 10 | 4.7 | 0.9 | 6 | 9.4 | 2.1 | 6 | 0.9* | 0.2 | 10 | 1.3# | 0.2 | 7 |
| 64 | 5.1 | 1.1 | 10 | 4.3 | 0.6 | 6 | 5.4 | 1.5 | 6 | 0.3* | 0.1 | 9 | 0.8#$ | 0.2 | 7 |
| 90 | 3.6 | 0.6 | 9 | 4.2 | 0.6 | 4 | 4.6 | 1.0 | 5 | 0.2* | 0.0 | 10 | 0.8#$ | 0.2 | 7 |

Testosterone assay LLOQ = 0.246 ng/mL;
@BLOQ values are calculated as 0.123 ng/mL, half of the LLOQ.
*Statistically significant (p < 0.05) Compound IV 100 mg/kg vs. Vehicle Control
Statistically significant (p < 0.05) Positive control (LHRH agonist) vs. Vehicle Control
$Statistically significant (p < 0.05) Positive control (LHRH agonist) vs. Compound IV 100 mg/kg Prostate volume was measured in live animals under anesthesia using a transrectal ultrasound (TRUS) procedure at baseline and Week 6. The width and height of prostate were recorded. Prostate volumes were calculated as width×width×height×pi/6 and were normalized to body weight. The wet weight of prostate was recorded at necropsy after trimming the tissue free of fat and extraneous tissue.

Results and Discussion:

Serum testosterone levels are presented in FIG. 15 and Tables 9 through 12. At baseline, the testosterone levels for all monkeys on the study were in the normal range for sexually mature adult male cynomolgus monkeys. However, testosterone levels were significantly reduced in monkeys receiving Compound IV at 100 mg/kg/day and in monkeys treated with positive control (LHRH agonist). Testosterone levels in the positive control (LHRH agonist) group illustrated a biphasic change, with an initial significant increase (i.e., flare) of 47.4% and 547% (p<0.01) on Days 1 and 3, respectively, followed by decreases of 3.6%, 67%, 73%, 83%, and 85% on Days 7, 14, 28, 64 and 90 (see FIG. 15 and Tables 9 to 12). A similar flare was not observed for any

TABLE 10

Percentage change (%) of mean serum testosterone levels compared to baseline; @ Estimated final concentrations.

| Day | Vehicle Control | Compound IV 1 mg/kg | Compound IV 10 mg/kg | Compound IV 100 mg/kg | Positive Control |
|---|---|---|---|---|---|
| 1 | 31 | 44 | 54 | 82 | 47 |
| 3 | 35 | 1.8 | 3.5 | −60 | 547 |
| 7 | −3.2 | −8.1 | 57 | −51 | −3.6 |
| 14 | −44 | −48 | 45 | −42 | −67 |
| 28 | −38 | −35 | 92 | −79 | −73 |
| 64 | −16 | −41 | 11 | −92 | −83 |
| 90 | −42 | −42 | −5.5 | −96 | −85 |

Testosterone assay LLOQ = 0.246 ng/mL;
@ BLQ values are calculated as 0.123 ng/mL, half of the LLOQ.

TABLE 11

Mean serum testosterone levels (ng/mL) in intact male monkeys after daily oral administration Compound IV; ^Quantifiable concentrations only

| Day | Vehicle Control | | | Compound IV 1 mg/kg | | | Compound IV 10 mg/kg | | | Compound IV 100 mg/kg | | | Positive control (LHRH agonist) | | |
|---|---|---|---|---|---|---|---|---|---|---|---|---|---|---|---|
| | Mean | SEM | N | Mean | SEM | N | Mean | SEM | N | Mean | SEM | N | Mean | SEM | N |
| 0 baseline | 6.1 | 1.2 | 10 | 7.3 | 1.0 | 6 | 4.9 | 0.6 | 6 | 4.4 | 0.6 | 10 | 4.9 | 0.9 | 7 |
| 1 | 8.0 | 1.7 | 10 | 11 | 1.6 | 6 | 7.6 | 1.1 | 6 | 8.0 | 2.2 | 10 | 7.2 | 0.8 | 7 |
| 3 | 8.2 | 2.3 | 10 | 7.4 | 1.2 | 6 | 5.1 | 1.1 | 6 | 1.8 | 0.5 | 10 | 32 | 3.8 | 7 |
| 7 | 5.9 | 1.2 | 10 | 6.7 | 0.8 | 6 | 7.7 | 1.9 | 6 | 2.2 | 0.7 | 9 | 4.7 | 2.6 | 7 |
| 14 | 3.4 | 0.5 | 10 | 3.8 | 0.4 | 6 | 7.1 | 1.6 | 6 | 2.6 | 0.9 | 9 | 1.6 | 0.2 | 7 |
| 28 | 3.8 | 0.6 | 10 | 4.7 | 0.9 | 6 | 9.4 | 2.1 | 6 | 0.9 | 0.2 | 10 | 1.3 | 0.2 | 7 |
| 64 | 5.1 | 1.1 | 10 | 4.3 | 0.6 | 6 | 5.4 | 1.5 | 6 | 0.3 | 0.1 | 9 | 0.8 | 0.2 | 7 |
| 90 | 3.6 | 0.6 | 9 | 4.2 | 0.6 | 4 | 4.6 | 1.0 | 5 | 0.2 | 0.1 | 4 | 0.8 | 0.2 | 7 |

Testosterone assay LLOQ = 0.246 ng/mL;
^BLQ values are excluded.

TABLE 12

Percentage change (%) of mean testosterone levels compared to baseline; ^ Quantifiable concentrations only.

| Day | Vehicle Control | Compound IV 1 mg/kg | Compound IV 10 mg/kg | Compound IV 100 mg/kg | Positive Control |
|---|---|---|---|---|---|
| 1 | 31 | 44 | 54 | 82 | 47 |
| 3 | 35 | 1.8 | 3.5 | −60 | 547 |
| 7 | −3.2 | −8.1 | 57 | −51 | −3.6 |
| 14 | −44 | −48 | 45 | −42 | −67 |
| 28 | −38 | −35 | 92 | −79 | −73 |
| 64 | −16 | −41 | 11 | −92 | −83 |
| 90 | −42 | −42 | −5.5 | −95 | −85 |

Testosterone assay LLOQ = 0.246 ng/mL;
^ BLQ values are excluded.

Serum PSA levels were also significantly suppressed by Compound IV within four weeks of treatment initiation. PSA reductions of 69% and 87% (in mean) were noted for monkeys receiving Compound IV at 10 mg/kg and 100 mg/kg for 4 weeks, whereas PSA levels were reduced by 60% in the positive control (LHRH agonist) group (FIG. 16 and Tables 13-16).

TABLE 13

Mean serum PSA levels (ng/mL) in intact male monkeys after daily oral administration of Compound IV; @Estimated final concentrations.

| | Vehicle Control | | | Compound IV 1 mg/kg | | | Compound IV 10 mg/kg | | | Compound IV 100 mg/kg | | | Positive control (LHRH agonist) | | |
|---|---|---|---|---|---|---|---|---|---|---|---|---|---|---|---|
| | Mean | SEM | N | Mean | SEM | N | Mean | SEM | N | Mean | SEM | N | Mean | SEM | N |
| Pre-dose | 1.1 | 0.2 | 10 | 1.0 | 0.2 | 6 | 0.8 | 0.1 | 6 | 1.0 | 0.1 | 10 | 1.0 | 0.1 | 7 |
| 4-week | 1.0 | 0.2 | 10 | 0.9 | 0.2 | 6 | 0.3* | 0.1 | 6 | 0.1$^{\&}$ | 0.1 | 10 | 0.4$^{\#\$}$ | 0.1 | 7 |

PSA assay LLOQ = 0.0575 ng/mL;
@BLQ values are calculated as 0.02875 ng/mL, half of the LLOQ.
*Statistically significant (p < 0.05) Compound IV 10 mg/kg vs. Vehicle Control
$^{\&}$Statistically significant (p < 0.05) Compound IV 100 mg/kg vs. Vehicle Control
$^{\#}$Statistically significant (p < 0.05) Positive control (LHRH agonist) vs. Vehicle Control
$^{\$}$Statistically significant (p < 0.05) Positive control (LHRH agonist) vs. Compound IV 100 mg/kg

TABLE 14

Percentage change (%) of mean PSA levels compared to baseline; @Estimated final concentrations.

| | Control | Compound IV 1 mg/kg | Compound IV 10 mg/kg | Compound IV 100 mg/kg | Positive control (LHRH agonist) |
|---|---|---|---|---|---|
| 4-week | −7.1 | −11 | −69 | −87 | −60 |

PSA assay LLOQ = 0.0575 ng/mL;
@BLQ values are calculated as 0.02875 ng/mL, half of the LLOQ.

TABLE 15

Mean serum PSA levels (ng/mL) in intact male monkeys after daily oral administration Compound IV; ^Quantifiable concentrations only.

| | Vehicle Control | | | Compound IV 1 mg/kg | | | Compound IV 10 mg/kg | | | Compound IV 100 mg/kg | | | Positive control (LHRH agonist) | | |
|---|---|---|---|---|---|---|---|---|---|---|---|---|---|---|---|
| | Mean | SEM | N | Mean | SEM | N | Mean | SEM | N | Mean | SEM | N | Mean | SEM | N |
| Pre-dose | 1.2 | 0.2 | 9 | 1.0 | 0.2 | 6 | 0.8 | 0.1 | 6 | 1.0 | 0.1 | 10 | 1.0 | 0.1 | 7 |
| 4-week | 1.1 | 0.1 | 9 | 0.9 | 0.2 | 6 | 0.3 | 0.1 | 5 | 0.3 | 0.1 | 4 | 0.4 | 0.1 | 7 |

PSA assay LLOQ = 0.0575 ng/mL;
^BLQ values are excluded in this table.

TABLE 16

Percentage change (%) of mean PSA levels compared to baseline; ^Quantifiable concentrations only.

| | Control | Compound IV 1 mg/kg | Compound IV 10 mg/kg | Compound IV 100 mg/kg | Positive Control |
|---|---|---|---|---|---|
| 4-week | −7.1 | −11 | −64 | −72 | −60 |

PSA assay LLOQ = 0.0575 ng/mL;
^ BLQ values are excluded in this table.

Prostate volumes were measured by TRUS periodically throughout the study. Results obtained after six weeks of treatment demonstrate a potent effect of Compound IV and positive control (LHRH agonist) on monkey prostate. Compound IV significantly suppressed prostate volumes by 25% and 45% at the 10 mg/kg and 100 mg/kg dose levels, respectively, whereas prostate volumes were reduced by 28% in the positive control (LHRH agonist) group (FIG. 17 and Tables 17 and 18).

TABLE 17

Mean prostate volumes (ratio) in male monkeys after daily oral administration Compound IV.

| | Vehicle Control | | | Compound IV 1 mg/kg | | | Compound IV 10 mg/kg | | | Compound IV 100 mg/kg | | | Positive control (LHRH agonist) | | |
|---|---|---|---|---|---|---|---|---|---|---|---|---|---|---|---|
| | Mean | SEM | N | Mean | SEM | N | Mean | SEM | N | Mean | SEM | N | Mean | SEM | N |
| 6-week | 438 | 78 | 10 | 468 | 78 | 6 | 327 | 33 | 6 | 242 | 28 | 10 | 315 | 47 | 7 |

TABLE 18

Percentage change (%) of mean prostate volumes compared to baseline.

| | Control | Compound IV 1 mg/kg | Compound IV 10 mg/kg | Compound IV 100 mg/kg | Positive Control |
|---|---|---|---|---|---|
| 6-week | 0 | 6.8 | −25 | −45 | −28 |

The Compound IV-related reductions in prostate volume were confirmed by the evaluation of prostate weight at necropsy. After thirteen weeks of treatment, Compound IV significantly reduced mean prostate weights by 24% and 21% in animals receiving 10 and 100 mg/kg/day, respectively (FIG. 18B and Tables 19 and 20).

TABLE 19

Mean prostate weights (grams) at necropsy in monkeys with daily oral administration Compound IV.

| | Vehicle Control | | | Compound IV 1 mg/kg | | | Compound IV 10 mg/kg | | | Compound IV 100 mg/kg | | |
|---|---|---|---|---|---|---|---|---|---|---|---|---|
| | Mean | SEM | N | Mean | SEM | N | Mean | SEM | N | Mean | SEM | N |
| 13-week | 1.8 | 0.2 | 3 | 1.8 | 0.4 | 3 | 1.3 | 0.1 | 3 | 1.4 | 0.1 | 3 |

TABLE 20

Percentage change (%) of mean prostate weights compared to baseline.

| | Control | Compound IV 1 mg/kg | Compound IV 10 mg/kg | Compound IV 100 mg/kg |
|---|---|---|---|---|
| 13-week | 0 | 1.7 | −24 | −21 |

No apparent effects on platelet aggregation, prothrombin time (PT) or activated partial thromboplastin time (APTT) were observed.

Example 17

Compound IV Studies on Humans

A study was conducted to determine the effect of Compound IV on human males. 12 subjects per cohort were examined in dosages of 100, 300, 600 and 1000 mg of Compound IV. Table 21 presents mean change of LH, serum PSA, free testosterone and total testosterone levels in men by administering Compound IV at dosages of 100, 300, 600 and 1000 mg. Dose dependent mean total testosterone levels (nmol/L) in humans were measured for a period between days 1-11 (FIG. 19). Total testosterone level decreased by 51.9% and 47.9% at dosages of 600 mg and 1000 mg, respectfully.

Dose dependent mean LH levels (IU/L) in humans were measured for a period between days 1-10 (FIG. 20). The LH levels increased by 20.7%, 46.9%, 27.6% and 29.2% at dosages of 100 mg, 300 mg, 600 mg and 1000 mg, respectfully.

Dose dependent mean free testosterone levels (pg/mL) in humans were measured for a period between days 1-10 (FIG. 21). The free testosterone levels decreased by 17.0%, 18.5%, 72.7% and 53.2% at dosages of 100 mg, 300 mg, 600 mg and 1000 mg, respectfully.

Dose dependent mean PSA levels (µg/L) in humans were measured for a period between days 1-10 (FIG. 22). The PSA levels decreased by 9.2%, 24.4%, 27.5% and 29.9% at dosages of 100 mg, 300 mg, 600 mg and 1000 mg, respectfully. No changes noted for 10 and 30 mg doses.

TABLE 21

Mean change from baseline

| | 100 mg | 300 mg | 600 mg | 1000 mg |
|---|---|---|---|---|
| Serum PSA | −9.2% | −24.4% | −27.5% | −29.9% |
| LH | 20.7% | 46.9% | 27.6% | 29.2% |
| Free Testosterone | −17.0% | −18.5% | −72.7% | −53.2% |
| Total Testosterone | 3.9% | 7.3% | −51.9% | −47.9% |

These data show declines in testosterone and PSA in the context of LH elevations during the early timepoints in this human trial. This supports the suppression of testosterone and corresponding anti-androgenic effects (PSA suppression) via mechanisms other than hypothalamus-pituitary-testes axis suppression. The mechanism for this LH-independent suppression could be, among others, direct action of Compound IV on adrenal or gonadal androgen synthesis or sequestration of serum T due to elevations in SHBG.

Example 18

Bioavailability of Compound IV

Compound IV was rapidly absorbed following oral dosing to rats, dogs and monkeys. The oral bioavailability of Compound IV in rats ranged from 6% to 25% depending on the formulation in which the dose was administered. Formulations using polyethylene glycol 300 (PEG300) generally produced higher exposures than microemulsions prepared in Tween 80 diluted in deionized water. In dogs, visual inspection of the plasma concentration-time profiles suggested that Compound IV undergoes enterohepatic recirculation as evidenced by a second peak in the terminal phase. Importantly, in dogs the exposure in the male 30 mg/kg PEG300 oral dose group exceeded the exposure necessary to produce the maximal effect on prostate reduction in the rat model of LH suppression. In monkeys, preliminary pharmacokinetic studies suggested that oral bioavailability in this species approximates or exceeds that in dogs, as evidenced by plasma concentrations of Compound IV and suppression of serum testosterone over a seven day period. As a whole, these data suggest that sufficient oral exposure can be achieved in two non-rodent animal species to produce the desired pharmacologic effect (based on AUC data). Further, endocrine data in rats and monkeys suggest that the pharmacologic effects of Compound IV are reversible (i.e., that serum concentrations of testosterone return to baseline or normal levels when treatment with Compound IV is stopped).

Thus, Compound IV was rapidly absorbed following oral dosing to rats, dogs and monkeys. The oral bioavailability of Compound IV ranged from 6 to 25% in rats and 3 to 12% in dogs depending on the formulation and route of administration. In monkeys, preliminary pharmacokinetic studies suggested that oral bioavailability in this species approximates or exceeds that in dogs, as evidenced by plasma concentrations of Compound IV and suppression of serum testosterone. Further, endocrine data in rats and monkeys (Example 10) indicated that the pharmacologic effects of Compound IV are reversible, with serum testosterone concentrations returning to baseline or normal levels when treatment with Compound IV is stopped

Example 19

Pharmacokinetics of Compound IV

Preliminary data from in vitro (mouse, rat, dog, monkey and human) and in vivo (rat) metabolism studies suggest that conjugation of Compound IV, its hydroxylated metabolite(s) and its N-dealkylated metabolite contribute to the overall disposition of Compound IV in animals and humans. The results of the interspecies comparison, although only qualitative, show that the overall metabolite profiles of the non-clinical species adequately reflect the profile generated in human liver microsomes. Based on these results, the rat and dog are appropriate rodent and nonrodent species, respectively, for pharmacology and toxicology evaluations. In vitro studies show Compound IV does not induce relevant CYP450 isoforms (CYP1A2, CYP2B6, or CYP3A4) and does not inhibit CYP1A2, CYP2C19, CYP2D6, or CYP3A4/5 at concentrations <30 µM. CYP2C9 is inhibited by Compound IV but only at high concentrations ($K_i$=8 µM), and potential pharmacokinetic drug-drug interactions are considered remote.

Example 20

Off Target Activity of Compound IV

Compound IV exerts little or no in vitro inhibitory effects ($IC_{50}$≥300 µM) on the hERG channel. The compound dose-dependently decreased APD50 and APD90 at concentrations of 10 and 100 µM in isolated canine Purkinje fibers in vitro. However, Compound IV did not affect hemodynamic or cardiac function (blood pressure, heart rate, electrocardiogram morphology or QT intervals) in telemetered dogs at any dose (up to 300 mg/kg). No neuropharmacological or pulmonary effects were observed. No significant effects were noted on renal function with a single oral dose of up to 30 mg/kg Compound IV. Only increased urine volume output and urinary excretion of potassium and chloride were observed at the highest dose tested (100 mg/kg). Oral administration of Compound IV at doses of 30 to 300 mg/kg in rats produced a significant increase in peristalsis, and oral administration of Compound IV at 30 mg/kg in rats produced a significant increase in gastrointestinal motility and gastric acidity (likely not due to effects on smooth muscle).

Compound IV was not mutagenic and did not induce structural or numeric chromosomal aberrations at concentrations up to 200 µM in human peripheral blood lymphocytes in vitro. Compound IV was well-tolerated by rats and dogs after single and repeated oral administration (up to 28 days). There were no pathologic changes observed in the kidney, liver, heart and other non-target-related organs. There were no serious physical signs, body weight effects, clinical pathology changes, ophthalmologic, electrocardiographic, or histopathologic changes associated with oral administration of Compound IV to male or female dogs for up to 28 days.

Example 21

Compound IV Reduces Testosterone to Castrate Level

A 56 day, proof of concept study of Compound IV was conducted in healthy young male volunteers. (Table 22 and Table 23 below). In subjects that were sufficiently compliant in taking Compound IV, as determined by blood levels of Compound IV, the study showed that 90% of the subjects reached castrate levels of total testosterone by Day 28 in the 1500 mg dose group. The free testosterone levels were reduced to levels below the levels expected from surgical castration or those expected from chemical castration with LHRH agonists or antagonists. This is due to a dose dependent increase in sex hormone binding globulin (SHBG) that is observed with Compound IV. SHBG tightly binds testosterone making it unavailable for activity within the cell and increasing the levels of SHBG decreases the testosterone available to act in the cell potentially providing a pharmacologic benefit with Compound IV that does not exist with surgical castration or with castration with LHRH agonists or antagonists.

TABLE 22

% Change from baseline to final observation in subjects that were sufficiently compliant[†] based on serum levels of Compound IV

| | 600 mg | 1000 mg | 1500 mg | Comments |
| --- | --- | --- | --- | --- |
| # of subjects in assessment | 18 | 12 | 12 | |
| # of subjects castrated | 0 | 9* | 11** | |
| % subjects castrated | 0% | 75% | 92% | |
| Total testosterone | +22.1 ± 51.9% | −63.0 ± 59.9% | −90.6 ± 9.67% | Dose dependent |
| p-value | 0.133 | 0.002 | <0.00000001 | |
| Free testosterone | −32.9 ± 43.2% | −86.4 ± 26.4% | −97.5 ± 1.64% | Dose dependent and even 600 mg dose reduced Free T |
| p-value | 0.003 | <0.00000001 | <0.00000001 | |
| serum PSA | −43.8 ± 21.1% | −42.8 ± 30.2% | −48.1 ± 17.0% | Not dose dependent, but variability in change is less at 1500 mg |
| p-value | 0.0544 | not calculated | 0.001 | |
| FSH | −48.4 ± 53.9% | −78.4 ± 29.4% | −89.7 ± 5.07% | Dose dependent |
| p-value | 0.143 | <0.0000001 | <0.0000001 | |
| SHBG | +363 ± 139% | +446 ± 130% | +591 ± 258% | Dose dependent |
| p-value | <0.00000001 | <0.00000001 | <0.00000001 | |
| BSAP | −18.7 ± 18.8% | −5.97 ± 31.6% | −21.1 ± 17.0% | Not dose dependent |
| p-value | 0.082 | 0.301 | 0.057 | |
| Osteocalcin | −32.8 ± 11.1% | −21.4 ± 14.4% | −18.2 ± 18.7% | |
| p-value | 0.050 | 0.015 | 0.194 | |

[†]The subjects included in this analysis are subjects that did not EDC (except for castration) and in whom non-compliance could not be confirmed.
*2 subjects reached castration and then escaped probably due to decreased compliance with study drug as determined by Compound IV levels.
**1 subject reached castration and then escaped.

TABLE 23

| | Castrated subjects[†] | |
| --- | --- | --- |
| | 1000 mg | 1500 mg |
| # of subjects castrated | 9* | 11** |
| Total testosterone | −94.7 ± 0.228% | −92.8 ± 0.65% |
| p-value | <0.000000001 | <0.000000001 |
| Free testosterone | −98.2 ± 0.146% | −97.7 ± 0.155% |
| p-value | <0.000000001 | <0.000000001 |
| serum PSA | −52 ± 28% | −43 ± 24% |
| p-value | 0.0523 | 0.001 |
| FSH | −91 ± 5.2% | −88 ± 4.8% |
| p-value | 0.00167 | 0.000006 |
| SHBG | 471 ± 102% | 524 ± 212% |
| p-value | 0.0000002 | <0.0000000001 |
| BSAP | 6.0 ± 29% | −19 ± 21% |
| p-value | 0.862 | 0.1475 |
| Osteocalcin | −20 ± 15% | −23 ± 17% |
| p-value | 0.0663 | 0.1228 |

[†]The subjects included in this analysis are subjects that did not EDC (except for castration) and in whom non-compliance could not be confirmed.
*2 subjects reached castration and then escaped probably due to decreased compliance with study drug as determined by Compound IV levels.
**1 subject reached castration and then escaped.

Example 22

Compound IV Studies on Castrated Monkeys—90 Days

Colony-bred cynomolgus macaques of Mauritius origin are obtained. The prospective study is designed as a 39-week oral pharmacology and toxicology evaluation of Compound IV in the male cynomolgus monkey with a 13-week interim period, comparing castrate versus non-castrate animals (Example 16). A total of 49 sexually mature male monkeys, 5 to 8 years of age, are randomly assigned to 7 groups prior to treatment initiation. Animals selected for groups 3-7 are castrated according to NIH guidelines. Groups include: 1) intact vehicle control, 2) intact positive control (LHRH agonist), 3) castrated vehicle control, 4) castrated 1 mg/kg Compound IV, 5) castrated 10 mg/kg Compound IV, 6) castrated 100 mg/kg Compound IV, and 7) castrated control (LHRH agonist).

Drug is delivered orally by cage-side administration once daily for 39 weeks with vehicle control article (Tween 80/PRANG™) for Groups 1, 2, 3 and 7 or Compound IV in vehicle for Groups 4, 5 and 6. Dose levels of Compound IV are 1, 10, and 100 mg/kg/day for Groups 4, 5 and 6, respectively. Oral doses are delivered in a 10 mL/kg dose volume as calculated based on most recent available body weight for each animal. Animals in Groups 2 and 7 also receive a once-daily subcutaneous injection of LHRH agonist (0.02 mL constant volume) for the 39 week study period. General appearance and clinical signs are observed and recorded daily. Routine evaluations and select other study investigations are performed as indicated in the study protocol. Select parameters include, but are not limited to, testosterone, prostate specific antigen (PSA), and prostate volume and weight.

Testosterone and total PSA levels are quantified in serum samples (following standard procedure) using an enzyme immunoassay (EIA) method and chemiluminescence immunoassay (LIA, ALPCO Diagnostics, Salem N.H.), respectively. Blood samples for testosterone evaluations are collected from all animals (in fasted state) at baseline (i.e., prior to commencement of treatment) and on days 1, 3, 7, 14, 28, 64, and 90. Blood samples for PSA determinations are collected from all animals (in fasted state) at baseline and during Week 6. For the purpose of discussion, results for samples with concentrations below the limit of quantitation (BLQ) for the testosterone and PSA assays are calculated as ½ of the lower limit of quantitation (LLOQ) of the assay, and are considered as "Estimated final concentrations". Prostate volume is measured in live animals under anesthesia using a transrectal ultrasound (TRUS) procedure at baseline and Week 6. The width and height of prostate were recorded. Prostate volumes are calculated as width×width×height×pi/6 and are normalized to body weight. The wet weight of prostate is recorded at necropsy after trimming the tissue free of fat and extraneous tissue.

Results and Discussion:

At baseline, the testosterone levels for all monkeys in groups 1 and 2 of the study are in the normal range for sexually mature adult male cynomolgus monkeys. However, at baseline, testosterone levels of all monkeys in groups 3-7 of the study are reduced to the castrate range for sexually mature adult male cynomolgus monkeys. Results show testosterone levels are significantly reduced in positive control group 2 monkeys receiving LHRH agonist. Testosterone levels in this intact positive control (LHRH agonist) group illustrate a biphasic change. A similar flare is not observed for any of the castrated animals treated with Compound IV. Dose and treatment duration are important to the pharmacologic action of Compound IV.

Unexpectedly, serum PSA levels are significantly suppressed by Compound IV in castrate animals (groups 4, 5 and 6) within four weeks of treatment initiation.

Prostate volumes are measured by TRUS periodically throughout the study. Intact Vehicle control shows minimal change between pre-dose and 4 weeks. Results demonstrate a potent effect of Compound IV on monkey prostate.

The Intact Vehicle Control shows results similar to those observed in Example 16. The Compound IV-related reductions in prostate volume are confirmed by the evaluation of prostate weight at necropsy. After thirteen weeks of treatment, Compound IV significantly reduces mean prostate weights in animals receiving doses of Compound IV.

No apparent effects on platelet aggregation, prothrombin time (PT) or activated partial thromboplastin time (APTT) are observed.

Example 23

Compound IV Studies on Humans with Prostate Cancer Undergoing ADT

A study is conducted to determine the effect of Compound IV on testosterone and PSA levels in human males undergoing ADT for prostate cancer, wherein ADT treatment results in subjects having castrate levels of testosterone. All subjects are required to show histological evidence of prostate cancer. Patients who had not undergone previous orchiectomy and are currently receiving Luteinizing hormone-releasing hormone analogues for chemical castration, are required to remain on this therapy for the course of the study.

12 subjects per cohort are examined at dosages of 100, 300, 600 and 1000 mg of Compound IV. Dose dependent mean total testosterone levels (nmol/L) in humans are measured for a period between days 1-11. See FIG. 26 for an overview of all the clinical studies on Compound IV.

Dose dependent mean free testosterone levels (pg/mL) in humans are measured for a period between days 1-10.

Dose dependent mean PSA levels (μg/L) in humans are measured for a period between days 1-10.

Example 24

Compound IV Studies on Healthy Human Subjects

Compound IV Toxicity Studies in Healthy Human Subjects

Single and multiple dose studies in healthy human subjects showed that Compound IV was well tolerated at single doses up to 1247 mg and at multiple doses up to 997 mg (10, 30, 100, 300, 609 and 997 mg) for up to 10 days. There were observations of elevated ALT levels above the upper limit of normal in four subjects in the multiple dose study (3 subjects in the 1000 mg group and 1 subject in the 600 mg group). The highest single observed value of ALT was 129 IU/L or 2.6 times the upper limit of normal. Aspartate aminotransferase levels were also elevated in this subject to 1.9 times the upper limit of normal. There were no observations of elevations in total bilirubin in any subject in the trial.

The Effect of Compound IV on Serum Testosterone Levels

Serum total testosterone levels were assessed throughout the multiple doses study. Total testosterone levels were decreased in 100% (10/10) of the subjects in the 600 mg dose group and 90% (9/10) of the subjects in the 997 mg dose group. The levels of total testosterone were decreased to below the lower limit of normal in 40% (4/10) of the subjects in the 600 mg dose group and 50% (5/10) of the subjects in the 1000 mg dose group. However, no subject had total testosterone levels below 1.73 nmol/L (castrate range) and the total testosterone levels of all subjects returned to normal within 6 days after discontinuation of Compound IV.

A proof of concept study (Study 1) to assess the effect of Compound IV on serum total and free testosterone in healthy young male volunteers wherein healthy male volunteers took 600 mg, 1000 mg or 1500 mg of Compound IV in solution form for 56 days, showed that in the 1000 and 1500 mg dose groups, some subjects had serum total testosterone levels within the castrate range (<1.73 nmol/L) and in the 600 mg dose arm, no subject had levels of serum total testosterone within castrate range (<1.73 nmol/L).

A second proof of concept study (Study 4) to assess the effect of Compound IV on serum total and free testosterone levels in healthy older male volunteers, has also been conducted. In this study, volunteers took 1000 mg, 1500 mg, or 2000 mg of Compound IV in a tablet form for 28 days continually. See FIG. 26 for an overview of all the clinical studies on Compound IV.

In both these studies, Compound IV showed a dose dependent increase in sex hormone binding globulin (SHBG). SHBG binds to testosterone resulting in a conjugate that is not available for binding to the androgen receptor and reducing the levels of testosterone that is available to bind to the androgen receptor (as indicated by levels of free testosterone). In each of the dose arms administered in the two studies, SHBG was increased by 300-600% over baseline and serum free testosterone was decreased. In men who are chemically castrated with Compound IV with total testosterone levels <50 ng/dL, levels of serum free testosterone are expected to be lower than the levels that are expected with surgical castration and administration of luteinizing hormone releasing hormone (LHRH) agonists.

A summary of the details of the various human studies is presented in FIG. 26.

Example 25

Compound IV Studies on Male Subjects with Prostate Cancer

The Effect of Compound IV on Total Serum Testosterone Levels, Free Testosterone Levels, PSA Levels, SHBG Levels, Hot Flashes, Bone Turnover and Insulin Resistance-Advanced Prostate Cancer Patients Study 2: Patients and Methods This was a prospective, randomized 1:1:1, Phase 2 open-label, multicenter, trial comprised of men with advanced prostate cancer (n=159) initiating ADT with either oral daily doses of 1000 mg Compound IV, oral daily doses of 2000 mg Compound IV, or leuprolide depot (Lupron Depot® 4 month). It was conducted according to the Declaration of Helsinki, approved by appropriate research ethics committees, and each patient provided signed informed consent prior to registration and randomization. Patient demographics are outlined in Table 24.

TABLE 24

Descriptive Statistics and Characteristics of the Study Population at Baseline

| Characteristic | Compound IV 1000 mg (n = 53) | | Compound IV 2000 mg (n = 55) | | Leuprolide Depot (n = 51) | | p-value** |
| --- | --- | --- | --- | --- | --- | --- | --- |
| | n | % | n | % | n | % | |
| Ethnicity | | | | | | | 0.7673 |
| Hispanic/Latino | 6 | 11.3 | 4 | 7.3 | 5 | 9.8 | |
| Non-Hispanic/Latino | 47 | 88.7 | 51 | 92.7 | 46 | 90.2 | |
| Race | | | | | | | 0.9861 |
| White | 41 | 77.4 | 42 | 76.4 | 41 | 80.4 | |
| Black or African American | 11 | 20.7 | 12 | 21.8 | 10 | 19.6 | |
| Asian | 1 | 1.9 | 1 | 1.8 | 0 | 0.0 | |
| Distant Metastasis | | | | | | | 0.6121 |
| M0 | 23 | 51.1 | 31 | 60.8 | 29 | 61.7 | |
| M1 | 3 | 6.7 | 5 | 9.8 | 5 | 10.6 | |
| MX | 19 | 42.2 | 15 | 29.4 | 13 | 27.7 | |
| Gleason Grade Primary Pattern | | | | | | | 0.6733 |
| 2 | 2 | 3.8 | 0 | 0.0 | 2 | 4.0 | |
| 3 | 22 | 42.3 | 26 | 48.1 | 28 | 56.0 | |
| 4 | 25 | 48.1 | 25 | 46.3 | 18 | 36.0 | |
| 5 | 3 | 5.8 | 3 | 5.6 | 2 | 4.0 | |
| Gleason Grade Secondary Pattern | | | | | | | 0.8694 |
| 2 | 1 | 1.9 | 1 | 1.9 | 1 | 2.0 | |
| 3 | 21 | 40.4 | 26 | 48.1 | 21 | 42.0 | |
| 4 | 25 | 48.1 | 18 | 33.3 | 21 | 42.0 | |
| 5 | 5 | 9.6 | 9 | 16.7 | 7 | 14.0 | |

| | mean | SD | mean | SD | mean | SD | p-value** |
| --- | --- | --- | --- | --- | --- | --- | --- |
| Age | 66.6 | 8.8 | 67.5 | 7.7 | 67.5 | 7.4 | 0.8260 |
| PSA* | 34.1 | 197.1 | 17.3 | 68.0 | 11.5 | 19.9 | 0.6175 |
| Testosterone, total | 377.9 | 195.0 | 388.2 | 129.6 | 394.8 | 157.1 | 0.8706 |
| Testosterone, free | 53.6 | 20.1 | 51.3 | 15.1 | 58.2 | 20.8 | 0.1719 |

The trial required each subject to remain on the study for at least 60 days. If a subject failed to reach total testosterone ≤50 ng/dL by day 60, they were discontinued from the study. Subjects that achieved castration by day 60 continued for up to 360 days to assess the safety of Compound IV over this dosing duration and to assess the maintenance of total testosterone levels ≤50 ng/dL.

The major inclusion criteria for the trial were: Males between 45-80 years of age; ECOG ≤2; screening serum total testosterone ≥150 ng/dL; no prior ADT (medical or surgical) unless the subject had been treated with LHRH agent for ≤6 months duration and that treatment was ≥1 years prior to screening. Key exclusion criteria included: history of abnormal blood clotting, Factor V Leiden mutation, thrombotic disease, stroke, deep vein thrombosis (DVT), or pulmonary embolus (PE); alanine aminotransferase (ALT) or aspartate aminotransferase (AST)>2 times the upper limit of normal (ULN); alkaline phosphatase >3 times ULN or total bilirubin levels >2 mg/dL at baseline; brain or spinal cord metastases; currently taking testosterone, testosterone-like agents or antiandrogens, including 5-alpha reductase inhibitors; saw palmetto, PC-SPES, diethylstilbesterol or other estrogen products within the previous 12 months prior to randomization; QTcB >480 msec.

The primary endpoint of the clinical trial was the proportion of patients that achieve ≤50 ng/dL total testosterone by Day 60. Secondary efficacy endpoints evaluated included serum concentrations of free testosterone, PSA, SHBG, safety and tolerability of Compound IV, incidence and frequency of hot flashes, serum bone turnover markers [bone specific alkaline phosphatase (BSAP) and c-terminal telopeptide (CTX)] and IGF-1 levels, an indicator of insulin resistance.

All serum hormone and PSA measurements were performed by a central laboratory utilizing standard techniques. Serum total testosterone concentrations were determined using a validated liquid chromatography-tandem mass spectrometry (LC/MS-MS) method. This is the assay platform that is current utilized for total testosterone by most major laboratories and provides values which are more accurate at the lower levels of testosterone found in women, children, hypogonadal men, and men on ADT. The percent free testosterone was determined by equilibrium dialysis. Free testosterone concentrations were calculated as the product of (total testosterone by LC/MS/MS) and (free fraction by equilibrium dialysis). This combination of approaches is considered to be the gold standard with which to measure free testosterone with excellent accuracy and validity (sensitivity and specificity).

Hot flash assessments were performed utilising a standard instrument to measure the frequency and severity of hot flashes, and data were compiled at baseline, Day 28 and Day 90. The men reported as experiencing hot flashes were those indicating any in the period between the respective time point and the prior patient visit. CTX (pg/ml) assayed by an electrochemiluminescent immunoassay and BSAP (U/L) assayed by immunoenzymatic methodology were measured as indicators of bone turnover. Serum IGF-1 levels were measured by liquid chromatography/mass spectrometry (LC/MS) at the same time each day (within a +/−60 minute window).

Statistical Analyses

Simple descriptive statistics and graphics were used to present the characteristics of the study population. One way Analysis of Variance (PROC GLM with CONTRAST statement) methods were used to compare total testosterone percent change from baseline to Day 28, Day 60 and Day 90. Kaplan Meier survival analysis was used to estimate the proportion of subjects that reached castrate levels by Day 60 in each treatment arm based upon time to total testosterone of ≤50 ng/dL. Fisher Exact tests were used to compare rate of hot flashes at Day 28 and Day 90 among the two Compound IV and the leuprolide arms. One way ANOVA methods were also used to compare CTX and BSAP changes from baseline to Day 120 between treatment groups. The intent-to-treat (ITT) population consisted of all randomized patients who received at least one dose of Compound IV or leuprolide depot. The castrate population included those individuals that reached testosterone levels of ≤50 ng/dL by Day 60. All p-values describe the comparison of both Compound IV arms to the leuprolide arm where p-values of <0.05 were considered significant. SAS 9.3 (SAS Institute Inc. Cary, N.C.) was used to perform all statistical analyses.

Total Serum Testosterone

A dose finding study (Study 2) comparing 1000 mg and 2000 mg Compound IV doses administered once daily with a four month depot formulation of leuprolide acetate, has been conducted. The primary objectives of the study were to assess the proportion of subjects that achieved castrate levels of serum total testosterone by Day 60 and maintained castrate levels from Day 60 to Day 360.

Fifty-two (52) subjects were randomized to the 1000 mg Compound IV dose arm. In the 1000 mg Compound IV dose arm in subjects that reached Day 60, 43.4% of the subjects achieved castration by Day 60 (i.e., total T<50 ng/dL; the dotted line in FIG. 47). However, this proportion of subjects reaching castration was too low to be considered clinically viable as androgen deprivation monotherapy.

Fifty-five (55) subjects were randomized to the 2000 mg Compound IV dose arm. In the 2000 mg dose arm among subjects that reached Day 60, 63.6% of the subjects achieved castration by Day 60. (FIG. 47)

Forty-nine (49) subjects were randomized to the leuprolide acetate dose arm. In the leuprolide treated arm among subjects that reached Day 60, 88.2% of these subjects achieved castration by Day 60. (FIG. 47) During the study, nine (9) subjects in the 1000 mg dose arm and two (2) subjects in the 2000 mg dose arm experienced a venous thromboembolism event (VTE).

Free Testosterone

As the biological activity of a hormone is mediated by its free concentration rather than its protein-bound concentration, a second objective of Study 2 was to compare the free testosterone levels. The percent free testosterone represents the ratio of free testosterone/total testosterone and is provided as a means to understand changes in free fraction that occurred during treatment with Compound IV.

The median levels of free testosterone were 0.4 pg/ml and 0.3 pg/ml in the 1000 mg and 2000 mg arms, respectively, as compared to 0.9 pg/ml for the leuprolide group at Day 120 (p values <0.03 for all comparisons) (FIG. 48). Similarly, the median levels of free testosterone in the men who were castrate (total testosterone ≤50 ng/dL) were 0.4 pg/mL for 1000 mg and 0.3 pg/mL for 2000 mg versus 0.8 pg/mL for the leuprolide treated men (p values <0.005 for all comparisons) (FIGS. 49A-C). While free testosterone concentrations are presented in FIG. 48, the percent (%) free testosterone is shown in FIG. 34.

PSA Levels

A third objective of Study 2 was to compare the reduction of PSA in response to treatment over time with 1000 mg (Compound IV), 2000 mg (Compound IV), and leuprolide acetate depot. FIG. 36 shows that despite fewer patients achieving castration with Compound IV, similar or greater reduction in serum PSA levels were observed in men treated with Compound IV compared to leuprolide, with statistically different differences between the groups observed at at least Days 7, 14, 21 and 28. Table 25 presents baseline PSA values.

TABLE 25

Serum Prostate Specific Antigen (PSA) (ug/L) Day 1 (Baseline)

|  | 1000 mg Compound IV (n = 53) | 2000 mg Compound IV (n = 55) | Lupron Depot ® (n = 50) |
|---|---|---|---|
| Mean | 34.1 | 17.3 | 11.5 |
| SD | 197.1 | 68.1 | 19.9 |
| Median | 4.6 | 4.0 | 6.1 |
| Range | (0.0, 1440.0) | (0.0, 501.2) | (0.1, 96.7) |

SHBG Levels

A fourth objective of Study 2 was to compare levels of SHBG with the reduction of free testosterone. Increases in SHBG correlated with the reduction of free testosterone. Estrogens are known to stimulate SHBG production by the liver. SHBG increases following Compound IV therapy were apparent as early as day 30 days (data not shown). As evident by the waterfall plots (FIG. 50), the men being treated with Compound IV had SHBG levels that significantly increased over those treated with leuprolide at all the time points measured. At Day 90, the men treated with 1000 mg and 2000 mg of Compound IV had median increases of 495% and 583% respectively compared to 5.0% in men on leuprolide (p<0.001). Comparisons show that administration of Compound IV increases SHBG, reducing unbound (free) testosterone towards undetectable.

Hot Flashes

Hot flashes are a common side effect in men on ADT. A fifth objective of study 2 was to compare the incidence and frequency of hot flashes in subjects administered Compound IV versus subjects administered leuprolide acetate depot. The results presented show that men administered Compound IV experienced less hot flashes compared to men who were administered leuprolide acetate depot.

The frequency of hot flashes was recorded from all treatment groups utilising an established patient reported outcome hot flash instrument. The patients were queried whether they experienced a hot flash during the period of time since their last visit. As illustrated in FIG. 40, at baseline, 3.8% (2/53), 0% (0/55) and 7.8% (4/51) of the men treated with 1000 mg Compound IV, 2000 mg Compound IV and leuprolide, respectively, reported having previously experienced a hot flash. Between baseline and the Day 28 visit, those hot flashes had increased to 25% (13/52), 12.8% (6/47) and 60.4% (29/48) of the men, respectively. Between Days 29 and 90, 18.8% (3/16), 5.6% (2/36) and 80.9% (38/47) of the men, respectively, had recorded at least one hot flash.

These results show that treatment with Compound IV resulted in a significantly lower (p<0.001 for Day 90 visits) rate of hot flashes that is at most, 25% of that observed in the leuprolide treated group.

At the baseline, there were no significant differences in the number of men reporting hot flashes in any of the treatment groups (p=0.065). The percentage of men who experienced a hot flash while receiving leuprolide increased significantly to 60.4% (p<0.0001) by Day 28 and increased further to 80.9% (p<0.0001) by Day 90. Although some subjects experienced hot flashes while receiving Compound IV, these men were a significantly lower percentage, 18.8 and 5.6% at the 1000 mg and 2000 mg doses of Compound IV respectively at day 90. As a result of an increased risk of venous thromboembolic events (VTEs) at these higher doses of Compound IV, the trial was stopped prior to its completion and not all of the men on the study reached the 90 day treatment date (99 evaluable). The study results are presented in Table 26 and FIG. 40.

TABLE 26

Number of men experiencing hot flashes

|  | 1000 mg Compound IV (n = 53) | 2000 mg Compound IV (n = 55) | Lupron Depot ® (n = 50) |
|---|---|---|---|
| Baseline | 3.8% (2/53) | 0% (0/55) | 7.8% (4/51) |
| Baseline to Day 28 | 25% (13/52) | 12.8% (6/47) | 60.4% (29/48) |
| Day 29 to Day 90 | 18.8% (3/16) | 5.6% (2/36) | 80.9% (38/47) |

Men with advanced prostate cancer, receiving Compound IV experienced a greater than 4-fold reduction in their reported hot flashes at day 90. Since hot flashes are a major side effect that impacts the quality of life in men on ADT, the ability to significantly decrease their likelihood would seem to be of great benefit.

Table 27 presents the results of a preliminary analysis of the incidence of hot flashes in men undergoing Androgen Deprivation Therapy with an Injectable LHRH Agonist (Lupron) versus an Oral Selective Estrogen Receptor Alpha Agonist (Compound IV):

TABLE 27

| Treatment | Total Number of Subjects Assessed | Number (Percent) of Subjects that Experienced a Hot Flash |
|---|---|---|
| Lupron Depot ® | 49 | 35 (71%) |
| Compound IV (2000 mg daily) | 41 | 2 (5%) |

Bone Turnover Markers

A sixth objective of Study 2 was comparing bone turnover markers in men treated with Compound IV. When comparing baseline to Day 120, C-terminal telopeptide (CTX) had a median increase of 42.3% in the men on leuprolide. In comparison, the men treated with Compound IV had a median decrease in CTX of −55.3% and −58% in the 1000 mg and 2000 mg arms, respectively. Similarly, another marker of bone turnover, bone specific alkaline phosphatase (BSAP) levels, also increased in the leuprolide treated group by a median of 4.1% as compared to decreasing in the 1000 mg and 2000 mg Compound IV treated men by medians of −26.3% and −22.6%, respectively. The waterfall plots demonstrate how the levels of these two biomarkers changed in individual patients (FIGS. 38 and 39). Mean changes for Compound IV treated groups were significantly different than leuprolide treated men for each bone parameter (p<0.001). A summary of the changes in bone turnover markers from baseline to day 120 is presented below in Table 28.

TABLE 28

|  | 1000 mg Compound IV (n = 53) | 2000 mg Compound IV (n = 55) | Lupron Depot ® (n = 51) |
|---|---|---|---|
| C-terminal telopeptides (pg/ml) | −55.3% | −58% | 42.3% |
| Bone specific alkaline phosphatase (U/L) | −26.3% | −22.6% | 4.1% |

Mean percentage change
p-value for all comparisons to Lupron Depot®<0.001

Patients receiving Compound IV experienced a significant decrease in markers of bone turnover indicating potential improvement and not a loss of bone on ADT. Since changes in bone mineral density are a major side effect that can negatively affect the quality of life in men on ADT, the improvements in bone turnover observed in men treated with Compound IV could be significant. Compound IV may have the ability to castrate with a significant lowering of free T and a decrease in PSA while minimizing the bone morbidity of standard ADT.

IGF-1

A seventh objective of Study 2 was the use of insulin-like growth factor 1 (IGF-1) as a metabolism marker of insulin resistance in men treated with Compound IV. Results are presented in Example 29 below.

Study 5: Naïve Prostate Cancer Patients

Another study (Study 5) to assess 1000 mg twice per day and 1500 mg twice daily loading doses of Compound IV for 28 days was conducted. Subjects that were castrate on Day 28 received either 1000 mg or 2000 mg Compound IV daily to maintain the castration.

Thirty (30) and 28 subjects were randomized to the 1500 mg BID and 1000 mg BID loading doses, respectively. Among the subjects that had reached Day 28, 90% (18/20) of the subjects in the 1500 mg BID dose group and 94% (17/18) of the subjects in the 1000 mg BID dose group had reached castrate levels of serum total testosterone. During this study, two (2) subjects in the 1500 mg BID dose group experienced a VTE, including one fatal pulmonary embolus (PE) and three (3) subjects in the 1000 mg BID dose group experienced a VTE. See FIG. 26 for an overview of all the clinical studies on Compound IV.

TABLE 29

Castration rates for treatment naïve prostate cancer patients receiving >14 days of Compound IV (Study 5)

| | Castration (%) | | | |
|---|---|---|---|---|
| | 1000 mg QD | 2000 mg QD | 1000 mg BID | 1500 mg BID | leuprolide acetate |
| D28 | 50 | 31 | 84.2 | 85.7 | 100 |
| D60 | 59.4 | 79.6 | — | — | 95.7 |
| Ever | 61.5 | 84.6 | 90 | 95.2 | 100 |

Figure 28A:
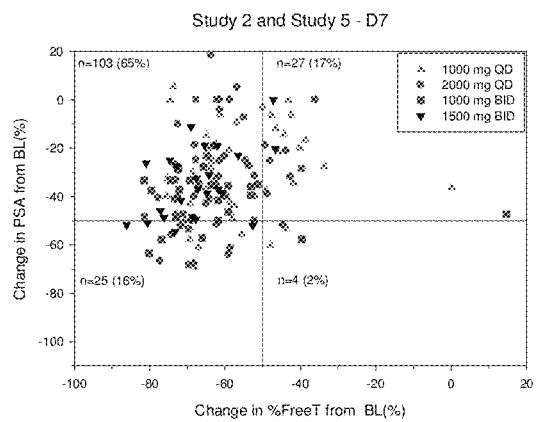
Figure 28B:
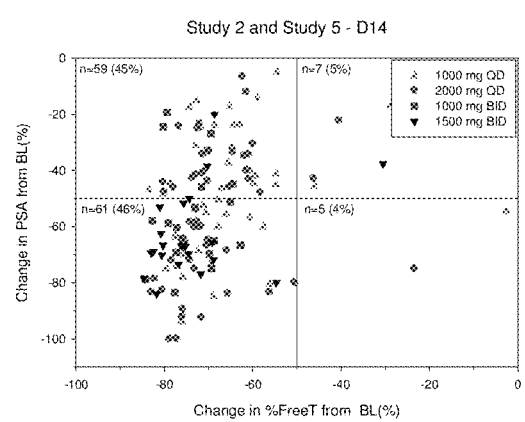
Figure 28C:
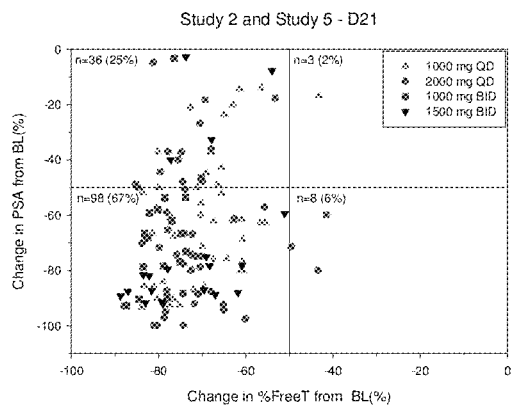
Figure 28D:
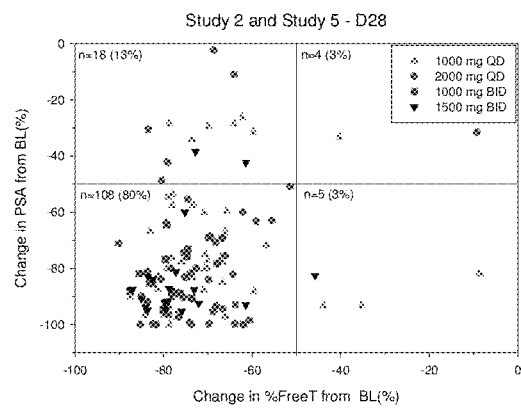

In treatment naïve patients, when looking at changes in % FreeT from baseline, 81% have at least a 50% reduction in % FreeT after only 7 days of therapy (FIG. 28A). This change in % FreeT is associated with reductions in PSA as therapy is extended to 14, 21 and 28 days. After a month (FIG. 28D) of Compound IV therapy, 80% of all patients have both at least a 50% reduction in % FreeT and a 50% reduction in PSA from baseline (i.e., data clustered in lower left quadrant in FIG. 28D). These patients meet the PCWG2 criteria for PSA response.

Reduction of 50% FreeT and 50% PSA at D28 is re-plotted as the change in SHBG vs. the change in PSA in FIG. 29. A wide range of SHBG induction is capable of >50% reduction in PSA.

In treatment naïve patients, both Compound IV and leuprolide therapy markedly increase the molar ratio of SHBG:Total T after 28 days of therapy (FIG. 31). Since Compound IV induces SHBG and reduces Total T, the molar ratio of SHBG to Total T is 3-7 fold higher than in leuprolide acetate treated patients. This increased molar ratio corresponds to a 70% drop in % FreeT at day 28 in Compound IV treated patients as opposed to only 20% reduction in leuprolide acetate treated men (FIG. 31). Also all doses of Compound IV show similar, rapid reductions in % FreeT suggesting that 1000 mg QD is an Emax dose and that lower doses of Compound IV are likely to reduce % FreeT. At 28 days, 28.3% of the men on Compound IV were below the cutoff of 0.5 pg/mL of free testosterone in comparison to 2.3% on leuprolide acetate. At 45 days, 50.9% of men on Compound IV were below the cutoff compared to 14.6% and at Day 120 on the study, 58.1% of the men on Compound IV were below the cutoff compared to 28.6%.

Based on clinical experience, the SHBG data from Study 1 and 2 was extrapolated to lower doses (FIG. 32) suggesting that even at 125 mg, 250 mg and 500 mg doses, SHBG can be elevated enough to significantly suppress % freeT and PSA.

Study 3 Compared to Study 2 (Preliminary Analysis): Decreased Free T and PSA in CRPC Patients (Study 3) Despite Lack of Decrease in Total T.

Men with CRPC (n=9) received 2000 mg Compound IV daily. The primary endpoint of the study was the proportion of subjects with a greater than or equal to 50% reduction in prostate specific antigen (PSA) from Day 1. Secondary endpoints included serum free T and SHBG which together with PSA were assessed at days 1, 15, 30, 60 and 90. Serum concentrations of total T, free T, SHBG and PSA were determined at baseline and during treatment.

TABLE 30

Characteristics of Men Treated with Compound IV or Leuprolide (ITT Population)

| | Treatment Group | | |
|---|---|---|---|
| | 1000 mg Compound IV (n = 53) | 2000 mg Compound IV (n = 55) | Lupron (n = 51) |
| No. Castrated (%) at Day 28 | 26 (49%) | 31 (56%) | 48 (94%) |
| No. Castrated (%) on both Day 28 and Day 60 | 16 (30%) | 28 (51%) | 43 (84%) |
| Total T, Free T and PSA reduction data based on subjects castrated on both day 28 and day 60 | | | |
| Mean Total T (ng/dL) at Day 28 | 25 ± 15 | 19 ± 9 | 14 ± 7 |
| Mean Free T (pg/ml) at Day 28 | 1.0 ± 0.8 | 0.7 ± 0.7 | 1.7 ± 1.1 |
| % Reduction on PSA at Day 28 | 84% | 73% | 56% |

Results

As indicated in Table 30 (above), in ADT naïve advanced prostate cancer patients, 28 days of 1000 mg or 2000 mg daily Compound IV or leuprolide therapy castrated (T<50 ng/dL) 50, 31 and 100% of patients, reducing mean serum total T in castrated patients to 25±15, 19±9 and 14±7 ng/dL, respectively. However, treatment with 1000 mg or 2000 mg Compound IV daily reduced mean free T levels to a greater extent (1.0±0.8 and 0.7±0.7 pg/mL, respectively) than leuprolide (1.7±1.1 pg/mL). Changes in PSA at 28 days were more closely associated with the observed changes in free T, with reductions of 84, 73 and 56% for 1000 mg, 2000 mg doses of Compound IV and leuprolide, respectively. In CRPC patients (Study 3), 2000 mg Compound IV daily did not further reduce serum total T levels, but did result in free T reductions and PSA decreases from baseline following 15 days of therapy in all of the men maintained on ADT with LHRH agonists alone.

TABLE 31

Percentage of Treated ADT Naïve Patients (Castrate Population) below the Free T Cutoff of 0.5 pg/ml (Study 2)

| | Time on Therapy (days) | | |
|---|---|---|---|
| | 28 | 45 | 120 |
| Compound IV | 28.3% | 50.9% | 58.1% |
| Leuprolide | 2.3% | 14.6% | 28.6% |

TABLE 32

Percentage of Treated Patients Already on ADT (ITT Population) Below the Free T Cutoff of 0.5 pg/ml (Study 3)

| | Time on Therapy (days) | | |
|---|---|---|---|
| | 15 | 30 | 60 |
| Compound IV | 85.7% | 66.7% | 100% |

In CRPC patients, 2000 mg Compound IV daily did not further reduce serum total T levels, but did result in free T reductions and PSA decreases from baseline following 15 days of therapy in all of the men maintained on ADT with LHRH agonists alone.

Conclusions

Although Compound IV and LHRH based ADT both reduce total serum T and PSA levels in ADT naïve advanced prostate cancer patients (Study 2), free T was rapidly reduced to a greater degree in the Compound IV treated patients. In men with CRPC (Study 3), Compound IV therapy resulted in significant reductions in free T and resultant PSA declines. The ability of Compound IV to reduce free T provides a unique mechanism to treat men with advanced prostate cancer and CRPC. The free T cutoff of 0.5 pg/ml can be utilized to determine differences in therapeutic efficacy. Men that responded to Compound IV had an approximately 200-600% increase in SHBG levels. At higher doses, Compound IV resulted in a higher VTE rate than that observed for leuprolide. Both actual and projected trough concentrations suggest that significant increases in serum SHBG and reductions in free T can be achieved with lower (125 to 500 mg) doses of Compound IV (Capesaris). As a selective ERα agonist, Compound IV has the potential to lower serum free T and avoid the estrogen deficiency related side effects of LHRH analogs, as well as those typically associated with nonselective estrogens. Detailed data are presented in Tables 24-32 and FIGS. 28-32, 34-40 and 47-50.

Example 26

Compound IV Studies on Male Subjects with Castration Resistant Prostate Cancer (CRPC) Undergoing ADT: Study 3

The Effect of Compound IV on Serum PSA Progression

When total testosterone is measured, the measurement includes SHBG bound testosterone, free testosterone and albumin bound testosterone. SHBG tightly binds testosterone while free testosterone and albumin bound testosterone are in equilibrium. Compound IV has been shown to increase SHBG and reduce free testosterone to levels below the levels achieved by LHRH agonists or antagonists or surgical castration.

A study (Study 3) was conducted to assess the effects of Compound IV on serum PSA progression in men with castration resistant prostate cancer who have been effectively treated with ADT and at the time of enrollment into this study have shown serum PSA progression. This study consisted of one dose arm with 9 subjects.

Summary of studies details is presented in FIG. 26.

The objectives of this study were: (a) to assess the effect of Compound IV on serum PSA levels in men with castration resistant prostate cancer maintained on androgen deprivation therapy (serum PSA response and serum PSA progression); (b) to assess the effect of Compound IV on serum free testosterone levels; (c) to assess the effect of Compound IV on SHBG; (d) to assess the effect of Compound IV on serum total testosterone; (e) to assess the effect of Compound IV on the development of new bone metastases; (f) to assess the effect of Compound IV on soft tissue metastases (visceral and lymph nodes); and (g) to assess the safety and tolerability of Compound IV in men with prostate cancer on androgen deprivation therapy.

The subjects were 12 male subjects over age 18 years with castration resistant prostate cancer, who were being treated with androgen deprivation therapy (chemical or surgical castration) for at least 6 months, that have serum PSA >2 ng/mL or >2 ng/mL and a 25% increase above the nadir after the initiation of androgen deprivation therapy (ADT) at study enrollment. The subjects were maintained on androgen deprivation therapy throughout the study.

To meet the definition of castrate resistant subjects must: (1) have had a serum PSA in the undetectable range on two successive occasions followed by a rise in serum PSA to >2 ng/ml, while on adequate androgen deprivation therapy; (2) have a castrate level of serum total testosterone (<50 ng/dL); (3) have a history of serum PSA response after initiation of ADT, (serum PSA response is at least a 90% reduction in serum PSA to <10 ng/mL OR undetectable level of serum PSA (<0.2 ng/mL)); (4) have rising serum PSA on two successive assessments at least 2 weeks apart and serum PSA levels >2 ng/mL or >2 ng/mL and a 25% increase above the nadir after the initiation of androgen deprivation therapy (ADT); and (5) be continued on androgen deprivation therapy throughout this study.

TABLE 33

Baseline hormone parameters for young healthy subjects, older treatment-naïve prostate cancer patients and castration resistant prostate cance patients from Studies 1, 2 and 5; and Study 3, respectively.

| | Parameter (Baseline, mean ± SD) | | |
|---|---|---|---|
| | Young Healthy (Study 1, n = 70) | Older Tx Naïve PC (Study 2, 5, n = 210) | CRPC on ADT (Study 3, n = 9) |
| Total T (ng/dL) | 615 ± 184 | 387 ± 161 | 7.8 ± 5.2 |
| Free T (pg/mL) | 15 ± 4.0** | 54 ± 18 | 0.9 ± 0.7 |
| % Free T | 0.25 ± 0.07** | 1.5 ± 0.4 | 1.1 ± 0.3 |
| SHBG (mg/L) | 3.3 ± 1.3 | 4.6 ± 2.2 | 5.1 ± 2.7 |
| FAI (x103) TT[mol]/SHBGv [mol] | 655 ± 188 | 293 ± 91 | 6.0 + 4.8 |

**Study 1 employed a RIA Free T method reporting reduced Free T levels when compared to the preferred dialysis method used in Study 2, 5 and 3.

The dose selected for the study was 2000 mg Compound IV. Four Compound IV tablets, 500 mg (2000 mg dose) were orally administered daily. This dose has been shown to increase SHBG and result in a significant reduction in free testosterone more quickly than the 1000 mg dose. Subjects received 2000 mg of Compound IV daily by mouth until study termination. Dosing was to be continued until their serum PSA had increased at least 25% and 2 ng/mL from the nadir at two successive sample times (approximately 30 days apart) after initiation of treatment with Compound IV. The prostate cancer working group (PCWG) definition of PSA progression was used (serum PSA has increased at least 25% and 2 ng/mL above the nadir after initiation of treatment with Compound IV on two successive sample times).

Assessments of serum PSA concentration were made at baseline and on Days 15, 30, and 60 (only 1 patient made it this far before study was terminated).

The study was terminated before PSA progression was observed for any of the subjects. However, had the study continued, the following protocol would have been followed: After the subject shows a serum PSA progression, the subject remains on drug for 30 days and has a follow up serum PSA assessment. If the serum PSA progression is NOT confirmed at this visit, the subject remains in the study and continues dosing with Compound IV. If the serum PSA progression is confirmed at this visit, the subject is discontinued from the study and End of Study visit assessments is conducted. A scheduled follow-up visit for subjects, takes place 30 days after the last dose of Compound IV.

Primary Endpoint:

The proportion of subjects with a 50% decline from baseline in serum PSA (confirmed by a second PSA assessment at least one week later).

Secondary Endpoints:

(1) time to serum PSA progression; (2) the proportion of subjects with a ≥90% decline from baseline in serum PSA; (3) change in serum free testosterone levels; (4) change in SHBG levels; (5) change in serum total testosterone levels; (6) change in RECIST criteria from baseline; (7) proportion of subjects with new bone metastases; (8) proportion of subjects with new or worsening soft tissue metastases (visceral and lymph nodes); (9) to assess the safety and tolerability Compound IV in men with prostate cancer on androgen deprivation therapy.

Drug Supply and Formulation:

Compound IV Tablets, 500 mg strength tablet formulated with micronized drug substance and 1% w/w SDS.

A flow chart describing study procedures can be found in FIG. 33.

Results

The trial was terminated early but out of the twelve subjects that were enrolled in this study, seven subjects were on study long enough to have evaluable data for efficacy. All seven of the subjects showed a reduction in serum PSA from baseline to Day 15. In all three subjects that had at least 30 days of exposure to Compound IV a >50% reduction in serum PSA was observed (FIG. 24).

Had the study continued, the following protocol would have been followed: Serum PSA response rate in men with castrate resistant prostate cancer maintained on androgen deprivation therapy who receive Compound IV is the primary outcome of the study and is assessed for all subjects. PSA response is defined as a 50% decline from baseline confirmed by a second PSA value 4±one week later. The proportion of subjects with PSA response is estimated and the exact 95% Blyth-Still-Casella confidence interval is computed. This estimate was constructed among subjects in the ITT population. This was done similarly for the proportion of subjects with >90% reduction in PSA from baseline.

Graphical depiction of percentage change in PSA via waterfall plots is presented in FIG. 24.

The Effect of Compound IV on SHBG Levels and the Relationship Between SHBG Levels and Free Testosterone Percentage In treatment naive patients from the Study 2 and Study 5 trials, baseline SHBG was induced by ~150-700% after 28 days of Compound IV therapy (FIG. 27A). SHBG induction was strongly correlated with reductions in % FreeT [Free T (pg/mL)/Total T (pg/mL)*100]. The regression of the relationship shows that a ~400% induction in SHBG was associated with ~75% reductions in % FreeT. A large number of treatment naive patients clustered in this range across all doses of Compound IV. Importantly this strong relationship was maintained in CRPC patients on concurrent ADT from Study 3 (FIG. 27B) even when looking at only 15 days of Compound IV therapy. Open symbols represent baseline (BL) and closed symbols are treated with Compound IV as described above.

The Effect of Compound IV on Free Testosterone Percentage (% FreeT) and the Relationship Between PSA Levels and Free Testosterone Percentage (% FreeT)

Like treatment naïve patients, the CRPC patients on Compound IV showed a rapid, greater than 50% reduction in % FreeT (Day 15) (FIG. 30). This corresponded with a greater than 50% reduction in PSA in 3 of 7 patients (closed data points) after only two weeks of Compound IV therapy, and 2 of 3 patients after 30 days (open data points). 85.7% (6 of 7), 66.7% (2 of 3), and 100% (1 of 1) of men reached the free T concentration cutoff of below 0.5 pg/mL on days 15, 30, and 60, respectively.

Subject Stopping Rules: When the serum PSA in a subject increases at least 2 ng/mL and 25% from the nadir after initiation of treatment with Compound IV, the subject remains on study. A follow up serum PSA is taken 30 days later. If the follow up assessment does NOT confirm the serum PSA progression, the subject remains on the study and continues dosing with Compound IV. If the follow up serum PSA progression confirms the serum PSA progression, the subject is discontinued from the study and the End of Study visit and Follow up visits is conducted.

Serum PSA Progression:

Serum PSA progression will be defined by the PCWG2 criteria. The PCWG2 criteria require a confirmation of suspected PSA progression in an evaluation 3-4 weeks following the PSA level that indicated possible progression. Time to PSA progression for confirmed instances will be time from initiation of study drug to the date of the first PSA level that indicated possible progression. Patients who die on the trial will be considered failures for PSA progression free survival. The time for patients who never progress (censored patients) will be the time from initiation of study drug until their last follow up date. The Kaplan-Meier method will be used to estimate PSA progression free survival and associated 95% confidence intervals at various time points. The median estimate of PSA progression free survival will be estimated if the median is realized.

Serum PSA progression (PCWG2 defined): If initial decline of serum PSA from baseline, then use as the date of progression occurred when the serum PSA has a 25% or greater increase and an absolute increase of 2 ng/ml or more from the nadir, but should be confirmed by a second serum PSA value obtained 3 or more weeks later. If no decline of serum PSA from baseline, then use as the date of progression occurred when the serum PSA has a 25% or greater increase and an absolute increase of 2 ng/ml or more after 12 weeks, but should be confirmed by a second serum PSA value obtained 3 or more weeks later.

Additional Serum PSA Analyses

1. Percentage change from baseline to every measured time point
2. Maximum decline at anytime on study (Percent change from baseline to nadir)
3. Duration of response (measured in days with at least a 50% reduction from baseline)

Free Testosterone:

The change from baseline to Day 15, Day 30, Day 90, and End of Study in free testosterone levels is assessed.

Total Testosterone:

The change from baseline to Day 15, Day 30, Day 90, and End of Study in total testosterone levels is assessed.

SHBG:

The change from baseline to Day 15, Day 30, Day 90, and End of Study in SHBG levels is assessed.

Example 27

Compound IV as a Secondary Hormone Therapy for Metastatic Castration Resistant Prostate Cancer (mCRPC): Study 6 Protocol Compound IV, is studied (Study 6) for the proposed indication secondary hormone therapy for metastatic castration resistant prostate cancer (mCRPC), for high risk non-metastatic castration resistant prostate cancer (nmCRPC) or advanced prostate cancer at high risk of progressing to CRPC, or any combination thereof.

Compound IV has been shown to increase serum SHBG and reduce serum free testosterone to levels below what has been observed with LHRH agonists or antagonists or surgical castration. Compared to leuprolide acetate treated group, the Compound IV group has been shown to have decreased bone turnover markers from baseline and to have a lower incidence of adverse events of hot flashes in men with advanced prostate cancer.

The effect of Compound IV as secondary hormonal therapy that reduces serum PSA and serum free testosterone levels in men with metastatic castration resistant prostate cancer maintained on androgen deprivation therapy is studied. The study assesses the effects of Compound IV on serum PSA response and serum PSA progression in men with mCRPC on ADT with LHRH agonists, LHRH antagonists, or orchidectomy. This study also assesses the VTE risk of lower doses of Compound IV. Secondary endpoints include serum free testosterone levels, adrenal gland androgen precursor production (DHEA and DHEAS levels), progression free survival, and skeletal related events (SRE).

Summary of study details is presented in FIG. 26.

Study objectives: (1) To assess the effect of Compound IV on serum PSA levels in men with metastatic castration resistant prostate cancer (mCRPC) maintained on androgen deprivation therapy (serum PSA response and serum PSA progression); (2) To assess the effect of Compound IV on serum free testosterone levels; (3) To assess the effect of Compound IV on serum SHBG; (4) To assess the effect of Compound IV on serum total testosterone; (5) To assess the effect of Compound IV on adrenal gland androgen precursor hormones (DHEA and DHEAS); (6) To assess the effect of Compound IV on the development of new bone metastases; (7) To assess the effect of Compound IV on soft tissue metastases (visceral and lymph nodes); (8) To assess the effects of Compound IV on skeletal related events; (9) To assess the effect of Compound IV on bone turnover markers; (10) To assess the incidence and frequency of hot flashes in men on Compound IV; (11) To assess the safety and tolerability Compound IV in men with prostate cancer on androgen deprivation therapy who have failed ADT.

75 subjects with castration resistant prostate cancer patients with radiographic evidence of metastatic disease (T any-N any-M1) are enrolled in the study. These subjects have a median life expectancy of less than 20 months, i.e. more serious disease than the other subjects with advanced prostate cancer enrolled in the previous studies. All subjects have been previously treated with androgen deprivation therapy (ADT), have responded to the ADT and currently have a serum PSA >2 ng/mL or >2 ng/mL and representing a 25% increase above the nadir achieved on the ADT. Subjects are maintained on ADT throughout the study.

Each subject receives daily doses of 125 mg Compound IV, 250 mg Compound IV, or 500 mg Compound IV administered orally, until their serum PSA increases at least 25% and 2 ng/mL from the nadir at two successive serum PSA assessments after initiation of treatment with Compound IV.

Compound IV 125 mg and 500 mg tablets are formulated with micronized Compound IV drug substance and 1% sodium dodecyl sulfate (SDS), and supplied in a 50-count high-density polyethylene (HDPE) bottle.

Enrollment into this study is staggered by 1 cycle (30 days) such that the first 25 subjects are enrolled into the 125 mg Compound IV dose arm. These subjects are evaluated for incidence of venous thromboembolic events (VTE). When the last subject in the 125 mg Compound IV dose arm has completed 1 cycle of therapy (30 days) in this dose arm and there is an acceptable incidence rate of VTE in this dose arm at that time (less than 3), enrollment is commenced in the 250 mg Compound IV dose arm. These subjects are evaluated for the incidence of VTE. When all 25 subjects in the 250 mg Compound IV dose arm have completed 1 cycle of therapy (30 days) in this dose arm and there is an acceptable incidence rate of VTE in this dose arm at that time (less than 3), enrollment into the 500 mg Compound IV dose arm (25 subjects) is commenced.

The 500 mg dose is expected to increase serum SHBG and result in a significant reduction in serum free testosterone. The lower doses, 125 mg and 250 mg, are expected to increase serum SHBG, but to a lesser extent, and are added to the protocol to determine the minimum effective dose of Compound IV to produce a serum PSA response. These doses may also have direct effects in reducing adrenal gland production of androgen precursors like DHEAS and DHEA which can be utilized by prostate cancer cells to produce testosterone or dihydrotestosterone (DHT).

125 mg Compound IV, 250 mg Compound IV, or 500 mg Compound IV will be administered daily to all subjects in the study until they have developed serum PSA progression (serum PSA has increased at least 25% and 2 ng/mL above the nadir at two successive sample times after initiation of treatment with Compound IV). At Day 90 if the subject does not have at least a 50% reduction in serum PSA from baseline and this confirmed on a second assessment, the subject will be discontinued from the study. The total duration of dosing may be greater than 360 days in subjects that do not show a serum PSA progression on study.

Subjects that show a serum PSA progression on two successive assessments after the initiation of treatment with Compound IV are discontinued from this study. At Day 90, any subject that does not show >50% reduction in serum PSA from baseline on two successive samples are discontinued from the study.

After the subject has shown a serum PSA progression, the subject remains on drug for 30 days and have a follow up serum PSA assessment. If the serum PSA progression is NOT confirmed at this visit, the subject remains in the study and continue dosing with Compound IV. If the serum PSA progression is confirmed at this visit, the subject is discontinued from the study and End of Study visit assessments is conducted.

Assessments of serum total testosterone, serum free testosterone, serum SHGB and serum PSA concentrations are made on Days 15, 30, and every 30 days until their serum PSA has increased at least 25% and 2 ng/mL from the nadir at two successive sample times after initiation of treatment with Compound IV. Bone turnover markers are assessed at baseline (Day 1), Day 90, and End of Study.

The incidence and frequency of hot flashes is assessed at baseline (Day 1), Day 30, Day 60, Day 90 and End of Study.

CT scan of abdomen/pelvis is conducted on Day 0, and every 90 days until End of Study to assess tumor progression and soft tissue or visceral metastases.

Bone scan is conducted on Day 0, and every 90 days until End of Study, to assess the development of new bone metastases.

Primary Endpoint:

The proportion of subjects with a 50% decline from baseline in serum PSA (confirmed by a second serum PSA assessment 30 days later) by Day 90 (with follow up confirmation by Day 120)

Secondary Endpoints:

(1) Time to serum PSA progression; (2) The proportion of subjects with a ≥90% decline from baseline in serum PSA; (3) The proportion of subjects with a ≥30% decline from baseline in serum PSA; (4) Change in serum free testosterone levels; (5) Change in serum SHBG levels; (6) Change in serum total testosterone levels; (7) Change in DHEA and DHEAS levels; (8) Time to progression (TTP) assessed by RECIST 1.1 (soft tissue) or by PCWG2 (bone metastases); (9) Progression free Survival (PFS) assessed by RECIST 1.1 (soft tissue) or by PCWG2 (bone metastases); (10) Change in bone turnover marker levels; (11) Change in incidence and frequency of hot flashes from baseline; (12) Time to new or worsening SREs; (13) Assess the safety and tolerability Compound IV in men with prostate cancer who have failed ADT.

To minimize the risk of VTEs in this study: (1) Subjects with a personal or family history of abnormal blood clotting or thrombotic disease (venous or arterial thrombotic events such as history of stroke, deep vein thrombosis (DVT), and/or pulmonary embolus (PE)) will be excluded from the study. (2) Any subjects with a modified activated protein C reaction ratio <2.5 and a Factor V Leiden mutation, an antithrombin level <80% of normal, a serum homocysteine level of >7 micromoles/liter, the presence of either antiphospholipid antibody, or a prothrombin gene mutation will be excluded from the study. (3) All subjects enrolled in this study, if not on aspirin or other anticoagulant therapy, will be required to take 81 mg of aspirin daily. Although reports on the effectiveness of aspirin to prevent VTEs have been conflicting, the recent literature supports the hypothesis that low dose aspirin is as effective as low molecular weight heparin for VTE prophylaxis. (4) All subjects enrolled in the study will have their VTE risk assessed using the Caprivi Venous Thromboembolism Risk Assessment Tool. The subject's VTE risk will be assessed at each visit and, should a change in risk be identified during the study, appropriate prevention will be instituted. More specifically, subjects that experience an event that makes them a high risk for a VTE, such as need for immobilization, long bone fracture, acute trauma, hospitalization, surgery, radiation, etc., will be closely monitored and instructed about the proper preventative measures to minimize their risks for VTE and, when indicated, subjects will be treated with prophylactic anticoagulation therapy. (5) All thromboembolic events or cardiovascular SAEs will be considered at least possibly related to Compound IV therapy and will be included in the trial stopping rules regardless of investigator attribution.

Subjects accepted for this study must:

Have castration resistant prostate cancer patients with radiographic evidence of metastatic disease (T any-N any-M1)

Have been treated with ADT (chemical or surgical) for at least 6 months

Have a castrate level of serum total testosterone (<50 ng/dL)

Have a history of serum PSA response on ADT. A serum PSA response is at least a 90% reduction in serum PSA from the serum PSA value prior to the initiation of treatment to <10 ng/mL OR undetectable level of serum PSA (<0.2 ng/mL).

Have a rising serum PSA on two successive assessments at least 2 weeks apart and serum PSA levels >2 ng/mL or >2 ng/mL and a 25% increase above the nadir from the ADT. If a subject has been treated with an antiandrogen and has shown a serum PSA progression, the subject will be required to stop the antiandrogen. Once the antiandrogen has been stopped (antiandrogen withdrawal), the subject should have at least two rising serum PSA levels at least 2 weeks apart.

Be continued on ADT throughout this study

Subjects must agree, if not already on anticoagulation therapy or aspirin, to take 81 mg aspirin daily throughout the duration of their participation in this study and for 30 days after completion of dosing with Compound IV. Clinic Visits: Potential study participants will visit the clinical research facility as needed for screening evaluations. Subjects will have study related visits at Enrollment (Day 1) and on Days 15 and 30. Subjects will return to the clinic every 30 days from Day 30 to Day 90. Those subjects who have at least a 50% reduction in serum PSA from baseline will remain on study and will return to the clinic every 30 days from Day 90 to Day 360 and then every 90 days after Day 360 until their serum PSA has increased at least 25% and 2 ng/mL from the nadir after initiation of treatment with Compound IV, and this finding is confirmed with a second serum PSA assessment or their disease has progressed (CT or bone scan).

A follow-up visit will be conducted 30 days after last dose.

When the serum PSA in a subject has increased at least 2 ng/mL and 25% from the nadir after initiation of treatment with Compound IV the subject will have met the criteria for disease progression. However, the subject should remain on study until a confirmatory follow-up serum PSA is taken 30 days later. If the follow-up assessment does NOT confirm the serum PSA progression, the subject should remain on the study and continue dosing with Compound IV. If the follow-up serum PSA confirms the serum PSA progression, the subject should be discontinued from the study and the End of Study visit and Follow-up visits should be conducted.

At Day 90, any subject that does not show a serum PSA reduction >50% from baseline will have a confirmatory assessment of serum PSA 30 days after Day 90. The subject should remain on study drug after Day 90 and up until the confirmatory assessment. At the confirmatory assessment if the serum PSA is reduced >50% from baseline, the subject will remain on the study and continue dosing with Compound IV. If in the confirmatory assessment the serum PSA is not reduced >50% from baseline, the subject will be discontinued from the study due to lack of efficacy. The End of Study visit and Follow-up visit should be conducted.

Subjects displaying evidence of progression of disease, as documented by CT imaging (RECIST 1.1 criteria) or two new lesions observed on bone scan, must be discontinued from the study.

Efficacy Analyses, Serum PSA, and Serum PSA Response

Serum PSA response at Day 90 will be the primary outcome and will be assessed for all subjects. Serum PSA response will be defined as >50% decline from baseline confirmed by a second serum PSA value within 14 days. The primary objective is to assess the serum PSA response rate in men with mCRPC maintained on ADT who receive Compound IV.

The proportion of subjects with serum PSA response will be estimated and the exact 95% Blyth-Still-Casella confidence interval computed.

This estimation will be performed among:
(1) subjects in the intent-to-treat (ITT) population with subjects who drop out prior to the Day 90 assessment considered non-responders, and
(2) subjects in the efficacy evaluable (EE) population.

Graphical depiction of percentage change in serum PSA from baseline to each PSA assessment (with emphasis on the Day 90 assessment) will be via waterfall plots as described below:

The percentage change in serum PSA from baseline to each assessment will be computed and the y axis will represent percentage change, the x axis will have a bar for each individual subject and the order of these bars will be from smallest percentage decrease in serum PSA (this could potentially be an increase for some subject(s)) to greatest percentage drop.

Serum PSA Progression

Serum PSA progression will be defined by the PCWG2 criteria, show below. The PCWG2 criteria require a confirmation of suspected serum PSA progression in an evaluation 3-4 weeks following the serum PSA level that indicated possible progression.

PSA progression free survival will be estimated by the method of Kaplan-Meier and associated 95% confidence intervals will be constructed. A subject's progression free survival will be the time from first dose of study the first date associated with a confirmed progression or death. Subjects who drop out or are lost to follow-up will be censored at their date of last contact. The median estimate of PSA progression free survival will be estimated if the median is realized.

Time to PSA progression will be estimated by the method of Kaplan-Meier and associated 95% confidence intervals will be constructed. A subject's time to progression will be the time from first dose of study medication until the first date associated with a confirmed progression. Subjects who die prior to progression will be censored on the date of death. Subjects who drop out or are lost to follow-up will be censored at their date of last contact. The median estimate of time to progression will be estimated if the median is realized.

The median estimate of serum PSA progression free survival will be estimated if the median is realized.

Serum PSA progression (PCWG2 defined):
If initial decline of serum PSA from baseline, then use as the date of progression occurred when the serum PSA has a 25% or greater increase and an absolute increase of
  2 ng/ml or more from the nadir, but should be confirmed by a second serum PSA value obtained 3 or more weeks later.
If no decline of serum PSA from baseline, then use as the date of progression occurred when the serum PSA has a 25% or greater increase and an absolute increase of 2 ng/ml or more after 12 weeks, but should be confirmed by a second serum PSA value obtained
  3 or more weeks later.

Serum Free Testosterone

The change in serum free testosterone levels from baseline to each scheduled assessment will be assessed. The change and percentage change from baseline to each scheduled assessment will be tested using a paired t-test if data are determined to be normally distributed; otherwise, an exact Wilcoxon signed-rank test will be used to compare change and percentage change from baseline to each scheduled assessment. This will be done until the number of subjects decreases below 5. Mixed model repeated measures models may be used to explore the change over time within each arm. Subject will be considered a random effect.

Serum SHBG

The change from baseline to each scheduled assessment in serum SHBG levels will be assessed. The change and percentage change from baseline to each scheduled assessment will be tested using a paired t-test if data are determined to be normally distributed; otherwise, an exact Wilcoxon signed-rank test will be used to compare change and percentage change from baseline to each scheduled assessment. This will be done until the number of subjects decreases below 5. Mixed model repeated measures models may be used to explore the change over time within each arm. Subject will be considered a random effect.

Serum Total Testosterone

The change from baseline to each scheduled assessment in serum testosterone levels will be assessed. The change and percentage change from baseline to each scheduled assessment will be tested using a paired t-test if data are determined to be normally distributed; otherwise, an exact Wilcoxon signed-rank test will be used to compare change and percentage change from baseline to each scheduled assessment. This will be done until the number of subjects decreases below 5. Mixed model repeated measures models may be used to explore the change over time within each arm. Subject will be considered a random effect.

DHEA and DHEAS

The change from baseline to each scheduled assessment in both DHEA and DHEAS levels will be assessed. The change and percentage change from baseline to each scheduled assessment will be tested using a paired t-test if data are determined to be normally distributed; otherwise, an exact Wilcoxon signed-rank test will be used to compare change and percentage change from baseline to each scheduled assessment. This will be done until the number of subjects decreases below 5. Mixed model repeated measures models may be used to explore the change over time within each arm. Subject will be considered a random effect.

Soft Tissue Progression (RECIST 1.1)

RECIST 1.1 criteria will be used to assess progression and response. Both TTP and PFS, as defined below, will be estimated among subjects.

Progression free survival (PFS) will be estimated by the method of Kaplan-Meier and associated 95% confidence intervals will be constructed. A subject's progression free survival will be the time from first dose of study medication until documented evidence of progression or death. Subjects who drop out or are lost to follow-up will be censored at their date of last contact.

The median estimate of PFS will be estimated if the median is realized.

Time to progression (TTP) will be estimated by the method of Kaplan-Meier and associated 95% confidence intervals will be constructed. A subject's time to progression will be the time from first dose of study medication until documented evidence of progression. Subjects who die prior to progression will be censored on the date of death. Subjects who drop out or are lost to follow-up will be censored at their date of last contact.

The median estimate of time to progression will be estimated if the median is realized.

Subjects' best responses will be determined and the proportion in CR, PR(PR+CR), SD, and PD will be estimated and the exact 95% Blyth-Still-Casella confidence interval computed.

Bone Progression

Both TTP and PFS, as defined below, will be estimated among subjects who present with measurable bone scan metastases.

Progression free survival (PFS) will be estimated by the method of Kaplan-Meier and associated 95% confidence intervals will be constructed. A subject's progression free survival will be the time from first dose of study medication until documented evidence of progression or death. Subjects who drop out or are lost to follow-up will be censored at their date of last contact.

The median estimate of PFS will be estimated if the median is realized.

Time to progression (TTP) will be estimated by the method of Kaplan-Meier and associated 95% confidence intervals will be constructed. A subject's time to progression will be the time from first dose of study medication until documented evidence of progression. Subjects who die prior to progression will be censored on the date of death. Subjects who drop out or are lost to follow-up will be censored at their date of last contact.

The median estimate of time to progression will be estimated if the median is realized.

Subjects' best responses will be determined and the proportion in CR, PR(PR+CR), SD, and PD will be estimated and the exact 95% Blyth-Still-Casella confidence interval computed.

Bone Turnover Markers

The change from baseline to each scheduled assessment for each bone turnover marker in each treatment group will be assessed. The mean, standard deviation, median, minimum, and maximum bone turnover marker levels will be summarized at each of these time points. The change from baseline to each time point will be summarized as well. A paired t-test will test within an arm as to whether the change from baseline to each time point is significantly different from zero. This will be done for ITT population. This will be done for observed cases and an LOCF analysis will be performed as well. Mixed model repeated measures models may be used to explore the change over time within each arm. Subject will be considered a random effect.

Hot Flashes

Subjects will be questioned regarding events of hot flashes (incidence and frequency).

The proportion of subjects experiencing any hot flashes will be tabulated by treatment group. The proportion of subjects experiencing hot flashes weekly or more often will be tabulated by treatment group. The proportion of subjects experiencing hot flashes daily or more often will be tabulated by treatment group. The proportion of subjects experiencing multiple hot flashes per day will be tabulated by treatment group.

The proportion of subjects experiencing moderate to very severe hot flashes will be tabulated by treatment group. The proportion of subjects experiencing severe to very severe hot flashes will be tabulated by treatment group.

Shift tables will express the change in severity from baseline to each assessment.

Skeletal Related Events (SREs)

SREs are a composite endpoint which includes pathologic fracture, spinal cord compression, and radiation or surgery to bone.

Skeletal related event free time will be estimated by the method of Kaplan-Meier and associated 95% confidence intervals will be constructed. A subject's skeletal related event free time will be the time from first dose of study medication until documented evidence of a new SRE or death. Subjects who drop out or are lost to follow-up will be censored at their date of last contact. This analysis will be repeated under the definition of an event as any of a new or worsening SRE or death.

The median estimate of Skeletal related event free time (new or worsening SRE) will be estimated if the median is realized.

Time to new skeletal related event will be estimated by the method of Kaplan-Meier and associated 95% confidence intervals will be constructed. A subject's time to new skeletal related event will be the time from first dose of study medication until documented evidence of a new skeletal related event. Subjects who die prior to a new skeletal related event will be censored on the date of death. Subjects who drop out or are lost to follow-up will be censored at their date of last contact. This analysis will be repeated under the definition of an event as either a new or worsening SRE.

The median estimate of time to new SRE (new or worsening SRE) will be estimated if the median is realized.

Example 28

Secondary Hormone Therapy for Metastatic Castration Resistant Prostate Cancer (mCRPC) (Based on Study 6 Protocol)

Estradiol, ethynyl estradiol, steroidal estrogen agonists and nonsteroidal estrogen agonists, is studied (Study 6) for the proposed indication secondary hormone therapy for metastatic castration resistant prostate cancer (mCRPC), non-metastatic castration resistant prostate cancer or maintenance of ADT therapy, or any combination thereof.

Estradiol, ethynyl estradiol, steroidal estrogen agonists and nonsteroidal estrogen agonists show an increase in serum SHBG and reduce serum free testosterone to levels below what has been observed with LHRH agonists or antagonists or surgical castration. Compared to leuprolide acetate treated group, estradiol, ethynyl estradiol, steroidal estrogen agonists and nonsteroidal estrogen agonist show decrease in bone turnover markers from baseline and have a lower incidence of adverse events of hot flashes in men with advanced prostate cancer.

The effect of estradiol, ethynyl estradiol, steroidal estrogen agonists and nonsteroidal estrogen agonists as secondary hormonal therapy that reduces serum PSA and serum free testosterone levels in men with metastatic castration resistant prostate cancer maintained on androgen deprivation therapy is studied. The study assesses the effects of estradiol, ethynyl estradiol, steroidal estrogen agonists and nonsteroidal estrogen agonist on serum PSA response and serum PSA progression in men with mCRPC on ADT with LHRH agonists, LHRH antagonists, or orchidectomy. This study also assesses the VTE risk of lower doses of estradiol, ethynyl estradiol, steroidal estrogen agonists and nonsteroidal estrogen agonist. Secondary endpoints include serum free testosterone levels, adrenal gland androgen precursor production (DHEA and DHEAS levels), progression free survival, and skeletal related events (SRE).

Study objectives: (1) To assess the effect of estradiol, ethynyl estradiol, steroidal estrogen agonists and nonsteroidal estrogen agonists on serum PSA levels in men with metastatic castration resistant prostate cancer (mCRPC) maintained on androgen deprivation therapy (serum PSA response and serum PSA progression); (2) To assess the effect of estradiol, ethynyl estradiol, steroidal estrogen agonists and nonsteroidal estrogen agonists on serum free testosterone levels; (3) To assess the effect of estradiol, ethynyl estradiol, steroidal estrogen agonists and nonsteroidal estrogen agonist on serum SHBG; (4) To assess the effect of estradiol, ethynyl estradiol, steroidal estrogen agonists and nonsteroidal estrogen agonists on serum total testosterone; (5) To assess the effect of estradiol, ethynyl estradiol, steroidal estrogen agonists and nonsteroidal estrogen agonists on adrenal gland androgen precursor hormones (DHEA and DHEAS); (6) To assess the effect of estradiol, ethynyl estradiol, steroidal estrogen agonists and nonsteroidal estrogen agonists on the development of new bone metastases; (7) To assess the effect of estradiol, ethynyl estradiol, steroidal estrogen agonists and nonsteroidal estrogen agonists on soft tissue metastases (visceral and lymph nodes); (8) To assess the effects of estradiol, ethynyl estradiol, steroidal estrogen agonists and nonsteroidal estrogen agonists on skeletal related events; (9) To assess the effect of estradiol, ethynyl estradiol, steroidal estrogen agonists and nonsteroidal estrogen agonists on bone turnover markers; (10) To assess the incidence and frequency of hot flashes in men on estradiol, ethynyl estradiol, steroidal estrogen agonists and nonsteroidal estrogen agonists; (11) To assess the safety and tolerability estradiol, ethynyl estradiol, steroidal estrogen agonists and nonsteroidal estrogen agonists in men with prostate cancer on androgen deprivation therapy who have failed ADT.

75 subjects with castration resistant prostate cancer patients with radiographic evidence of metastatic disease (T any-N any-M1) are enrolled in the study. These subjects have a median life expectancy of less than 20 months, i.e. more serious disease than the other subjects with advanced prostate cancer enrolled in the previous studies. All subjects have been previously treated with androgen deprivation therapy (ADT), have responded to the ADT and currently have a serum PSA >2 ng/mL or >2 ng/mL and representing a 25% increase above the nadir achieved on the ADT. Subjects are maintained on ADT throughout the study.

Each subject receives daily doses of 125 mg, 250 mg or 500 mg estradiol, ethynyl estradiol, steroidal estrogen agonists or nonsteroidal estrogen agonists, administered orally, until their serum PSA increases at least 25% and 2 ng/mL from the nadir at two successive serum PSA assessments after initiation of treatment with estradiol, ethynyl estradiol, steroidal estrogen agonists or nonsteroidal estrogen agonists.

The 500 mg dose is expected to increase serum SHBG and result in a significant reduction in serum free testosterone. The lower doses, 125 mg and 250 mg, are expected to increase serum SHBG, but to a lesser extent, and are added to the protocol to determine the minimum effective dose of estradiol, ethynyl estradiol, steroidal estrogen agonists or nonsteroidal estrogen agonists to produce a serum PSA response. These doses may also have direct effects in reducing adrenal gland production of androgen precursors like DHEAS and DHEA which can be utilized by prostate cancer cells to produce testosterone or dihydrotestosterone (DHT).

125 mg, 250 mg, or 500 mg estradiol, ethynyl estradiol, steroidal estrogen agonists or nonsteroidal estrogen agonists will be administered daily to all subjects in the study until they have developed serum PSA progression (serum PSA has increased at least 25% and 2 ng/mL above the nadir at two successive sample times after initiation of treatment with estradiol, ethynyl estradiol, steroidal estrogen agonists or nonsteroidal estrogen agonists). At Day 90 if the subject does not have at least a 50% reduction in serum PSA from baseline and this confirmed on a second assessment, the subject will be discontinued from the study. The total duration of dosing may be greater than 360 days in subjects that do not show a serum PSA progression on study.

Assessments of serum total testosterone, serum free testosterone, serum SHGB and serum PSA concentrations are made on Days 15, 30, and every 30 days until their serum PSA has increased at least 25% and 2 ng/mL from the nadir at two successive sample times after initiation of treatment with Compound IV. Bone turnover markers are assessed at baseline (Day 1), Day 90, and End of Study.

The incidence and frequency of hot flashes is assessed at baseline (Day 1), Day 30, Day 60, Day 90 and End of Study.

CT scan of abdomen/pelvis is conducted on Day 0, and every 90 days until End of Study to assess tumor progression and soft tissue or visceral metastases.

Bone scan is conducted on Day 0, and every 90 days until End of Study, to assess the development of new bone metastases.

Primary Endpoint:

The proportion of subjects with a 50% decline from baseline in serum PSA (confirmed by a second serum PSA assessment 30 days later) by Day 90 (with follow up confirmation by Day 120)

Secondary Endpoints:

(1) Time to serum PSA progression; (2) The proportion of subjects with a ≥90% decline from baseline in serum PSA; (3) The proportion of subjects with a ≥30% decline from baseline in serum PSA; (4) Change in serum free testosterone levels; (5) Change in serum SHBG levels; (6) Change in serum total testosterone levels; (7) Change in DHEA and DHEAS levels; (8) Time to progression (TTP) assessed by RECIST 1.1 (soft tissue) or by PCWG2 (bone metastases); (9) Progression free Survival (PFS) assessed by RECIST 1.1 (soft tissue) or by PCWG2 (bone metastases); (10) Change in bone turnover marker levels; (11) Change in incidence and frequency of hot flashes from baseline; (12) Time to new or worsening SREs; (13) Assess the safety and tolerability Compound IV in men with prostate cancer who have failed ADT.

Serum Free Testosterone

The change in serum free testosterone levels from baseline to each scheduled assessment will be assessed. The change and percentage change from baseline to each scheduled assessment will be tested using a paired t-test if data are determined to be normally distributed; otherwise, an exact Wilcoxon signed-rank test will be used to compare change and percentage change from baseline to each scheduled assessment. This will be done until the number of subjects decreases below 5. Mixed model repeated measures models may be used to explore the change over time within each arm. Subject will be considered a random effect.

Serum SHBG

The change from baseline to each scheduled assessment in serum SHBG levels will be assessed. The change and percentage change from baseline to each scheduled assessment will be tested using a paired t-test if data are determined to be normally distributed; otherwise, an exact Wilcoxon signed-rank test will be used to compare change and percentage change from baseline to each scheduled assessment. This will be done until the number of subjects decreases below 5. Mixed model repeated measures models may be used to explore the change over time within each arm. Subject will be considered a random effect.

Serum Total Testosterone

The change from baseline to each scheduled assessment in serum testosterone levels will be assessed. The change and percentage change from baseline to each scheduled assessment will be tested using a paired t-test if data are determined to be normally distributed; otherwise, an exact Wilcoxon signed-rank test will be used to compare change and percentage change from baseline to each scheduled assessment. This will be done until the number of subjects decreases below 5. Mixed model repeated measures models may be used to explore the change over time within each arm. Subject will be considered a random effect.

DHEA and DHEAS

The change from baseline to each scheduled assessment in both DHEA and DHEAS levels will be assessed. The change and percentage change from baseline to each scheduled assessment will be tested using a paired t-test if data are determined to be normally distributed; otherwise, an exact Wilcoxon signed-rank test will be used to compare change and percentage change from baseline to each scheduled assessment. This will be done until the number of subjects decreases below 5. Mixed model repeated measures models may be used to explore the change over time within each arm. Subject will be considered a random effect.

Soft Tissue Progression (RECIST 1.1)

RECIST 1.1 criteria will be used to assess progression and response. Both TTP and PFS, as defined below, will be estimated among subjects.

Progression free survival (PFS) will be estimated by the method of Kaplan-Meier and associated 95% confidence intervals will be constructed. A subject's progression free survival will be the time from first dose of study medication until documented evidence of progression or death. Subjects who drop out or are lost to follow-up will be censored at their date of last contact. The median estimate of PFS will be estimated if the median is realized.

Time to progression (TTP) will be estimated by the method of Kaplan-Meier and associated 95% confidence intervals will be constructed. A subject's time to progression will be the time from first dose of study medication until documented evidence of progression. Subjects who die prior to progression will be censored on the date of death. Subjects who drop out or are lost to follow-up will be censored at their date of last contact.

The median estimate of time to progression will be estimated if the median is realized.

Subjects' best responses will be determined and the proportion in CR, PR(PR+CR), SD, and PD will be estimated and the exact 95% Blyth-Still-Casella confidence interval computed.

Bone Progression

Both TTP and PFS, as defined below, will be estimated among subjects who present with measurable bone scan metastases.

Progression free survival (PFS) will be estimated by the method of Kaplan-Meier and associated 95% confidence intervals will be constructed. A subject's progression free survival will be the time from first dose of study medication until documented evidence of progression or death. Subjects who drop out or are lost to follow-up will be censored at their date of last contact.

The median estimate of PFS will be estimated if the median is realized.

Time to progression (TTP) will be estimated by the method of Kaplan-Meier and associated 95% confidence intervals will be constructed. A subject's time to progression will be the time from first dose of study medication until documented evidence of progression. Subjects who die prior to progression will be censored on the date of death. Subjects who drop out or are lost to follow-up will be censored at their date of last contact.

The median estimate of time to progression will be estimated if the median is realized.

Subjects' best responses will be determined and the proportion in CR, PR(PR+CR), SD, and PD will be estimated and the exact 95% Blyth-Still-Casella confidence interval computed.

Bone Turnover Markers

The change from baseline to each scheduled assessment for each bone turnover marker in each treatment group will be assessed. The mean, standard deviation, median, minimum, and maximum bone turnover marker levels will be summarized at each of these time points. The change from baseline to each time point will be summarized as well. A paired t-test will test within an arm as to whether the change from baseline to each time point is significantly different from zero. This will be done for ITT population. This will be done for observed cases and an LOCF analysis will be performed as well. Mixed model repeated measures models may be used to explore the change over time within each arm. Subject will be considered a random effect.

Hot Flashes

Subjects will be questioned regarding events of hot flashes (incidence and frequency). The proportion of subjects experiencing any hot flashes will be tabulated by treatment group. The proportion of subjects experiencing hot flashes weekly or more often will be tabulated by treatment group. The proportion of subjects experiencing hot flashes daily or more often will be tabulated by treatment group. The proportion of subjects experiencing multiple hot flashes per day will be tabulated by treatment group.

The proportion of subjects experiencing moderate to very severe hot flashes will be tabulated by treatment group. The proportion of subjects experiencing severe to very severe hot flashes will be tabulated by treatment group.

Shift tables will express the change in severity from baseline to each assessment.

Skeletal Related Events (SREs)

SREs are a composite endpoint which includes pathologic fracture, spinal cord compression, and radiation or surgery to bone.

Skeletal related event free time will be estimated by the method of Kaplan-Meier and associated 95% confidence intervals will be constructed. A subject's skeletal related event free time will be the time from first dose of study medication until documented evidence of a new SRE or death. Subjects who drop out or are lost to follow-up will be censored at their date of last contact. This analysis will be repeated under the definition of an event as any of a new or worsening SRE or death. The median estimate of Skeletal related event free time (new or worsening SRE) will be estimated if the median is realized.

Time to new skeletal related event will be estimated by the method of Kaplan-Meier and associated 95% confidence intervals will be constructed. A subject's time to new skeletal related event will be the time from first dose of study medication until documented evidence of a new skeletal related event. Subjects who die prior to a new skeletal related event will be censored on the date of death. Subjects who drop out or are lost to follow-up will be censored at their date of last contact. This analysis will be repeated under the definition of an event as either a new or worsening SRE.

The median estimate of time to new SRE (new or worsening SRE) will be estimated if the median is realized.

Example 29

Compound IV Decreases Serum IGF-1 Levels
(Study 2)

Serum IGF-1 Levels are Decreased in Men with Advanced Prostate Cancer Treated with the ERα Agonist, Compound IV The insulin pathway and, in particular, insulin-like growth factor-1 (IGF-1), has been implicated in the development of prostate cancer, and serum IGF-1 levels have been associated with advanced disease. Compound IV, an ERα agonist that is being evaluated for the treatment of advanced prostate cancer, reduces serum total testosterone (T) and free T and increases SHBG. Study 2 compared the effects of Compound IV and leuprolide on serum IGF-1 levels in men with advanced prostate cancer treated with ADT.

Methods

In the study, men with advanced prostate cancer (n=159) received 1000 mg or 2000 mg of Compound IV daily or leuprolide. Serum samples were collected from all of the men in the study and serum IGF-1 levels (ng/ml) were analyzed by a reference laboratory. All p values describe the comparison of Compound IV treatment groups to the leuprolide treated men.

Results

Through day 90, in men receiving the 1000 mg and 2000 mg doses of Compound IV, serum IGF-1 levels were decreased by more than 70 ng/ml (greater than 50%), while levels stayed constant or increased slightly in men on leuprolide (p<0.001). As a result of an increased risk of venous thromboembolic events (VTEs) at these higher doses of Compound IV, the trial was stopped prior to its completion, and not all of the men in the study reached the 90 day treatment date (92 men reached that date). The study results are presented in Table 34, and FIGS. 41-43 for IGF-1 levels at days 60, 90, and 180, respectively.

TABLE 34

Changes in IGF-1 Levels

| | 1000 mg Compound IV (n = 53) | 2000 mg Compound IV (n = 55) | Lupron Depot ® (n = 51) |
|---|---|---|---|
| Day 1 to Day 28 | −75.2 ± 25.6 | −78.6 ± 38.3 | 4.5 ± 39.8 |
| Day 1 to Day 60 | −73.7 ± 29.2 | −77.7 ± 39.9 | 0.3 ± 26.3 |
| Day 1 to Day 90 | −73.1 ± 25.1 | −72.7 ± 24.9 | −1.3 ± 30.2 |
| Day 1 to Day 360 | −35.2 ± 40.5 | −33.4 ± 45.2 | 6.1 ± 31.4 |

Conclusions

In men with advanced prostate cancer, the ERα agonist, Compound IV, can decrease the active form of testosterone, serum free T, to significantly lower levels than leuprolide. Patients receiving Compound IV experienced a significant decrease in serum IGF-1. Since changes in insulin metabolism are involved in regulating prostate cancer as well as bone and systemic metabolism, the observed decreases in IGF-1 could be significant.

Example 30

Secondary Hormone Therapy with 125 mg Compound IV Decreased Free Testosterone to Levels Similar to Orchiectomy in Men with Metastatic Castration Resistant Prostate Cancer (mCRPC) (Study 6 Results)

Methods:

In a Phase 2 open label study (Study 6 described in Examples 27 and 28), the initial 38 men with mCRPC were continued on their current form of ADT along with a low dose of compound of formula IV, 125 mg, for at least 90 days. Exclusion criteria included men at increased risk for venous thrombolic events (VTE).

Baseline subject parameters for men on the Study 6 were representative of men with metastatic, castrate resistant prostate cancer (mCRPC). Serum total testosterone levels reflected ongoing androgen deprivation therapy. All patients had levels below 50 ng/dL serum total testosterone (cut-off established in registration trials) with most (90%) having levels below 20 ng/dL, which is the serum value thought to more closely reflective of circulating testosterone following surgical orchiectomy. Mean baseline SHBG values were slightly elevated at 5.73 mg/dL compared to 4.58 mg/dL in Study 2 (See Example 25 above), also reflecting an androgen depleted hormonal milieu relative to ADT naive patients in Study 2.

Patient baseline characteristics for the initial 33 subjects are presented below in Tables 35-29.

TABLE 36

Patient Age

Age at Date of First Treatment

| N | Minimum | Median | Maximum | Mean | Std Dev |
|---|---|---|---|---|---|
| 31 | 52.00 | 71.00 | 88.00 | 70.32 | 9.05 |

TABLE 36-continued

Patient Age

Starting Parameters for PSA, SHBG and T

| PARAMETER | N Obs | N | Minimum | Median | Maximum | Mean | Std Dev |
|---|---|---|---|---|---|---|---|
| PROSTATE SPECIFIC ANTIGEN (ug/L) | 33 | 33 | 3.00 | 20.10 | 2542.70 | 233.52 | 566.69 |
| SEX HORMONE BINDING GLOBULIN (mg/L) | 33 | 33 | 2.28 | 4.94 | 17.01 | 5.73 | 3.17 |
| TESTOSTERONE, TOTAL (ng/dL) | 33 | 32 | 2.00 | 10.50 | 29.00 | 11.03 | 6.52 |
| TESTOSTERONE, FREE (pg/mL) | 33 | 32 | 0.20 | 0.90 | 4.60 | 1.19 | 0.91 |

TABLE 37

Total Serum Testosterone

| Total T | Frequency | Percent |
|---|---|---|
| 20 ng/dL or above | 3 | 9.09 |
| Below 20 ng/dL | 30 | 90.91 |

TABLE 38

Free Serum Testosterone

| Free T | Frequency | Percent |
|---|---|---|
| 0.9 pg/mL or above | 16 | 48.48 |
| Below 0.9 pg/mL | 17 | 51.52 |

TABLE 39

Patient Origin

| Country | Frequency | Percent |
|---|---|---|
| Hungary | 7 | 21.21 |
| USA | 26 | 78.79 |

Results:

The initial 15 patients in this trial reached 90 days on study and were evaluated for select trial endpoints. Additional patient data was evaluated for select trial endpoints at given time points and combined with that of the initial 15 patients.

Testosterone

Eleven of the 15 men began the study with suboptimal castration (free T>0.7 pg/ml) and 91% (10/11) of these men became optimally castrated by day 90 (FIG. 45). The expanded result database provided clear proof of concept in a metastatic CRPC population, wherein 27 of 30 patients showed reductions in free T despite being "castrate" under definitions established by contemporary ADT based upon serum total T. 24 of 30 patients receiving 125 mg Compound IV reported maximum free T reductions greater than 50% from baseline. (FIG. 51) These changes were significantly different from baseline (Table 40 below) following 90 days of therapy.

TABLE 40

Free testosterone levels at day 90 in current patients.

| DAY OF VISIT | N | RANGE | MEDIAN | MEAN | STANDARD DEVIATION | P-VALUE |
|---|---|---|---|---|---|---|
| DAY 1 (Baseline) | 33 | (0.20, 4.60) | 0.80 | 1.17 | 0.90 | — |
| DAY 90 | 20 | (0.30, 1.20) | 0.45 | 0.57 | 0.31 | — |
| CHANGE FROM BASELINE TO DAY 90 | 20 | (−3.90, 0.30) | −0.50 | −0.74 | 0.98 | 0.0002 |
| % CHANGE FROM BASELINE TO DAY 90 | 20 | (−84.80, 150.00) | −57.14 | −34.59 | 54.53 | 0.0035 |

Sex Hormone Binding Globulin (SHBG)

Of the initial 15 patients, all treated men had SHBG levels increased to ≥150% of Day 0 (FIG. 44). Consistent with the findings of previous trials performed in primarily hormone naïve patients, reductions in free T appear to be driven by treatment mediated elevations in SHBG. Almost all of the men receiving Compound IV had at least doublings of their SHBG levels. Only a single patient reported decreased serum SHBG levels following Compound IV therapy confirming the desired mode of drug action in a heavily treated metastatic CRPC population at the 125 mg dose level. (FIG. 52)

Changes in Prostate Specific Antigen (PSA) from Baseline

Of the initial 15 patients, 4/15 patients had >45% decrease in PSA (FIG. 36). Almost all men treated with 125 mg Compound IV, had decreases in their serum PSA levels. Since these men have aggressive, metastatic prostate cancer, there are some men (6) in this population that do not respond to Compound IV and have continually increasing PSA levels. All but one of these patients had rising PSA, despite marked Free T reductions, suggesting their disease was truly hormone refractory and unlikely to respond to further modulation of the AR-axis. 24 patients do report a PSA decrease in response to therapy with the largest percentage decreases occurring primarily after at least 1 month of treatment. (FIG. 53)

Hot Flashes

The addition of an estrogen to the hormonal milieu of a castrated male is expected to mitigate the hot flashes associated with estrogen deficiency resulting from castration. The data from 18 evaluable patients with hot flashes before starting the study is presented here. A measure of hot flashes included both frequency and severity. Improvement in both frequency and severity of hot flashes was observed in 22% of the patients (4/18). Improvement of frequency or severity and stability with respect to other measurements was observed in 11% of the patients (2/18). Stability in frequency and severity was observed in 50% of the patients (9/18). A worsening of either frequency or severity was observed in 17% of the patients (3/18). At this point, 33% percent of the evaluable patients in Study 6 reported improvements in hot flash frequency or severity on 125 mg Compound IV therapy and an additional 50% remained stable. Table 41 shows changes in hot flashes from base line.

TABLE 41

Change in Hot Flashes (Frequency, Severity)

| Hot flashes at Baseline | (Better, Better) | | (Better, Stable) | | (Better, Worse) | | (Stable, Stable) | | (Stable, Worse) | | (Worse, Worse) | |
|---|---|---|---|---|---|---|---|---|---|---|---|---|
| | n | % | n | % | n | % | n | % | n | % | n | % |
| No | 0 | | 0 | | 0 | | 7 | 77.78 | 0 | | 2 | 22.22 |
| Yes | 3 | 18.75 | 3 | 18.75 | 1 | 6.25 | 6 | 37.50 | 1 | 6.25 | 2 | 12.50 |

FIG. 54 provides a summary of these results.

Bone Turnover Markers

Improvement and stability of bone turnover markers were observed in at least 73% (8 of 11 evaluable subjects for bone turnover markers; data not shown) of treated men in the initial group. Reflecting the anti-resorptive capacity of an estrogen, 125 mg Compound IV therapy resulted in reduced bone turnover as measured by serum c-terminal telopeptide (CTx) and bone specific alkaline phosphatase. 60% and 52% of evaluable patients reported reductions in CTX and bone specific alkaline phosphatase, respectively, suggesting 125 mg Compound IV has bone sparing properties in a heavily treated CRPC population as seen in Tables 42 and 43 below and in FIGS. 55A and 55B. These properties have been demonstrated to result in a decreased fracture rate as well as risk of bone metastases.

TABLE 42

CTx

| | Increased | Decreased | Unchanged |
|---|---|---|---|
| # of patients (%) | 5/20 (25%) | 12/20 (60%) | 3/20 (15%) |

TABLE 43

BSAP

| | Increased | Decreased | Unchanged |
|---|---|---|---|
| # of patients (%) | 8/21 (38%) | 11/21 (52%) | 2/21 (10%) |

Adverse Effects (AE)

While some patients experienced AEs, none were vascular related and there were no SAEs or VTEs. Table 44 presents the most frequent adverse events observed in 34 subjects.

TABLE 44

| Adverse Event | Frequency (%) |
|---|---|
| Gynecomastia (grade 2) | 4 (12%) |
| Gynecomastia/breast tenderness (grade 1) | 4 (12%) |
| Loss of appetite | 3 (9%) |
| Bone pain | 3 (9%) |
| Nausea | 2 (6%) |
| VTE | 0 |

No deep vein thrombosis events (DVTs) have been reported on 125 mg Compound IV therapy.

Conclusions

The majority of patients enrolled in this Phase 2 study had suboptimal levels of free T while on an LHRH agonist that were further lowered by compound of formula IV administration. Compound of formula IV treatment resulted in stabilisation and/or improvement in reported hot flashes and bone turnover, two major side effects of ADT. These preliminary findings show that 125 mg of compound of formula IV was clinically effective and was well tolerated.

Example 31

Secondary Hormone Therapy with 250 mg Compound IV Decreased Free Testosterone to Levels Similar to Orchiectomy in Men with Metastatic Castration Resistant Prostate Cancer (mCRPC) (Study 6 Results)

Methods:

In a Phase 2 open label study (Study 6 described in Examples 27 and 28), 20 men with high risk (non-metastatic) nmCRPC and mCRPC were continued on their current form of ADT along with a 250 mg dose of Compound IV, for at least 90 days. Men at increased risk for venous thromboembolic events (VTE) were excluded. The primary endpoint of this trial was the proportion of men with a PSA decline of ≥50%, while secondary endpoints include serum total and free T, SHBG, bone turnover and hot flashes.

Results:

The initial 20 patients (1 nmCRPC and 19 mCRPC) of the cohort receiving daily 250 mg completed 90 days on study and were evaluable. The principal mechanism of drug action, induction of SHBG, was confirmed in these patients with median SHBG levels of 297% of baseline. This was increased compared to subjects treated with 125 mg of Compound IV in Study 6 (Table 45) suggesting SHBG levels are dose responsive.

TABLE 45

Clinical response rates in Study 6 using 125 mg and 250 mg of Compound IV.

| Values | 125 mg cohort | 250 mg cohort* |
|---|---|---|
| PSA response | 4/38 ≥ 50% (11%) | 6/20 ≥ 50% (30%) |
| SHBG | Mean -196%<br>Median - 158% | Mean - 294%<br>Median - 297% |
| Hot flashes in men experiencing them on Day 1 | 7/24 improved (29%)<br>12/24 stable (50%) | 4/11 improved (36%)<br>5/11 stable (45%) |
| Bone turnover (CTX) | 69% are decreased (improved) | 13/16 (81%) are decreased (improved) |

*20 patients have reached Day 90 study; 19 patients were mCPRC and 1 patient was nmCRPC.

This is consistent with observations from other trials reported herein. The percentage change in SHBG for each subject at their study visits for nineteen subjects on 250 mg is shown in FIG. 56. 250 mg of Compound IV daily impacts testosterone levels in an additive fashion compared to LHRH agents alone. 4/4 subjects with total T levels >20 ng/dL fell below that level while on study and 9/10 subjects with serum free T levels >0.7 pg/ml fell below that level on study, consistent with observations with the 125 mg dose (as presented below).

Additional Suppression of Serum Testosterone in Men on ADT with Optimal Testosterone Responses to ADT (i.e., Total T<20 ng/dL or Free T<0.7 pg/mL).

Total Testosterone:
   Patient with >20 ng/dL (Day 1) that goes to <20 ng/dL
   125 mg cohort-3/3-100%
   250 mg cohort-4/4-100%
   Patient with >20 ng/dL (Day 1) does NOT go to <20 ng/dL
   125 mg cohort-0/3-0%
   250 cohort-0/4-0%
Free Testosterone:
   Patient with >0.7 pg/ml (Day 1) goes to <0.7 pg/mL
   125 mg cohort-22/25 (88%)
   250 mg cohort-9/10 (90%)
   Patient with <0.7 pg/ml free T (Day 1)
   125 mg cohort-13
   250 mg cohort-10

The percentage change in total and free serum T levels for each subject on 250 mg at each study visit are indicated in FIG. 57 and FIG. 58.

Six of 20 (30%) subjects on 250 mg, compared to 4/38 (11%) on 125 mg, experienced ≥50% decrease in their PSA level (Table 45). Seventeen of 20 (85%) on 250 mg had any level of PSA decline (FIG. 59).

The bone turnover biomarker collagen C-telopeptide (CTX) decreased in 81% of subjects on 250 mg, compared to 69% on 125 mg, suggesting a potential dose relationship (Table 45). The percentage change in the bone turnover markers for subjects on 250 mg is shown in FIGS. 60A and 60B.

Suppression of hot flashes, another estrogen deficiency side effect of ADT, was comparable for subjects on 250 mg and 125 mg doses (Table 45 (both cohorts) and FIG. 61 (data for 250 mg cohort only)) and in both cases a percentage of men entering the study with hot flashes demonstrated improvement in either the severity or frequency of their hot flashes. 250 mg of Compound IV daily was generally well tolerated with one reported drug related serious adverse events (SAE) and seven reported the following adverse events (AE's):

| AE's: | |
|---|---|
| Nipple Tenderness | Grade 1 |
| Nipple Pain | Grade 1 |
| Sensitivity of Mammila | Grade 1 |
| Bilateral Breast Tenderness | Grade 1 |
| Gynecomastia | Grade 2 |
| Diarrhea | Grade 1 |

SAE's:
   Phlebothrombosis-Grade 3-possibly drug related-patient required hospitalization.
   Dehydration, vertigo, weakness (not drug related but required hospitalization and the patient has recovered).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating, suppressing, reducing the incidence of, reducing the severity of, or inhibiting the progression of castration resistant prostate cancer (CRPC) and its symptoms, or increasing the overall or progression-free survival of men with castration resistant prostate cancer (CRPC) comprising administering a therapeutically effective amount of a compound of formula I, or its isomer, pharmaceutically acceptable salt, pharmaceutical product, polymorph, hydrate or any combination thereof:

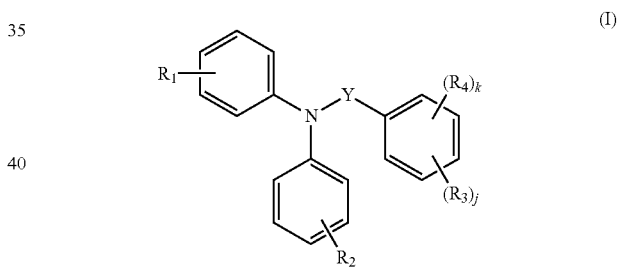

(I)

wherein
   Y is C(O) or $CH_2$;
   $R_1$ and $R_2$ are each independently hydrogen, halogen, hydroxyl, alkoxy, cyano, nitro, $CF_3$, $N(R)_2$, sulfonamide, $SO_2R$, alkyl, haloalkyl, aryl, O-Alk-$NR_5R_6$ or O-Alk-heterocycle in which the heterocycle is a 3-7 membered substituted or unsubstituted heterocyclic ring, optionally aromatic;
   $R_3$ and $R_4$ are each independently hydrogen, halogen, hydroxyalkyl, hydroxyl, alkoxy, cyano, nitro, $CF_3$, NHCOR, $N(R)_2$, sulfonamide, $SO_2R$, alkyl, haloalkyl, aryl or protected hydroxyl;
   R is alkyl, hydrogen, haloalkyl, dihaloalkyl, trihaloalkyl, $CH_2F$, $CHF_2$, $CF_3$, $CF_2CF_3$, aryl, halogen, alkenyl, CN, $NO_2$, or OH;
   $R_5$ and $R_6$ are independently hydrogen, phenyl, an alkyl group of 1 to 6 carbon atoms, a 3 to 7 membered cycloalkyl, a 3 to 7 membered heterocycle, or a 5 to 7 membered aryl; or $R_5$ and $R_6$ form a 3 to 7 membered ring with the nitrogen atom to which they are attached;
   j and k are each independently 1-4; and
   Alk is a linear alkyl of 1-7 carbons, a branched alkyl of 1-7 carbons, or a cyclic alkyl of 3-8 carbons.

2. The method of claim 1, wherein said compound of formula I is selected from:

II.
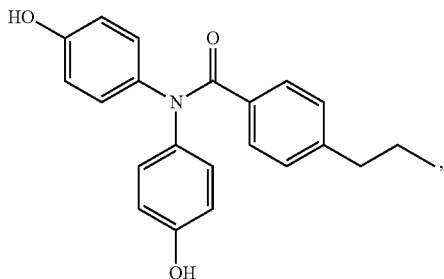

III.
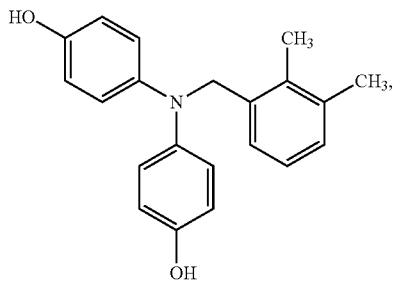

IV.
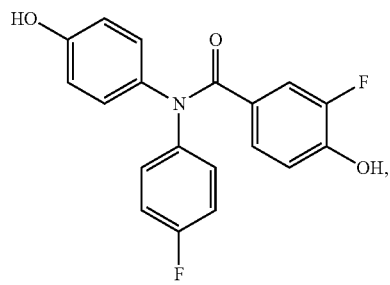

V.
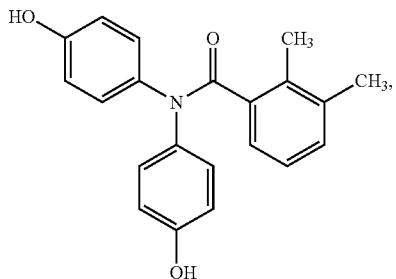

VII.
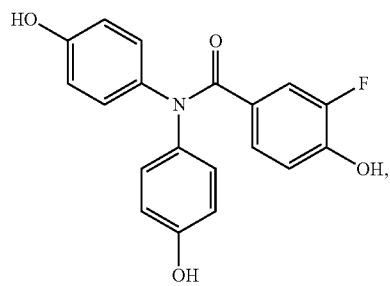

-continued

VIII.
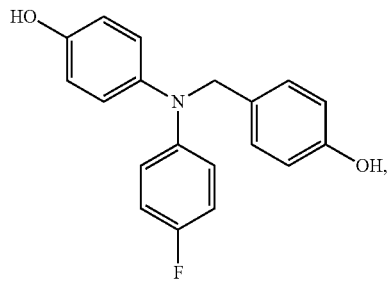

XI.
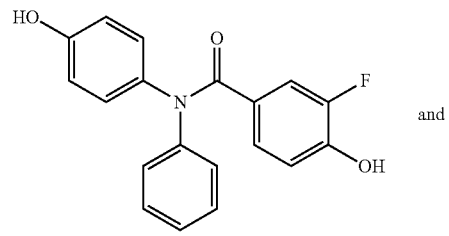

and

XII.
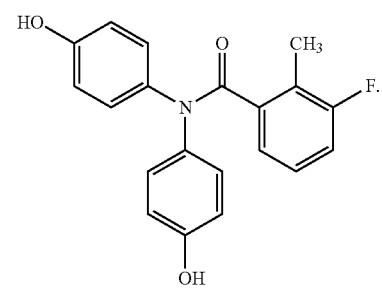

3. The method of claim 1, wherein said compound of formula I is Compound IV:

IV
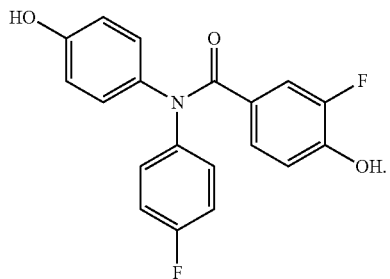

4. The method of claim 1, wherein said subject further receives androgen deprivation therapy (ADT).

5. The method of claim 1, wherein said method lowers the prostate specific antigen (PSA) levels.

6. The method of claim 1, wherein said method increases the levels in serum of sex or steroidal hormone binding globulin (SHBG).

7. The method of claim 1, wherein said method increases radiographic progression free survival (rPFS) in a subject having metastatic cancer.

8. The method of claim 1, wherein said method increases metastasis-free survival (MFS) in a subject having non-metastatic cancer.

9. The method of claim 1, wherein said method decreases symptomatic bone fractures in said subject.

10. The method of claim 1, wherein said CRPC is metastatic CRPC (mCRPC).

11. The method of claim 1, wherein said CRPC is non-metastatic CRPC (nmCRPC).

12. The method of claim 11, wherein said nmCRPC is high-risk nmCRPC.

13. The method of claim 4, wherein said administering of said compound reduces or ameliorates side effects associated with said androgen deprivation therapy (ADT).

14. The method of claim 13, wherein said side effects are selected from the group consisting of: hot flashes, gynecomastia, increased body fat, bone loss, decreased bone mineral density, and increased risk of bone fracture.

15. The method of claim 1, wherein said compound or its isomer, pharmaceutically acceptable salt, pharmaceutical product, hydrate or any combination thereof, is administered at a dose of 40 mg per day, 80 mg per day, 125 mg per day, 250 mg per day or 500 mg per day.

* * * * *